US010934595B2

(12) United States Patent
Faruki et al.

(10) Patent No.: US 10,934,595 B2
(45) Date of Patent: Mar. 2, 2021

(54) METHODS FOR SUBTYPING OF LUNG ADENOCARCINOMA

(71) Applicants: GeneCentric Therapeutics, Inc., Research Triangle Park, NC (US); The University of North Carolina at Chapel Hill, Chapel Hill, NC (US)

(72) Inventors: Hawazin Faruki, Durham, NC (US); Myla Lai-Goldman, Durham, NC (US); Greg Mayhew, Durham, NC (US); Jonathan Serody, Duham, NC (US); Charles Perou, Carrboro, NC (US); David Neil Hayes, Chapel Hill, NC (US)

(73) Assignees: GeneCentric Therapeutics, Inc., Research Triangle Park (NC); The University of North Carolina at Chapel Hill, Chapel Hill, NC (US)

( * ) Notice: Subject to any disclaimer, the term of this patent is extended or adjusted under 35 U.S.C. 154(b) by 103 days.

(21) Appl. No.: 16/302,167

(22) PCT Filed: May 17, 2017

(86) PCT No.: PCT/US2017/033110

§ 371 (c)(1),
(2) Date: Nov. 16, 2018

(87) PCT Pub. No.: WO2017/201165

PCT Pub. Date: Nov. 23, 2017

(65) Prior Publication Data

US 2019/0338365 A1 Nov. 7, 2019

Related U.S. Application Data

(60) Provisional application No. 62/337,591, filed on May 17, 2016, provisional application No. 62/337,645, filed on May 17, 2016, provisional application No. 62/396,587, filed on Sep. 19, 2016, provisional application No. 62/420,836, filed on Nov. 11, 2016, provisional application No. 62/425,717, filed on Nov. 23, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 4,843,155 | A | 6/1989 | Chomczynski |
| 5,384,261 | A | 1/1995 | Winkler et al. |
| 5,445,934 | A | 8/1995 | Fodor et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,770,722 | A | 6/1998 | Lockhart et al. |
| 5,789,162 | A | 8/1998 | Dower et al. |
| 5,800,992 | A | 9/1998 | Fodor et al. |
| 5,854,033 | A | 12/1998 | Lizardi |
| 5,856,174 | A | 1/1999 | Lipshutz et al. |
| 5,874,219 | A | 2/1999 | Rava et al. |
| 5,922,591 | A | 7/1999 | Anderson et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,344,316 | B1 | 2/2002 | Lockhart et al. |
| 6,524,581 | B1 | 2/2003 | Adamis |
| 7,473,767 | B2 | 1/2009 | Dimitrov |
| 8,492,094 | B2 | 7/2013 | Dimitrov et al. |
| 2003/0092009 | A1 | 5/2003 | Palm |
| 2004/0009489 | A1 | 1/2004 | Golub et al. |
| 2006/0024692 | A1 | 2/2006 | Nakamura et al. |
| 2010/0233695 | A1 | 9/2010 | Hayes et al. |
| 2015/0140017 | A1 | 5/2015 | Dhodapkar et al. |
| 2017/0114416 | A1 | 4/2017 | Faruki et al. |
| 2019/0203296 | A1 | 7/2019 | Faruk et al. |
| 2019/0338366 | A1 | 11/2019 | Faruki et al. |

FOREIGN PATENT DOCUMENTS

| | | | |
|---|---|---|---|
| WO | WO 2003/029273 | A2 | 4/2003 |
| WO | WO 2004/031413 | A2 | 4/2004 |
| WO | WO 2008/151110 | A2 | 12/2008 |

(Continued)

OTHER PUBLICATIONS

Hou et al (PLoS One. 2010. 6(4): e10312, p. 1-12 (Year: 2010).*
ALIMTA® (Pemetrexed disodium) Eli Lilly & Co., Indianapolis, IN prescribing information. http://pi.lilly.com/us/alimta-pi.pdf, 31 pages (2018).
American Cancer Society. Cancer Facts and Figures, retrieved Sep. 25, 2018 from https://www.cancer.org/research/cancer-facts-statistics/all-cancer-facts-figures/cancer-facts-figures-2014.html, 6 pages.
AVASTIN® (Bevacizumab) Genetech Inc, San Francisco, CA prescribing information (2018). Retrieved online Oct. 10, 2018 at https://www.gene.com/download/pdf/avastin_prescribing.pdf, 41 pages.
Barany, "Cloning, overexpression and nucleotide sequence of a thermostable DNA ligase-encoding gene," Proc. Natl. Acad. Sci. USA 88:189-193 (1991).

(Continued)

*Primary Examiner* — Carla J Myers
(74) *Attorney, Agent, or Firm* — Cooley LLP

(57) ABSTRACT

Methods and compositions are provided for determining a subtype of lung adenocarcinoma (AD) of an individual by detecting the expression level of at least one classifier biomarker selected from a group of gene signatures for lung adenocarcinoma. Also provided herein are methods and compositions for determining the response of an individual with an adenocarcinoma subtype to a therapy such as immunotherapy.

11 Claims, 34 Drawing Sheets

Specification includes a Sequence Listing.

(56) References Cited

FOREIGN PATENT DOCUMENTS

| | | |
|---|---|---|
| WO | WO 2015/184461 | 6/2015 |
| WO | WO 2016/168446 A1 | 10/2016 |
| WO | WO 2017/201164 A1 | 11/2017 |
| WO | WO 2017/201165 A1 | 11/2017 |

OTHER PUBLICATIONS

Bibikova et al., "Quantitative gene expression profiling in formalin-fixed, paraffin-embedded tissues using universal bead arrays," Am J. Pathol 165:1799-1807 (2004).

Bild AH, Yao G, Chang JT, et al. Oncogenic pathway signatures in human cancers as a guide to targeted therapies. Nature 439(7074): 353-357 (2006).

Bindea et al., "Spatiotemporal dynamics of intratumoral immune cells reveal the immune landscape in human cancer," Immunity 39(4); 782-795 (2013).

Bolstad et al., "A comparison of normalization methods for high density oligonucleotide array data based on variance and bias," Bioinformatics Bioinformatics 19(2):185-193 (2003).

Brenner et al., "Gene expression analysis by massively parallel signature sequencing (MPSS) on microbead arrays," Nat. Biotech. 18:630-34, 2000.

Broomhead DS, Jones R, King GP., "Comment on Singular-value decomposition and embedding dimension," Phys Rev A Gen Phys. Jun 15;37(12):5004-5005 (1988).

Calabrese et al., "Serpin B4 lsoform Overexpression is Associated with Aberrant Epithelial Proliferation and Lung Cancer in Idiopathic Pulmonary Fibrosis," Pathology 44(3):192-198 (2012).

Cancer Genome Atlas Research Network. "Comprehensive genomic characterization of squamous cell lung cancers." Nature 489.7417 (2012): 519-525.

Cao et al., "Role of LKB1-CRTC1 on glycosylated COX-2 and response to COX-2 inhibition in lung cancer," JNatl Cancer Inst. 2015;107(1):1-11.

Clark et al., "Suppression of nonspecific binding of avidin-biotin complex (ABC) to proteins electroblotted to nitrocellulose paper," J Histochem Cytochem 34:1509-1512 (1986).

Collisson E., et al., "Comprehensive Molecular Profiling of Lung Adenocarcinoma," Nature 511(7511):543-550 (2014).

Cronin et al., "Measurement of gene expression in archival paraffin-embedded tissues: development and performance of a 92-gene reverse transcriptase-polymerase chain reaction assay,"Am. J Pathol. 164(1):35-42 (2004).

Dabney AR ClaNC: Point-and-click software for classifying microarrays to nearest centroids. Bioinformatics. 2006;22: 122-123.

Dabney, "Classification of microarrays to nearest centroids," Bioinformatics 21(22):4148-4154 (2005).

Ettinger et al., "Non-small cell lung cancer, version 2.2013." J Natl Compr Canc Netw. Jun. 1, 2013;11(6):645-53; quiz 653.

Extended European Search Report issued by the European Patent Office for Application No. 16780736.1, dated Nov. 9, 2018, 13 pages.

Fan et al., "A Versatile Assay for High-Throughput Gene Expression Profiling on Universal Array Matrices," Genome Res. 14:878-885 (2004).

Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).

Faruki H, et al., "Validation of the Lung Subtyping Panel in Multiple Fresh-Frozen and Formalin-Fixed, Paraffin-Embedded Lung Tumor Gene Expression Data Sets," Archives Path & Lab Med. Oct. 2015.

Fennell et al., "Association between Gene Expression Profile and Clinical Outcome of Pemetrexed-Based Treatment in Patients ,with Advanced Non-Small Cell Lung Cancer: Exploratory Results from a Phase II study," Plos one Sep. 14, 2014 9(9): e107455, 8 pages.

Fishel and Kaufman et al., "Meta-analysis of gene expression data: a predictor-based approach ," Bioinformatics 23(13): 1599-606 ( 2007).

Forero et al., "Expression of the MHC class II pathway in triple negative breast cancer tumor cells is associated with a good prognosis and infiltrating lymphocytes," Cancer Immunol Res 4(5):390-399 2016.

Foundation Medicine Solid Tumor Mutation Panel accessed Oct. 2014, 2 pages.

Fox et al., "Formaldehyde Fixation," J Histochem Cytochem 33:845-853 (1985).

Friedman et al., "Regularization Paths for Generalized Linear Models via Coordinate Descent,"Journal of statistical software 33(1): 1-22 (2010).

Geiss et al., "Direct multiplexed measurement of gene expression with color-coded probe pairs," Nat. Biotechnol. 26:317-325 (2008).

Grilley-Olson et al. Validation of interobserver agreement in lung cancer assessment: hematoxylin-eosin diagnostic reproducibility for non small cell lung cancer. Arch Pathol Lab Med 2013; 137: 32-40.

Guatelli et al., "Isothermal, in vitro amplification of nucleic acids by a multienzyme reaction modeled after retroviral replication," Proc Natl Acad Sci U S A. 87(5):1874-1878 (1990).

Hast et al., Cancer-derived mutations in KEAP1 impair NRF2 degradation but not ubiquitination. Cancer Res 2014; 74(3): 808-817.

Hayes DN, Monti S, Parmigiani G, et al. Gene expression profiling reveals reproducible human lung adenocarcinoma subtypes in multiple independent patient cohorts. J Clin Oncol 24(31): 5079-5090 (2006).

Hubbell, "Robust estimators for expression analysis," Bioinformatics (2002) 18(12):1585-1592.

International Search Report and Written Opinion issued by the International Searching Authority for Application No. PCT/US2015/033611, dated Sep. 14, 2015, 10 pages.

International Search Report and Written Opinion issued by the International Searching Authority for Application No. PCT/US2016/027503, dated Jul. 14, 2016, 10 pages.

International Search Report and Written Opinion issued by the International Searching Authority for Application No. PCT/US2017/033107, dated Oct. 23, 2017, 21 pages.

International Search Report and Written Opinion issued by the International Searching Authority for Application No. PCT/US2017/033110, dated Oct. 20, 2017, 21 pages.

Irizarry et al., "Exploration, normalization, and summaries of high density oligonucleotide array probe level data," Biostatistics Apr. 4(2): 249-64 (2003).

Koyama et al., STK11/LKB1 deficiency promotes neutrophil recruitment and proinflammatory cytokine production to suppress T-cell activity in the lung tumor microenvironment. Cancer Res 76(5): 999-1008 (2016).

Kratz JR, et al., "A practical molecular assay to predict survival in resected non-squamous, non-small-cell lung cancer: development and international validation studies," Lancet 379(9818):823-832 (2012).

Kwoh et al., "Transcription-based amplification system and detection of amplified human immunodeficiency virus type 1 with a bead-based sandwich hybridization format (TI RNA polymerase/in vitro nucleic acid amplification)," Proc. Natl. Acad. Sci. USA, 86:1173-1177 (1989).

Landegren et al., "A ligase-mediated gene detection technique," Science, 241(4869):1077-1080 (1988), retrieved from http://science.sciencemag.org/ on Oct. 29, 2018+A71.

Lee ES, et al., "Prediction of recurrence-free survival in postoperative non-small cell lung cancer patients by using an integrated model of clinical information and gene expression." Clinical Cancer Research 14(22):7397-7404 (2008).

Li and Dewey, "RSEM: accurate transcript quantification from RNA-Seq data with or without a reference genome," BMC Bioinformatics 2011 12:323, 16 pages.

McGhee and von Hippel, "Formaldehyde as a probe of DNA structure. II. Reaction with endocyclic imino groups of DNA bases," Biochemistry 14:1281-1296 (1975).

Mukhopadhyay S., "Utility of Small Biopsies for Diagnosis of Lung Nodules: Doing More with Less," Modern Pathology, 25(1):S43-S57 (2012).

(56) References Cited

OTHER PUBLICATIONS

Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Nielsen, "A comparison of PAM50 intrinsic subtyping with immunohistochemistry and clinical prognostic factors in tamoxifen-treated estrogen receptor-positive breast cancer," Clin Cancer Res. Nov. 1, 2010;16(21):5222-32. doi: 10.1158/1078-0432.CCR-10-1282. Epub Sep. 13, 2010, Downloaded from clincancerres.aacrjournals.org on Oct. 10, 2018.
Niki, T., et al., "Expression of Vascular Endothelial Growth Factors A, B. C, and D and Their Relationships to Lymph Node Status in Lung Adenocarcinoma," Clinical Cancer Research 6(6):2431-2439 (2000).
Paolillo et al., "Small molecule integrin antagonists in cancer therapy," Mini Rev Med Chem 12:1439-1446 (2009).
Parzen, "On Estimation of a Probability Density Function and Mode," Stanford University, 1065-1076 (1962).
Prasad et al., "Differential Expression of Degradome Components in Cutaneous Squamous Cell Carcinomas," Modern Pathology 27:495-957 (2014).
Quinlan, "Induction of Decision Trees," Machine Learning 1(1):81-106 (1986).
Raponi et al. "Gene expression signatures for predicting prognosis of squamous cell and adenocarcinomas of the lung," Cancer Res 66(7): 466-472 (2006).
Rekhtman et al., "Distinct profile of driver mutations and clinical features in immunomarker-defined subsets of pulmonary large-cell carcinoma," Mod Pathol 26(4): 511-22 (2013).
Rekhtman et al., "Immunnohistochemical algorithm for differentiation of lung adenocarcinoma and squamous cell carcinoma based on large series of whole-tissue sections with validation in small specimens," Modern Path. 24:1348-1359 (2011).
Ringnér, M., et al., "Prognostic and Chemotherapy Predictive Value of Gene-Expression Phenotypes in Primary Lung Adenocarcinoma," Clinical Cancer Research 22(1):218-229 (2015).
Robin et al., "pROC: an open source package for R and S+ to analyze and compare ROC curves," BMC bioinformatic 12:77 (2011), 8 pages.
Roepman P, et al. An immune response enriched 72-gene prognostic profile for early stage non-small-cell lung cancer. Clinical Cancer Research 15.1:284-290 (2009).
Rossi G, Mengoli MC, Cavazza A, et al. Large cell carcinoma of the lung: clinically oriented classification integrating immunohistochemistry and molecular biology. Virchows Arch. 2014; 464: 61-68. DOI 10.1007/s00428-013-1501-6.
Rouskin et al., "Genome-wide probing of RNA structure reveals active unfolding of mRNA structures in vivo," Nature 505, pp. 701-705 (2014).
Rousseaux S, et al. Ectopic activation of germline and placental genes identifies aggressive metastasis-prone lung cancers. Sci Transl Med. 5(186):186ra66 (2013).
Rupp G and Locker J., University of Pittsburgh School of Medicine, "Purification and analysis of RNA from paraffin embedded tissues," BioTechniques 6(1):56-60 (1988).
Schabath et al., "Differential association of STK11 and TP53 with KRAS mutation-associated gene expression, proliferation, and immune surveillance in lung adenocarcinoma," Oncogene 35(24):3209-3216, Author manuscript, 13 pages (2016).
Schafer, G., et al., *Homo sapiens* Vascular Endothelial Growth Factor D (FIGF) Gene, Promoter Region and 5' UTR. National Center fnr Biotechnology Information. Genbank Entry. Jan. 3, 2005 [retrieved on Sep. 27, 2017] Retrieved from the Internet: <URL: https://www.ncbi.nlm.nih.gov/nucleotide/58223364?report=genbank&log$=nuclalign&blast_rank=5&RID=WWYAJBVM015>; pp. 1-2.
Shedden K, Taylor JMG, Enkemann SA, et al. Gene expression-based survival prediction in lung adenocarcinoma: a multi-site, blinded validation study: director's challenge consortium for the molecular classification of lung adenocarcinoma. Nat Med 14(8): 822-827 (2008). doi: 10.1038/nm. 1790.
Skoulidis et al., "Co occuring genomic alterations define major subsets of KRAS-mutant lung adenocarcinoma with distinct biology, immune profiles, and therapeutic vulnerabilities," Cancer Discov 5(8): 860-77 (2015).
Smyth, G. K., Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Smyth, G. K., "Linear Models and Empirical Bayes Methods for Assessing Differential Expression in Microarray Experiments," Stat. Appi. Genet. Mol. Biol. 3: Article 3, 28 pages (2004).
Statistical analyses R 3.2.0 software (http://www.R-project.org) retrieved online Jan. 7, 2019 at http://www.R-project.org, 3 pages.
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229.
Tang et al., "Advances in lung adenocarcinoma classification: a summary of the new international multidisciplinary classification system (IASLC/ATS/ERS) ," J Thorac Dis 2014;6(S5):S489-S501.
The Clinical Lung Cancer Genome Project (CLCGP) and Network Genomic Medicine (NGM). A genomics-based classification of human lung tumors. Sci Transl Med 5, 209ra153, 28 pages (2013).
Thunnissen et al., "Reproducibility of histopathological subtypes and invasion in pulmonary adenocarcinoma. An international interobserver study," Mod Pathol 2012; 25(12):1574-1583. DOI: 10.1038/modpathol.2012.106 Epub Jul. 20, 2012.
Thunnissen et al., "Correlation of immunohistochemical staining p63 and TTF-1 with EGFR and K-ras mutational spectrum and diagnostic reproducibility in non small cell lung carcinoma," Virchows Arch 2012; 46(6)1:629-38.
Thunnissen et al., "Reproducibility of histopathological diagnosis in poorly differentiated NSCLC: an international multiobserver study," J Thorac Oncol 2014; 9(9): 1354-1362.
Tibshirani et al., "Diagnosis of multiple cancer types by shrunken centroids of gene expression," Proc. Natl. Acad. Sci. USA 99(10):6576-6572) (2002).
Tomida S., et al., "Relapse-related molecular signature in lung adenocarcinomas identifies patients with dismal prognosis," J Clin Oncol 27(17): 2793-99 (2009).
Trapnell et al., "Transcript assembly and quantification by RNA-Seq reveals unannotated transcripts and isoform switching during cell differentiation," Nature biotechnology 28(5):511-515 (2010).
Trapnell et al., "TopHat: discovering splice junctions with RNA-Seq.," Bioinformatics 25(9):1105-11 (2009).
Travis et al., "Diagnosis of lung cancer in small biopsies and cytology: implications of the 2011 International Association for the Study of Lung Cancer/American Thoracic Society/European Respiratory Society classification," Arch Pathol Lab Med 2013; 137(5):668-84.
Travis and Rekhtman, "Pathological diagnosis and classification of lung cancer in small biopsies and cytology: strategic management of tissue for molecular testing," Sem Resp and Crit Care Med 32(1): 22-31 (2011).
Travis et al., "International Association for the study of lung cancer/American Thoracic Society/European Respiratory Society International multidisciplinary classification of lung adenocarcinoma," J Thorac Oncol, 6:244-285 (2011).
Travis et al., "New pathologic classification of lung cancer: relevance for clinical practice and clinical trials," J Clin Oncol 31:992-1001 (2013).
Velculescu et al., "Characterization of the yeast transcriptome," Cell 88(2):243-251 (1997).
Velculescu et al., "Serial analysis of gene expression," Science 270(5235):484-487 (1995), retrieved from http://science.sciencemag.org/ on Oct. 29, 2018.
Vermeulen, Pediatric Primitive Neuroectodermal Tumors of the Central Nervous System Differentially Express Granzyme Inhibitors. PLoS One. 11(3):1-8 (2016).

(56) References Cited

OTHER PUBLICATIONS

Wilkerson et al., Lung Squamous Cell Carcinoma mRNA Expression Subtypes are Reproducible, Clinically Important and Correspond to Different Normal Cell Types. Clinical Clin Cancer Res 16(19):4864-4875 (2010).
Wilkerson et al., "Differential pathogenesis of lung adenocarcinoma subtypes involving sequence mutations, copy number, chromosomal instability, and methylation," PLoS One. 2012; 7(5) e36530. Doi:10.1371/joumal.pone.0036530, 13 pages.
Wilkerson et al., "Prediction of lung cancer histological types by RT-qPCR gene expression in FFPE specimens," J Molec Diagn 15(4):485-497 (2013).
Wilkerson, M.D. et al. Supplemental Figure S2, Journal of Molecular Diagnostics 15(4):485 (Jul. 2013; online May 22, 2013), 1 page.
Wistuba et al., "Validation of a proliferation-based expression signature as prognostic marker in early stage lung adenocarcinoma," Clin Cancer Res 19(22):6261-6271 (2013), Downloaded from clincancerres.aacrjournals.org on Oct. 10, 2018.
Wold, et al., "Genome expression and mRNA maturation at late stages of productive adenovirus type 2 infection," J Virol. Nov. 1976;20(2):465-77.
Wu and Wallace, "The ligation amplification reaction (LAR)—amplification of specific DNA sequences using sequential rounds of template dependent ligation.," Genomics, 4(4):560-569 (1989).
Yang et al, "Normalization for cDNA microarray data: a robust composite method addressing single and multiple slide systematic variation,"Feb. 15, 2002;30(4):e15, 10 pages.
Zhang et al., "Assessment of VEGF-D Expression Measured by lmmunohistochemical Staining and F-18 FDG Uptake on PET as Biological Prognostic Factors for Recurrence in Patients with Surgically Resected Lung Adenocarcinoma," Annals of Nuclear Medicine. 24(7):533-540 (2010).
Zhu CQ, et al., "Prognostic and predictive gene signature for adjuvant chemotherapy in resected non-small-cell lung cancer," J Clin Oncol 28(29); 4417-4424 (2010).
Bhattacharjee et al., Classification of Human Lung Carcinomas by mRNA Expression Profiling Reveals Distinct Adenocarcinoma Subclasses, PNAS 98(24):13790-13795 (2001).
Charych et al., Intra-tumoral immune 1 cell mobilization and anti-tumor activity after treatment with the engineered cytokine NKTR-214 in multiple preclinical mouse tumor models, European Journal of Cancer vol. 69, Jan. 1, 2016, Poster (Board P132), No. 306, 1 page.
Extended European Search Report issued by the European Patent Office for Application No. 17800090.7, dated Jan. 27, 2020, 6pages.
Extended European Search Report issued by the European Patent Office for Application No. 17800091.5, dated Jan. 28, 2020, 7 pages.
Filosso et al., "Adenosquamous lung carcinomas: A histologic subtype with poor prognosis," Lung Cancer, 74:25-29 (2011).
Han et al., "RNA sequencing identifies novel markers of non-small cell lung cancer," Lung Cancer 84:229-23 (2014).
Kuang et al., "The prognostic value of platelet endothelial cell adhesion molecule-I in non-small-cell lung cancer patients," Med. Oncol. 30:536 (2013).
Lee et al, "Multiregion gene expression profiling reveals heterogeneity in molecular subtypes and immunotherapy response signatures in lung cancer," Modern Pathology, Nature Publishing Group, GB, 31(6):947-955 (2018).
"Rare lung cancers," Breathe (Sheffield, England), 11(4):323-330 (2015).

* cited by examiner

Lung Cancer Subtyping

FIG. 2

| Characteristic | TCGA[2] | Shedden[6] | Tomida[7] | UNC[1] | GeneCentric |
|---|---|---|---|---|---|
| Total # of samples | 515 | 442 | 117 | 116 | 88 |
| Tissue preservation | Fresh Frozen | Fresh Frozen | Fresh Frozen | Fresh Frozen | FFPE |
| Subtype | | | | | |
| bronchioid | 188 | 159 | 45 | 47 | 26 |
| magnoid | 154 | 161 | 40 | 40 | 29 |
| squamoid | 173 | 122 | 32 | 29 | 33 |
| Gender | | | | | |
| Female/Male/NA | 274/237/4 | 219/223/0 | 57/60/0 | 63/53/0 | |
| Age of diagnosis | | | | | |
| Median/(Range) | 66/(38-88) | 65/(33-87) | 61/(32-84) | 65/(41-90) | |
| Age not available | 35 | 0 | 0 | 0 | |
| Stage | | | | | |
| I | 276 | 276 | 79 | 73 | 42 |
| II | 123 | 95 | 13 | 21 | 7 |
| III | 84 | 68 | 25 | 19 | 15 |
| IV | 27 | 0 | 0 | 2 | 24 |
| Stage not available | 5 | 3 | 0 | 1 | 0 |
| Smoking ever | | | | | |
| yes | 346 | 300 | 61 | 82 | |
| no | 2 | 49 | 56 | 11 | |
| Smoking status not available | 167 | 93 | 0 | 23 | |

FIG. 5 (continued)
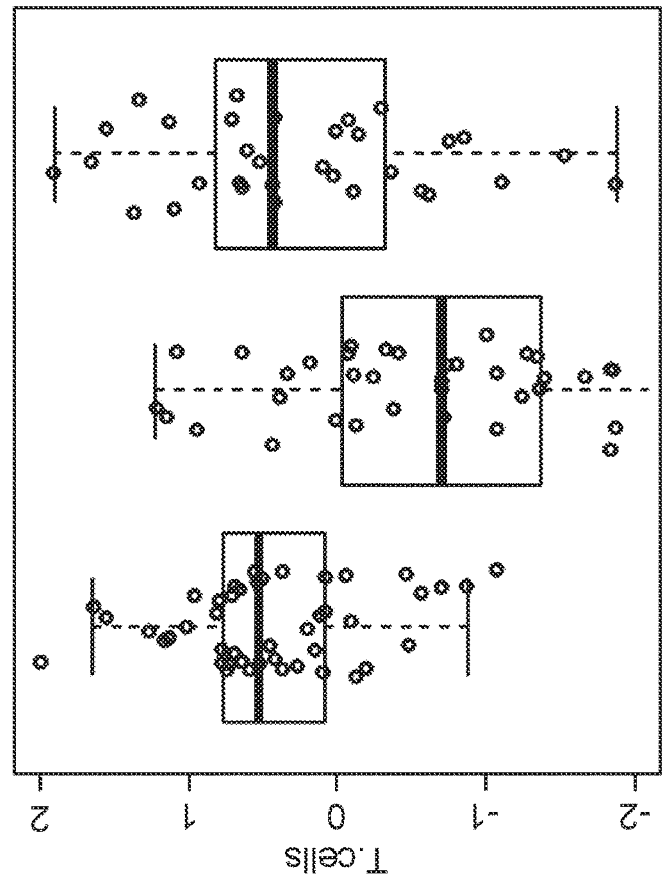
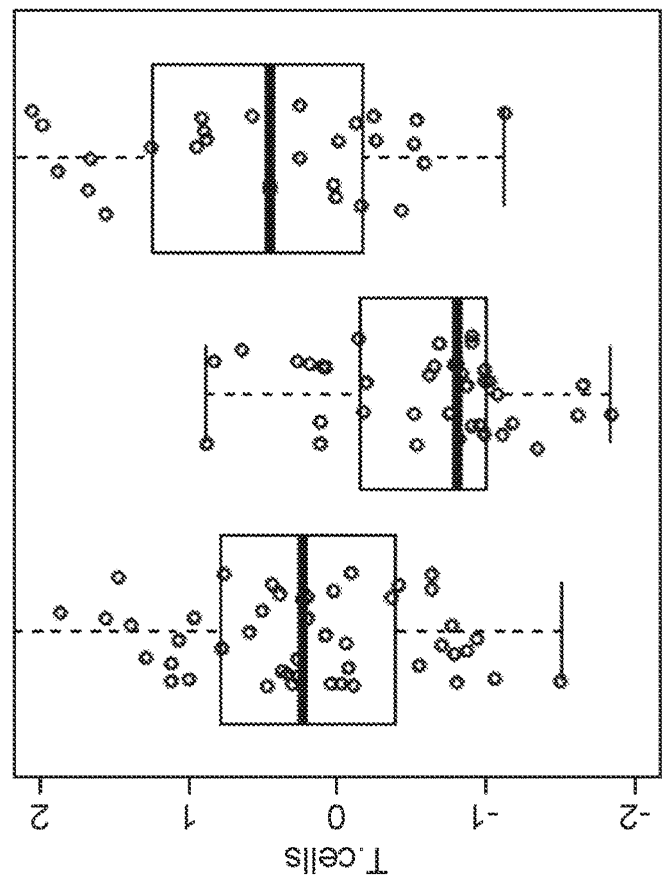

TCGA AD n=515

FIG. 13

Gold standard (rows) vs clanc48 (columns)

| | | bronchioid | magnoid | squamoid |
|---|---|---|---|---|
| GeneCentric FFPE | bronchioid | 23 | 0 | 3 |
| | magnoid | 1 | 23 | 5 |
| | squamoid | 3 | 2 | 28 |
| shedden | bronchioid | 151 | 5 | 3 |
| | magnoid | 16 | 126 | 19 |
| | squamoid | 7 | 6 | 109 |
| tcga | bronchioid | 175 | 3 | 10 |
| | magnoid | 12 | 120 | 22 |
| | squamoid | 9 | 11 | 153 |
| tomida | bronchioid | 43 | 2 | 0 |
| | magnoid | 4 | 28 | 8 |
| | squamoid | 2 | 8 | 22 |
| unc | bronchioid | 44 | 3 | 0 |
| | magnoid | 0 | 38 | 2 |
| | squamoid | 1 | 3 | 25 |

Agreement

| | GeneCentric FFPE | shedden | tcga | tomida | unc |
|---|---|---|---|---|---|
| Agree | 0.84 | 0.87 | 0.87 | 0.79 | 0.92 |

TCGA AD n=515
PDL1 Association Strength
0.00
0.05
0.10
0.15
0.20
0.25
0.30
0.35
Subtype Association Strength
B cells
T cells
T helper cells
Tcm
Tem
Th1 cells
Th2 cells
TFH
Th17 cells
TReg
CD8 T cells
Tgd
Cytotoxic cells AC IFN
p-value=1.1e-20
IFN
AC PDL1
p-value=1.3e-35
PDL1
AC PDL2
p-value=9.4e-33
PDL2
AC PDCD1
p-value=1.4e-13
PDCD1
AC CTLA4
p-value=1.7e-10
CTLA4
AC MHCII
p-value2.7e-45
MHCII
TRU
PP
PI
Subtype
3
2
1
0
-1
-3

FIG. 19
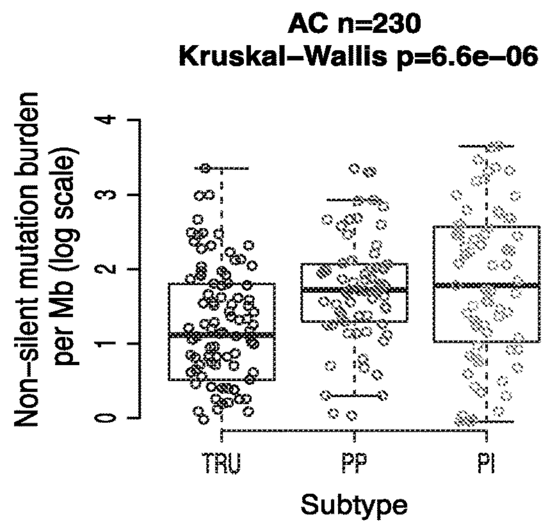
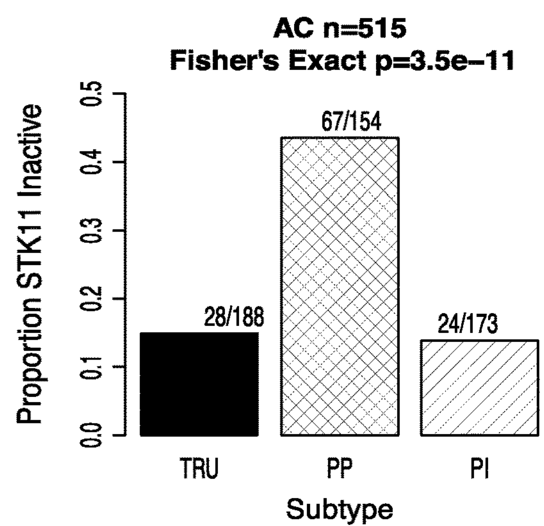
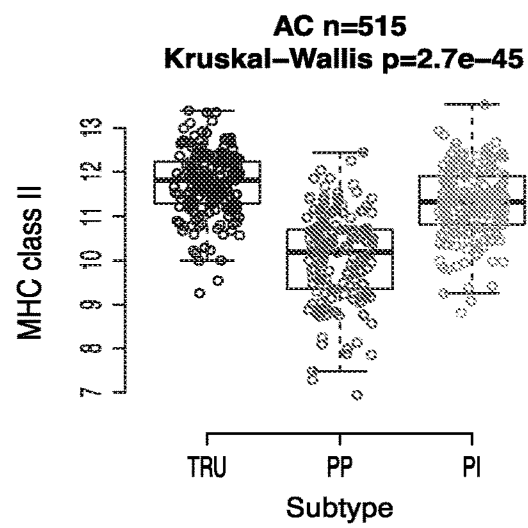

TCGA AD n=515

METHODS FOR SUBTYPING OF LUNG ADENOCARCINOMA

CROSS REFERENCE

This application is a national phase of International Application No. PCT/US2017/033110, filed May 17, 2017, which claims priority from U.S. Provisional Application No. 62/337,591 filed May 17, 2016, U.S. Provisional Application No. 62/337,645 filed May 17, 2016, U.S. Provisional Application No. 62/396,587 filed Sep. 19, 2016, U.S. Provisional Application No. 62/420,836 filed Nov. 11, 2016, and U.S. Provisional Application No. 62/425,717 filed Nov. 23, 2016, each of which is incorporated by reference herein in its entirety for all purposes.

FIELD OF THE INVENTION

The present invention relates to methods for determining an adenocarcinoma subtype of a lung sample and for predicting the response to a treatment for a patient inflicted with specific subtypes of lung cancer.

STATEMENT REGARDING SEQUENCE LISTING

The Sequence Listing associated with this application is provided in text format in lieu of a paper copy, and is hereby incorporated by reference into the specification. The name of the text file containing the Sequence Listing is GNCN_009_01WO_SeqList_ST25.txt. The text file is 194 KB, and was created on May 16, 2017, and is being submitted electronically via EFS-Web.

BACKGROUND OF THE INVENTION

Lung cancer is the leading cause of cancer deaths in both the United States and worldwide. Approximately 172,000 tumors of the lung were diagnosed in 2005 with an estimated 163,000 deaths, more than colon, breast, and prostate combined. At least 75% of patients present with locally advanced disease. Although there has been much effort to improve screening using technology such as high-resolution CT, these methods often produce false positive results and usually do not change outcome. Thus, even small tumors detected early present a significant threat to patients with postoperative 5-year survival rates for stage I lung cancer estimated between 47 to 63 percent. For patients with advanced disease the prognosis is worse with median survivals well under a year. In general, palliative therapy is effective but not sustainable and the average impact on overall survival is approximately 3 months.

At the population level, the underlying cause of lung cancer is clearly tobacco use, with 90% of all lung cancers attributed directly to smoking. Smoking is so tightly correlated with lung cancer that it confounds definitive association with most other risk factors; although asbestos, radon, and a number of lung irritants are generally accepted as lung cancer risk factors. A genetic association is strongly suspected, however, the exact mechanism remains to be determined outside of a select group of rare Mendelian cancer syndromes. Despite many classification schemes and ongoing clinical trials, there has been overall disappointing progress in the field of clinical diagnostics and therapeutics.

Most lung cancers are classified as non-small cell lung carcinoma (NSCLC) (>85%), which is a diverse group with subtypes occurring throughout the respiratory tract. Adenocarcinoma (AD) and squamous cell carcinomas (SCC or SQ), the two main subtypes of NSCLC, are diagnosed at near equal frequency but are often found at different locations with SCC occurring more centrally. The 6th edition of the consensus classification of lung cancers developed by the World Health Organization (WHO) describes no fewer than 90 malignant morphologic classes and variants. There can often be heterogeneity, especially in larger tumors >1.5 cm, making morphological classification more difficult and leading to designations such as adeno-squamous carcinoma. Further, studies of histologic diagnosis reproducibility have shown limited intra-pathologist agreement and inter-pathologist agreement. Variability in morphology, limited tissue samples, and the need for assessment of a growing list of therapeutically targeted markers pose challenges to the current diagnostic standard. This is further highlighted by the idea that differentiation among various morphologic subtypes of lung cancer can be essential in guiding patient management and additional molecular testing can be used to identify specific therapeutic target markers.

Currently, gene expression based lung adenocarcinoma (AD) subtyping has been primarily restricted to a research protocol involving the extraction of RNA from fresh frozen lung tumors, followed by application of a nearest centroid predictor using quantitative gene expression of over 500 genes. Gene expression based adenocarcinoma subtyping has been shown to classify adenocarcinoma tumors into 3 biologically distinct subtypes (Terminal Respiratory Unit (TRU; formerly referred to as Bronchioid), Proximal Inflammatory (PI; formerly referred to as Squamoid), and Proximal Proliferative (PP; formerly referred to as Magnoid)) which can vary in their genomic profiles including gene expression, mutational spectrum, and copy number alterations. Further, these three subtypes can vary in their prognosis, in their distribution of smokers vs. nonsmokers, in their prevalence of EGFR alterations, ALK rearrangements, TP53 mutations, in their angiogenic features, and in their immunogenic response features. Despite evidence of prognostic and predictive benefits from AD subtyping, the requirement for gene expression of >500 genes in combination with complex bioinformatics analyses, has hindered the application of AD subtyping in drug development and/or in the clinic.

Cancer immunosurveillance is the principle that the immune system can identify precancerous and cancerous cells and kill these cells before they become clinically relevant, which has been demonstrated in immunodeficient mouse models. Innate and adaptive immune responses can work together to either promote or inhibit cancer growth, and evasion of immune destruction is an emerging hallmark of cancer. Historically, methods of immune stimulation were not effective for lung cancer patients in the clinic. Deficiencies in tumor antigen expression and presentation on antigen presenting cells (APCs), infiltration of immunosuppressive cells and cytokines, and ineffective T-cell activation can lead to immunosuppression at the tumor site. Advances in the understanding of cancer and the immune system have led to effective therapies that activate antitumor responses, even in tumors that have highly developed methods of immune evasion, such as lung cancer. However the high immunosuppressive effects caused by lung tumors limit the beneficial effects of these advances due to a delicate balance between immunoactivation and immunosuppression in a patient. For example, in NSCLC, the role of immunosuppressive cells hampering immune activation is high, which is suggested to be related to the type of tumor, advanced stage of the disease, and the tumor load.

Therefore, developing a method to effectively distinguish intrinsic lung adenocarcinoma subtypes is critical for clinical diagnosis and disease management. Accordingly, new methods are needed to further define populations that might be likely to respond to immunotherapy. The present invention addresses these and other needs in the field for determining a prognosis or disease outcome for adenocarcinoma patient populations based in part on the adenocarcinoma subtype (Terminal Respiratory Unit (TRU), Proximal Inflammatory (PI), Proximal Proliferative (PP)) of the patient. The methods of the invention provide a means for determining the cellular and molecular origins of lung cancer (e.g., subtyping AD) and can provide for more accurate diagnosis and applicable treatments as compared to diagnostic methods known in the art.

SUMMARY OF THE INVENTION

In one aspect, provided herein is a method for determining an adenocarcinoma (AD) subtype of a lung tissue sample obtained from a patient, the method comprising detecting an expression level of at least one classifier biomarker of Table 1, wherein the detection of the expression level of the classifier biomarker specifically identifies a Terminal Respiratory Unit (TRU), Proximal Proliferative (PP), or Proximal Inflammatory (PI) AD subtype. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference AD TRU sample, expression data of the at least one classifier biomarkers of Table 1 from a reference AD PP sample, expression data of the at least one classifier biomarkers of Table 1 from a reference AD PI sample or a combination thereof; and classifying the sample as TRU, PP or PI subtype based on the results of the comparing step. In some cases, the comparing step comprises applying a statistical algorithm which comprises determining a correlation between the expression data obtained from the sample and the expression data from the at least one training set(s); and classifying the sample as a TRU, PP or PI subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers specific for at least one classifier biomarker of Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises at least two classifier biomarkers, at least 8 classifier biomarkers, at least 16 classifier biomarkers, at least 24 classifier biomarkers, at least 32 classifier biomarkers, at least 40 classifier biomarkers, or at least 48 classifier biomarkers of Table 1. In some cases, the at least one classifier biomarker comprises all the classifier biomarkers of Table 1.

In another aspect, provided herein is a method for determining an adenocarcinoma (AD) subtype of a lung tissue sample obtained from a patient comprising detecting an expression level of at least one nucleic acid molecule that encodes a classifier biomarker having a specific expression pattern in lung cancer cells, wherein the classifier biomarker is selected from the group consisting of the classifier genes set forth in Table 1, the method comprising: (a) isolating nucleic acid material from a lung tissue sample from a patient; (b) mixing the nucleic acid material with oligonucleotides that are substantially complementary to portions of nucleic acid molecule of the classifier biomarker; and (c) detecting expression of the classifier biomarker. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference AD TRU sample, expression data of the at least one classifier biomarkers of Table 1 from a reference AD PP sample, expression data of the at least one classifier biomarkers of Table 1 from a reference AD PI sample or a combination thereof; and classifying the sample as TRU, PP or PI subtype based on the results of the comparing step. In some cases, the comparing step comprises applying a statistical algorithm which comprises determining a correlation between the expression data obtained from the sample and the expression data from the at least one training set(s); and classifying the sample as a TRU, PP or PI subtype based on the results of the statistical algorithm. In some cases, the detecting the expression level comprises performing qRT-PCR or any hybridization-based gene assays. In some cases, the expression level is detected by performing qRT-PCR. In some cases, the detection of the expression level comprises using at least one pair of oligonucleotide primers specific for at least one classifier biomarker of Table 1. In some cases, the method further comprises predicting the response to a therapy for treating a subtype of lung adenocarcinoma (AD) based on the detected expression level of the classifier biomarker. In some cases, the therapy is chemotherapy, angiogenesis inhibitors and/or immunotherapy. In some cases, the subtype of lung AD is TRU and the therapy is chemotherapy or angiogenesis inhibitor. In some cases, the subtype of lung AD is PP and the therapy is chemotherapy. In some cases, the subtype of lung AD is PI and the therapy is an immunotherapy. In some cases, the sample is a formalin-fixed, paraffin-embedded (FFPE) lung tissue sample, fresh or a frozen tissue sample, an exosome, wash fluids, cell pellets or a bodily fluid obtained from the patient. In some cases, the bodily fluid is blood or fractions thereof, urine, saliva, or sputum. In some cases, the at least one nucleic acid molecule that encodes a classifier biomarker comprises a plurality of nucleic acid molecules that encode a plurality of classifier biomarkers. In some cases, the plurality of classifier biomarkers comprises at least two classifier biomarkers, at least 5 classifier biomarkers, at least 10 classifier biomarkers, at least 20 classifier biomarkers or at least 30 classifier biomarkers of Table 1. In some cases, the at least one classifier biomarker comprises all the classifier biomarkers of Table 1.

In yet another aspect, provided herein is a method of detecting a biomarker in a lung tissue sample obtained from a patient, the method comprising measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In one aspect, provided herein is a method of detecting a biomarker in a lung tissue sample obtained from a patient, the method consisting essentially of measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In another aspect, provided herein is a method of detecting a biomarker in a lung tissue sample obtained from a patient, the method consisting of measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In another aspect, provided herein is a method of determining whether an adenocarcinoma patient is likely to respond to immunotherapy, the method comprising, determining the adenocarcinoma subtype of a lung tissue sample from the patient, wherein the adenocarcinoma subtype is selected from the group consisting of squamoid (proximal inflammatory), bronchoid (terminal respiratory unit) and magnoid (proximal proliferative); and based on the subtype, assessing whether the patient is likely to respond to immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have adenocarcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1.

In yet another aspect, provided herein is a method for selecting an adenocarcinoma patient for immunotherapy, the method comprising, determining an adenocarcinoma subtype of a lung tissue sample from the patient, based on the subtype; and selecting the patient for immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have adenocarcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1.

In one aspect, provided herein is a method of treating lung cancer in a subject, the method comprising: measuring the expression level of at least one biomarker nucleic acid in a lung cancer sample obtained from the subject, wherein the at least one biomarker nucleic acid is selected from a set of biomarkers listed in Table 1, wherein the presence, absence and/or level of the at least one biomarker indicates a subtype of the lung cancer; and administering an immunotherapeutic agent based on the subtype of the lung cancer. In some cases, the lung cancer sample is an adenocarcinoma lung cancer sample, In some cases, the at least one biomarker nucleic acid selected from the set of biomarkers comprises, consists essentially of or consists of at least two biomarker nucleic acids, at least 8 biomarker nucleic acids, at least 16 biomarker nucleic acids, at least 32 biomarker nucleic acids, or all 48 biomarker nucleic acids of Table 1. In some cases, the lung tissue sample was previously diagnosed as being adenocarcinoma. In some cases, the previous diagnosis was by histological examination. In some cases, the method further comprises measuring the expression of at least one biomarker from an additional set of biomarkers. In some cases, the additional set of biomarkers comprise gene expression signatures of Innate immune Cells (IIC), Adaptive immune Cells (AIC), one or more individual immune biomarkers, one or more interferon(IFN) genes, one or more major histocompatibility complex, class II (MHC ii) genes or a combination thereof. In some cases, the additional set of biomarkers comprises genes selected from Tables 4A, 4B, 5, 6, 7, or a combination thereof. In some cases, the gene expression signatures of AICs are selected from Table 4A. In some cases, the gene expression signature of IICs are selected from Table 4B. In some cases, the one or more individual immune biomarkers are selected from Table 5. In some cases, the one or more IFN genes are selected from Table 6. In some cases, the one or more MHCII genes are selected from Table 7. In some cases, the measuring the expression level is conducted using an amplification, hybridization and/or sequencing assay. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the subject's adenocarcinoma subtype is selected from squamoid (proximal inflammatory), bronchoid (terminal respiratory unit) or magnoid (proximal proliferative). In some cases, the lung cancer subtype is proximal inflammatory and wherein the immunotherapeutic agent comprises a checkpoint inhibitor. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the at least one biomarker nucleic acid is a plurality of biomarker nucleic acids, wherein the plurality of biomarker nucleic acids comprises at least one biomarker nucleic acid listed in Table 1 in combination with one or more biomarker nucleic acids from a publically available lung adenocarcinoma dataset, wherein the presence, absence and/or level of the plurality of biomarker nucleic acids indicates a subtype of the lung cancer. In some cases, the at least one biomarker nucleic acid is a plurality of biomarker nucleic acids, wherein the plurality of biomarker nucleic acids comprises all of the biomarker nucleic acids listed in Table 1 in combination with one or more biomarker nucleic acids from a publically available lung adenocarcinoma dataset, wherein the presence, absence and/or level of the plurality of biomarker nucleic acids indicates a subtype of the lung cancer. In some cases, the publically available lung adenocarcinoma dataset is TCGA Lung AD RNAseq dataset.

BRIEF DESCRIPTION OF THE DRAWINGS

FIG. 2 illustrates the lung AD datasets used in the study described in Example 1.

FIGS. 7A-7B show survival associations of immune cell signatures and markers by AD subtype in the TCGA cohort (FIG. 7A) or the TGCA, Shedden and Tomida cohorts (FIG. 7B). Subtype specific immune marker hazard ratios and 95% confidence intervals were for 5 year overall survival in the TCGA cohort (n=515 AD) for FIG. 7A.

FIG. 13 illustrates agreement of AD subtype prediction by the 48 gene signature provided herein with the 506-gene classifier to define the gold standard subtype for multiple validation datasets. The agreement with the gold standard (TCGA) is 87%. The agreement with Shedden, Tomida, UNC, and FFPE is 87%, 79%, 92%, and 84%, respectively.

FIG. 19 illustrates Adenocarcinoma (AD) subtype non-silent mutation burden, STK11 inactivation (mutation and/or deletion) in AD, and MHC class II signature, with Kruskal-Wallis association test p-values. TRU=Terminal Respiratory Unit, PP=Proximal Proliferative, PI=Proximal Inflammatory, MHC II=Major Histocompatibility Class II gene signature.

DETAILED DESCRIPTION OF THE INVENTION

Overview

Figure 1:
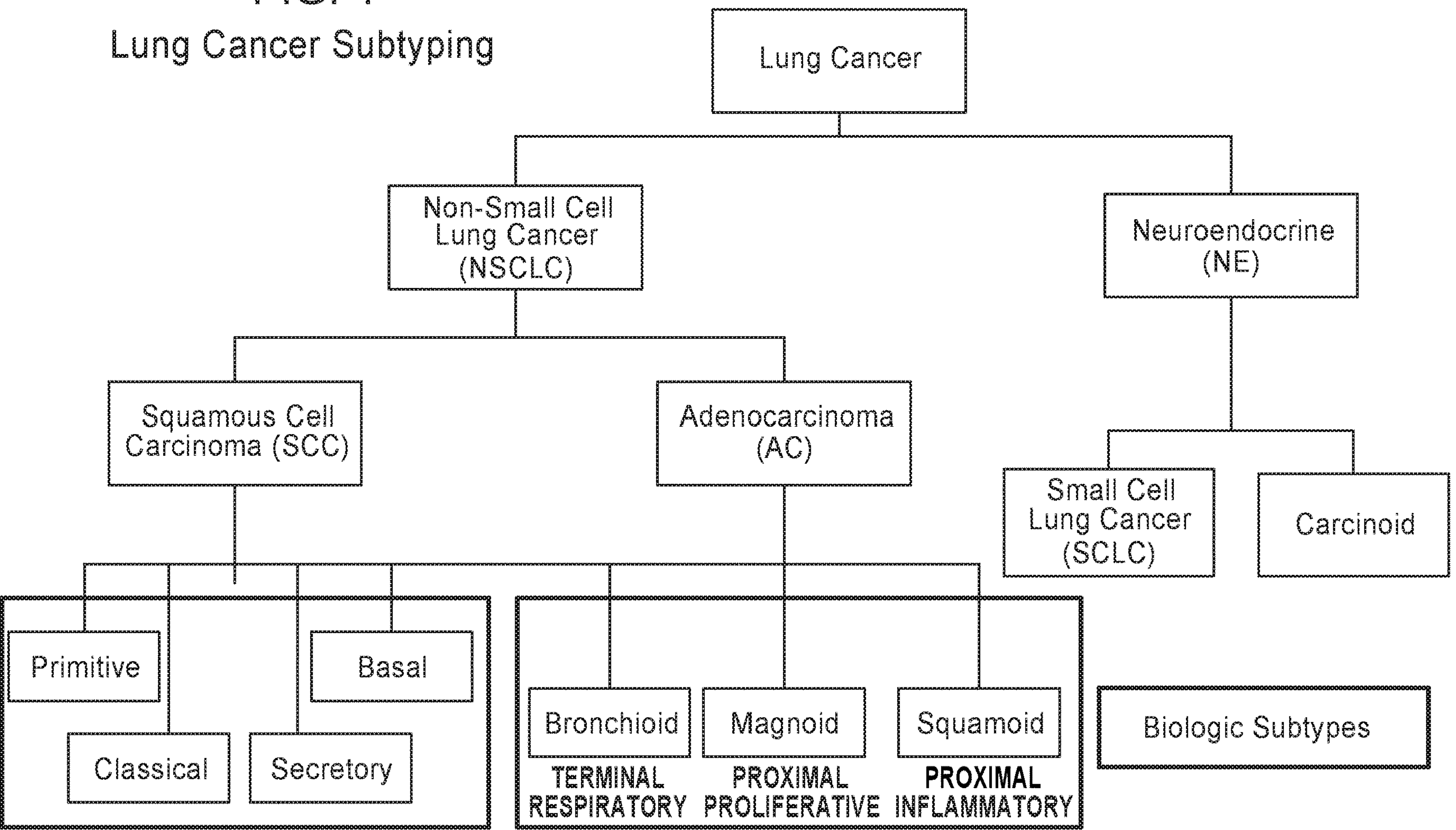
FIG. 1 illustrates lung cancer subtyping and the biologic subtypes of squamous cell carcinoma (SCC or SQ) and Adenocarcinoma (AC or AD).

The present invention provides kits, compositions and methods for identifying or diagnosing lung cancer. That is, the methods can be useful for molecularly defining subsets of lung cancer, specifically lung adenocarcinoma (AD). The methods provide a classification of lung cancer that can be prognostic and predictive for therapeutic response. While a useful term for epidemiologic purposes, "lung cancer" may not refer to a specific disease, but rather can represent a heterogeneous collection of tumors of the lung, bronchus, and pleura. For practical purposes, lung cancer can generally be divided into two histological subtypes-small cell lung cancer (SCLC) and non-small cell lung cancer (NSCLC). These main tumor types can present at different frequencies, can have different anatomic locations, can have different predilections for metastasis, may respond differently to therapy, and may likely be derived from different cell progenitors.

"Determining an adenocarcinoma subtype" can include, for example, diagnosing or detecting the presence and type of lung adenocarcinoma, monitoring the progression of the disease, and identifying or detecting cells or samples that are indicative of subtypes.

In one embodiment, lung cancer status is assessed through the evaluation of expression patterns, or profiles, of a plurality of classifier genes or biomarkers in one or more subject samples. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the invention. Accordingly, a subject can be diagnosed with lung adenocarcinoma (including subtypes, or grades thereof), can present with one or more symptoms of lung AD cancer, or a predisposing factor, such as a family (genetic) or medical history (medical) factor, for lung cancer, can be undergoing treatment or therapy for lung cancer, or the like. Alternatively, a subject can be healthy with respect to any of the aforementioned factors or criteria. It will be appreciated that the term "healthy" as used herein, is relative to lung cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more other cancers.

As used herein, an "expression profile" or a "biomarker profile" or "gene signature" comprises one or more values corresponding to a measurement of the relative abundance, level, presence, or absence of expression of a discriminative or classifier gene or biomarker. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject. The term subject can be used interchangeably with patient. The patient can be a human patient. The one or more biomarkers of the biomarker profiles provided herein are selected from one or more biomarkers of Table 1.

As used herein, the term "determining an expression level" or "determining an expression profile" or "detecting an expression level" or "detecting an expression profile" as used in reference to a biomarker or classifier means the application of a biomarker specific reagent such as a probe, primer or antibody and/or a method to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

In one embodiment, the "expression profile" or a "biomarker profile" or "gene signature" associated with the gene cassettes or classifier genes described herein (e.g., Tables 1 and 2) can be useful for distinguishing between normal and tumor samples. In another embodiment, the tumor samples are lung adenocarcinoma (AD). In another embodiment, AD can be further classified as bronchioid, squamoid, and magnoid based upon an expression profile determined using the methods provided herein. The characterization of bronchioid, squamoid, and magnoid adenocarcinomas using tumor biopsy tissue has been described in Hayes et al. (2006) *J. Clin Oncol.* 24(31):5079-90Expression profiles using the classifier genes disclosed herein (e.g., Table 1) can provide valuable molecular tools for specifically identifying lung adenocarcinoma subtypes, and for evaluating therapeutic efficacy in treating lung adenocarcinoma. Accordingly, the invention provides methods for screening and classifying a subject for molecular AD subtypes and methods for monitoring efficacy of certain therapeutic treatments for lung AD.

In some instances, a single classifier gene provided herein is capable of identifying subtypes of lung adenocarcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

In some instances, a single classifier gene as provided herein is capable of determining lung adenocarcinoma subtypes with a sensitivity or specificity of at least about 70%, at least about 71%, at least about 72%, about 73%, about 74%, about 75%, about 76%, about 7'7%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

The present invention also encompasses a system capable of distinguishing various subtypes of lung adenocarcinoma not detectable using current methods. This system c a n b e capable of processing a large number of subjects and subject variables such as expression profiles and other diagnostic criteria. The methods described herein can also be used for "pharmacometabonomics," in analogy to pharmacogenomics, e.g., predictive of response to therapy. In this embodiment, subjects could be divided into "responders" and "nonresponders" using the expression profile as evidence of "response," and features of the expression profile could then be used to target future subjects who would likely respond to a particular therapeutic course.

The expression profile can be used in combination with other diagnostic methods including histochemical, immunohistochemical, cytologic, immunocytologic, and visual diagnostic methods including histologic or morphometric evaluation of lung tissue.

In various embodiments of the present invention, the expression profile derived from a subject is compared to a reference expression profile. A "reference expression profile" can be a profile derived from the subject prior to treatment or therapy; can be a profile produced from the subject sample at a particular time point (usually prior to or following treatment or therapy, but can also include a particular time point prior to or following diagnosis of lung cancer); or can be derived from a healthy individual or a pooled reference from healthy individuals. A reference expression profile can be generic for lung cancer, or can be specific to different subtypes of lung adenocarcinoma.

The reference expression profile can be compared to a test expression profile. A "test expression profile" can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from a subject that has TRU, PP, or PI subtype.

The classifier biomarkers of the invention can include nucleic acids (RNA, cDNA, and DNA) and proteins, and variants and fragments thereof. Such biomarkers can include DNA comprising the entire or partial sequence of the nucleic acid sequence encoding the biomarker, or the complement of such a sequence. The biomarkers described herein can include RNA comprising the entire or partial sequence of any of the nucleic acid sequences of interest, or their non-natural cDNA products, obtained synthetically in vitro in a reverse transcription reaction. The biomarker nucleic acids can also include any expression product or portion thereof of the nucleic acid sequences of interest. A biomarker protein can be a protein encoded by or corresponding to a DNA biomarker of the invention. A biomarker protein can comprise the entire or partial amino acid sequence of any of the biomarker proteins or polypeptides. The biomarker nucleic acid can be extracted from a cell or can be cell free or extracted from an extracellular vesicular entity such as an exosome.

A "classifier biomarker" or "biomarker" or "classifier gene" can be any gene or protein whose level of expression in a tissue or cell is altered compared to that of a normal or healthy cell or tissue. For example, a "classifier biomarker" or "biomarker" or "classifier gene" can be any gene or protein whose level of expression in a tissue or cell is altered in a specific lung adenocarcinoma subtype. The detection of the biomarkers of the invention can permit the determination of the specific subtype. The "classifier biomarker" or "biomarker" or "classifier gene" may be one that is up-regulated (e.g. expression is increased) or down-regulated (e.g. expression is decreased) relative to a reference or control as provided herein. The reference or control can be any reference or control as provided herein. In some embodiments, the expression values of genes that are up-regulated or down-regulated in a particular subtype of lung adenocarcinoma can be pooled into one gene cassette. The overall expression level in each gene cassette is referred to herein as the "'expression profile" and is used to classify a test sample according to the subtype of lung adenocarcinoma. However, it is understood that independent evaluation of expression for each of the genes disclosed herein can be used to classify tumor subtypes without the need to group up-regulated and down-regulated genes into one or more gene cassettes. In some cases, as shown in Table 2, a total of 48 biomarkers can be used for AD subtype determination. For each AD subtype, 8 of the 16 biomarkers can be negatively correlated genes while 8 can be positively correlated genes which can be selected as the gene signature of a specific AD subtype.

The classifier biomarkers of the invention include any gene or protein that is selectively expressed in lung adenocarcinoma, as defined herein above. Sample biomarker genes are listed in Table 1 or 2, below. In Table 2, the first column of the table represents the biomarker list selected for distinguishing Terminal Respiratory Unit (TRU). The middle column of the table represents the biomarker list selected for distinguishing Proximal Proliferative (PP). The last column of the table represents the biomarker list selected for distinguishing Proximal Inflammatory (PI).

The relative gene expression levels as represented by the tsat as described herein of the classifier biomarkers for lung AD subtyping are shown in Table 1. In one embodiment, the gene expression levels of the classifier biomarkers for lung adenocarcinoma subtyping are shown in Table 1. In one embodiment, all 48 genes can be used to classify the subtypes of AD. In one embodiment, the first 16 genes are the selected gene signature biomarkers for Terminal Respiratory Unit, with gene numbers 1-8 up-regulated and gene numbers 9-16 down-regulated compared to a non-TRU sample. In another embodiment, gene numbers 17-32 are the selected gene signature biomarkers specific for Proximal Proliferative (PP), with gene numbers 17-24 up-regulated and gene numbers 25-32 down-regulated compared to a non-PP sample. In yet another embodiment, gene numbers 33-48 are the selected gene signature biomarkers specific for Proximal Inflammatory (PI), with gene numbers 33-40 up-regulated and gene numbers 41-48 down-regulated compared to a non-PI sample.

TABLE 1

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* | SEQ ID NO: |
|---|---|---|---|---|---|---|---|
| 1 | FIGF | C-fos-induced growth factor | 2.129901586 | −1.173222174 | −1.545843019 | AY874421.1 | 1 |
| 2 | CTSH | Cathepsin H | 1.099895637 | −0.797376345 | −0.531006607 | NM_004390.4 | 2 |
| 3 | SCTR | Secretin receptor | 2.043898366 | −1.911062476 | −1.836386831 | NM_002980.2 | 3 |
| 4 | CYP4B1 | Cytochrome P450 family 4 subfamily B member 1 | 2.462733828 | −1.447070454 | −1.481195844 | NM_001319161.1 | 4 |
| 5 | GPR116 | G protein-coupled receptor 116 | 1.289460077 | −0.972597916 | −0.731487829 | AY140958.1 | 5 |
| 6 | ADH1B | Alcohol dehydrogenase 1B (class I) | 2.013525076 | −1.580299515 | −1.094580574 | NM_001286650.1 | 6 |
| 7 | CBX7 | Chromobox 7 | 0.728027298 | −0.698222051 | −0.243583657 | NM_175709.3 | 7 |
| 8 | HLF | Hepatic leukemia factor | 1.479193357 | −1.28826965 | −1.018563422 | M95585.1 | 8 |
| 9 | CEP55 | Centrosomal protein 55 | −1.524932169 | 0.5743319 | 0.580921528 | NM_018131.4 | 9 |
| 10 | TPX2 | Tpx2, Microtubule-associated | −1.704080763 | 0.587761579 | 0.583674937 | NM_012112.4 | 10 |
| 11 | BUB1B | BUB1 mitotic checkpoint serine/threonin kinase B | −1.531514951 | 0.769199954 | 0.543731288 | AF107297.1 | 11 |
| 12 | KIF4A | Kinesin family member 4A | −1.794045266 | 0.570328759 | 0.599399471 | NM_012310.4 | 12 |
| 13 | CCNB2 | Cyclin B2 | −1.442466223 | 0.602807712 | 0.526093335 | NM_004701.3 | 13 |
| 14 | KIF14 | Kinesi family member 14 | −1.66445145 | 0.762295222 | 0.543132477 | NM_014875.2 | 14 |
| 15 | MELK | Maternal embryonic leucine zipper kinase | −1.685012297 | 0.584181432 | 0.694064307 | NM_014791.3 | 15 |
| 16 | KIF11 | Kinesin family member 11 | −1.183768087 | 0.693181955 | 0.481955763 | NM_004523.3 | 16 |
| 17 | FGL1 | Fibrinogen like 1 | −0.978882607 | 4.89751413 | −1.958269455 | NM_004467.3 | 17 |
| 18 | PBK | PDZ binding kinase | −1.407694417 | 1.278522857 | 0.404652088 | NM_018492.3 | 18 |
| 19 | HSPD1 | Heat shock protein family D (Hsp60) member 1 | −0.469703958 | 0.624572377 | 0.111400174 | NM_002156.4 | 19 |

TABLE 1-continued

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* | SEQ ID NO: |
|---|---|---|---|---|---|---|---|
| 20 | TDG | Thymine DNA glycosylase | −0.351189471 | 0.60348929 | 0.076442589 | NM_003211.4 | 20 |
| 21 | PRC1 | Protein regulator of cytokinesis 1 | −1.159074285 | 0.797575854 | 0.461100041 | NM_003981.3 | 21 |
| 22 | DUSP4 | Dual specificity phosphatase 4 | −0.704273045 | 1.933259798 | −0.283343923 | NM_001394.6 | 22 |
| 23 | GTPBP4 | GTP binding protein 4 | −0.467281005 | 0.543583167 | 0.038904486 | NM_012341.2 | 23 |
| 24 | ZWINT | ZW10 interacting kinetochore protein | −1.062801846 | 0.741405035 | 0.418738839 | NM_007057.3 | 24 |
| 25 | TLR2 | Toll like receptor 2 | 0.672774085 | −1.389004155 | 0.098176794 | NM_001318787.1 | 25 |
| 26 | CD74 | CD74 molecule | 0.689011729 | −1.365243826 | 0.239872217 | NM_001025159.2 | 26 |
| 27 | HLA-DPB1 | Major histocompatibility complex, class II, DP beta 1 | 0.70548523 | −1.431001558 | 0.157288388 | M83664.1 | 27 |
| 28 | HLA-DPA1 | Major histocompatibility, complex class II, DP alpha 1 | 0.620746458 | −1.622212879 | 0.206805676 | NM_033554.3 | 28 |
| 29 | HLA-DRA | Major histocompatibility complex, class II, DR alpha | 0.47615106 | −1.517000712 | 0.209882138 | NM_019111.4 | 29 |
| 30 | ITGB2 | Integrin subunit beta 2 | 0.227015125 | −1.489015066 | 0.473986644 | NM_000211.4 | 30 |
| 31 | FAS | Fas cell surface death receptor | 0.120924174 | −1.244937359 | 0.608312102 | KM114217.1 | 31 |
| 32 | HLA-DRB1 | Major histocompatibility complex, class II, DR beta 1 | 0.561088415 | −1.639812592 | 0.272965507 | NM_002124.3 | 32 |
| 33 | PLAU | Plasminogen activator, urokinase | −0.723116671 | −0.71054832 | 1.628730403 | NM_002658.4 | 33 |
| 34 | GBP1 | Guanylate binding protein 1 | −0.302372654 | −0.688857626 | 1.204326606 | NM_002053.2 | 34 |
| 35 | DSE | Dermatan sulfate epimerase | −0.101374419 | −0.602077696 | 0.748133278 | NM_013352.3 | 35 |
| 36 | CCDC109B | Coiled-coil domain containing 109B | −0.13855818 | −0.703783616 | 0.7964386 | BC002633.2 | 36 |
| 37 | TGFBI | Transforming growth factor beta induced | −0.328357044 | −0.746331889 | 1.164873128 | NM_000358.2 | 37 |
| 38 | CXCL10 | C-X-C motif chemokine ligand 10 | −0.434345777 | −0.62067894 | 1.70756508 | NM_001565.3 | 38 |
| 39 | LGALS1 | Lectin, galactoside binding soluble 1 | −0.291230377 | −0.549722715 | 0.957730776 | NM_002305.3 | 39 |
| 40 | TUBB6 | Tubulin beta 6 class V | −0.153163739 | −0.328431543 | 0.781293298 | NM_032525.2 | 40 |
| 41 | GJB1 | Gap junction protein beta 1 | 1.567852415 | 0.672938467 | −3.61601989 | NM_001097642.2 | 41 |
| 42 | RAP1GAP | RAP1 GTPase activating protein | 1.019990653 | 0.138302482 | −1.426817837 | NM_001145658.1 | 42 |
| 43 | CACNA2D2 | Calcium voltage-gated channel auxiliary subunit alpha2delta 2 | 1.610819757 | −0.126189977 | −2.357279793 | NM_001005505.2 | 43 |
| 44 | SELENBP1 | Selenium binding protein 1 | 1.0475958 | −0.331350331 | −1.209058454 | NM_003944.3 | 44 |
| 45 | TFCP2L1 | Transcription factor CP2-like 1 | 0.218606218 | 0.952552471 | −1.320932951 | NM_014553.2 | 45 |
| 46 | SORBS2 | Sorbin and SH3 domain containing 2 | 0.603086366 | 0.462888705 | −1.412139816 | NM_001270771.1 | 46 |
| 47 | UNC13B | Unc-13 homolog B | 0.293706669 | 0.418115853 | −0.978505828 | NM_006377.3 | 47 |
| 48 | TACC2 | Transforming acidic coiled coil containing protein 2 | 0.206302979 | 0.928437713 | −0.822332116 | AF220152.2 | 48 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Classifier Biomarkers Selected for Terminal Respiratory Unit, Proximal Proliferative, and Proximal Inflammatory

| Terminal Respiratory Unit (TRU) | Proximal Proliferative (PP) | Proximal Inflammatory (PI) |
|---|---|---|
| CEP55 | TLR2 | GJB1 |
| TPX2 | CD74 | RAP1GAP |
| BUB1B | HLA-DPB1 | CACNA2D2 |
| KIF4A | HLA-DPA1 | SELENBP1 |
| CCNB2 | HLA-DRA | TFCP2L1 |
| KIF14 | ITGB2 | SORBS2 |
| MELK | FAS | UNC13B |
| KIF11 | HLA-DRB1 | TACC2 |
| HLF | ZWINT | TUBB6 |
| CBX7 | GTPBP4 | LGALS1 |
| ADH1B | DUSP4 | CXCL10 |
| GPR116 | PRC1 | TGFBI |
| CYP4B1 | TDG | CCDC109B |
| SCTR | HSPD1 | DSE |
| CTSH | PBK | GBP1 |
| FIGF | FGL1 | PLAU |

Diagnostic Uses

In one embodiment, the methods and compositions provided herein allow for the differentiation of the three subtypes of adenocarcinoma: (1) Terminal Respiratory Unit (TRU), formerly referred to as bronchioid; (2) Proximal Proliferative (PP), formerly referred to as magnoid; and (3) Proximal Inflammatory (PI), formerly referred to as squamoid, with fewer genes needed that the molecular AD subtyping methods known in the art.

In general, the methods provided herein are used to classify a lung cancer sample as a particular lung cancer subtype (e.g. subtype of adenocarcinoma). In one embodiment, the method comprises measuring, detecting or determining an expression level of at least one of the classifier biomarkers of any publically available Lung AD expression dataset. In one embodiment, the method comprises detecting or determining an expression level of at least one of the classifier biomarkers of Table 1 in a lung cancer sample obtained from a patient or a subject. The lung cancer sample for the detection or differentiation methods described herein can be a sample previously determined or diagnosed as an adenocarcinoma sample. The previous diagnosis can be based on a histological analysis. The histological analysis can be performed by one or more pathologists.

In one embodiment, the measuring or detecting step is at the nucleic acid level by performing RNA-seq, a reverse transcriptase polymerase chain reaction (RT-PCR) or a hybridization assay with oligonucleotides that are substantially complementary to portions of cDNA molecules of the at least one classifier biomarker (such as the classifier biomarkers of Table 1) under conditions suitable for RNA-seq, RT-PCR or hybridization and obtaining expression levels of the at least one classifier biomarkers based on the detecting step. The expression levels of the at least one of the classifier biomarkers are then compared to reference expression levels of the at least one of the classifier biomarker (such as the classifier biomarkers of Table 1) from at least one sample training set. The at least one sample training set can comprise, (i) expression levels of the at least one biomarker from a sample that overexpresses the at least one biomarker, (ii) expression levels from a reference squamoid (proximal inflammatory), bronchioid (terminal respiratory unit) or magnoid (proximal proliferative) sample, or (iii) expression levels from an adenocarcinoma free lung sample, and classifying the lung tissue sample as a squamoid (proximal inflammatory), bronchioid (terminal respiratory unit) or a magnoid (proximal proliferative) subtype. The lung cancer sample can then be classified as a bronchioid, squamoid, or magnoid subtype of adenocarcinoma based on the results of the comparing step. In one embodiment, the comparing step can comprise applying a statistical algorithm which comprises determining a correlation between the expression data obtained from the lung tissue or cancer sample and the expression data from the at least one training set(s); and classifying the lung tissue or cancer sample as a squamoid (proximal inflammatory), bronchioid (terminal respiratory unit) or a magnoid (proximal proliferative) subtype based on the results of the statistical algorithm.

In one embodiment, the method comprises probing the levels of at least one of the classifier biomarkers provided herein, such as the classifier biomarkers of Table 1 at the nucleic acid level, in a lung cancer sample obtained from the patient. The lung cancer sample can be a sample previously determined or diagnosed as an adenocarcinoma sample. The previous diagnosis can be based on a histological analysis. The histological analysis can be performed by one or more pathologists. The probing step, in one embodiment, comprises mixing the sample with one or more oligonucleotides that are substantially complementary to portions of cDNA molecules of the at least one classifier biomarkers provided herein, such as the classifier biomarkers of Table 1 under conditions suitable for hybridization of the one or more oligonucleotides to their complements or substantial complements; detecting whether hybridization occurs between the one or more oligonucleotides to their complements or substantial complements; and obtaining hybridization values of the at least one classifier biomarkers based on the detecting step. The hybridization values of the at least one classifier biomarkers are then compared to reference hybridization value(s) from at least one sample training set. For example, the at least one sample training set comprises hybridization values from a reference TRU adenocarcinoma, PP adenocarcinoma, and/or PI adenocarcinoma sample. The lung cancer sample is classified, for example, as TRU, PP, or PI based on the results of the comparing step.

The lung tissue sample can be any sample isolated from a human subject or patient. For example, in one embodiment, the analysis is performed on lung biopsies that are embedded in paraffin wax. In one embodiment, the sample can be a fresh frozen lung tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid for use in the methods provided herein. The extracellular sources can be cell-free DNA and/or exosomes. In one embodiment, the sample can be a cell pellet or a wash. This aspect of the invention provides a means to improve current diagnostics by accurately identifying the major histological types, even from small biopsies. The methods of the invention, including the RT-PCR methods, are sensitive, precise and have multianalyte capability for use with paraffin embedded samples. See, for example, Cronin et al. (2004) *Am. J Pathol.* 164 (1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

In one embodiment, the sample used herein is obtained from an individual, and comprises formalin-fixed paraffin-embedded (FFPE) tissue. However, other tissue and sample types are amenable for use herein. In one embodiment, the other tissue and sample types can be fresh frozen tissue, wash fluids, or cell pellets, or the like. In one embodiment, the sample can be a bodily fluid obtained from the individual. The bodily fluid can be blood or fractions thereof (e.g., serum, plasma), urine, sputum, saliva or cerebrospinal fluid (CSF). A biomarker nucleic acid as provided herein can be extracted from a cell or can be cell free or extracted from an extracellular vesicular entity such as an exosome.

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a lung tissue sample, for example, an adenocarcinoma sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., *Science,* 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The numbers of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a biomarker of interest is detected at the nucleic acid level via detection of non-natural cDNA molecules.

In some embodiments, the method for lung cancer AD subtyping includes detecting expression levels of a classifier biomarker set. In some embodiments, the detecting includes all of the classifier biomarkers of Table 1 at the nucleic acid level or protein level. In another embodiment, a single or a subset of the classifier biomarkers of Table 1 are detected, for example, from about 8 to about 16. For example, in one embodiment, from about 5 to about 10, from about 5 to about 15, from about 5 to about 20, from about 5 to about 25, from about 5 to about 30, from about 5 to about 35, from about 5 to about 40, from about 5 to about 45, from about 5 to about 48 of the biomarkers in Table 1 are detected in a method to determine the lung cancer AD subtype. In another embodiment, each of the biomarkers from Table 1 is detected in a method to determine the lung cancer subtype. In another embodiment, 16 of the biomarkers from Table 1 are selected as the gene signatures for a specific lung cancer AD subtype.

The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene provided herein, such as the classifier biomarkers listed in Table 1.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or (3-Actin. Alternatively, normalization can be based on the mean or median signal of all of the assayed biomarkers or a large subset thereof (global normalization approach).

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

As explained above, in one embodiment, once the mRNA is obtained from a sample, it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. PCR can be performed with the forward and/or reverse primers comprising sequence complementary to at least a portion of a classifier gene provided herein, such as the classifier biomarkers in Table 1. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. For example, the forward and/or reverse primers comprising sequence complementary to at least a portion of a classifier gene provided herein, such as the classifier biomarkers from Table 1 can comprise tail sequence. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (ii) adapter sequences are added to the ends of cDNA molecules to make DNA sequences that do not exist in vivo, (iii) the error rate associated with amplification further creates DNA sequences that do not exist in vivo, (iv) the disparate structure of the cDNA molecules as compared to what exists in nature, and (v) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3.0 \times 10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Another method of biomarker level analysis at the nucleic acid level is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, "quantitative PCR" (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising the sequences of the invention may be used.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers provided herein, such as the classifier biomarkers of Table 1 (or subsets thereof, for example 8 to 16, 16 to 32, or 32 to 48 biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, lung adenocarcinoma subtypes can be evaluated using levels of protein expression of one or more of the classifier genes provided herein, such as the classifier biomarkers listed in Table 1. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel et al, eds, 1994*, Current Protocols in Molecular Biology*, Vol. I, John Wiley & Sons, Inc., New York, which is incorporated by reference herein in its entirety).

In one embodiment, antibodies specific for biomarker proteins are utilized to detect the expression of a biomarker protein in a body sample. The method comprises obtaining a body sample from a patient or a subject, contacting the body sample with at least one antibody directed to a biomarker that is selectively expressed in lung cancer cells, and detecting antibody binding to determine if the biomarker is expressed in the patient sample. A preferred aspect of the present invention provides an immunocytochemistry technique for diagnosing lung cancer subtypes. One of skill in the art will recognize that the immunocytochemistry method described herein below may be performed manually or in an automated fashion.

As provided throughout, the methods set forth herein provide a method for determining the lung cancer AD subtype of a patient. Once the biomarker levels are determined, for example by measuring non-natural cDNA biomarker levels or non-natural mRNA-cDNA biomarker complexes, the biomarker levels are compared to reference values or a reference sample, for example with the use of statistical methods or direct comparison of detected levels, to make a determination of the lung cancer molecular AD subtype. Based on the comparison, the patient's lung cancer sample is AD classified, e.g., as TRU, PP, or PI.

In one embodiment, expression level values of the at least one classifier biomarkers provided herein, such as the classifier biomarkers of Table 1 are compared to reference expression level value(s) from at least one sample training set, wherein the at least one sample training set comprises expression level values from a reference sample(s). In a further embodiment, the at least one sample training set comprises expression level values of the at least one classifier biomarkers provided herein, such as the classifier biomarkers of Table 1 from a proximal inflammatory (squamoid), proximal proliferative (magnoid), a terminal respiratory unit (bronchioid) sample, or a combination thereof.

In a separate embodiment, hybridization values of the at least one classifier biomarkers provided herein, such as the classifier biomarkers of Table 1 are compared to reference hybridization value(s) from at least one sample training set, wherein the at least one sample training set comprises hybridization values from a reference sample(s). In a further embodiment, the at least one sample training set comprises hybridization values of the at least one classifier biomarkers provided herein, such as the classifier biomarkers of Table 1 from a proximal inflammatory (squamoid), proximal proliferative (magnoid), a terminal respiratory unit (bronchioid) sample, or a combination thereof. Methods for comparing detected levels of biomarkers to reference values and/or reference samples are provided herein. Based on this comparison, in one embodiment a correlation between the biomarker levels obtained from the subject's sample and the reference values is obtained. An assessment of the lung cancer AD subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear descriminant analysis (LDA) (see, for example, Nillson, 1965); K-nearest neighbour analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, each of which is herein incorporated by reference in its entirety.

In other embodiments, an unsupervised training approach is employed, and therefore, no training set is used.

Referring to sample training sets for supervised learning approaches again, in some embodiments, a sample training set(s) can include expression data of a plurality or all of the classifier biomarkers (e.g., all the classifier biomarkers of Table 1) from an adenocarcinoma sample. The plurality of classifier biomarkers can comprise at least two classifier biomarkers, at least 8 classifier biomarkers, at least 16 classifier biomarkers, at least 24 classifier biomarkers, at least 32 classifier biomarkers, at least 40 classifier biomarkers, or at least 48 classifier biomarkers of Table 1. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human lung tissue sample and the expression data from the adenocarcinoma training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method is employed for the statistical algorithm as described in Mullins et al. (2007) Clin Chem. 53(7):1273-9, and based on gene expression data, which is herein incorporated by reference in its entirety.

Results of the gene expression performed on a sample from a subject (test sample) may be compared to a biological sample(s) or data derived from a biological sample(s) that is known or suspected to be normal ("reference sample" or "normal sample", e.g., non-adenocarcinoma sample). In some embodiments, a reference sample or reference gene expression data is obtained or derived from an individual known to have a particular molecular subtype of adenocarcimona, i.e., squamoid (proximal inflammatory), bronchioid (terminal respiratory unit) or magnoid (proximal proliferative).

The reference sample may be assayed at the same time, or at a different time from the test sample. Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., lung adenocarcinoma subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the lung cancer subtype. For example, it may be determined that a confidence level of greater than 90% may be a useful predictor of the lung cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the lung adenocarcinoma subtype in some cases can be improved through the application of algorithms designed to normalize and or improve the reliability of the gene expression data. In some embodiments of the present invention, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the lung adenocarcinoma subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among subtypes such as squamoid (proximal inflammatory) positive, bronchioid (terminal respiratory unit) positive or magnoid (proximal proliferative) positive, and then "testing" the accuracy of the classifier on an independent test set. Therefore, for new, unknown samples the classifier can be used to predict, for example, the class (e.g., squamoid vs bronchioid vs magnoid) in which the samples belong.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments of the present invention, data from probe-sets may be excluded from analysis if they are not identified at a detectable level (above background).

In some embodiments of the present disclosure, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−l) degrees of freedom. (N−l)*Probe-set Variance/(Gene Probe-set Variance). Chi-Sq(N−l) where N is the number of input CEL files, (N−l) is the degrees of freedom for the Chi-Squared distribution, and the "probe-set variance for the gene" is the average of probe-set variances across the gene. In some embodiments of the present invention, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment, further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, and/or varying molecular subtypes of adenocarcinoma (e.g., squamoid, bronchioid, magnoid)) are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods of the present invention to rank the markers provided by the classifier algorithm.

A statistical evaluation of the results of the biomarker level profiling may provide a quantitative value or values indicative of one or more of the following: molecular subtype of adenocarcinoma (squamoid, bronchioid or magnoid); the likelihood of the success of a particular therapeutic intervention, e.g., angiogenesis inhibitor therapy, chemotherapy, or immunotherapy. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases, the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the lung adenocarcinoma subtype and proposed therapies.

In one embodiment, the results of the gene expression profiling may be classified into one or more of the following: squamoid (proximal inflammatory) positive, bronchioid (terminal respiratory unit) positive, magnoid (proximal proliferative) positive, squamoid (proximal inflammatory) negative, bronchioid (terminal respiratory unit) negative, magnoid (proximal proliferative) negative; likely to respond to angiogenesis inhibitor, immunotherapy or chemotherapy; unlikely to respond to angiogenesis inhibitor, immunotherapy or chemotherapy; or a combination thereof.

In some embodiments of the present invention, results are classified using a trained algorithm. Trained algorithms of the present invention include algorithms that have been developed using a reference set of known gene expression values and/or normal samples, for example, samples from individuals diagnosed with a particular molecular subtype of adenocarcinoma. In some cases, a reference set of known gene expression values are obtained from individuals who have been diagnosed with a particular molecular subtype of adenocarcinoma, and are also known to respond (or not respond) to angiogenesis inhibitor therapy. In some cases, a reference set of known gene expression values are obtained from individuals who have been diagnosed with a particular molecular subtype of adenocarcinoma, and are also known to respond (or not respond) to immunotherapy. In some cases, a reference set of known gene expression values are obtained from individuals who have been diagnosed with a particular molecular subtype of adenocarcinoma, and are also known to respond (or not respond) to chemotherapy.

Algorithms suitable for categorization of samples include but are not limited to k-nearest neighbor algorithms, support vector machines, linear discriminant analysis, diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to angiogenesis inhibitor therapy. A false positive in this case occurs when the person tests positive, but actually does respond. A false negative, on the other hand, occurs when the person tests negative, suggesting they are unlikely to respond, when they actually are likely to respond. The same holds true for classifying a lung cancer subtype.

The positive predictive value (PPV), or precision rate, or post-test probability of disease, is the proportion of subjects with positive test results who are correctly diagnosed as likely or unlikely to respond, or diagnosed with the correct lung cancer subtype, or a combination thereof. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate $(\alpha)=FP/(FP+TN)$-specificity; False negative rate $(\beta)=FN/(TP+FN)$-sensitivity; Power=sensitivity=$1-\beta$; Likelihood-ratio positive=sensitivity/(1−specificity); Likelihood-ratio negative=(1−sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the lung tissue sample as a particular lung cancer subtype based on the comparison of biomarker levels in the sample and reference biomarker levels, for example present in at least one training set. In some embodiments, the lung tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmablegate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 5 to about 10, from about 8 to about 16, from about 5 to about 15, from about 5 to about 20, from about 5 to about 25, from about 5 to about 30, from about 5 to about 35, from about 5 to about 40, from about 5 to about 45, from about 5 to about 48 biomarkers (e.g., as disclosed in Table 1) is capable of classifying subtypes of lung adenocarcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein (e.g., in Table 1) can be used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, a single biomarker, or from about 5 to about 10, from about 8 to about 16, from about 5 to about 15, from about 5 to about 20, from about 5 to about 25, from about 5 to about 30, from about 5 to about 35, from about 5 to about 40, from about 5 to about 45, from about 5 to about 48 biomarkers (e.g., as disclosed in Table 1) is capable of classifying lung adenocarcinoma subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein can be used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

Classifier Gene Selection

Figure 8:
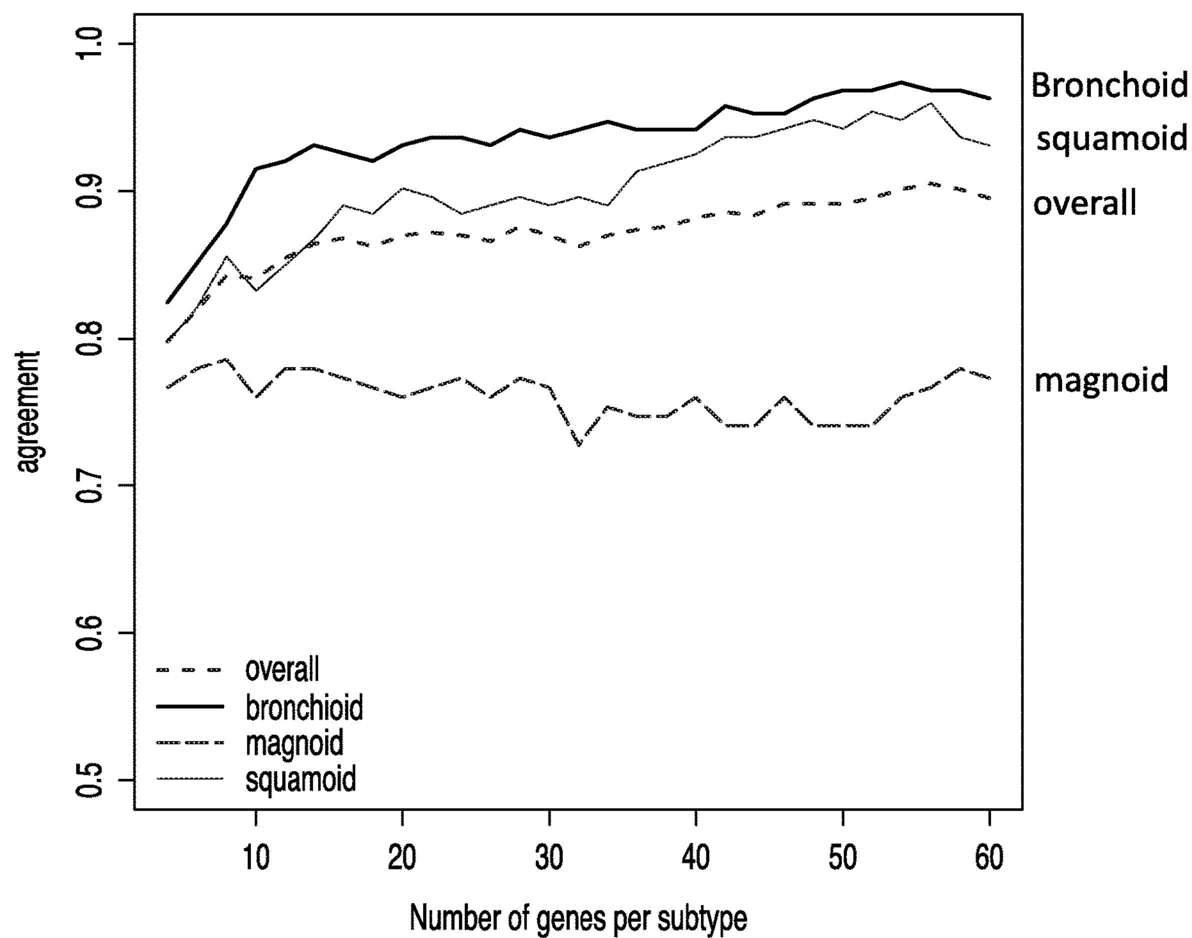
FIG. 8 illustrates a five-fold cross validation study performed from the Cancer Genome Atlas (TCGA) on an RNASeq lung adenocarcinoma (AD) dataset. For determining an optimal number of genes to include for subtyping AD. Terminal Respiratory Unit (TRU) is formerly referred to as bronchioid. Proximal Proliferative (PP) is formerly referred to as magnoid. Proximal Inflammatory (PI) is formerly referred to as squamoid.
Figure 9:
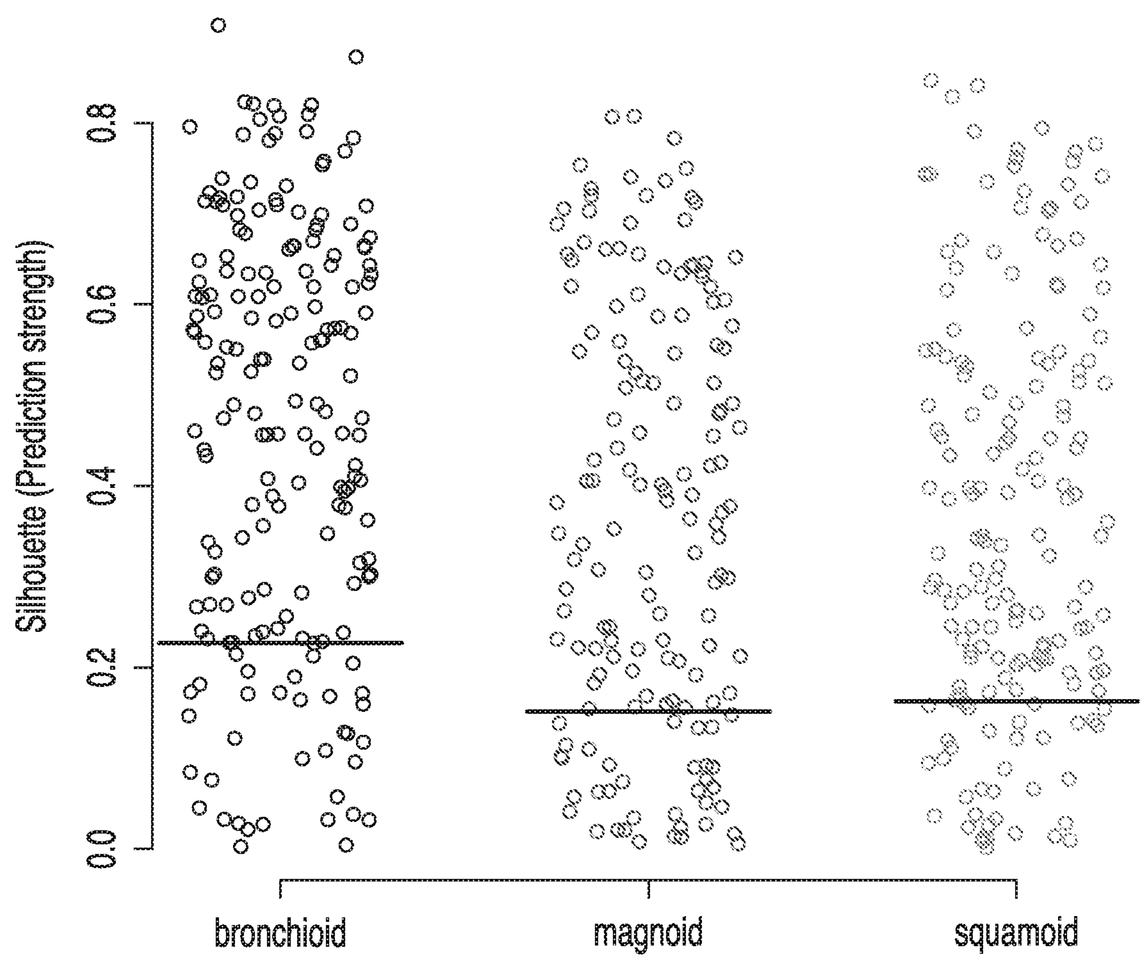
FIG. 9 illustrates the selection of prototype samples by silhouette score for gene signature training of the AD predictor described herein.

In one embodiment, the methods and compositions provided herein are useful for determining the AD subtype of a sample (e.g., lung tissue sample) from a patient by analyzing the expression of a set of biomarkers, whereby the set of biomarkers comprise a fewer number of biomarkers that methods known in the art for molecularly classifying lung AD subtype. In some cases, the set of biomarkers is less than 250, 240, 230, 220, 210, 200, 150, 100, 95 or 90 biomarkers. In some cases, the set of biomarkers is less than 50 biomarkers. In some cases, the set of biomarkers is the set of 48 biomarkers listed in Table 1. In some cases, the set of biomarkers is a sub-set of biomarkers listed Table 1. The biomarkers or classifier genes useful in the methods and compositions provided herein can be selected from one or more lung adenocarcinoma datasets from one or more databases. The databases can be public databases. In one embodiment, classifier genes (e.g., one or more genes listed in Table 1 and Table 2) useful in the methods and compositions provided herein for detecting or diagnosing lung adenocarcinoma subtypes were selected from a lung adenocarcinoma RNAseq dataset from The Cancer Genome Atlas (TCGA). In one embodiment, classifier genes useful for the methods and compositions provided herein such as those in Table 1 are selected by subjecting a large set of classifier genes to an in silico based process in order to determine the minimum number of genes whose expression profile can be used to determine an AD subtype of sample obtained from a subject. In some cases, the large set of classifier genes can be a lung AD RNAseq dataset such as, for example, from TCGA. In some cases, the large set of classifier genes can be 506-gene classifier described herein, whereby the 506-gene classifier can serve to define gold standard subtype. The in silico process for selecting a gene cassette as provided herein for determining lung AD subtype of a sample from a patient can comprise, applying or using a Classifying arrays to Nearest Centroid (CLaNC) algorithm with modification on the standard 506 classifier genes to choose an equal number of negatively and positively correlated genes for each subtype. For determination of the optimal number of genes (e.g, 16 per subtype as shown in Table 1) to include in the signature, the process can further comprise performing a 5-fold cross validation using TCGA lung adenocarcinoma dataset as provided herein to produce cross-validation curves as shown in FIG. 8. To get the final list of gene classifiers, the method can further comprise applying the Classifying arrays to Nearest Centroid (CLaNC) to the entire TCGA data set minus 20% of samples with the lowest gold standard subtype prediction strength, and removing an equal number from each subtype such as shown in FIG. 9.

In one embodiment, the method further comprises validating the gene classifiers. Validation can comprise testing the expression of the classifiers in several fresh frozen publicly available array and RNAseq datasets and calling the subtype based on said expression levels and subsequently comparing the expression with the gold standard subtype calls as defined by the previously published 506-gene signature. Final validation of the gene signature (e.g., Table 1) can then be performed in a newly collected RNAseq dataset of archived formalin-fixed paraffin-embedded (FFPE) adenocarcinoma samples to assure comparable performance in the FFPE samples. In one embodiment, the classifier biomarkers of Table 1 were selected based on the in silico CLaNC process described herein. The gene symbols and official gene names are listed in column 2 and column 3, respectively.

In one embodiment, the methods of the invention require the detection of at least 1, at least 2, at least 3, at least 4, at least 5, at least 6, at least 7, at least 8, at least 9, at least 10, at least 11, at least 12, at least 13, at least 14, at least 15, or up to 16 classifier biomarkers in a lung cancer cell sample obtained from a patient which expression is altered in order to identify a TRU, a PP, or a PI lung adenocarcinoma subtype. The same applies for other classifier gene expression datasets as provided herein.

In another embodiment, the methods of the invention require the detection of a total of at least 1, at least 2, at least 5, at least 8, at least 10, at least 16, at least 20, at least 30, at least 32, or up to 48 classifier biomarkers out of the 48 gene biomarkers of Table 1 in a lung cancer cell sample (e.g., lung AD sample) obtained from a patient in order to identify a TRU, a PP, or a PI lung adenocarcinoma subtype. The same applies for other classifier gene expression datasets as provided herein.

In one embodiment, at least 1, at least 2, at least 3, at least 4, at least 5, at least 6, at least 7, or up to 8 biomarkers of Table 1 are "up-regulated" in a specific subtype of lung adenocarcinoma. In another embodiment, at least 1, at least 2, at least 3, at least 4, at least 5, at least 6, at least 7, or up to 8 biomarkers of Table 1 are "down-regulated" in a specific subtype of lung adenocarcinoma. The same applies for other classifier gene expression datasets as provided herein.

In one embodiment, the expression level of an "up-regulated" biomarker as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker as provided herein is decreased by about 0.8-fold, about 1.4-fold, about 2-fold, about 2.6-fold, about 3.2-fold, about 3.6-fold, about 4-fold, and any values in between.

It is recognized that additional genes or proteins can be used in the practice of the invention. For example, vimentin, a member of the intermediate filament family of proteins can be used to identify the adenocarcinoma subtype Proximal Proliferative (magnoid), and SMA can be used to identify Proximal Inflammatory (squamoid) subtype. In general, genes useful in classifying the subtypes of lung adenocarcinoma, include those that are independently capable of distinguishing between normal versus tumor, or between different classes or grades of lung cancer. A gene is considered to be capable of reliably distinguishing between subtypes if the area under the receiver operator characteristic (ROC) curve is approximately 1.

Clinical/Therapeutic Uses

In one embodiment, a method is provided herein for determining a disease outcome or prognosis for a patient suffering from cancer. In some cases, the cancer is lung cancer. The disease outcome or prognosis can be measured by examining the overall survival for a period of time or intervals (e.g., 0 to 36 months or 0 to 60 months). In one embodiment, survival is analyzed as a function of subtype (e.g., for lung cancer, adenocarcinoma (TRU, PI, and PP)). Relapse-free and overall survival can be assessed using standard Kaplan-Meier plots as well as Cox proportional hazards modeling.

In one embodiment, upon determining a patient's lung cancer subtype, the patient is selected for suitable therapy, for example chemotherapy or drug therapy with an angiogenesis inhibitor or immunotherapy. In one embodiment, upon determining a patient's lung cancer subtype, the patient is administered a suitable therapeutic agent, for example chemotherapeutic agent(s) or an angiogenesis inhibitor or immunotherapeutic agent(s). In one embodiment, the therapy is immunotherapy, and the immunotherapeutic agent is a checkpoint inhibitor, monoclonal antibody, biological response modifier, therapeutic vaccine or cellular immunotherapy.

The methods of present invention are also useful for evaluating clinical response to therapy, as well as for endpoints in clinical trials for efficacy of new therapies. The extent to which sequential diagnostic expression profiles move towards normal can be used as one measure of the efficacy of the candidate therapy.

In one embodiment, the methods of the invention also find use in predicting response to different lines of therapies based on the subtype of lung adenocarcinoma (AD). For example, chemotherapeutic response can be improved by more accurately assigning tumor subtypes. Likewise, treatment regimens can be formulated based on the tumor subtype. For example, clinical trials have shown convincing evidence that the VEGF inhibitor, bevacizumab, can be effective in the treatment of NSCLC.

In one embodiment, the Terminal Respiratory Unit (TRU) subtype may have enhanced response to EGFR inhibitors and Pemetrexed. In another embodiment, Proximal Proliferative (PP) can have enhanced response to chemotherapy. In another embodiment, Proximal Inflammatory (PI) can have enhanced response to immunotherapy. In another embodiment, all subtypes can have enhanced response to chemotherapies, angiogenesis inhibitor treatments, and immunotherapies.

Angiogenesis Inhibitors

In one embodiment, upon determining a patient's lung adenocarcinoma subtype, the patient is selected for drug therapy with an angiogenesis inhibitor.

In one embodiment, the angiogenesis inhibitor is a vascular endothelial growth factor (VEGF) inhibitor, a VEGF receptor inhibitor, a platelet derived growth factor (PDGF) inhibitor or a PDGF receptor inhibitor.

Each biomarker panel can include one, two, three, four, five, six, seven, eight or more biomarkers usable by a classifier (also referred to as a "classifier biomarker") to assess whether an adenocarcinoma patient is likely to respond to angiogenesis inhibitor therapy; to select an adenocarcinoma patient for angiogenesis inhibitor therapy; to determine a "hypoxia score" and/or to subtype an adenocarcinoma sample as squamoid (also referred to as proximal inflammatory), bronchioid (also referred to as terminal respiratory unit) or magnoid (also referred to as proximal proliferative) molecular subtype. As used herein, the term "classifier" can refer to any algorithm for statistical classification, and can be implemented in hardware, in software, or a combination thereof. The classifier can be capable of 2-level, 3-level, 4-level, or higher, classification, and can depend on the nature of the entity being classified. One or more classifiers can be employed to achieve the aspects disclosed herein.

In general, methods of determining whether an adenocarcinoma patient is likely to respond to angiogenesis inhibitor therapy, or methods of selecting an adenocarcinoma patient for angiogenesis inhibitor therapy are provided herein. In one embodiment, the method comprises assessing whether the patient's adenocarcinoma subtype is squamoid (proximal inflammatory), bronchioid (terminal respiratory unit) or magnoid (proximal proliferative) using the methods described herein (e.g., assessing the expression of one or more classifier biomarkers of Table 1) and probing an adenocarcinoma sample from the patient for the levels of at least five biomarkers selected from the group consisting of RRAGD, FABP5, UCHL1, GAL, PLOD, DDIT4, VEGF, ADM, ANGPTL4, NDRG1, NP, SLC16A3, and C14ORF58 (see Table 3) at the nucleic acid level. In a further embodiment, the probing step comprises mixing the sample with five or more oligonucleotides that are substantially complementary to portions of nucleic acid molecules of the at least five biomarkers under conditions suitable for hybridization of the five or more oligonucleotides to their complements or substantial complements, detecting whether hybridization occurs between the five or more oligonucleotides to their complements or substantial complements; and obtaining hybridization values of the sample based on the detecting steps. The hybridization values of the sample are then compared to reference hybridization value(s) from at least one sample training set, wherein the at least one sample training set comprises (i) hybridization value(s) of the at least five biomarkers from a sample that overexpresses the at least five biomarkers, or overexpresses a subset of the at least five biomarkers, (ii) hybridization values of the at least five biomarkers from a reference squamoid (proximal inflammatory), bronchioid (terminal respiratory unit) or magnoid (proximal proliferative) sample, or (iii) hybridization values of the at least five biomarkers from an adenocarcinoma free lung sample. A determination of whether the patient is likely to respond to angiogenesis inhibitor therapy, or a selection of the patient for angiogenesis inhibitor is then made based upon (i) the patient's adenocarcinoma subtype and (ii) the results of comparison.

TABLE 3

Biomarkers for hypoxia profile

| Name | Abbreviation | GenBank Accession No. |
|---|---|---|
| RRAGD | Ras-related GTP binding D | BC003088 |
| FABP5 | fatty acid binding protein 5 | M94856 |
| UCHL1 | ubiquitin carboxyl-terminal esterase L1 | NM_004181 |
| GAL | Galanin | BC030241 |
| PLOD | procollagen-lysine, 2-oxoglutarate 5-dioxygenase lysine hydroxylase | M98252 |
| DDIT4 | DNA-damage-inducible transcript 4 | NM_019058 |
| VEGF | vascular endothelial growth factor | M32977 |
| ADM | Adrenomedullin | NM_001124 |
| ANGPTL4 | angiopoietin-like 4 | AF202636 |
| NDRG1 | N-myc downstream regulated gene 1 | NM_006096 |
| NP | nucleoside phosphorylase | NM 000270 |
| SLC16A3 | solute carrier family 16 monocarboxylic acid transporters, member 3 | NM_004207 |
| C14ORF58 | chromosome 14 open reading frame 58 | AK000378 |

The aforementioned set of thirteen biomarkers, or a subset thereof, is also referred to herein as a "hypoxia profile".

In one embodiment, the method provided herein includes determining the levels of at least five biomarkers, at least six biomarkers, at least seven biomarkers, at least eight biomarkers, at least nine biomarkers, or at least ten biomarkers, or five to thirteen, six to thirteen, seven to thirteen, eight to thirteen, nine to thirteen or ten to thirteen biomarkers selected from RRAGD, FABP5, UCHL1, GAL, PLOD, DDIT4, VEGF, ADM, ANGPTL4, NDRG1, NP, SLC16A3, and C14ORF58 in an adenocarcinoma sample obtained from a subject. Biomarker expression in some instances may be normalized against the expression levels of all RNA transcripts or their expression products in the sample, or against a reference set of RNA transcripts or their expression products. The reference set as explained throughout, may be an actual sample that is tested in parallel with the adenocarcinoma sample, or may be a reference set of values from a database or stored dataset. Levels of expression, in one embodiment, are reported in number of copies, relative fluorescence value or detected fluorescence value. The level of expression of the biomarkers of the hypoxia profile together with adenocarcinoma subtype as determined using the methods provided herein can be used in the methods described herein to determine whether a patient is likely to respond to angiogenesis inhibitor therapy.

In one embodiment, the levels of expression of the thirteen biomarkers (or subsets thereof, as described above, e.g., five or more, from about five to about 13), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, angiogenesis inhibitor treatments include, but are not limited to an integrin antagonist, a selectin antagonist, an adhesion molecule antagonist, an antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1), a basic fibroblast growth factor antagonist, a vascular endothelial growth factor (VEGF) modulator, a platelet derived growth factor (PDGF) modulator (e.g., a PDGF antagonist).

In one embodiment of determining whether a subject is likely to respond to an integrin antagonist, the integrin antagonist is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-113 (IL-1β), monocyte chemotactic protein-1 (MCP-1) and a vascular endothelial growth factor (VEGF)), as described in U.S. Pat. No. 6,524,581, incorporated by reference in its entirety herein.

The methods provided herein are also useful for determining whether a subject is likely to respond to one or more of the following angiogenesis inhibitors: interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with salvia and schisandra chinensis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In another embodiment, a method is provided for determining whether a subject is likely to respond to one or more endogenous angiogenesis inhibitors. In a further embodiment, the endogenous angiogenesis inhibitor is endostatin, a 20 kDa C-terminal fragment derived from type XVIII collagen, angiostatin (a 38 kDa fragment of plasmin), a member of the thrombospondin (TSP) family of proteins. In a further embodiment, the angiogenesis inhibitor is a TSP-1, TSP-2, TSP-3, TSP-4 and TSP-5. Methods for determining the likelihood of response to one or more of the following angiogenesis inhibitors are also provided a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN), (e.g., IFN-α, IFN-β, IFN-γ), a chemokine, e.g., a chemokine having the C-X-C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein.

In one embodiment, a method for determining the likelihood of response to one or more of the following angiogenesis inhibitors is provided is angiopoietin-1, angiopoietin-2, angiostatin, endostatin, vasostatin, thrombospondin, calreticulin, platelet factor-4, TIMP, CDAI, interferon α, interferon β,vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and schisandra *chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In yet another embodiment, the angiogenesis inhibitor can include pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), motesanib, or a combination thereof. In another embodiment, the angiogenesis inhibitor is a VEGF inhibitor. In a further embodiment, the VEGF inhibitor is axitinib, cabozantinib, aflibercept, brivanib, tivozanib, ramucirumab or motesanib. In yet a further embodiment, the angiogenesis inhibitor is motesanib.

In one embodiment, the methods provided herein relate to determining a subject's likelihood of response to an antagonist of a member of the platelet derived growth factor (PDGF) family, for example, a drug that inhibits, reduces or modulates the signaling and/or activity of PDGF-receptors (PDGFR). For example, the PDGF antagonist, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-0 aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

Upon making a determination of whether a patient is likely to respond to angiogenesis inhibitor therapy, or selecting a patient for angiogenesis inhibitor therapy, in one embodiment, the patient is administered the angiogenesis inhibitor. The angiogenesis in inhibitor can be any of the angiogenesis inhibitors described herein.

Immunotherapy

In one embodiment, provided herein is a method for determining whether an adenocarcinoma (AD) lung cancer patient is likely to respond to immunotherapy by determining the subtype of AD of a sample obtained from the patient and, based on the AD lung cancer subtype, assessing whether the patient is likely to respond to immunotherapy. In another embodiment, provided herein is a method of selecting a patient suffering from AD for immunotherapy by determining an AD subtype of a sample from the patient and, based on the AD subtype, selecting the patient for immunotherapy. The determination of the AD subtype of the sample obtained from the patient can be performed using any method for subtyping AD known in the art. In one embodiment, the sample obtained from the patient has been previously diagnosed as being AD, and the methods provided herein are used to determine the AD subtype of the sample. The previous diagnosis can be based on a histological analysis. The histological analysis can be performed by one or more pathologists. In one embodiment, the AD subtyping is performed via gene expression analysis of a set or panel of biomarkers or subsets thereof in order to generate an expression profile. The gene expression analysis can be performed on a lung cancer sample (e.g., lung cancer AD sample) obtained from a patient in order to determine the presence, absence or level of expression of one or more biomarkers selected from a publically available lung cancer database described herein and/or Table 1 provided herein. The AD subtype can be selected from the group consisting of squamoid (proximal inflammatory), bronchioid (terminal respiratory unit) and magnoid (proximal proliferative). The immunotherapy can be any immunotherapy provided herein. In one embodiment, the immunotherapy comprises administering one or more checkpoint inhibitors. The checkpoint inhibitors can be any checkpoint inhibitor provided herein such as, for example, a checkpoint inhibitor that targets PD-1, PD-LI or CTLA4.

As disclosed herein, the biomarkers panels, or subsets thereof, can be those disclosed in any publically available AD gene expression dataset or datasets. In one embodiment, the lung cancer is AD and the biomarker panel or subset thereof is, for example, the cancer genome atlas (TCGA) lung AD RNAseq gene expression dataset (n=515). In one embodiment, the lung cancer is AD and the biomarker panel or subset thereof is, for example, the AD gene expression dataset (n=442) disclosed in Shedden et al. (Nat Med 2008; 14(8): 822-827), the contents of which are herein incorporated by reference in its entirety. In one embodiment, the lung cancer is AD and the biomarker panel or subset thereof is, for example, the AD gene expression dataset (n=117) disclosed in Tomida et al. (J Clin Oncol 2009; 27(17):2793-2799), the contents of which are herein incorporated by reference in its entirety. In one embodiment, the lung cancer is AD and the biomarker panel or subset thereof is, for example, the AD gene expression dataset (n=116) disclosed in Wilkerson et al. (PLoS One 2012; 7(5):e36530), the contents of which are herein incorporated by reference in its entirety. In one embodiment, the lung cancer is AD and the biomarker panel or subset thereof is, for example, the AD gene expression dataset disclosed in Table 1. In one embodiment, the lung cancer is AD and the biomarker panel or subset thereof is, for example, the AD gene expression dataset disclosed in Table 1 in combination with one or more biomarkers from a publically available AD expression dataset. In Table 2, the first column of the table represents the biomarker list for distinguishing Terminal Respiratory Unit (TRU). The middle column of the table represents the biomarker list for distinguishing Proximal Proliferative (PP). The last column of the table represents the biomarker list for distinguishing Proximal Inflammatory (PI). In some cases, as shown in Table 2, a total of 48 biomarkers can be used for AD subtype determination. For each AD subtype, 8 of the 16 biomarkers can be negatively correlated genes, while 8 can be positively correlated genes which can be selected as the gene signature of a specific AD subtype.

In some embodiments, the method for lung cancer subtyping (e.g., AD subtyping) includes detecting expression levels of a classifier biomarker set. The classifier biomarker set can be a set of biomarkers from a publically available database such as, for example, TCGA lung AD RNASeq gene expression dataset(s) or any other dataset provided herein. In some embodiments, the detecting includes all of the classifier biomarkers of Table 1 or any other dataset provided herein at the nucleic acid level or protein level. In another embodiment, a single classifier biomarker of Table 1 or a subset of the classifier biomarkers of Table 1 or any other dataset provided herein are detected, for example, from about five to about twenty. In another embodiment, a single classifier biomarker of Table 1 or a subset of the classifier biomarkers of Table 1 and/or any other dataset provided herein are detected, for example, from about 16 to about 48. In another embodiment, all of the classifier biomarkers of Table 1 or any other dataset provided herein are detected. In another embodiment, at least one or all of the classifier biomarkers of Table 1 in combination with one or more classifier biomarkers of any other AD dataset provided herein are detected. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene from a dataset provided herein alone or in combination.

In one embodiment, from about 1 to about 5, about 5 to about 10, from about 5 to about 15, from about 5 to about 20, from about 5 to about 25, from about 5 to about 30, from about 5 to about 35, from about 5 to about 40, from about 5 to about 45, from about 5 to about 50, from about 5 to about 55, from about 5 to about 60, from about 5 to about 65, from about 5 to about 70, from about 5 to about 75, or from about 5 to about 80 of the biomarkers in any of the AD gene expression datasets provided herein, including, for example, Table 1 for an AD lung sample are detected in a method to determine the lung cancer subtype as provided herein. In another embodiment, each of the biomarkers from any one of the AD gene expression datasets provided herein, including, for example, Table 1 for an AD lung sample are detected in a method to determine the lung cancer subtype as provided herein.

In one embodiment, the methods provided herein further comprise determining the presence, absence or level of immune activation in an AD subtype. The presence or level of immune cell activation can be determined by creating an expression profile or detecting the expression of one or more biomarkers associated with innate immune cells and/or adaptive immune cells associated with each AD subtype in a sample (e.g., lung cancer sample) obtained from a patient. In one embodiment, immune cell activation associated with an AD subtype is determined by monitoring the immune cell signatures of Bindea et al (Immunity 2013; 39(4); 782-795), the contents of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. The presence or a detectable level of immune activation (Innate and/or Adaptive) associated with an AD subtype can indicate or predict that a patient with said AD subtype may be amendable to immunotherapy. The immunotherapy can be treatment with a checkpoint inhibitor as provided herein. In one embodiment, the PI subtype of AD has immune expression. In one embodiment, a method is provided herein for detecting the expression of at least one classifier biomarker provided herein in a sample (e.g., lung cancer AD sample) obtained from a patient further comprises administering an immunotherapeutic agent following detection of immune activation as provided herein in said sample.

In one embodiment, the method comprises determining a subtype of a lung cancer AD sample and subsequently determining a level of immune cell activation of said subtype. In one embodiment, the subtype is determined by determining the expression levels of one or more classifier biomarkers using sequencing (e.g., RNASeq), amplification (e.g., qRT-PCR) or hybridization assays (e.g., microarray analysis) as described herein. The one or more biomarkers can be selected from a publically available database (e.g., TCGA lung AD RNASeq gene expression datasets or any other publically available AD gene expression datasets provided herein). In some embodiments, the biomarkers of Table 1 can be used to specifically determine the subtype of an AD lung sample obtained from a patient. In one embodiment, the level of immune cell activation is determined by measuring gene expression signatures of immunomarkers. The immunomarkers can be measured in the same and/or different sample used to subtype the lung cancer sample as described herein. The immunomarkers that can be measured can comprise, consist of, or consistently essentially of innate immune cell (IIC) and/or adaptive immune cell (AIC) gene signatures, interferon (IFN) gene signatures, individual immunomarkers, major histocapability complex class II (MEW class II) genes or a combination thereof. The gene expression signatures for both IICs and AICs can be any known gene signatures for said cell types known in the art. For example, the immune gene signatures can be those from Bindea et al. (Immunity 2013; 39(4); 782-795). In one embodiment, the immunomarkers for use in the methods provided herein are selected from Table 4A and/or Table 4B. The individual immunomarkers can be CTLA4, PDCD1 and CD274 (PD-L1). In one embodiment, the individual immunomarkers for use in the methods provided herein are selected from Table 5. The immunomarkers can be one or more interferon (INF) genes. In one embodiment, the immunomarkers for use in the methods provided herein are selected from Table 6. The immunomarkers can be one or more MHCII genes. In one embodiment, the immunomarkers for use in the methods provided herein are selected from Table 7. In yet another embodiment, the immunomarkers for use in the methods provided herein are selected from Tables 4A, 4B, 5, 6, 7, or a combination thereof.

TABLE 4A

Adaptive immune cell (AIC) gene signature immunomarkers for use in the methods provided herein.

| | Cell Type | | |
|---|---|---|---|
| | B cells | T cells | T helper cells |
| Human Gene (Gene Name; GenBank Accession No.*) | ABCB4 (ATP binding cassette subfamily B member 4; NM_000443) | BCL11B (B-cell lymphoma/leukaemia 11B; AJ404614.1) | ANP32B (acidic nuclear phosphoprotein 32 family member B; NM_006401.2) |
| | BACH2 (BTB domain and CNC homolog 2; NM_021813.3) | CD2 (CD2 molecule; NM_001328609.1) | ASF1A (anti-silencing function 1A histone chaperone; NM_014034.2) |
| | BCL11A (B-cell CLL/lymphoma 11A; NM_022893.3) | CD28 (CD28 molecule; NM_001243078.1) | ATF2 (activating transcription factor 2; NM_001256093.1) |
| | BLK (BLK proto-oncogene, Src family tyrosine kinase; NM_001715.2) | CD3D (CD3d molecule; NM_000732.4) | BATF (basic leucine zipper ATF-like transcription factor; NM_006399.3) |
| | BLNK (B-cell linker; NM_013314.3) | CD3E (CD3e molecule; NM_000733.3) | C13orf34 (aurora borealis; EU834129.1) |
| | CCR9 (C-C motif chemokine receptor 9; NM_031200.2) | CD3G (CD3g molecule; NM_000073.2) | CD28 (CD28 molecule; NM_006139.3) |
| | CD19 (CD19 molecule; NM_001178098.1) | CD6 (CD6 molecule; NM_006725.4) | DDX50 (DEAD-box helicase 50; NM_024045.1) |
| | CD72 (CD72 molecule; NM_001782.2) | CD96 (CD96 molecule; NM_198196.2) | FAM111A (family with sequence similarity 111 member A; NM_022074.3) |
| | COCH (cochlin; NM_001135058.1) | GIMAP5 (GTPase, IMAP family member 5; NM_018384.4) | FRYL (FRY like transcription coactivator; NM_015030.1) |

TABLE 4A-continued

Adaptive immune cell (AIC) gene signature immunomarkers for use in the methods provided herein.

| | | |
|---|---|---|
| CR2 (complement C3d receptor 2; NM_001006658.2) | ITM2A (integral membrane protein 2A; NM_004867.4) | FUSIP1 (serine and arginine rich splicing factor 10; NM_006625.5) |
| DTNB (dystrobrevin beta; NM_021907.4) | LCK (LCK proto-oncogene, Src family tyrosine kinase; NM_001042771.2) | GOLGA8A (golgin A8 family member A; NM_181077.3) |
| FAM30A (family with sequence similarity 30, member A; NR_026800.2) | NCALD (neurocalcin delta; NM_001040624.1) | ICOS (inducible T-cell costimulator; NM_012092.3) |
| FCRL2 (Fc receptor like 2; NM_030764.3) | PRKCQ (protein kinase C theta; NM_006257.4) | ITM2A (integral membrane protein 2A; NM_004867.4) |
| GLDC (glycine decarboxylase; NM_000170.2) | SH2D1A (SH2 domain containing 1A; NM_002351.4) | LRBA (LPS responsive beige-like anchor protein; NM_001199282.2) |
| GNG7 (G protein subunit gamma 7; NM_052847.2) | SKAP1 (src kinase associated phosphoprotein 1; NM_001075099.1) | NAP1L4 (nucleosome assembly protein 1 like 4; NM_005969.3) |
| HLA-DOB (major histocompatibility complex, class II, DO beta; NM_002120.3) | TRA (T cell receptor alpha delta locus; NG_001332.3) | NUP107 (nucleoporin 107; NM_020401.3) |
| HLA-DQA1 (major histocompatibility complex, class II, DQ alpha 1; NM_002122.3) | TRAC (nuclear receptor corepressor 2; NM_006312.5) | PHF10 (PHD finger protein 10; NM_018288.3) |
| IGHA1 (immunoglobulin heavy locus; NG_001019.6) | TRAT1 (T cell receptor associated transmembrane adaptor 1; NM_016388.3) | PPP2R5C (protein phosphatase 2 regulatory subunit B', gamma; NM_001161725.1) |
| IGHG1 (immunoglobulin heavy locus; NG_001019.6) | TRBC1 (T cell receptor beta locus; NG_001333.2) | RPA1 (replication protein A1; NM_002945.3) |
| IGHM (immunoglobulin heavy locus; NG_001019.6) | | SEC24C (SEC24 homolog C, COPII coat complex component; NM_004922.3) |
| IGKC (immunoglobulin kappa locus, proximal V-cluster and J-C cluster; NG_000834.1) | | SLC25A12 (solute carrier family 25 member 12; NM_003705.4) |
| IGL (immunoglobulin lambda locus; NG_000002.1) | | TRA (T cell receptor alpha delta locus; NG_001332.3) |
| KIAA0125 (family with sequence similarity 30, member A; NR_026800.2) | | UBE2L3 (ubiquitin conjugating enzyme E2 L3; NM_003347.3) |
| MEF2C (myocyte enhancer factor 2C; NM_001308002.1) | | YME1L1 (YME1 like 1 ATPase; NM_001253866.1) |
| MICAL3 (microtubule associated monooxygenase, calponin and LIM domain containing 3; NM_001136004.3) | | |
| MS4A1 (membrane spanning 4-domains A1; NM_021950.3) | | |

TABLE 4A-continued

| Adaptive immune cell (AIC) gene signature immunomarkers for use in the methods provided herein. | | | |
|---|---|---|---|
| | OSBPL10 (oxysterol binding protein like 10; NM_017784.4) | | |
| | PNOC (prepronociceptin; NM_001284244.1) | | |
| | QRSL1 (glutaminyl-tRNA synthase (glutamine-hydrolyzing)-like 1; NM_018292.4) | | |
| | SCN3A (sodium voltage-gated channel alpha subunit 3; NM_001081677.1) | | |
| | SLC15A2 (solute carrier family 15 member 2; XM_017007074.1) | | |
| | SPIB (Spi-B transcription factor; NM_001244000.1) | | |
| | TCL1A (T-cell leukemia/lymphoma 1A; NM_001098725.1) | | |
| | TNFRSF17 (TNF receptor superfamily member 17; NM_001192.2) | | |

| | Cell Type | | |
|---|---|---|---|
| | Tcm | Tem | Th1 cells |
| Human Gene (Gene Name; GenBank Accession No.*) | AQP3 (aquaporine 3; NM_004925.4) | AKT3 (AKT serine/threonine kinase 3; NM_005465.4) | APBB2 (amyloid beta precursor protein binding family B member 2; NM_001166054.1) |
| | ATF7IP (activating transcription factor 7 interacting protein; NM_181352.1) | C7orf54 (staphylococcal nuclease and tudor domain containing 1 (SND1); NG_051199.1) | APOD (apolipoprotein D; NM_001647.3) |
| | ATM (ATM serine/threonine kinase; NM_000051.3) | CCR2 (C-C motif chemokine receptor 2; NM_001123396.1) | ATP9A (ATPase phospholipid transporting 9A; NM_006045.2) |
| | CASP8 (caspase 8; NM_001228.4) | DDX17 (DEAD-box helicase 17; NM_006386.4) | BST2 (bone marrow stromal cell antigen 2; NM_004335.3) |
| | CDC14A (cell division cycle 14A; NM_003672.3) | EWSR1 (EWS RNA binding protein 1; NM_013986.3) | BTG3 (BTG anti-proliferation factor 3; NM_001130914.1) |
| | CEP68 (centrosomal protein 68; NM_015147.2) | FLI1 (Fli-1 proto-oncogene, ETS transcription factor; NM_002017.4) | CCL4 (C-C motif chemokine ligand 4; NM_002984.3) |
| | CG030 (BRCA2 region, mRNA sequence CG030; U50531.1) | GDPD5 (glycerophosphodiester phosphodiesterase domain containing 5; NM_030792.6) | CD38 (CD38 molecule; NM_001775.3) |
| | CLUAP1 (clusterin associated protein 1; NM_015041.2) | LTK (leukocyte receptor tyrosine kinase; NM_002344.5) | CD70 (CD70 molecule; NM_001252.4) |
| | CREBZF (CREB/ATF bZIP transcription factor; | MEFV (Mediterranean fever; | CMAH (cytidine monophospho-N-acetylneuraminic |

TABLE 4A-continued

Adaptive immune cell (AIC) gene signature immunomarkers for use in the methods provided herein.

| | | |
|---|---|---|
| NM_001039618.2) | NM_000243.2) | acid hydroxylase, pseudogene; NR_002174.2) |
| CYLD (CYLD lysine 63 deubiquitinase; NM_015247.2) | NFATC4 (nuclear factor of activated T-cells 4; NM_001136022.2) | CSF2 (colony stimulating factor 2; NM_000758.3) |
| CYorf15B (taxilin gamma pseudogene, Y-linked; NR_045128.1) | PRKY (protein kinase, Y-linked, pseudogene; NR_028062.1) | CTLA4 (cytotoxic T-lymphocyte associated protein 4; NM_005214.4) |
| DOCK9 (dedicator of cytokinesis 9; NM_015296.2) | TBC1D5 (TBC1 domain family member 5; NM_001134381.1) | DGKI (diacylglycerol kinase iota; NM_004717.3) |
| FOXP1 (forkhead box P1; NM_032682.5) | TBCD (tubulin folding cofactor D; NM_005993.4) | DOK5 (docking protein 5; NM_018431.4) |
| FYB (FYN binding protein; NM_001465.4) | TRA (T cell receptor alpha delta locus; NG_001332.3) | DPP4 (dipeptidyl peptidase 4; NM_001935.3) |
| HNRPH1 (heterogeneous nuclear ribonucleoprotein H1 (H); NM_001257293.1) | VIL2 (ezrin; NM_003379.4) | DUSP5 (dual specificity phosphatase 5; NM_004419.3) |
| INPP4B (inositol polyphosphate-4-phosphatase type II B; NM_003866.3) | | EGFL6 (EGF like domain multiple 6; NM_015507.3) |
| KLF12 (Kruppel like factor 12; NM_007249.4) | | GGT1 (gamma-glutamyltransferase 1; NM_013421.2) |
| LOC202134 (family with sequence similarity 153 member B; NM_001265615.1) | | HBEGF (heparin binding EGF like growth factor; NM_001945.2) |
| MAP3K1 (mitogen-activated protein kinase kinase kinase 1, E3 ubiquitin protein ligase; NM_005921.1) | | IFNG (interferon gamma; NM_000619.2) |
| MLL (lysine (K)-specific methyltransferase 2A; NM_005933.3) | | IL12RB2 (interleukin 12 receptor subunit beta 2; NM_001319233.1) |
| NEFL (neurofilament, light polypeptide; NM_006158.4) | | IL22 (interleukin 22; NM_020525.4) |
| NFATC3 (nuclear factor of activated T-cells 3; NM_173165.2) | | LRP8 (LDL receptor related protein 8; NM_017522.4) |
| PCM1 (pericentriolar material 1; NM_001315507.1) | | LRRN3 (leucine rich repeat neuronal 3; NM_018334.4) |
| PCNX (pecanex homolog 1; NM_014982.2) | | LTA (lymphotoxin alpha; NM_000595.3) |
| PDXDC2 (pyridoxal dependent decarboxylase domain containing 2, pseudogene; NR_003610.1) | | SGCB (sarcoglycan, beta (43 kDa dystrophin-associated glycoprotein); NM_000232.4) |
| PHC3 (polyhomeotic homolog 3; NM_001308116.1) | | SYNGR3 (synaptogyrin 3; NM_004209.5) |
| POLR2J2 (RNA polymerase II subunit J2; NM_032959.5) | | ZBTB32 (zinc finger and BTB domain containing 32; NM_014383.2) |
| PSPC1 (paraspeckle component 1; | | |

TABLE 4A-continued

| Adaptive immune cell (AIC) gene signature immunomarkers for use in the methods provided herein. |
|---|
| NM_001042414.2)<br>REPS1 (RALBP1 associated Eps domain containing 1; NM_001128617.2)<br>RP11-74E24.2 (zinc finger CCCH-type domain-containing-like; NM_001271675.1)<br>RPP38 (ribonuclease P/MRP subunit p38; NM_001265601.1)<br>SLC7A6 (solute carrier family 7 member 6; NM_003983.5)<br>SNRPN (small nuclear ribonucleoprotein polypeptide N; NM_022807.3)<br>ST3GAL1 (ST3 beta-galactoside alpha-2,3-sialyltransferase 1; NM_173344.2)<br>STX16 (syntaxin 16; NM_001204868.1)<br>TIMM8A (translocase of inner mitochondrial membrane 8 homolog A; NM_001145951.1)<br>TRAF3IP3 (TRAF3 interacting protein 3; NM_001320144.1)<br>TXK (TXK tyrosine kinase; NM_003328.2)<br>USP9Y (ubiquitin specific peptidase 9, Y-linked; NG_008311.1) |

| | Cell Type | | | |
|---|---|---|---|---|
| | Th2 cells | TFH | Th17 cells | TReg |
| Human Gene (Gene Name; GenBank Accession No.*) | ADCY1 (adenylate cyclase 1; NM_001281768.1) | B3GAT1 (beta-1,3-glucuronyltransferase 1; NM_018644.3) | IL17A (interleukin 17A; NM_002190.2) | FOXP3 (forkhead box P3; NM_014009.3) |
| | AHI1 (Abelson helper integration site 1; NM_001134831.1) | BLR1 (c-x-c chemokine receptor type 5; EF444957.1) | IL17RA (interleukin 17 receptor A; NM_014339.6) | |
| | AI582773 (tn17d08.x1 NCI_CGAP_Brn25 *Homo sapiens* cDNA clone; AI582773.1) | C18orf1 (low density lipoprotein receptor class A domain containing 4; NM_181481.4) | RORC (RAR related orphan receptor C; NM_001001523.1) | |
| | ANK1 (ankyrin 1; NM_020476.2) | CDK5R1 (cyclin dependent kinase 5 regulatory subunit 1; NM_003885.2) | | |
| | BIRC5 (baculoviral IAP repeat containing 5; NM_001012271.1) | CHGB (chromogranin B; NM_001819.2) | | |
| | CDC25C (cell division cycle 25C; NM_001318098.1) | CHI3L2 (chitinase 3 like 2; NM_001025199.1) | | |
| | CDC7 (cell | CXCL13 (C—X—C | | |

TABLE 4A-continued

Adaptive immune cell (AIC) gene signature immunomarkers for use in the methods provided herein.

| | |
|---|---|
| division cycle 7; NM_001134420.1) | motif chemokine ligand 13; NM_006419.2) |
| CENPF (centromere protein F; NM_016343.3) | HEY1 (hes related family bHLH transcription factor with YRPW motif 1; NM_001282851.1) |
| CXCR6 (killer cell lectin like receptor B1; NM_002258.2) | HIST1H4K (histone cluster 1 H4 family member k; NM_003541.2) |
| DHFR (dihydrofolate reductase; NM_001290354.1) | ICA1 (islet cell autoantigen 1; NM_001136020.2) |
| EVI5 (ecotropic viral integration site 5; NM_001308248.1) | KCNK5 (potassium two pore domain channel subfamily K member 5; NM_003740.3) |
| GATA3 (GATA binding protein 3; NM_001002295.1) | KIAA1324 (KIAA1324; NM_001284353.1) |
| GSTA4 (glutathione S-transferase alpha 4; NM_001512.3) | MAF (MAF bZIP transcription factor; NM_001031804.2) |
| HELLS (helicase, lymphoid-specific; NM_001289074.1) | MAGEH1 (MAGE family member H1; NM_014061.4) |
| IL26 (interleukin 26; NM_018402.1) | MKL2 (MKL1/myocardin like 2; NM_014048.4) |
| LAIR2 (leukocyte associated immunoglobulin like receptor 2; NM_021270.4) | MYO6 (myosin VI; NM_001300899.1) |
| LIMA1 (LIM domain and actin binding 1; NM_001243775.1) | MYO7A (myosin VIIA; NM_001127179.2) |
| MB (myoglobin; NM_203377.1) | PASK (PAS domain containing serine/threonine kinase; NM_001252119.1) |
| MICAL2 (microtubule associated monooxygenase, calponin and LIM domain containing 2; NM_001282663.1) | PDCD1 (programmed cell death 1; NM_005018.2) |
| NEIL3 (nei like DNA glycosylase 3; NM_018248.2) | POMT1 (protein O-mannosyltransferase 1; NM_001136114.1) |
| PHEX (phosphate regulating endopeptidase homolog, X-linked; NM_000444.5) | PTPN13 (protein tyrosine phosphatase, non-receptor type 13; NM_080685.2) |
| PMCH (pro-melanin concentrating hormone; NM_002674.3) | PVALB (parvalbumin; NM_001315532.1) |
| PTGIS (I2 synthase; NM_000961.3) | SH3TC1 (SH3 domain and tetratricopeptide repeats 1; NM_018986.4) |

TABLE 4A-continued

Adaptive immune cell (AIC) gene signature immunomarkers for use in the methods provided herein.

| | |
|---|---|
| SLC39A14 (solute carrier family 39 member 14; NM_001135153.1) | SIRPG (signal regulatory protein gamma; NM_018556.3) |
| SMAD2 (SMAD family member 2; NM_001135937.2) | SLC7A10 (solute carrier family 7 member 10; NM_019849.2) |
| SNRPD1 (small nuclear ribonucleoprotein D1 polypeptide; NM_001291916.1) | SMAD1 (SMAD family member 1; NM_001003688.1) |
| WDHD1 (WD repeat and HMG-box DNA binding protein 1; NM_001008396.2) | ST8SIA1 (ST8 alpha-N-acetyl-neuraminide alpha-2,8-sialyltransferase 1; NM_001304450.1) |
| | STK39 (serine/threonine kinase 39; NM_013233.2) |
| | THADA (THADA, armadillo repeat containing; NM_001271644.1) |
| | TOX (thymocyte selection associated high mobility group box; NM_014729.2) |
| | TSHR (thyroid stimulating hormone receptor; NM_000369.2) |
| | ZNF764 (zinc finger protein 764; NM_001172679.1) |

| | Cell Type | | |
|---|---|---|---|
| | CD8 T cells | Tgd | Cytotoxic cells |
| Human Gene (Gene Name; GenBank Accession No.*) | ABT1 (activator of basal transcription 1; NM_013375.3) | C1orf61 (chromosome 1 open reading frame 61; NM_006365.2) | APBA2 (amyloid beta precursor protein binding family A member 2; NM_005503.3) |
| | AES (amino-terminal enhancer of split; NM_198969.1) | CD160 (CD160 molecule; NM_007053.3) | APOL3 (apolipoprotein L3; NM_014349.2) |
| | APBA2 (amyloid beta precursor protein binding family A member 2; NM_001130414.1) | FEZ1 (Fasciculation And Elongation Protein Zeta 1; AF123659.1) | CTSW (cathepsin W; NM_001335.3) |
| | ARHGAP8 (Rho GTPase activating protein 8; NM_001198726.1) | TARP (TCR gamma alternate reading frame protein; NM_001003806.1) | DUSP2 (dual specificity phosphatase 2; NM_004418.3) |
| | C12orf47 (MAPKAPK5 antisense RNA 1; NR_015404.1) | TRD (T cell receptor alpha delta locus; NG_001332.3) | GNLY (granulysin; NM_012483.3) |
| | C19orf6 (transmembrane protein 259; NM_001033026.1) | TRGV9 (T cell receptor gamma V region 9; X69385.1) | GZMA (granzyme A; NM_006144.3) |
| | C4orf15 (HAUS augmin like complex subunit 3; NM_001303143.1) | | GZMH (granzyme H; NM_001270781.1) |
| | CAMLG (calcium modulating ligand; | | KLRB1 (killer cell lectin like |

TABLE 4A-continued

| Adaptive immune cell (AIC) gene signature immunomarkers for use in the methods provided herein. | |
|---|---|
| NM_001745.3) | receptor B1; NM_002258.2) |
| CD8A (CD8a molecule; NM_001768.6) | KLRD1 (killer cell lectin like receptor D1; NM_001114396.1) |
| CD8B (CD8b molecule; NM_001178100.1) | KLRF1 (killer cell lectin like receptor F1; NM_001291822.1) |
| CDKN2AIP (CDKN2A interacting protein; NM_001317343.1) | KLRK1 (killer cell lectin like receptor K1; NM_007360.3) |
| DNAJB1 (DnaJ heat shock protein family (Hsp40) member B1; NM_001313964.1) | NKG7 (natural killer cell granule protein 7; NM_005601.3) |
| FLT3LG (fms related tyrosine kinase 3 ligand; NM_001278638.1) | RORA (RAR related orphan receptor A; NM_134262.2) |
| GADD45A (growth arrest and DNA damage inducible alpha; NM_001199742.1) | RUNX3 (runt related transcription factor 3; NM_004350.2) |
| GZMM (granzyme M; NM_001258351.1) | SIGIRR (single Ig and TIR domain containing; NM_001135054.1) |
| KLF9 (Kruppel like factor 9; NM_001206.2) | WHDC1L1 (WAS protein homolog associated with actin, golgi membranes and microtubules pseudogene 3; NR_003521.1) |
| LEPROTL1 (leptin receptor overlapping transcript-like 1; NM_001128208.1) | ZBTB16 (zinc finger and BTB domain containing 16; NM_001018011.1) |
| LIME1 (Lck interacting transmembrane adaptor 1; NM_017806.3) | |
| MYST3 (MYST histone acetyltransferase (monocytic leukemia) 3; NM_006766.4) | |
| PF4 (platelet factor 4; NM_002619.3) | |
| PPP1R2 (protein phosphatase 1 regulatory inhibitor subunit 2; NM_001291504.1) | |
| PRF1 (perforin 1; NM_005041.4) | |
| PRR5 (proline rich 5; NM_181333.3) | |
| RBM3 (RNA binding motif (RNP1, RRM) protein 3; NM_006743.4) | |
| SF1 (splicing factor 1; NM_004630.3) | |
| SFRS7 (serine and arginine rich splicing factor 7; NM_001031684.2) | |

TABLE 4A-continued

| Adaptive immune cell (AIC) gene signature immunomarkers for use in the methods provided herein. |
|---|
| SLC16A7 (solute carrier family 16 member 7; NM_001270622.1) |
| TBCC (tubulin folding cofactor C; NM_003192.2) |
| THUMPD1 (THUMP domain containing 1; NM_017736.4) |
| TMC6 (transmembrane channel like 6; NM_001321185.1) |
| TSC22D3 (TSC22 domain family member 3; NM_001318470.1) |
| VAMP2 (vesicle associated membrane protein 2; NM_014232.2) |
| ZEB1 (zinc finger E-box binding homeobox 1; NM_001128128.2) |
| ZFP36L2 (ZFP36 ring finger protein like 2; NM_006887.4) |
| ZNF22 (zinc finger protein 22; NM_006963.4) |
| ZNF609 (zinc finger protein 609; NM_015042.1) |
| ZNF91 (zinc finger protein 91; NM_001300951.1) |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 4B

Innate immune cell (IIC) gene signature immunomarkers for use in the methods provided herein.

| | Cell Type | | |
|---|---|---|---|
| | NK cells | NK CD56dim cells | NK CD56bright cells |
| Human Gene (Gene Name; GenBank Accession No.*) | ADARB1 (adenosine deaminase, RNA specific B1; NM_001112) | EDG8 (sphingosine-1-phosphate receptor 5; NM_001166215.1) | BG255923 (lysophosphatidylcholine acyltransferase 4; NM_153613.2) |
| | AF107846 (neuroendocrine-specific Golgi protein p55; AF107846.1) | FLJ20699 (cDNA FLJ20699 fis, clone KAIA2372; AK000706.1) | DUSP4 (dual specificity phosphatase 4; NM_057158.3) |
| | AL080130 (cDNA DKFZp434E033 (from clone DKFZp434E033); AL080130.1) | GTF3C1 (general transcription factor IIIC subunit 1; NM_001286242.1) | FOXJ1 (forkhead box J1; NM_001454.3) |
| | ALDH1B1 (aldehyde dehydrogenase 1 family member B1; NM_000692.4) | GZMB (granzyme B; NM_004131.4) | MADD (MAP kinase activating death domain; NM_001135944.1) |
| | ARL6IP2 (atlastin GTPase 2; NM_001330461.1) | IL21R (interleukin 21 receptor; NM_181079.4) | MPPED1 (metallophosphoesterase domain containing 1, mRNA; NM_001044370.1) |
| | BCL2 (apoptosis regulator (BCL2); NM_000633.2) | KIR2DL3 (killer cell immunoglobulin like receptor, two Ig | MUC3B (mucin 3B cell surface associated; JQ511939.1) |

TABLE 4B-continued

| Innate immune cell (IIC) gene signature immunomarkers for use in the methods provided herein. | | |
|---|---|---|
| | domains and long cytoplasmic tail 3; NM_015868.2) | |
| CDC5L (cell division cycle 5 like; NM_001253.3) | KIR2DS1 (killer cell immunoglobulin like receptor, two Ig domains and short cytoplasmic tail 1; NM_014512.1) | NIBP (NIK and IKKbetta-binding protein; AY630619.1) |
| FGF18 (fibroblast growth factor 18; NM_003862.2) | KIR2DS2 (killer cell immunoglobulin like receptor, two Ig domains and short cytoplasmic tail 2; NM_001291700.1) | PLA2G6 (phospholipase A2 group VI; NM_001004426.1) |
| FUT5 (fucosyltransferase 5; NM_002034.2) | KIR2DS5 (killer cell immunoglobulin like receptor, two Ig domains and short cytoplasmic tail 5; NM_014513.2) | RRAD (Ras related glycolysis inhibitor and calcium channel regulator; NM_001128850.1) |
| FZR1 (fizzy/cell division cycle 20 related 1; XM_005259573.4) | KIR3DL1 (killer cell immunoglobulin like receptor, three Ig domains and long cytoplasmic tail 1; NM_013289.2) | SEPT6 (septin 6; NM_145802.3) |
| GAGE2 (G antigen 2; NM_001127212.1) | KIR3DL2 (killer cell immunoglobulin like receptor, three Ig domains and long cytoplasmic tail 2; NM_006737.3) | XCL1 (X-C motif chemokine ligand 1; NM_002995.2) |
| IGFBP5 (insulin like growth factor binding protein 5; NM_000599.3) | KIR3DL3 (killer cell immunoglobulin like receptor, three Ig domains and long cytoplasmic tail 3; NM_153443.4) | |
| LDB3 (LIM domain binding 3; NM_001171611.1) | KIR3DS1 (killer cell immunoglobulin like receptor, three Ig domains and short cytoplasmic tail 1; NM_001083539.2) | |
| LOC643313 (similar to hypothetical protein LOC284701; XM_933043.1) | SPON2 (spondin 2; NM_001199021.1) | |
| LOC730096 (hypothetical protein LOC730096; NC_000022.9) | TMEPAI (prostate transmembrane protein, androgen induced 1; NM_199169.2) | |
| MAPRE3 (microtubule associated protein RP/EB family member 3; NM_001303050.1) | | |
| MCM3AP (minichromosome maintenance complex component 3 associated protein; NM_003906.4) | | |
| MRC2 (mannose receptor C type 2; NM_006039.4) | | |
| NCR1 (natural cytotoxicity triggering receptor 1; NM_001242357.2) | | |
| NM_014114 (PRO0097 protein; NM_014114.1) | | |
| NM_014274 (transient receptor potential cation channel, subfamily V, member 6; NM_014274.3) | | |
| NM_017616 (KN motif and ankyrin repeat domains 2; NM_015493.6) | | |
| PDLIM4 (PDZ and LIM domain 4; NM_003687.3) | | |

TABLE 4B-continued

| Innate immune cell (IIC) gene signature immunomarkers for use in the methods provided herein. |
| --- |
| PRX (periaxin; NM_020956.2) |
| PSMD4 (proteasome 26S subunit, non-ATPase 4; NM_001330692.1) |
| RP5-886K2.1 (neuronal thread protein AD7c-NTP; AF010144.1) |
| SLC30A5 (solute carrier family 30 member 5; NM_001251969.1) |
| SMEK1 (protein phosphatase 4 regulatory subunit 3A; NM_001284280.1) |
| SPN (sialophorin; NM_003123.4) |
| TBXA2R (thromboxane A2 receptor; NM_001060.5) |
| TCTN2 (tectonic family member 2; NM_001143850.2) |
| TINAGL1 (tubulointerstitial nephritis antigen like 1; NM_001204415.1) |
| XCL1 (X-C motif chemokine ligand 1; NM_002995.2) |
| XCL2 (X-C motif chemokine ligand 2; NM_003175.3) |
| ZNF205 (zinc finger protein 205; NM_001278158.1) |
| ZNF528 (zinc finger protein 528; NM_032423.2) |
| ZNF747 (zinc finger protein 747; NM_023931.3) |

| | Cell Type | |
| --- | --- | --- |
| | DC | iDC |
| Human Gene (Gene Name; GenBank Accession No.*) | CCL13 (C-C motif chemokine ligand 13; NM_005408.2) | ABCG2 (ATP-binding cassette, sub-family G (WHITE), member 2 (Junior blood group); NM_001257386.1) |
| | CCL17 (C-C motif chemokine ligand 17; NM_002987.2) | BLVRB (biliverdin reductase B; NM_000713.2) |
| | CCL22 (C-C motif chemokine ligand 22; NM_002990.4) | CARD9 (caspase recruitment domain family member 9; NM_052814.3) |
| | CD209 (CD209 molecule; NM_001144899.1) | CD1A (CD1a molecule; NM_001763.2) |
| | HSD11B1 (hydroxysteroid 11-beta dehydrogenase 1; NM_001206741.1) | CD1B (CD1b molecule; NM_001764.2) |
| | NPR1 (natriuretic peptide receptor 1; NM_000906.3) | CD1C (CD1c molecule; NM_001765.2) |
| | PPFIBP2 (PPFIA binding protein 2; XR_930917.2) | CD1E (CD1e molecule; NM_001185115.1) |
| | | CH25H (cholesterol 25-hydroxylase; NM_003956.3) |
| | | CLEC10A (C-type lectin domain family 10 member A; NM_001330070.1) |
| | | CSF1R (colony stimulating factor 1 receptor; NM_001288705.1) |
| | | CTNS (cystinosin, lysosomal cystine transporter; NM_001031681.2) |
| | | F13A1 (factor XIII a subunit; AH002691.2) |
| | | FABP4 (fatty acid binding |

TABLE 4B-continued

| Innate immune cell (IIC) gene signature immunomarkers for use in the methods provided herein. | | | |
|---|---|---|---|
| | | | protein 4; NM_001442.2)<br>FZD2 (frizzled class receptor 2; NM_001466.3)<br>GSTT1 (glutathione S-transferase theta 1; NM_001293814.1)<br>GUCA1A (guanylate cyclase activator 1A; NM_001319062.1)<br>HS3ST2 (heparan sulfate (glucosamine) 3-O-sulfotransferase 2; NM_006043.1)<br>LMAN2L (lectin, mannose binding 2 like; NM_001322355.1)<br>MMP12 (matrix metallopeptidase 12; NM_002426.5)<br>MS4A6A (membrane spanning 4-domains A6A; NM_001330275.1)<br>NM_021941 (chromosome 21 open reading frame 97; NM_021941.1)<br>NUDT9 (nudix hydrolase 9; NM_001248011.1)<br>PPARG (peroxisome proliferator activated receptor gamma; NM_005037.5)<br>PREP (prolyl endopeptidase; NM_002726.4)<br>RAP1GAP (RAP1 GTPase activating protein; NM_001330383.1)<br>SLC26A6 (solute carrier family 26 member 6; NM_001281733.1)<br>SLC7A8 (solute carrier family 7 member 8; NR_049767.1)<br>SYT17 (synaptotagmin 17; NM_001330509.1)<br>TACSTD2 (tumor-associated calcium signal transducer 2; NM_002353.2)<br>TM7SF4 (dendrocyte expressed seven transmembrane protein; NM_001257317.1)<br>VASH1 (vasohibin 1; NM_014909.4) |

| | Cell Type | | |
|---|---|---|---|
| | aDC | pDC | Eosinophils |
| Human Gene (Gene Name; GenBank Accession No.*) | CCL1 (Chemokine (C-C motif) ligand 1; NM_002981) | IL3RA (interleukin 3 receptor subunit alpha; NM_001267713.1) | ABHD2 (abhydrolase domain containing 2; NM_007011.7) |
| | EBI3 (Epstein-Barr virus induced 3; NM_005755.2) | | ACACB (acetyl-CoA carboxylase beta; NM_001093.3) |
| | INDO (indoleamine-pyrrole 2,3 dioxygenase; AY221100.1) | | C9orf156 (tRNA methyltransferase O; NM_001330725.1) |
| | LAMP3 (lysosomal associated membrane protein 3; NM_014398.3) | | CAT (catalase; NM_001752.3) |

TABLE 4B-continued

| Innate immune cell (IIC) gene signature immunomarkers for use in the methods provided herein. | |
|---|---|
| OAS3 (2'-5'-oligoadenylate synthetase 3; NM_006187.3) | CCR3 (C-C motif chemokine receptor 3; NM_178329.2) |
| | CLC (Charcot-Leyden crystal galectin; NM_001828.5) CYSLTR2 (cysteinyl leukotriene receptor 2; NM_001308471.1) EMR1 (EGF-like module containing mucin-like hormone receptor-like 1; DQ217942.1) EPN2 (eosin 2; NM_001102664.1) GALC (galactosylceramidase; NM_000153.3) GPR44 (orphan G protein-coupled receptor; AF118265.1) HES1 (hes family bHLH transcription factor 1; NM_005524.3) HIST1H1C (histone cluster 1 H1 family member c; NM_005319.3) HRH4 (histamine receptor H4; NM_001143828.1) IGSF2 (immunoglobulin superfamily, member 2; BC130327.1) IL5RA (interleukin 5 receptor subunit alpha; NM_001243099.1) KBTBD11 (kelch repeat and BTB domain containing 11; NM_014867.2) KCNH2 (potassium voltage-gated channel, subfamily H (eag-related), member 2; NM_000238.3) LRP5L (LDL receptor related protein 5 like; NM_001135772.1) MYO15B (myosin XVB; NM_001309242.1) RCOR3 (REST corepressor 3; NM_001136224.2) RNASE2 (ribonuclease A family member 2; NM_002934.2) RNU2 (U2 snRNA; U57614.1) RRP12 (ribosomal RNA processing 12 homolog; NM_001284337.1) SIAH1 (siah E3 ubiquitin protein ligase 1; NM_003031.3) SMPD3 (sphingomyelin phosphodiesterase 3; NM_018667.3) SYNJ1 (synaptojanin 1; NM_001160302.1) TGIF1 (TGFB induced |

TABLE 4B-continued

| Innate immune cell (IIC) gene signature immunomarkers for use in the methods provided herein. | | | |
|---|---|---|---|
| | | | factor homeobox 1; NM_174886.2) |
| | | | THBS1 (thrombospondin 1; NM_003246.3) |
| | | | THBS4 (thrombospondin 4; NM_001306213.1) |
| | | | TIPARP (TCDD inducible poly(ADP-ribose) polymerase; NM_001184718.1) |
| | | | TKTL1 (transketolase like 1; NM_001145934.1) |

| | Cell Type | | |
|---|---|---|---|
| | Macrophages | Mast cells | Neutrophils |
| Human Gene (Gene Name; GenBank Accession No.*) | APOE (apolipoprotein E; NM_001302691.1) | ABCC4 (ATP binding cassette subfamily C member 4; NM_001301829.1) | ALPL (alkaline phosphatase, liver/bone/kidney; NM_001127501.3) |
| | ATG7 (autophagy related 7; NM_001144912.1) | ADCYAP1 (adenylate cyclase activating polypeptide 1; NM_001117.4) | BST1 (bone marrow stromal cell antigen 1; NM_004334.2) |
| | BCAT1 (branched chain amino acid transaminase 1; NM_001178094.1) | CALB2 (calbindin 2; NM_001740.4) | CD93 (CD93 molecule; NM_012072.3) |
| | CCL7 (C-C motif chemokine ligand 7; NM_006273.3) | CEACAM8 (carcinoembryonic antigen related cell adhesion molecule 8; NM_001816.3) | CEACAM3 (carcinoembryonic antigen related cell adhesion molecule 3; NM_001277163.2) |
| | CD163 (CD163 molecule; NM_203416.3) | CMA1 (chymase 1, mast cell; NM_001308083.1) | CREB5 (cAMP responsive element binding protein 5; NM_001011666.2) |
| | CD68 (CD68 molecule; NM_001040059.1) | CPA3 (carboxypeptidase A3; NM_001870.3) | CRISPLD2 (cysteine rich secretory protein LCCL domain containing 2; NM_031476.3) |
| | CD84 (CD84 molecule; NM_001184881.1) | CTSG (cathepsin G; NM_001911.2) | CSF3R (colony stimulating factor 3 receptor; NM_172313.2) |
| | CHI3L1 (chitinase 3 like 1; NM_001276.2) | ELA2 (neutrophil elastase; EU617980.1) | CYP4F3 (cytochrome P450 family 4 subfamily F member 3; NM_001199209.1) |
| | CHIT1 (chitinase 1; NM_001270509.1) | GATA2 (GATA binding protein 2; NM_001145661.1) | DYSF (dysferlin; NM_001130455.1) |
| | CLEC5A (C-type lectin domain family 5 member A; NM_001301167.1) | HDC (histidine decarboxylase; NM_002112.3) | FCAR (Fc fragment of IgA receptor; NM_133278.3) |
| | COL8A2 (collagen type VIII alpha 2 chain; NM_001294347.1) | HPGD (hydroxyprostaglandin dehydrogenase 15-(NAD); NM_001256307.1) | FCGR3B (Fc fragment of IgG receptor IIIb; NM_001271035.1) |
| | COLEC12 (collectin subfamily member 12; NM_130386.2) | KIT (KIT proto-oncogene receptor tyrosine kinase; NM_000222.2) | FLJ11151 (hypothetical protein FLJ11151; BC006289.2) |
| | CTSK (cathepsin K; NM_000396.3) | LOC339524 (long intergenic non-protein coding RNA 1140; NR_026985.1) | FPR1 (formyl peptide receptor 1; NM_001193306.1) |
| | CXCL5 (C—X—C motif chemokine ligand 5; NM_002994.4) | LOH11CR2A (BCSC-1 isoform; AY366508.1) | FPRL1 (formyl peptide receptor-like receptor; M84562.1) |
| | CYBB (cytochrome b- | MAOB (monoamine | G0S2 (G0/G1 switch 2; |

TABLE 4B-continued

| Innate immune cell (IIC) gene signature immunomarkers for use in the methods provided herein. | | |
|---|---|---|
| 245 beta chain; NM_000397.3) | oxidase B; NM_000898.4) | NM_015714.3) |
| DNASE2B (deoxyribonuclease 2 beta; NM_058248.1) | MLPH (melanophilin; NM_001042467.2) | HIST1H2BC (histone cluster 1 H2B family member c; NM_003526.2) |
| EMP1 (epithelial membrane protein 1; NM_001423.2) | MPO (myeloperoxidase; NM_000250.1) | HPSE (heparanase; NM_001098540.2) |
| FDX1 (ferredoxin 1; NM_004109.4) | MS4A2 (membrane spanning 4-domains A2; NM_001256916.1) | IL8RA (interleukin 8 receptor alpha; L19591.1) |
| FN1 (fibronectin 1; NM_001306131.1) | NM_003293 (tryptase alpha/beta 1; NM_003294.3) | IL8RB (interleukin-8 receptor type B; U11878.1) |
| GM2A (GM2 ganglioside activator; NM_000405.4) | NR0B1 (nuclear receptor subfamily 0 group B member 1; NM_000475.4) | KCNJ15 (potassium voltage-gated channel subfamily J member 15; NM_001276438.1) |
| GPC4 (glypican 4; NM_001448.2) | PGDS (hematopoietic prostaglandin D synthase; NM_014485.2) | KIAA0329 (tectonin beta-propeller repeat containing 2; NM_014844.4) |
| KAL1 (anosmin 1; NM_000216.3) | PPM1H (protein phosphatase, Mg2+/Mn2+ dependent 1H; NM_020700.1) | LILRB2 (leukocyte immunoglobulin like receptor B2; NR_103521.2) |
| MARCO (macrophage receptor with collagenous structure; NM_006770.3) | PRG2 (proteoglycan 2, pro eosinophil major basic protein; NM_001302927.1) | MGAM (maltase-glucoamylase; NM_004668.2) |
| ME1 (malic enzyme 1; NM_002395.5) | PTGS1 (prostaglandin-endoperoxide synthase 1; NM_000962.3) | MME (membrane metalloendopeptidase; NM_007289.2) |
| MS4A4A (membrane spanning 4-domains A4A; NM_001243266.1) | SCG2 (secretogranin II; NM_003469.4) | PDE4B (phosphodiesterase 4B; NM_001297440.1) |
| MSR1 (macrophage scavenger receptor 1; NM_138716.2) | SIGLEC6 (sialic acid binding Ig like lectin 6; NM_198845.5) | S100A12 (S100 calcium binding protein A12; NM_005621.1) |
| PCOLCE2 (procollagen C-endopeptidase enhancer 2; NM_013363.3) | SLC18A2 (solute carrier family 18 member A2; NM_003054.4) | SIGLEC5 (sialic acid binding Ig like lectin 5; NM_003830.3) |
| PTGDS (prostaglandin D2 synthase; NM_000954.5) | SLC24A3 (solute carrier family 24 member 3; NM_020689.3) | SLC22A4 (solute carrier family 22 member 4; NM_003059.2) |
| RAI14 (retinoic acid induced 14; NM_001145525.1) | TAL1 (T-cell acute lymphocytic leukemia 1; X51990.1) | SLC25A37 (solute carrier family 25 member 37; NM_001317812.1) |
| SCARB2 (scavenger receptor class B member 2; NM_001204255.1) | TPSAB1 (tryptase alpha/beta 1; NM_003294.3) | TNFRSF10C (TNF receptor superfamily member 10c; NM_003841.3) |
| SCG5 (secretogranin V; NM_001144757.2) | TPSB2 (tryptase beta 2; NM_024164.5) | VNN3 (vanin 3; NM_001291703.1) |
| SGMS1 (sphingomyelin synthase 1; NM_147156.3) | | |
| SULT1C2 (sulfotransferase family 1C member 2; NM_176825.2) | | |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 5

Individual Immunomarkers for use in the methods provided herein.

| Gene Name | Abbreviation | GenBank Accession No.* |
|---|---|---|
| Programmed Death Ligand 1 | PDL1 | NM_014143 |
| programmed death ligand 2 | PDL2 | AY254343 |
| programmed cell death 1 | PDCD1 | NM_005018 |
| cytotoxic T-lymphocyte associated protein 4 | CTLA4 | NM_005214 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 6

Interferon (IFN) Genes for use in the methods provided herein.

| Gene Name | Abbreviation | GenBank Accession No.* |
|---|---|---|
| Chemokine (C—X—C Motif) Ligand 10 | CXCL10 | NM_001565 |
| C—X—C motif chemokine ligand 9 | CXCL9 | NM_002416 |
| interferon alpha inducible protein 27 | IFI27 | NM_001130080 |
| interferon induced protein with tetratricopeptide repeats 1 | IFIT1 | NM_001548 |
| interferon induced protein with tetratricopeptide repeats 2 | IFIT2 | NM_001547 |
| interferon induced protein with tetratricopeptide repeats 3 | IFIT3 | NM_001549 |
| MX dynamin like GTPase 1 | MX1 | NM_001144925 |
| MX dynamin like GTPase 2 | MX2 | XM_005260983 |
| 2'-5'-oligoadenylate synthetase 1 | OAS1 | NM_016816 |
| 2'-5'-oligoadenylate synthetase 2 | OAS2 | NM_016817 |
| signal transducer and activator of transcription 1 | STAT1 | NM_007315 |
| signal transducer and activator of transcription 2 | STAT2 | NM_005419 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 7

MHC class II genes for use in the methods provided herein.

| Name | Abbreviation | GenBank Accession No.* |
|---|---|---|
| CD74 | *Homo sapiens* CD74 molecule (CD74) | NM_001025159 |
| CIITA | class II major histocompatibility complex transactivator | NM_001286402 |
| CTSH | cathepsin H | NM_004390 |
| HLA-DMA | *Homo sapiens* major histocompatibility complex, class II, DM alpha | NM_006120 |
| HLA-DPA1 | *Homo sapiens* major histocompatibility complex, class II, DP alpha 1 | NM_033554 |
| HLA-DPB1 | Human MHC class II lymphocyte antigen (HLA-DP) beta chain | M83664 |
| HLA-DQA1 | *Homo sapiens* major histocompatibility complex, class II, DQ alpha 1 | NM_002122 |
| HLA-DRB1 | *Homo sapiens* major histocompatibility complex, class II, DR beta 1 | NM_002124 |
| HLA-DRB5 | *Homo sapiens* major histocompatibility complex, class II, DR beta 5 | NM_002125 |
| HLA-DRB6 | *Homo sapiens* major histocompatibility complex, class II, DR beta 6 | NR_001298 |
| NCOA1 | *Homo sapiens* nuclear receptor coactivator 1 | NM_003743 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

In one embodiment, upon determining a patient's AD lung cancer subtype using any of the methods and classifier biomarkers panels or subsets thereof as provided herein alone or in combination with determining expression of one or more immune cell markers as provided herein, the patient is selected for treatment with or administered an immunotherapeutic agent. The immunotherapeutic agent can be a checkpoint inhibitor, monoclonal antibody, biological response modifiers, therapeutic vaccine or cellular immunotherapy.

In another embodiment, the immunotherapeutic agent is a checkpoint inhibitor. In some cases, a method for determining the likelihood of response to one or more checkpoint inhibitors is provided. In one embodiment, the checkpoint inhibitor is a PD-1/PD-LI checkpoint inhibitor. The PD-1/PD-LI checkpoint inhibitor can be nivolumab, pembrolizumab, atezolizumab, durvalumab, lambrolizumab, or avelumab. In one embodiment, the checkpoint inhibitor is a CTLA-4 checkpoint inhibitor. The CTLA-4 checkpoint inhibitor can be ipilimumab or tremelimumab. In one embodiment, the checkpoint inhibitor is a combination of checkpoint inhibitors such as, for example, a combination of one or more PD-1/PD-LI checkpoint inhibitors used in combination with one or more CTLA-4 checkpoint inhibitors.

In one embodiment, the immunotherapeutic agent is a monoclonal antibody. In some cases, a method for determining the likelihood of response to one or more monoclonal antibodies is provided. The monoclonal antibody can be directed against tumor cells or directed against tumor products. The monoclonal antibody can be panitumumab, matuzumab, necitumunab, trastuzumab, amatuximab, bevacizumab, ramucirumab, bavituximab, patritumab, rilotumumab, cetuximab, immu-132, or demcizumab.

In yet another embodiment, the immunotherapeutic agent is a therapeutic vaccine. In some cases, a method for determining the likelihood of response to one or more therapeutic vaccines is provided. The therapeutic vaccine can be a peptide or tumor cell vaccine. The vaccine can target MAGE-3 antigens, NY-ESO-1 antigens, p53 antigens, survivin antigens, or MUC1 antigens. The therapeutic cancer vaccine can be GVAX (GM-CSF gene-transfected tumor cell vaccine), belagenpumatucel-L (allogeneic tumor cell vaccine made with four irradiated NSCLC cell lines modified with TGF-beta2 antisense plasmid), MAGE-A3 vaccine (composed of MAGE-A3 protein and adjuvant AS15), (1)-BLP-25 anti-MUC-1 (targets MUC-1 expressed on tumor cells), CimaVax EGF (vaccine composed of human recombinant Epidermal Growth Factor (EGF) conjugated to a carrier protein), WT1 peptide vaccine (composed of four Wilms' tumor suppressor gene analogue peptides), CRS-207 (live-attenuated *Listeria monocytogenes* vector encoding human mesothelin), Bec2/BCG (induces anti-GD3 antibodies), GV1001 (targets the human telomerase reverse transcriptase), tergenpumatucel-L (consists of human lung cancer cells genetically modified to include a mouse gene to which the immune system responds strongly), TG4010 (targets the MUC1 antigen), racotumomab (anti-idiotypic antibody which mimicks the NGcGM3 ganglioside that is expressed on multiple human cancers), tecemotide (liposomal BLP25; liposome-based vaccine made from tandem repeat region of MUC1) or DRibbles (a vaccine made from nine cancer antigens plus TLR adjuvants).

In one embodiment, the immunotherapeutic agent is a biological response modifier. In some cases, a method for determining the likelihood of response to one or more biological response modifiers is provided. The biological response modifier can trigger inflammation such as, for example, PF-3512676 (CpG 7909) (a toll-like receptor 9 agonist), CpG-ODN 2006 (downregulates Tregs), *Bacillus* Calmette-Guerin (BCG), *mycobacterium* vaccae (SRL172) (nonspecific immune stimulants now often tested as adjuvants). The biological response modifier can be cytokine therapy such as, for example, IL-2+tumor necrosis factor alpha (TNF-alpha) or interferon alpha (induces T-cell proliferation), interferon gamma (induces tumor cell apoptosis), or Mda-7 (IL-24) (Mda-7/IL-24 induces tumor cell apoptosis and inhibits tumor angiogenesis). The biological response modifier can be a colony-stimulating factor such as, for example granulocyte colony-stimulating factor. The biological response modifier can be a multi-modal effector such as, for example, multi-target VEGFR: thalidomide and analogues such as lenalidomide and pomalidomide, cyclophosphamide, cyclosporine, denileukin diftitox, talactoferrin, trabecetedin or all-trans-retinmoic acid.

In one embodiment, the immunotherapy is cellular immunotherapy. In some cases, a method for determining the likelihood of response to one or more cellular therapeutic agents. The cellular immunotherapeutic agent can be dendritic cells (DCs) (ex vivo generated DC-vaccines loaded with tumor antigens), T-cells (ex vivo generated lymphokine-activated killer cells; cytokine-induce killer cells; activated T-cells; gamma delta T-cells), or natural killer cells.

In some cases, specific subtypes of AD have different levels of immune activation (e.g., innate immunity and/or adaptive immunity) such that subtypes with elevated or detectable immune activation (e.g., innate immunity and/or adaptive immunity) are selected for treatment with one or more immunotherapeutic agents described herein. In one embodiment, the PP subtype of AD has low immune activation (e.g., innate immunity and/or adaptive immunity) as compared to other AD subtypes or lung cancer subtypes. In some cases, specific subtypes of AD have high or elevated levels of immune activation. In some cases, the PI subtype of AD has elevated levels of immune activation (e.g., innate immunity and/or adaptive immunity) as compared to other AD subtypes or lung cancer subtypes. In one embodiment, AD subtypes with low levels of or no immune activation (e.g., innate immunity and/or adaptive immunity) are not selected for treatment with one or more immunotherapeutic agents described herein.

Detection Methods

In one embodiment, the methods and compositions provided herein allow for the detection of at least one nucleic acid in a lung cancer sample (e.g. adenocarcinoma lung cancer sample) obtained from a subject. The at least one nucleic acid can be a classifier biomarker provided herein. In one embodiment, the at least one nucleic acid detected using the methods and compositions provided herein are selected from Table 1. In one embodiment, the methods of detecting the nucleic acid(s) (e.g., classifier biomarkers) in the lung cancer sample obtained from the subject comprises, consists essentially of, or consists of measuring the expression level of at least one or a plurality of biomarkers using any of the methods provided herein. The biomarkers can be selected from Table 1. In some cases, the plurality of biomarker nucleic acids comprises, consists essentially of or consists of at least two biomarker nucleic acids, at least 8 biomarker nucleic acids, at least 16 biomarker nucleic acids, at least 24 biomarker nucleic acids, at least 32 biomarker nucleic acids, or all 48 biomarkers nucleic acids of Table 1. The detection can be at the nucleic acid level. The detection can be by using any amplification, hybridization and/or sequencing assay disclosed herein.

In another embodiment, the methods and compositions provided herein allow for the detection of at least one nucleic acid or a plurality of nucleic acids in a lung cancer sample (e.g. adenocarcinoma lung cancer sample) obtained from a subject such that the at least one nucleic acid is or the plurality of nucleic acids are selected from the biomarkers listed in Table 1 and the detection of at least one biomarker from a set of biomarkers whose presence, absence and/or level of expression is indicative of immune activation. The set of biomarkers for indicating immune activation can be gene expression signatures of and/or Adaptive Immune Cells (AIC) (e.g., Table 4A) and/or Innate immune Cells (IIC) (e.g., Table 4B), individual immune biomarkers (e.g., Table 5), interferon genes (e.g., Table 6), major histocompatibility complex, class II (MHC II) genes (e.g., Table 7) or a combination thereof. The gene expression signatures of both IIC and AIC can be any gene signatures known in the art such as, for example, the gene signature listed in Bindea et al. (Immunity 2013; 39(4); 782-795). The detection can be at the nucleic acid level. The detection can be by using any amplification, hybridization and/or sequencing assay disclosed herein.

Kits

Kits for practicing the methods of the invention can be further provided. By "kit" can encompass any manufacture (e.g., a package or a container) comprising at least one reagent, e.g., an antibody, a nucleic acid probe or primer, etc., for specifically detecting the expression of a biomarker of the invention. The kit may be promoted, distributed, or sold as a unit for performing the methods of the present invention. Additionally, the kits may contain a package insert describing the kit and methods for its use.

In one embodiment, kits for practicing the methods of the invention are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the invention. The kits may comprise at least 2, at least 3, at least 4, at least 5, at least 6, at least 7, at least 8, at least 9, at least 10, or more antibodies for use in the methods of the invention.

EXAMPLES

The present invention is further illustrated by reference to the following Examples. However, it should be noted that these Examples, like the embodiments described above, are illustrative and are not to be construed as restricting the scope of the invention in any way.

Example 1—Immune Cell Activation Differences Among Lung Adenocarcinoma Intrinsic Subtypes and Variable Correlation with CD274 (PD-L1) Expression Introduction Gene expression based subtyping in Lung Adenocarcinoma (AD) classifies AD tumors into distinct subtypes with variable biologic and clinical features. Gene expression based subtyping has consistently identified 3 distinct biologic types in Lung AD, Terminal Respiratory Unit (TRU), formerly Bronchioid, Proximal Proliferative (PP), formerly Magnoid, and Proximal Inflammatory (PI), formerly Squamoid (1,2)) (see FIG. 1). AD subtypes demonstrate key differences in genomic alterations, tumor drivers, prognosis, and likely response to various therapies (1-2).

Methods

Using previously published Bindea et al. (3) immune cell gene signatures (24 in total) and AD subtyping gene expression signatures (1-2), several publically available lung AD datasets (2, 4 and 5) and 1 recently collected gene expression dataset (see FIG. 2), were examined for immune cell features in relation to AD subtypes. This investigation of immune differences by subtype used the 24 immune cell gene signatures from Bindea et al [3] that each had a varying number of genes and were classified as adaptive or innate immunity cell signatures (see Table 4A-4B). Adaptive Immune Cell (AIC) signatures (Table 4A) included Tcells, Central Memory T cells (Tcm), Effector Memory T cells (Tem), I helper cell (Th), Type 1 T helper cells (Th1), Type 2 T helper cells (Th2), T follicular helper cells (Tfh), T helper 17 cells (Th17), T Regulatory Cells (Treg), Gamma Delta T cells (Tgd), CD8 Tcells, Cytotoxic T cells, B cells, and innate Immune Cell (IIC) signatures (Table 4B) included Natural Killer (NK), NK CD56dim cells, NK CD56bright cells, Dendritic cells (DC), Immature Dendritic Cells (iDC), Dendritic Cells (pDC), Activated Dendritic Cells(aDC), Mast cells, Eosinophils, Macrophages, and Neutrophils. In addition to the gene expression signatures of both innate Immune Cells (IIC) and Adaptive Immune Cells (AIC), a 13 gene IFN signature (IFN; Table 6), a 13-gene MEW class II signature score (Forero [6]; Table 7) as well as single gene immune biomarkers in Table 5 (CTLA4, PDCD1, CD274 (PD-L1), and PDCDLG2 (PD-L2)) were examined in the 3 AD subtypes (TRU, PP, and PI)

The AD datasets included several publically available lung cancer gene expression data sets as described above and a newly collected adenocarcinoma dataset of Formalin Fixed Paraffin Embedded (FFPE) lung tumor samples (n=88). The newly collected AD dataset of 88 formalin fixed paraffin embedded (FFPE) samples were archived residual lung tumor samples collected under an approved IRB protocol at the University of North Carolina at Chapel Hill (UNC-CH). FFPE sample sections (3 10 um sections) were macrodissected prior to RNA extraction. Transcriptome-enriched RNAseq was performed using Illumina's RNA-Access kits (San Diego, Calif.) with input of 100 ng/sample. Sequence data was aligned using hg19 as reference and the transcriptome was built using cufflinks (Trapnell 2010). Cuff compare was used to annotate the transcriptome and gene expression counts were calculated.

For AD, 4 published and 1 recently collected gene expression data sets (i.e., GeneCentric expression data set) of lung adenocarcinoma samples with a total of 1278 patient samples were used. The published data sets included TCGA [2], Shedden et al [4], Tomida et al [5], and Wilkerson et al [1], derived from fresh frozen specimens. The GeneCentric expression data set was derived from Formalin Fixed Paraffin Embedded (FFPE) specimens. For TCGA, upper quantile normalized RSEM data was downloaded from Firehose and log 2 transformed. Affymetrix Cel files from Shedden et al [4] were downloaded from the caIntegrator website and robust multi-array average expression measures were generated using the Affy package in R. Normalized Agilent array data was downloaded from the Gene Expression Omnibus (GEO) website for Tomida et al [5] (GSE13213) and Wilkerson et al [1] (GSE26939).

To determine adenocarcinoma subtype (TRU, PP, and PI), the published 506-gene nearest centroid classifier as described previously in Wilkerson et al [1] was used. After median centering of genes in the signature, each sample was assigned the subtype corresponding to the centroid with which it was maximally correlated. (Pearson)

Figure 3:
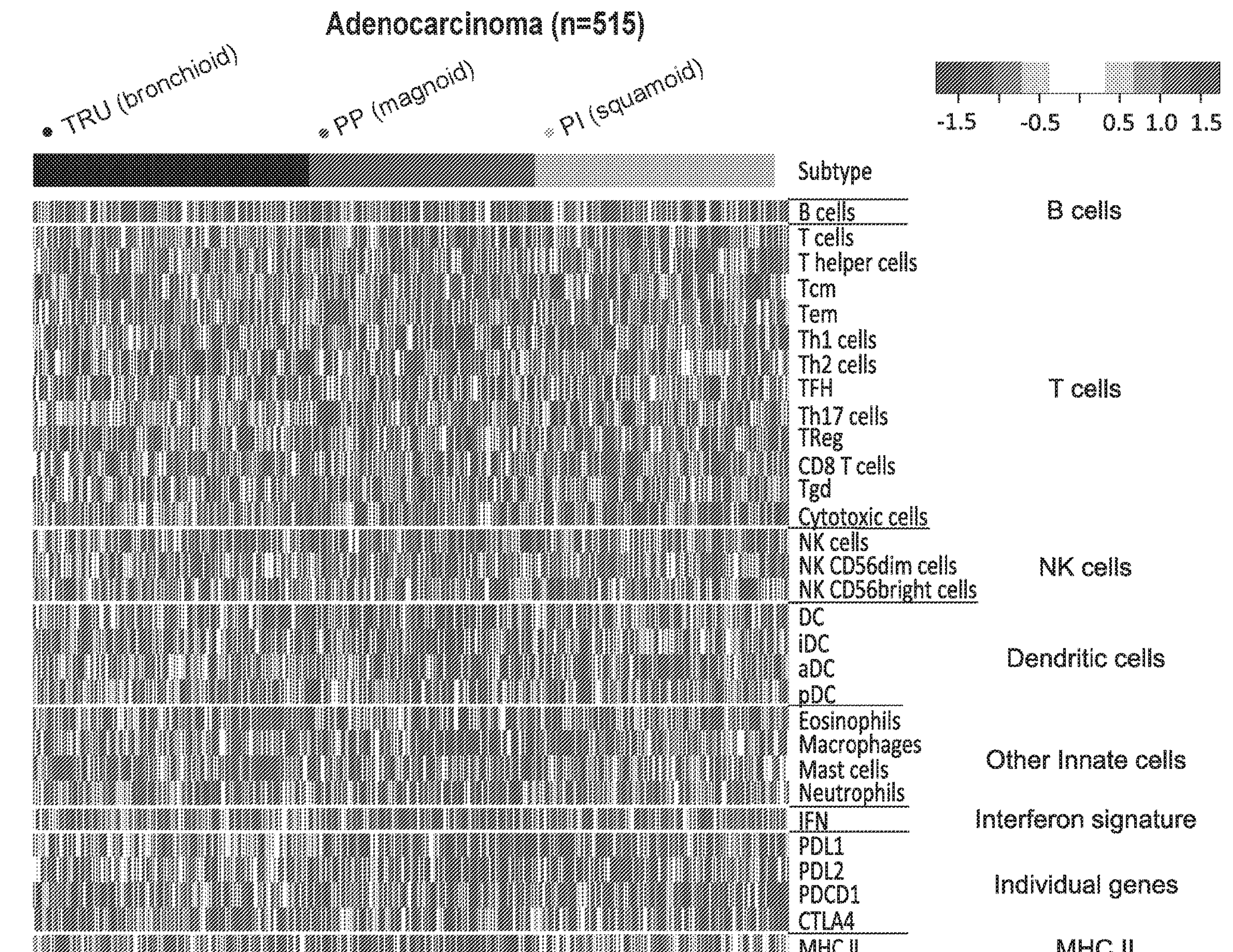
FIG. 3 illustrates a heatmap of immune cell signatures expression (i.e., Bindea et al reference from Example 1), other immune markers and individual immune markers in the Cancer Genome Atlas (TCGA) Lung AD dataset. TRU=Terminal Respiratory Unit, PP=Proximal Proliferative, PI=Proximal Inflammatory.
Figure 4:
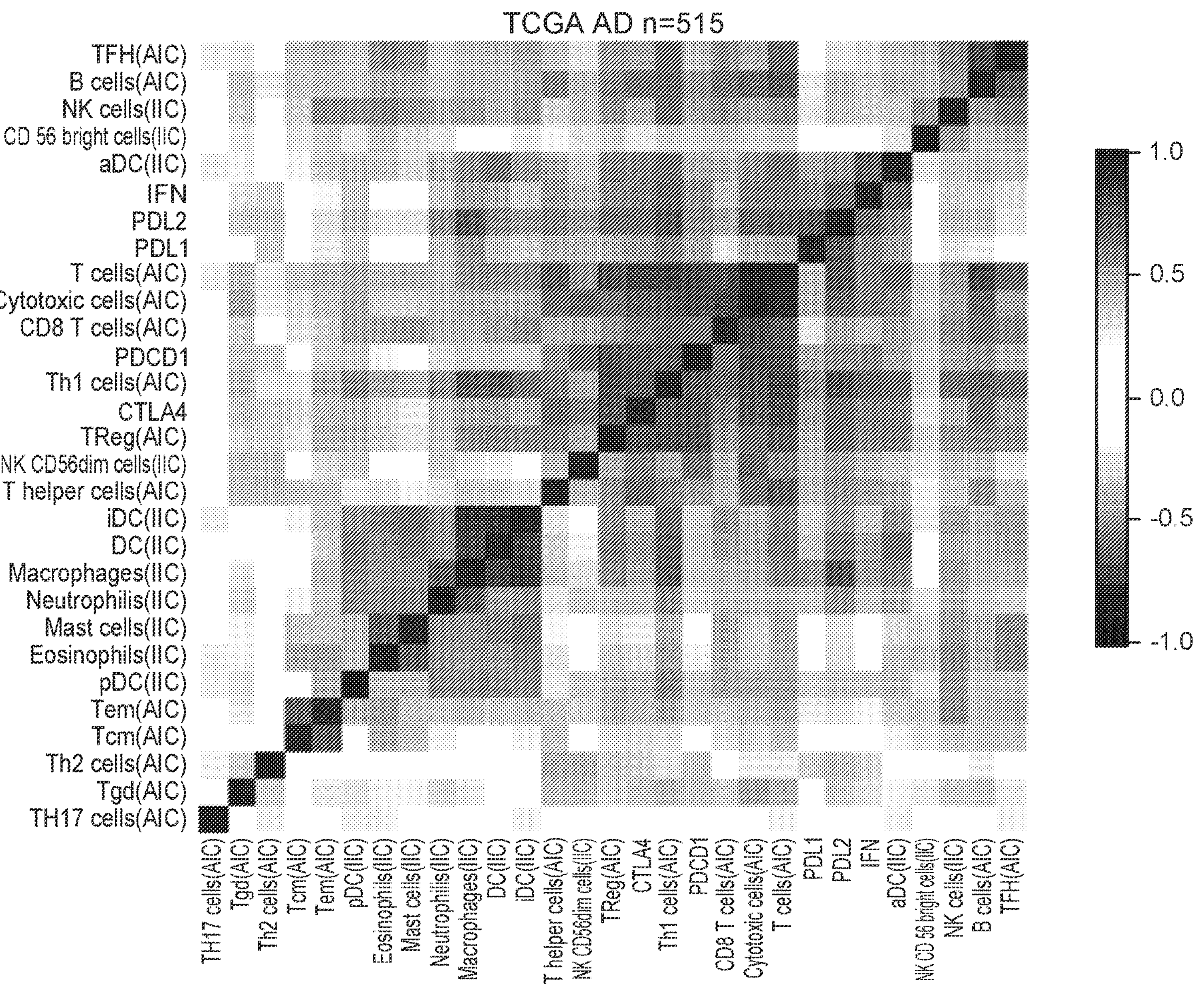
FIG. 4 illustrates correlation matrices of immune cell signatures in the TCGA AD dataset where signatures were arranged by hierarchical clustering. White means no correlation.

Using the TCGA data for adenocarcinoma, correlations were assessed among the 30 markers by plotting matrices of pairwise Spearman rank correlation coefficients where markers were ordered by hierarchical clustering (see FIG. 4). To investigate overall immunity marker trends by subtype, expression heatmaps were plotted where samples were arranged by subtype and markers were grouped according to ordering in Bindea et al [3] (see FIG. 3). To evaluate the reproducibility of immunity marker differences among the subtypes, normalized T cell signatures were plotted by subtype for each data set (see FIG. 5).

immune cell signature associations with tumor subtype and with CD274 expression were evaluated using linear regression. More specifically, to assess the prediction strength of subtype as a predictor of immune markers relative to that of PD-L1, a linear regression model of each signature with subtype the sole predictor, and again with PD-L1 the sole predictor, was fitted in the TCGA dataset. PD-L1 expression was treated as a low/medium/high categorical variable with equal proportions in each group. Scatter plots of adjusted R-squared when subtype was the predictor against adjusted R-squared when PD-L1 was the predictor were inspected for overall trends (see FIG. 6).

Using non-silent mutation burden per Mb data, available in the supplementary information from TCGA adenocarcinoma (Lawrence 2013), mutation burden-Tcell expression associations was investigated using the Kruskal Wallis test and the Spearman correlation coefficients, respectively. For TCGA adenocarcinoma, STK11 CNV and mutation status were downloaded from Firehose, and STK11 inactivation-subtype association was evaluated using Fisher's exact test. Here, a sample was called inactive when it was reported as deleted and/or mutated. To test whether STK11 in AD showed evidence of association after adjusting for subtype, a linear model for Tcell expression was fit with inactive STK11 in AD as sole predictors and again following adjustment for subtype.

Subtype and immune signature associations with a 13-gene MHC class II signature [Forero [6]; Table 7], calculated as an average of all genes in the list (Table 7), were investigated using the Kruskal-Wallis test. For immune signature-MHC class II associations, Spearman correlation coefficients were calculated.

Hierarchical clustering of immune signatures and pairwise signature correlations were also analyzed. Survival signature associations of Stages I-III samples were evaluated with stratified cox proportional hazard models allowing for different baseline hazards in each dataset. More specifically, immune marker-survival associations in the TCGA data sets were tested, overall and separately within each subtype, using Cox proportional hazards models. Immune markers were centered and scaled to have mean 0 and variance 1, and stage IV patients were excluded. Evaluations within a specific subtype adjusted for stage, and overall evaluations adjusted for both stage and subtype. Forest plots showing hazard ratios and confidence intervals for each signature were made (see FIGS. 7A and 7B). All statistical analyses were conducted using R 3.2.0 software (http://www.R-project.org).

Results

Figure 18:
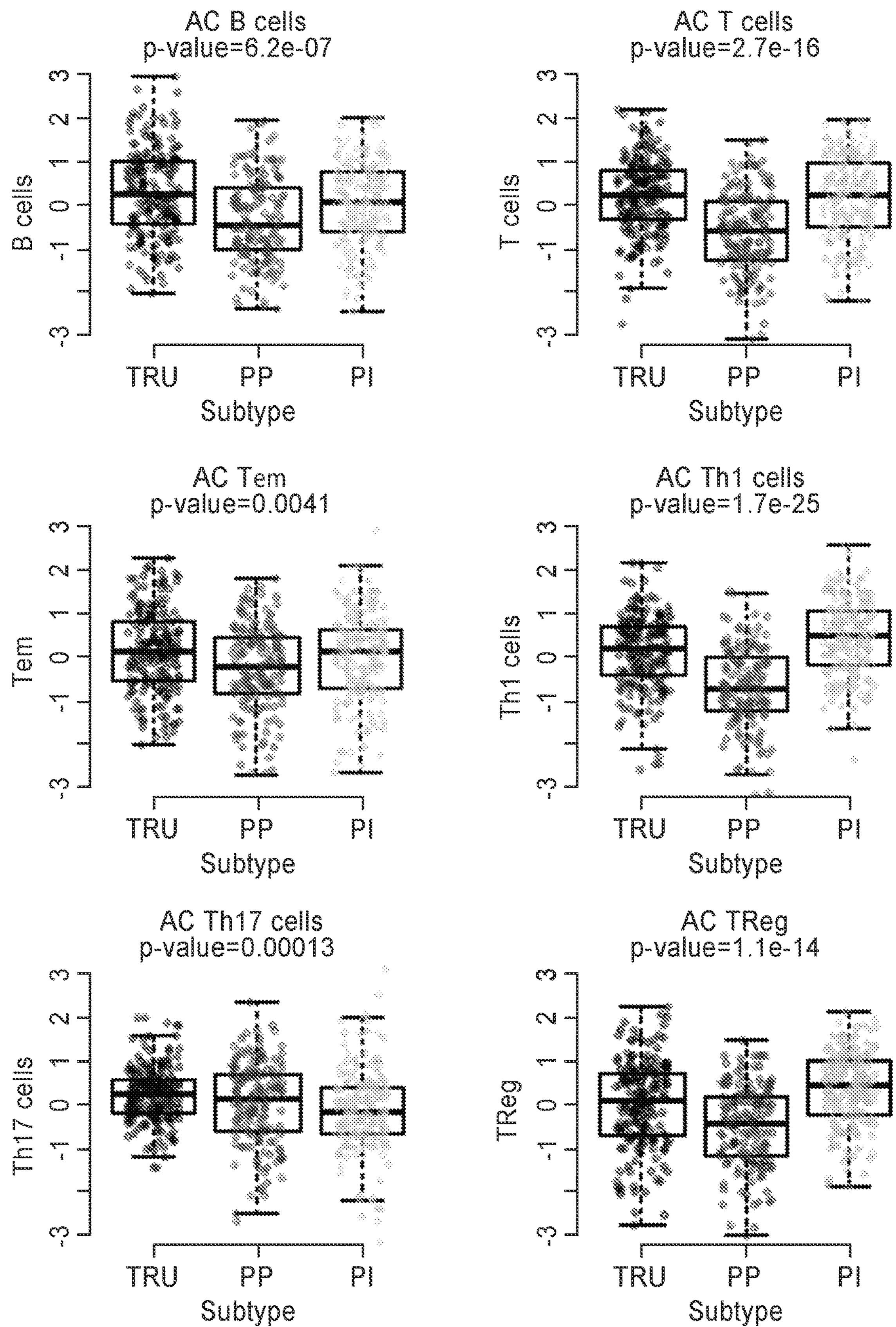
FIG. 18 illustrates box plots of all the immune cells and immunomarkers (i.e., IFN genes, MHCII genes and individual immunomarkers PDL1, PDL2, PDCD1 and CTLA4) by AD. TRU=Terminal Respiratory Unit, PP=Proximal Proliferative, PI=Proximal Inflammatory. AC=adenocarcinoma.
Figure 18:
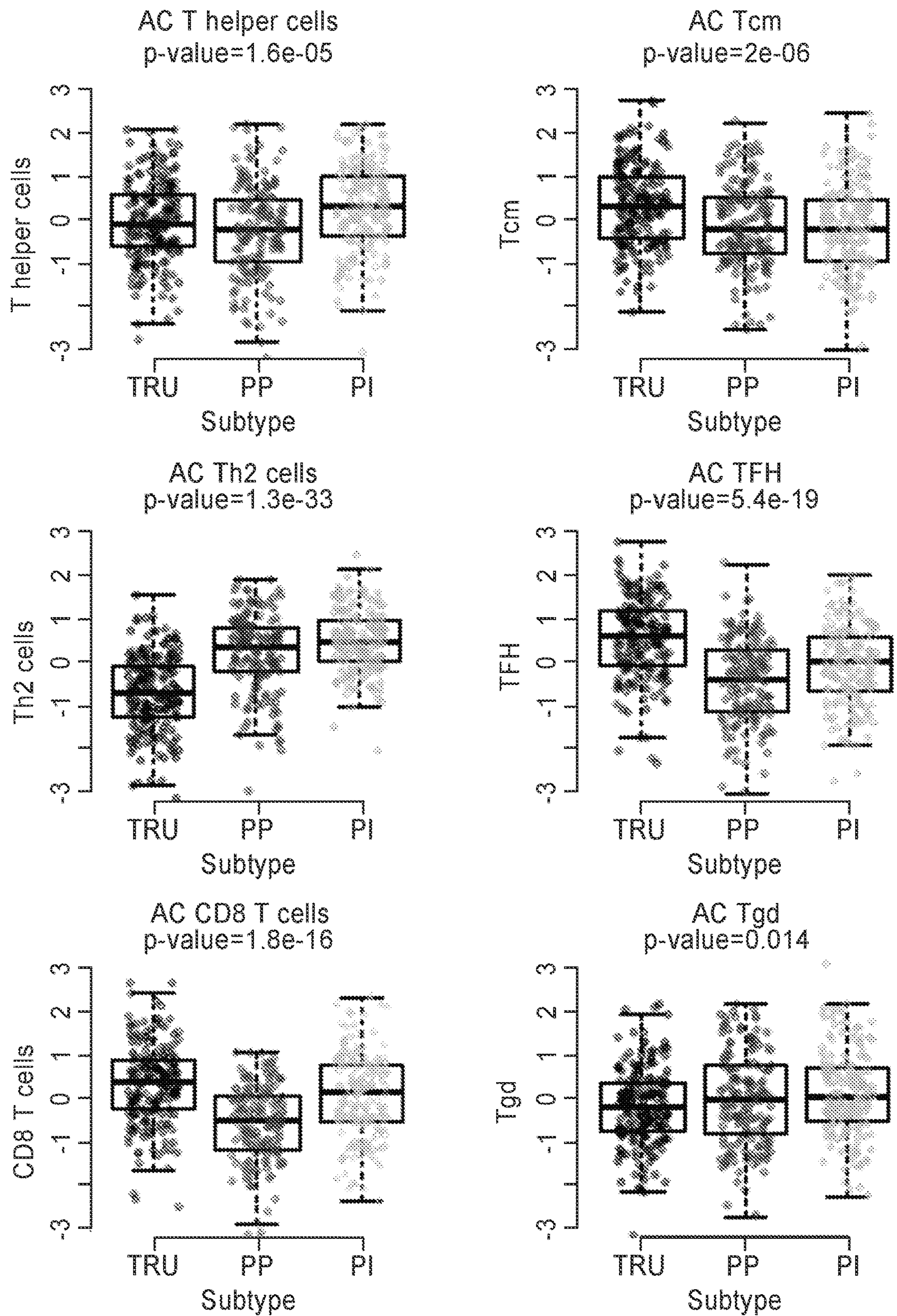
Figure 18:
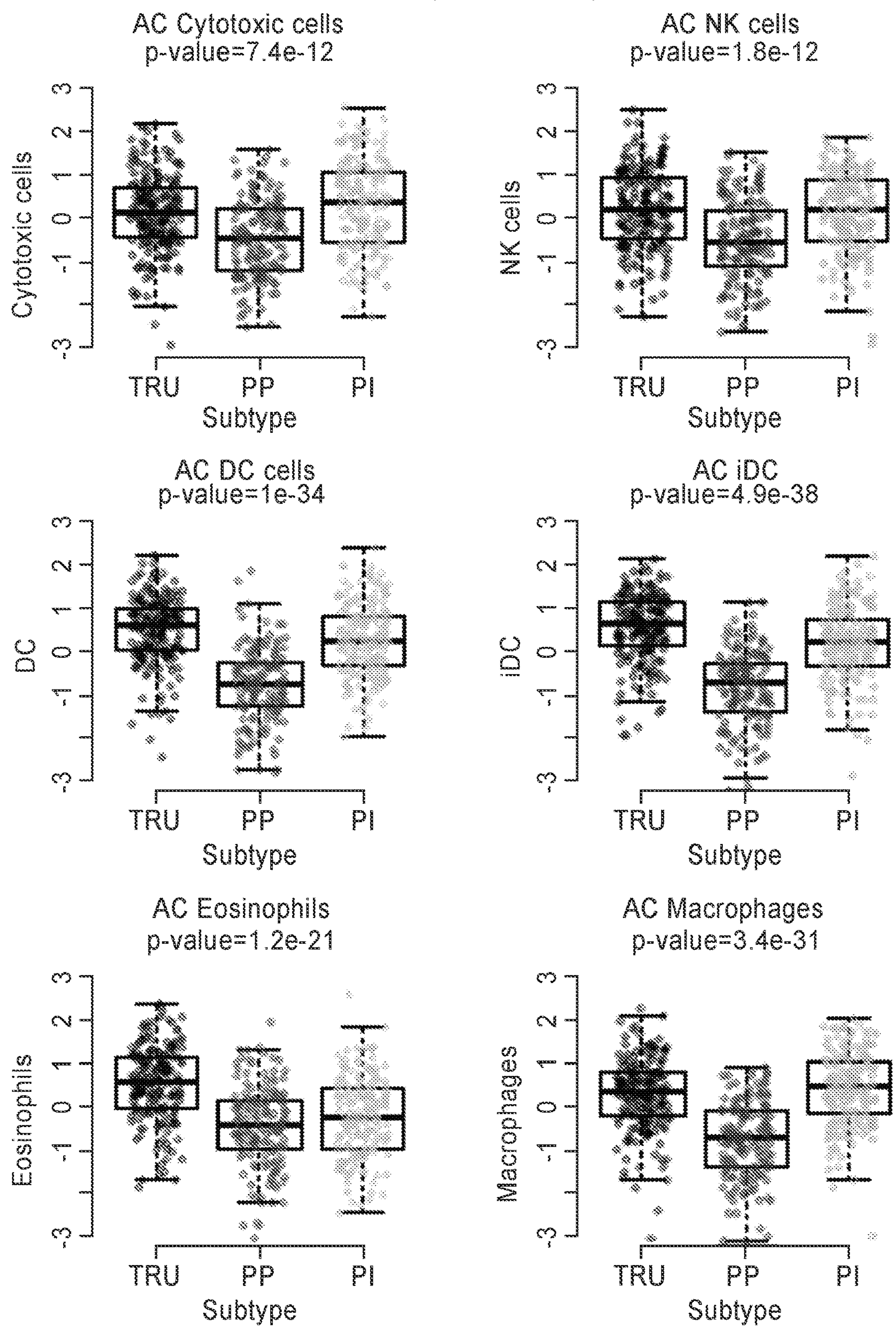
Figure 18:
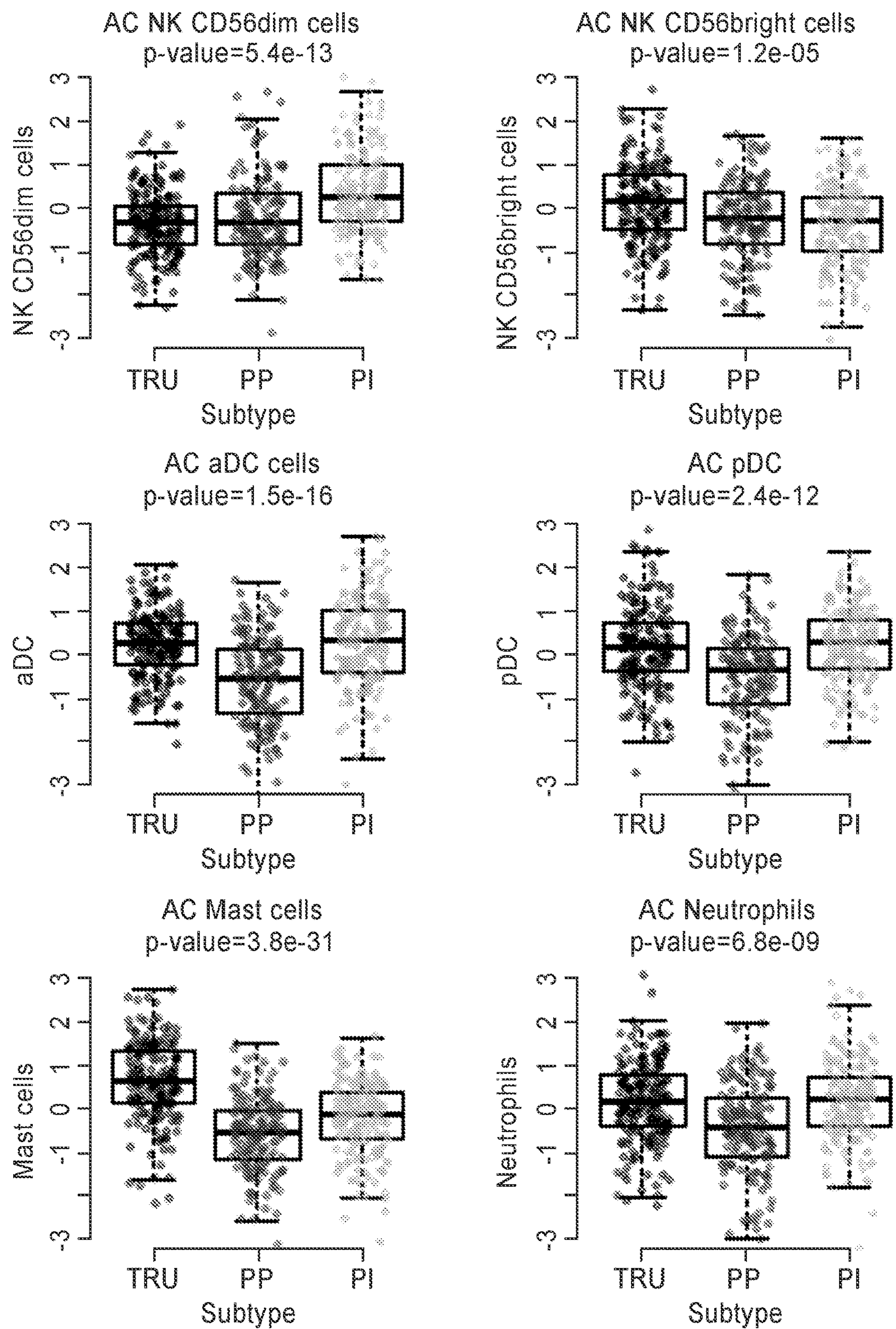
Figure 18:
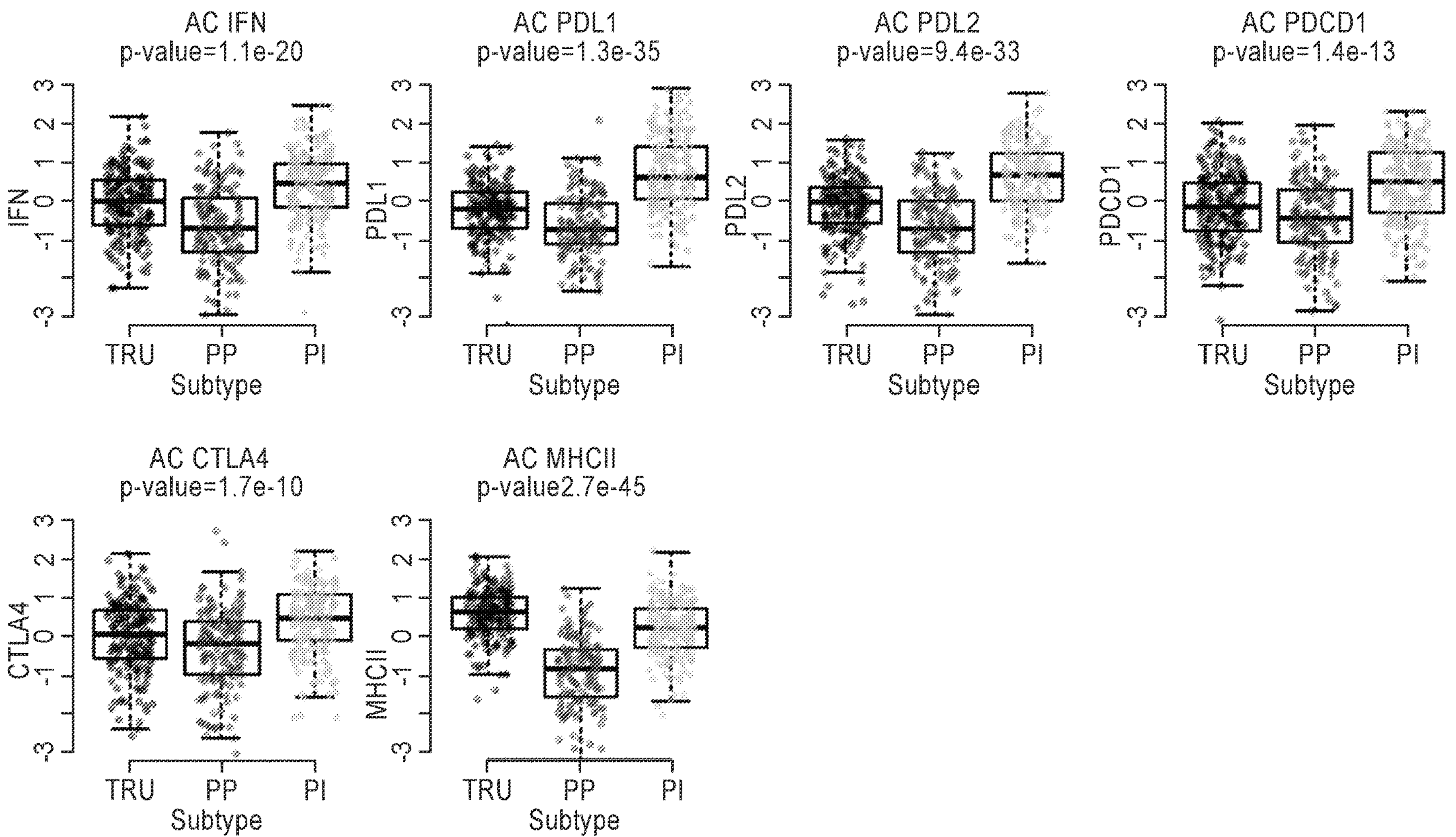

Heatmap analysis and unsupervised hierarchical clustering of immune cell gene signatures provided separation of intrinsic subtypes of AD (see FIGS. 3 and 4). Examination of Immune cell gene signatures (both AIC and IIC) as well as individual immune gene markers revealed clear differences among the AD subtypes (see FIG. 3). In AD, immune expression was consistently lower in the PP subtype for most cell types examined. Expression was similar in TRU and PI for most T cells but could be differentiated between TRU and PI by greater expression of some innate immune cells (dendritic cells, NK CD56bright, mast cells, eosinophils) and several adaptive immune cells (Bcells, TFH, Tcm, Th17, CD8 Tcells) in the TRU subtype, while the PI subtype showed higher expression of Th1 and Th2, Treg, cytotoxic Tcells and NKCD56dim cells (box plots of all the immune cells and markers by AD subtype can be found in FIG. 18). Immunotherapy targets, CTLA4 and CD274 (PD-L1), demonstrated consistently higher expression in the PI subtype across multiple datasets (box plot supplemental FIG. 18). In the PP tumors, both adaptive and innate immune cells expression as well as immunotherapy target expression was depressed relative to other AD. (FIG. 18).

Overall, immune activation was most prominent in the PI subtype of AD demonstrating activation of both innate as well as adaptive immune cells. In contrast, the PP subtype of AD demonstrated lower immune activation Using hierarchical clustering, correlation matrices revealed clustering of adaptive immune cells and innate immune cells (see FIG. 4). In AD, adaptive immune features such as T cells, cytotoxic cells, CD8 cells, Th1 cells, PDCD1, CTLA4, and Tregs had high pairwise correlations and similarly for innate immune cells, including iDC, DC, macrophages, neutrophils, mast cells, and eosinophils are correlated (FIG. 4).

Figure 6:
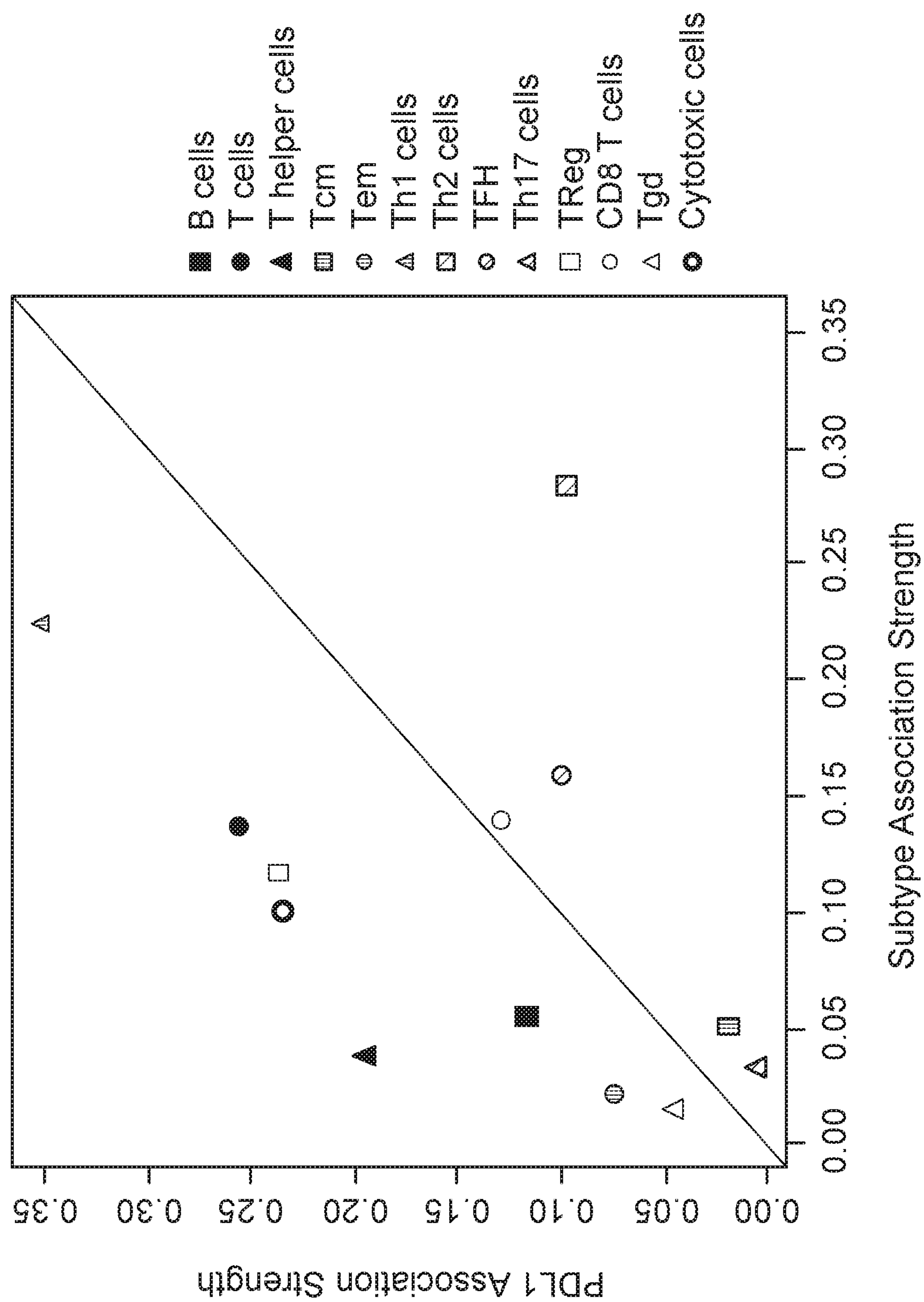
FIG. 6 illustrates association (adjusted R-squared) between CD274 (PD-L1) expression and adaptive immune cell (AIC) signatures in an Adenocarcinoma (AD) evaluation of the TCGA dataset. Association was consistently greater for subtypes than for PD-L1. Tcm=central memory T cells, Tem=Effector Memory T cells, Th1=Type 1 T helper cells, Th2=Type 2 T helper cells, TFH=T follicular helper cells, Th17=T helper 17 cells, Treg=Tregulatory cells, Tgd=Gamma Delta Tcells.

Strength of association of CD274 (PD-L1) expression with adaptive immune cell signatures, as compared to AD subtype was conducted. As shown in FIG. 6, for AD subtypes, association strengths (adjusted R squared) were mixed showing CD274 association greater for some cells (Bcells, Tcells, Th1, Treg, cytotoxic cells, Thelper, Tem, Tgd) while AD subtype association greater for others (TFH, Th2, CD8, Th17, and Tcm).

Figure 5:
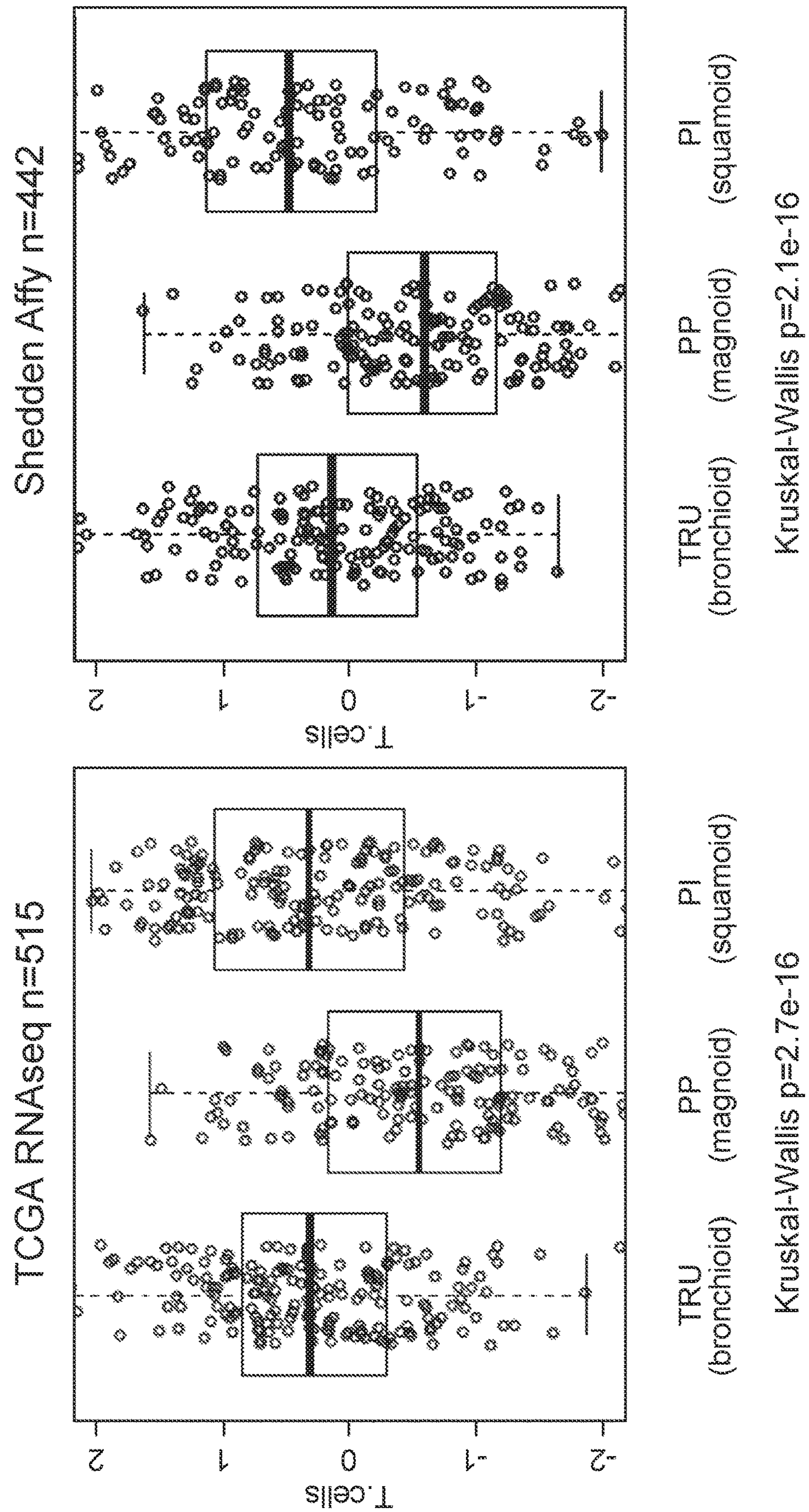
FIG. 5 illustrates reproducibility of T cell signature gene expression subtype patterns across multiple AD datasets as described in Example 1. TRU=Terminal Respiratory Unit, PP=Proximal Proliferative, PI=Proximal Inflammatory. RNAseq (Illumina, San Diego, Calif.) and microarrays from both Affymetrix (Santa Clara, Calif.) and Agilent (Santa Clara, Calif.).
Figure 5:
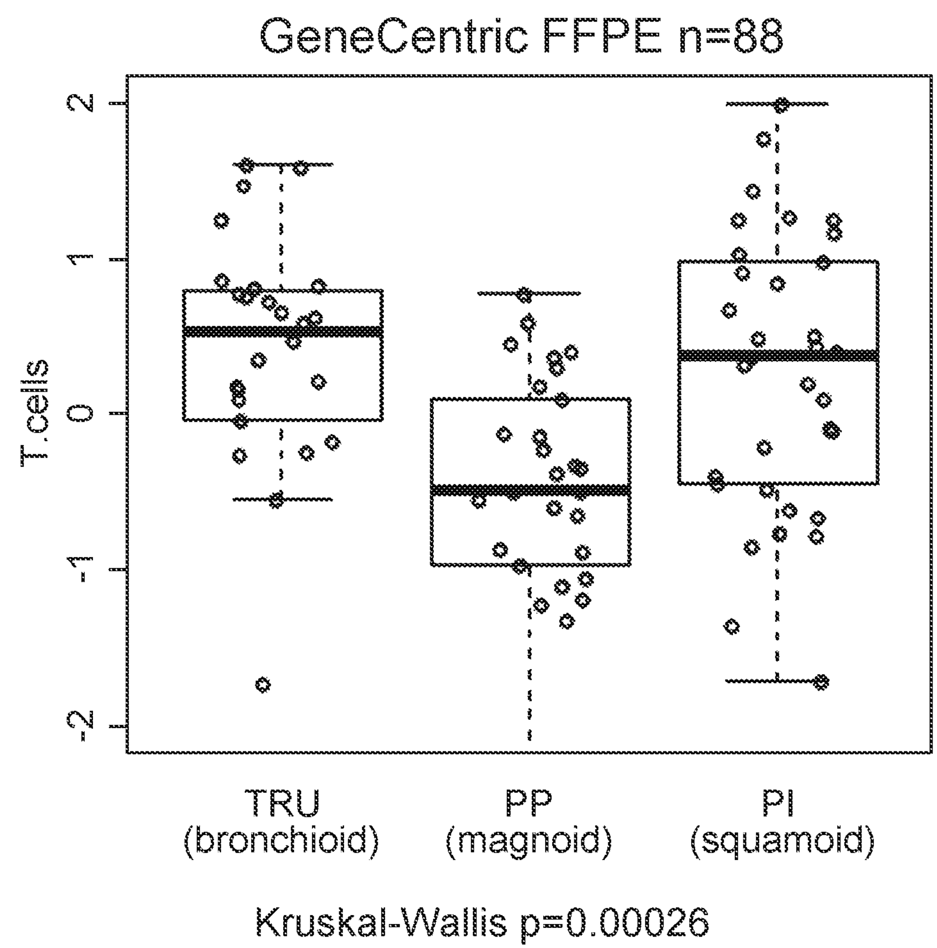

Immune cell signatures were primarily evaluated in the TCGA datasets, however AD subtype immune differences, as measured by the immune cell signatures, were found to be very reproducible across multiple datasets (see FIG. 5). T cell immune cell signature expression subtype differences in AD subtypes were remarkably reproducible across a variety of gene expression datasets derived from both frozen and FFPE samples and involving a variety of gene expression platforms including RNAseq (Illumina, San Diego, Calif.) and microarrays from both Affymetrix (Santa Clara, Calif.) and Agilent (Santa Clara, Calif.). Overall, immune cell signature gene expression patterns were consistent across multiple AD (see FIG. 5) datasets.

Non-silent mutation burden in the TCGA AD data differed by subtype with PI showing the highest burden and TRU the lowest burden (FIG. 19). The PI subtype, which is enriched for TP53 mutations, was associated with elevated immune cell expression, however, TRU had the lowest mutation burden despite having relatively high immune expression. Mutation burden was not strongly correlated with Tcell immune cell expression in AD datasets (Spearman correlation=−0.07 in AD).

Several other genomic features such as loss of STK11 in AD (Cao [7], Shabath [8], Koyama [9]) have been suggested as possible contributors to reduced immune response in NSCLC. STK11 inactivation was enriched in the low immune response adenocarcinoma PP subtype. STK11 inactivation in AD were associated with lower immune cell expression, however after adjustment for subtype using linear regression, STK11 was not a significant predictor (STK11 in AD p=0.0007 to p=0.43 following adjustment for subtype).

The association of immune cell expression in AD lung cancer with MHC class II genes was investigated using a published 13 gene MHC class II signature (Forero [6]). MHC class II gene expression was strongly correlated with several immune cells in AD including T-cell expression (Spearman correlation=0.66 in AD), B-cell expression (Spearman correlation=0.5 in AD) and DC expression (Spearman correlation=0.69 in AD). WIC class II gene expression was significantly higher in tumor adjacent normal lung tissue as compared with tumor and was differentially expressed across tumor subtypes (FIG. 19). In a linear model of the MHC class II signature as a predictor of T-cell immune cell expression, MHC class II remained significant following adjustment for AD subtype (p<1E-50 for MHC II).

Figure 7A:
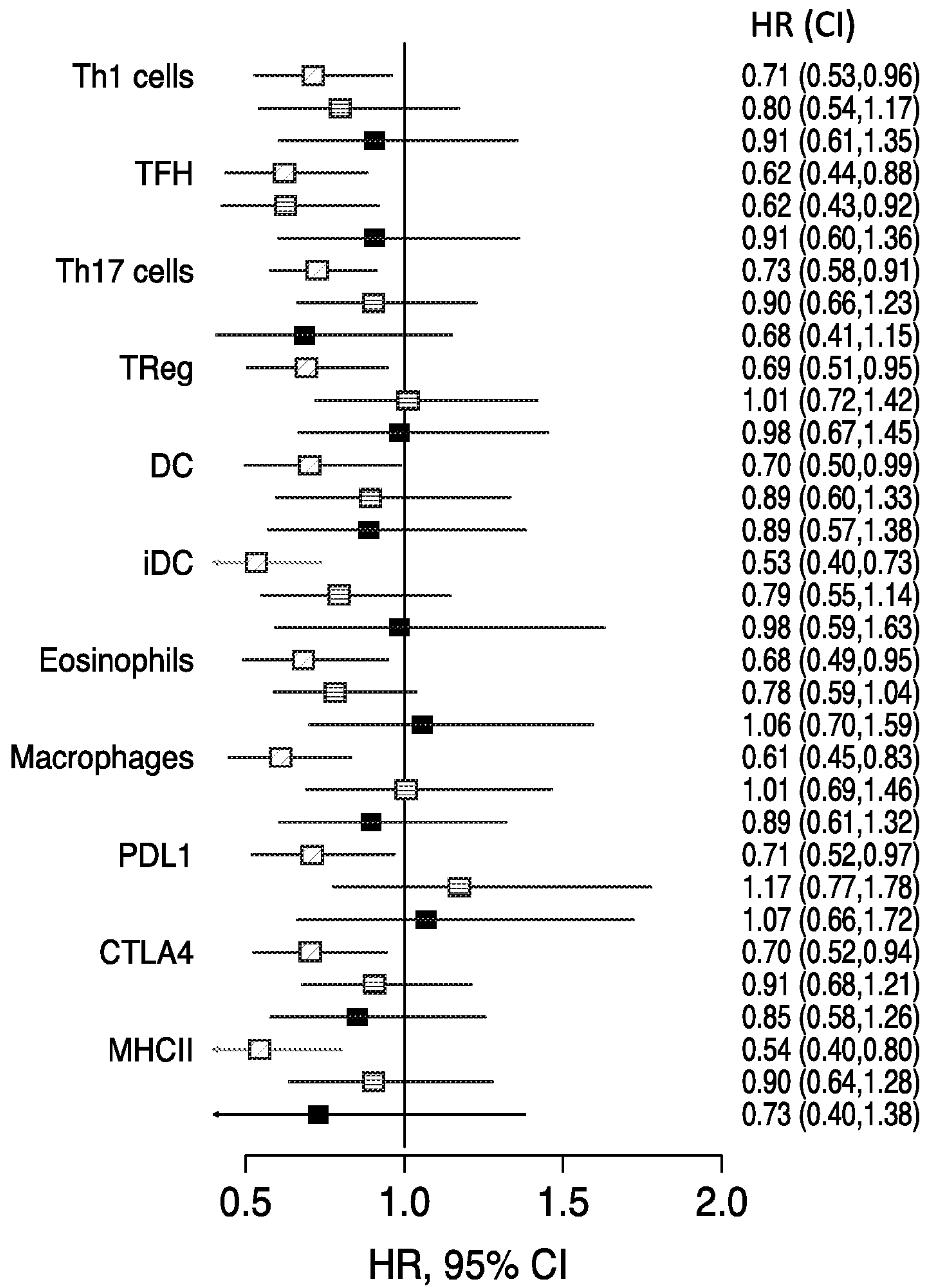
FIGS. 7A-7B illustrate signature-survival associations overall and by subtype as described in Example 1. Hazard Ratios (HR) and confidence intervals (CI) calculated from stratified cox models correspond to a unit increase in the normalized immune marker and were adjusted for pathological stage. Subtype specific HR's were adjusted for stage (overall adjusted by stage and subtype) and only immune features with significant associations (nominal $p<0.05$) for at least one subtype are shown. AD=Adenocarcinoma, TRU=Terminal Respiratory Unit, PP=Proximal Proliferative, PI=Proximal Inflammatory, MHC II=Major Histocompatibility Class II gene signature, Th1=Type 1 T helper cells, Th2=Type 2 T helper cells, TFH=T follicular helper cells, Th17=T helper 17 cells, Treg=Tregulatory cells, DC=Dendritic cells, iDC=Immature Dendritic Cells.
Figure 7B:
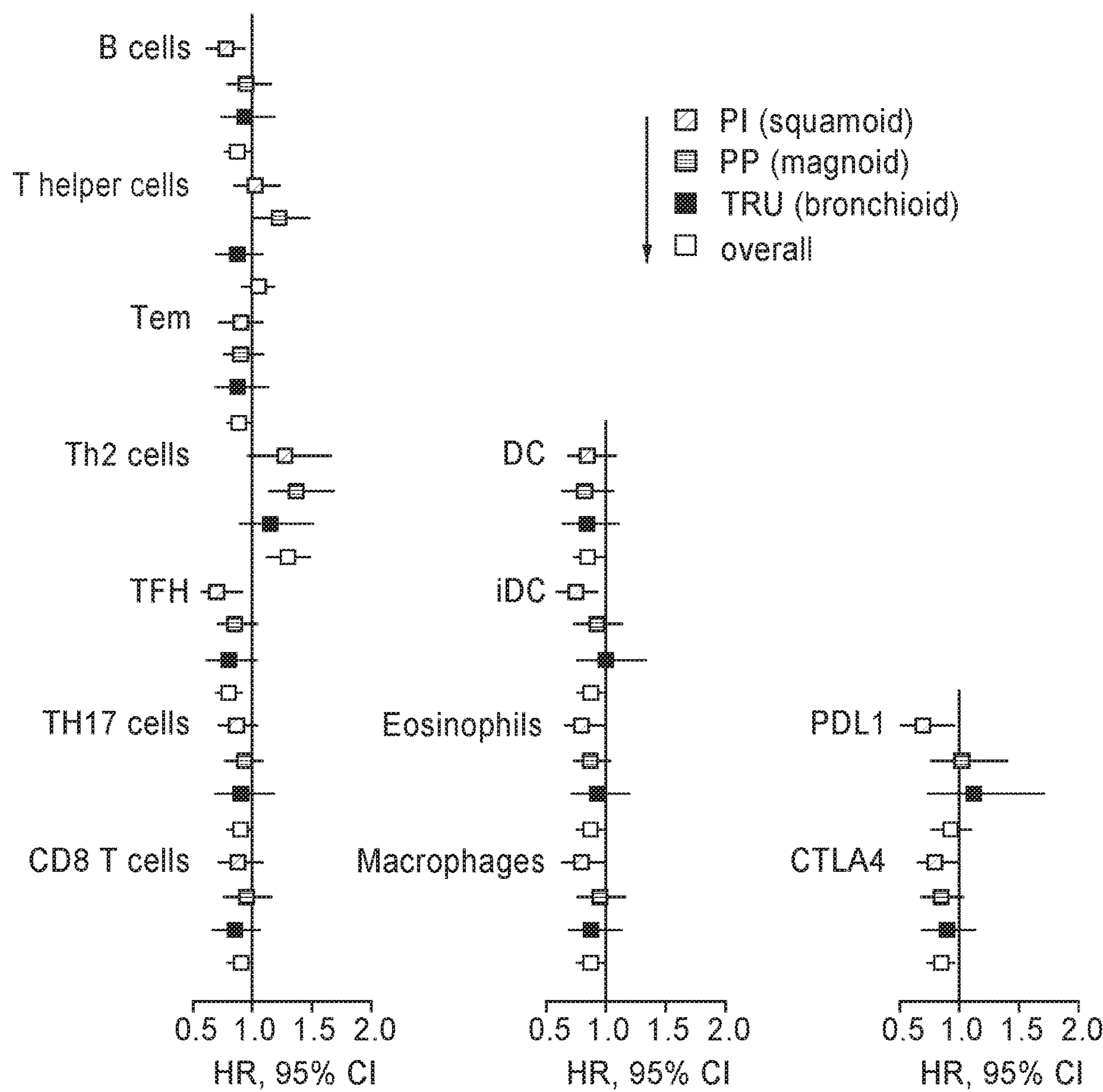

Using cox proportional hazard models, subtype specific hazard ratios (HRs) for one unit of increased expression were calculated. Subtype specific HRs were adjusted for pathologic stage and confidence intervals (CI) were calculated. Hazard ratios and confidence intervals for markers that were significant (nominal p-value<0.05) for at least one subtype are shown in FIGS. 7A-7B. The HR and CI for cell signatures or genes showing significant survival associations for one or more of the subtypes are shown in FIGS. 7A-7B. For AD subtypes, a unit increase in expression of many innate and adaptive immune cells, CD274 (PD-L1) MHC class II signature, and CTLA4 was significantly associated with improved survival in the PI subtype of AD but not in other subtypes (FIGS. 7A-7B). Overall, survival analysis of immune cell signatures suggested T Helper 17 and T Follicular Helper immune cells predicted improved survival in AD (p<0.001) (see FIG. 7A-7B).

Conclusion

Lung AD gene expression subtypes vary in their immune landscape. Intrinsic biologic subtypes of AD reveal key differences in immune cell activation, which were not always correlated with CD274 expression and demonstrated variable association with survival. AD PP subtype showed minimal immune infiltration (depressed immune cell expression) suggesting reduced response to immunoRX. The AD PI subtype showed immune feature expression associated with improved survival. Further, non-silent mutation burden was not correlated with immune cell expression across subtypes; however, MHC class II gene expression was highly correlated. Increased immune and MHC II gene expression was associated with improved survival in the TRU and PI subtype of AD.

INCORPORATION BY REFERENCE

The following references are incorporated by reference in their entireties for all purposes.

1.) Wilkerson M D, et al. PLoS One 2012; 7(5): e36530. PMID 22590557

2.) TCGA Lung AdenoC. Nature 2014; 511(7511): 543-550. PMID 25079552

3.) Bindea et al., Immunity 2013; 39(4): 782-95. PMID 24138885

4.) Shedden K. et al. Nat Med 2008; 14(8): 822-827. PMID 18641660

5.) Tomida S, et al. J Clin Oncol 2009; 27(17): 2793-99. PMID 19414676

6.) Forero A, Li Y, Dongquan C, et al. Expression of the MHC class II pathway in triple negative breast cancer tumor cells is associated with a good prognosis and infiltrating lymphocytes. Cancer Immunol Res 2016; 4(5): 390-399.

7.) Cao C, Gao R, Zhang M, er al. Role of LKB1-CRTC1 on glycosylated COX-2 and response yto COX-2 inhibition in lung cancer. J Natl Cancer Inst. 2015; 107(1):1-11.

8.) Shabath M B, Welsh E A, Fultp W J, et al. Differential association of STK11 and TP53 with KRAS mutation-associated gene expression, proliferation, and immune surveillance in lung adenocarcinoma. Oncogene. 2015:1-8.

9.) Koyama S, Akbey E A, Li Y, et al. STK11/LKB1 deficiency promotes neutrophil recruitment and proinflammatory cytokine production to suppress T-cell activity in the lung tumor microenvironment. *Cancer Res* 2016; 76(5): 999-1008.

Example 2—Development and Validation of the Lung Adenocarcinoma Subtyping Signature Background Several genomic studies have demonstrated three distinct intrinsic lung adenocarcinoma subtypes that can vary in their genomic profiles including gene expression, mutational spectrum, and copy number alterations [1-3]. The three biologic AD subtypes TRU, PP, and PI differ not only in their genomic features, but also demonstrate potentially important differences in clinical features [1-4]. The gene expression subtypes of AD can demonstrate significant differences in tumor differentiation, likelihood of distant recurrence, stage specific survival, underlying tumor drivers and inflammatory response [1-4] and may not be readily distinguishable by standard morphology-based techniques (microscopy & immunohistochemistry). Potential response differences to chemotherapy [2], Pemetrexed [5], and/or EGFR inhibitor therapies have also been suggested [2]. Enrichment for EGFR over-expression was demonstrated in the terminal respiratory unit (TRU) subtype [2, 3]. Greater frequency of KRAS mutations, in combination with LKB1/STK11 deletions, are more likely in the proximal proliferative (PP) subtype [2, 3]. TP53 mutations and immune gene activation are hallmarks of the proximal inflammatory (PI) subtype [2-4]. Preliminary data may demonstrate potential for enhanced response to EGFR inhibitors in the TRU subtype, enhanced response to chemotherapy in the PP subtype, enhanced Pemetrexed response in the TRU subtype, and potential response to immunotherapy in the PI subtype [2-6]. The emerging data suggests that AD classification by gene expression subtype may provide valuable information complementing drug target mutation testing and informing lung cancer patient management.

Objective

Lung Adenocarcinoma (AD) subtyping has been primarily restricted to a research protocol involving the extraction of RNA from Fresh Frozen lung tumors, followed by application of a nearest centroid predictor using quantitative gene expression of over 500 genes. Despite evidence of prognostic and predictive benefits from adenocarcinoma subtyping, the need for Fresh Frozen tissue, the requirement for gene expression of >500 genes in combination with complex bioinformatic analyses, has hindered the application of AD subtyping in drug development and/or the clinic. The goal of this study was to develop a robust and efficient gene signature (with fewer genes needed) for differentiating the three subtypes of adenocarcinoma (Terminal Respiratory Unit (TRU); formerly referred to as Bronchioid, Proximal Proliferative (PP); formerly referred to as Magnoid, and Proximal Inflammatory (PI); formerly referred to as Squamoid). The new efficient gene signature may serve to reliably subtype AD from fresh frozen or FFPE tumor samples, making it amenable for diagnostic applications and/or drug development using any of the available quantitative RNA platforms (qRT-PCR, RNAseq, Affymetrix or Agilent Arrays). Development of the 48 gene signature for differentiating the subtypes of adenocarcinoma was performed as described in the methods herein.

Methods

Using the 515 lung adenocarcinoma The Cancer Genome Atlas (TCGA) RNAseq dataset for training and the 506-gene classifier to define gold standard subtype, a 48-gene signature was developed that maintains low misclassification rates when applied to several independent test sets. Starting with the standard 506 classifier genes, the Classifying arrays to Nearest Centroid (CLaNC) [7] algorithm was used with modification to select an equal number of negatively and positively correlated genes for each subtype. The optimal number of genes (16 per subtype) to include in the signature was chosen based on 5-fold cross validation curves was performed using the TCGA lung adenocarcinoma dataset (see FIG. 8). Selection of prototype samples for training of the predictor is shown in FIG. 9, whereby to get the final list of 48 genes, the CLaNC was applied to the entire TCGA data set minus 20% of samples with the lowest gold standard subtype prediction strength, removing an equal number from each subtype (FIG. 9). The 48-gene signature was then tested in several Fresh Frozen publicly available array and RNAseq datasets [2, 8, 9] and results were compared with the gold standard subtype calls as defined by the previously published 506-gene signature [2]. Final validation of the 48-gene signature (Table 1) was then performed in a newly collected RNAseq dataset of archived FFPE adenocarcinoma samples to assure comparable performance in FFPE samples.

In order to validate the consistent performance of the selected 48 gene signature, the newly collected FFPE samples were lung adenocarcinoma (AD) residual archived samples (primarily surgical samples) that had been collected under an IRB approved protocol at the University of North Carolina in Chapel Hill, N.C. The samples were reviewed by a pathologist for tumor cells and three 10 μm tissue sections were macrodissected prior to extraction to enrich for tumor cells. RNA was quantitated and 100 ng was input per sample. Sequencing libraries were constructed using Illumina RNA-Access kits that enrich for the transcriptome. Sequencing libraries were under quality control by using a BA analyzer and quantified using qPCR. Sequence data was generated on an Illumina HiSeq platform (50 bp PE, 20-30 million reads) and was under quality control by using fastQC. Sequence results were aligned against hg19 reference sequence using STAR aligner and the transcriptome was built using Cufflinks [10]. Cuffcompare was used to annotate the transcriptome and counts of various expressed genes were calculated. RSEM expression count estimates were upper quartile normalized and log 2 transformed following the approach used in the Cancer Genome Atlas lung adenocarcinoma analysis [3, 11].

Results

Figure 10:
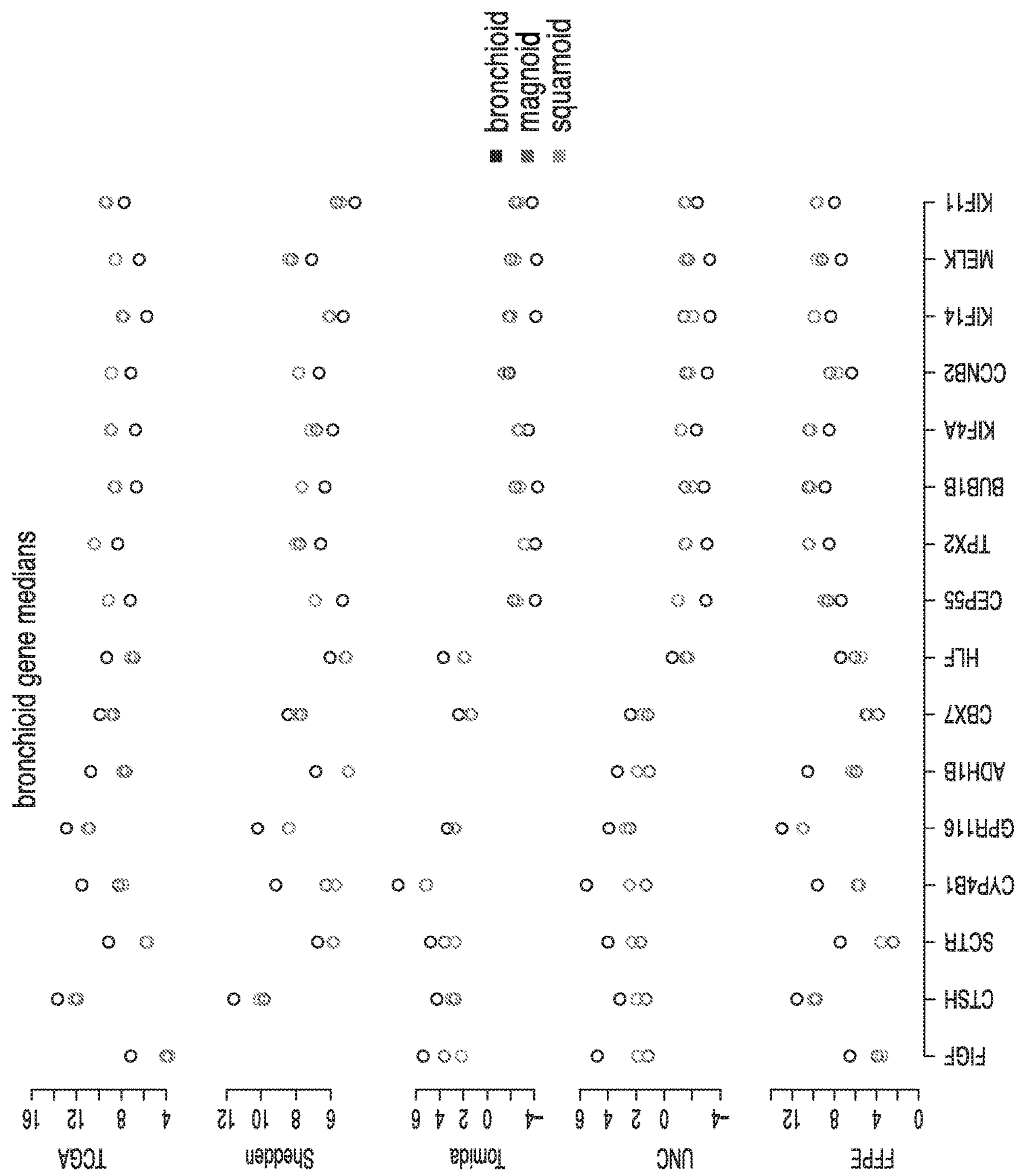
FIG. 10 illustrates the median gene expression of a subset of 16 genes from the 48 gene classifier selected for differentiating bronchioid samples (Terminal Respiratory Unit).
Figure 11:
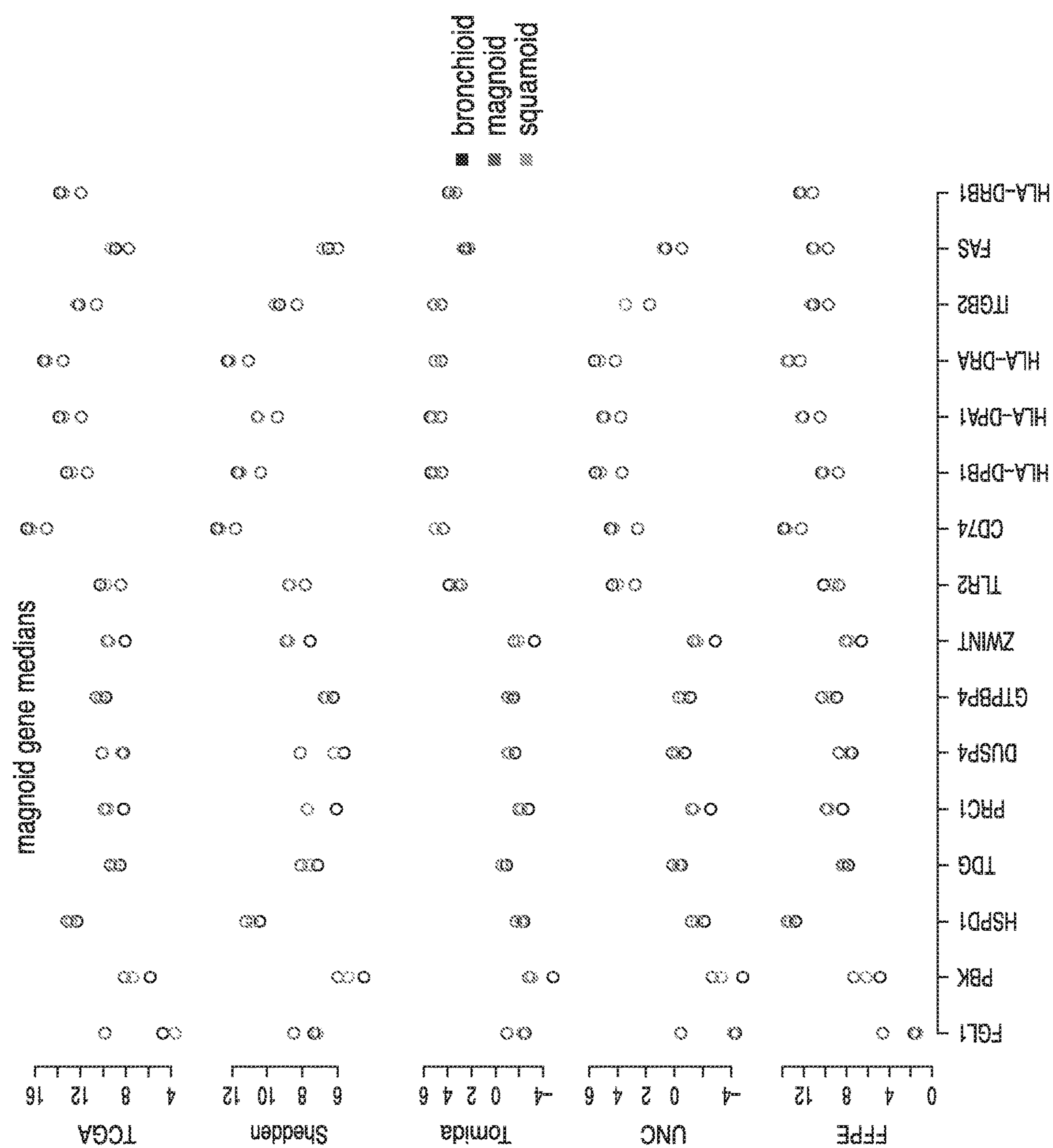
FIG. 11 illustrates the median gene expression of a subset of 16 genes from the 48 gene classifier selected for differentiating magnoid samples (Proximal Proliferative).
Figure 12:
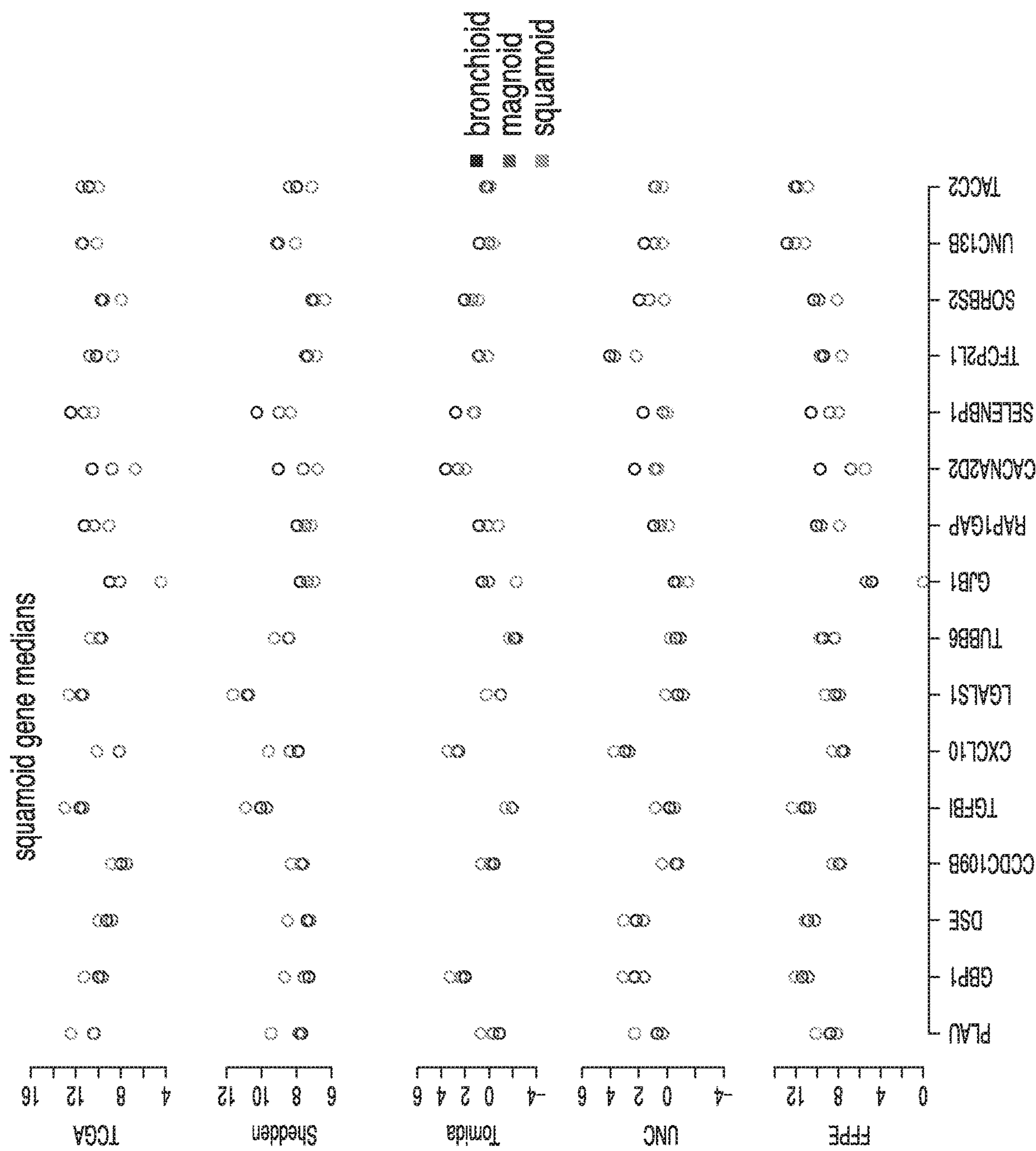
FIG. 12 illustrates the median gene expression of a subset of 16 genes from the 48 gene classifier selected for differentiating squamoid samples (Proximal Inflammatory).

The 48 gene signature gene list developed in this study is shown in Table 2, while the T statistics for the 48 gene signature gene list for each AD subtype can be found in Table 1. The median gene expression of the 16 genes selected for each AD subtype (bronchioid, magnoid, squamoid) is shown in FIGS. 10, 11, and 12, respectively. Agreement of subtype calls using the 48 gene signature with the published 506 gene signature subtype call in several different test datasets is shown in FIG. 13. The newly developed 48 gene signature demonstrated agreement of 0.84 in the newly collected FFPE dataset and a range of 0.79-0.92 in the other 3 Fresh Frozen test datasets. Below is a summary of the test datasets, the types of the RNA platforms, and the numbers of the adenocarcinoma samples used.

| Reference | RNA Platform | Adenocarcinoma Samples |
|---|---|---|
| TCGA Adenocarcinoma | RNAseq | 515 |
| Shedden et al. | Affymetrix Arrays | 442 |
| Tomida et al. | Agilent Arrays | 117 |
| Newly collected UNC FFPE samples | RNAseq | 88 |

Conclusion

Development and validation of an efficient 48 gene signature for AD subtyping was described. The resulting 48 gene signature maintains low misclassification rates when applied to several independent test sets. Thus, the new signature reliably subtypes AD from fresh frozen or FFPE tumor samples and can perform reliably using gene expression data generated from a variety of platforms including RNAseq and Arrays.

INCORPORATION BY REFERENCE

The following references are incorporated by reference in their entireties for all purposes.

1.) Hayes D N, Monti S, Parmigiani G, et al. Gene expression profiling reveals reproducible human lung adenocarcinoma subtypes in multiple independent patient cohorts. J Clin Oncol 2006. 24(31): 5079-5090.

2.) Wilkerson M, Yin X, Walter V, et al. Differential pathogenesis of lung adenocarcinoma subtypes involving sequence mutations, copy number, chromosomal instability, and methylation. PLoS ONE. 2012; 7(5) e36530. Doi:10.1371/journal.pone.0036530.

3.) Cancer Genome Atlas Research Network. Comprehensive molecular profiling of lung adenocarcinoma. Nature 511.7511 (2014): 543-550.

4.) Ringner M, Jonsson G, Staaf J. Prognostic and Chemotherapy Predictive Value of Gene-Expression Phenotypes in Primary Lung Adenocarcinoma. Clin Cancer Research 2016; 22(1): 218-29.

5.) Fennell D A, Myrand S P, Nguyen T S, Ferry D, Kerr K M, et al. Association between Gene Expression Profile and Clinical Outcome of Pemetrexed-Based Treatment in Patients with Advanced Non-Small Cell Lung Cancer: Exploratory Results from a Phase II study. PLOS one 2014; September 14 9(9): e107455.

6.) Skoulidis F, Byers L A, Diao L, Papadimitrakopoulou V A, Tong P, et al. Co-occuring genomic alterations define major subsets of KRAS-mutant lung adenocarcinoma with distinct biology, immune profiles, and therapeutic vulnerabilities. Cancer Discov 2015; Aug. 5(8): 860-77.

7.) Dabney A R. ClaNC: Point-and-click software for classifying microarrays to nearest centroids. Bioinformatics. 2006; 22: 122-123. doi:10.1093/bioinformatics/bti756

8.) Shedden K, Taylor JMG, Enkemann S A, et al. Gene expression-based survival prediction in lung adenocarcinoma: a multi-site, blinded validation study: director's challenge consortium for the molecular classification of lung adenocarcinoma. Nat Med 2008. 14(8): 822-827. doi: 10.1038/nm.1790.

9.) Tomida S, Takeuchi T, Shimada Y, Arima C, Maatsuo K, et al. Relapse-Related Molecular Signature Identifies Patients With Dismal Prognosis. J Clin Oncol 2009; 27(17): 2793-99.

10.) Trapnell C, Williams B A, Pertea Mortazavi A, Kwan van Baren M J, et al. Transcript assembly and quantification by RNA-Seq reveals unannotated transcripts and isoform switching during cell differentiation. Nature biotechnology 2010; 28(5):511-5.

11.) Li B, and Dewey C N. RSEM: accurate transcript quantification from RNA-Seq data with or without a reference genome. BMC Bioinformatics 2011, 12:323 doi:10.1186/1471-2105-12-323

Example 3—Immune Cell Activation Differences Among Lung Adenocarcinoma Intrinsic Subtypes as Determined Using Lung Adenocarcinoma Subtyping 48 Gene Signature from Example 2

Methods

Using previously published Bindea et al. (3) immune cell gene signatures (24 in total) and the Lung AD subtyping gene signature described in Example 2 for subtyping AD, several publically available lung AD datasets (1-2, 4-5; see FIG. 2), were examined for immune cell features in relation to AD subtypes as determined using the lung AD gene signature described in Example 2. Gene expression signatures of both Innate Immune Cells (IIC) and Adaptive Immune Cells (AIC), a 13 gene IFN signature (IFN), as well as single gene immune biomarkers (CTLA4, PDCD1, and CD274 (PD-L1), PDCDLG2 (PD-L2)) were examined in the 3 AD subtypes (TRU, PP, and PI). Immune cell signature associations with tumor subtype and with CD274 expression were evaluated using linear regression. Hierarchical clustering of immune signatures and pairwise signature correlations were also analyzed. Survival signature associations of Stages I-III samples were evaluated with stratified cox proportional hazard models allowing for different baseline hazards in each dataset.

Results

Figure 14:
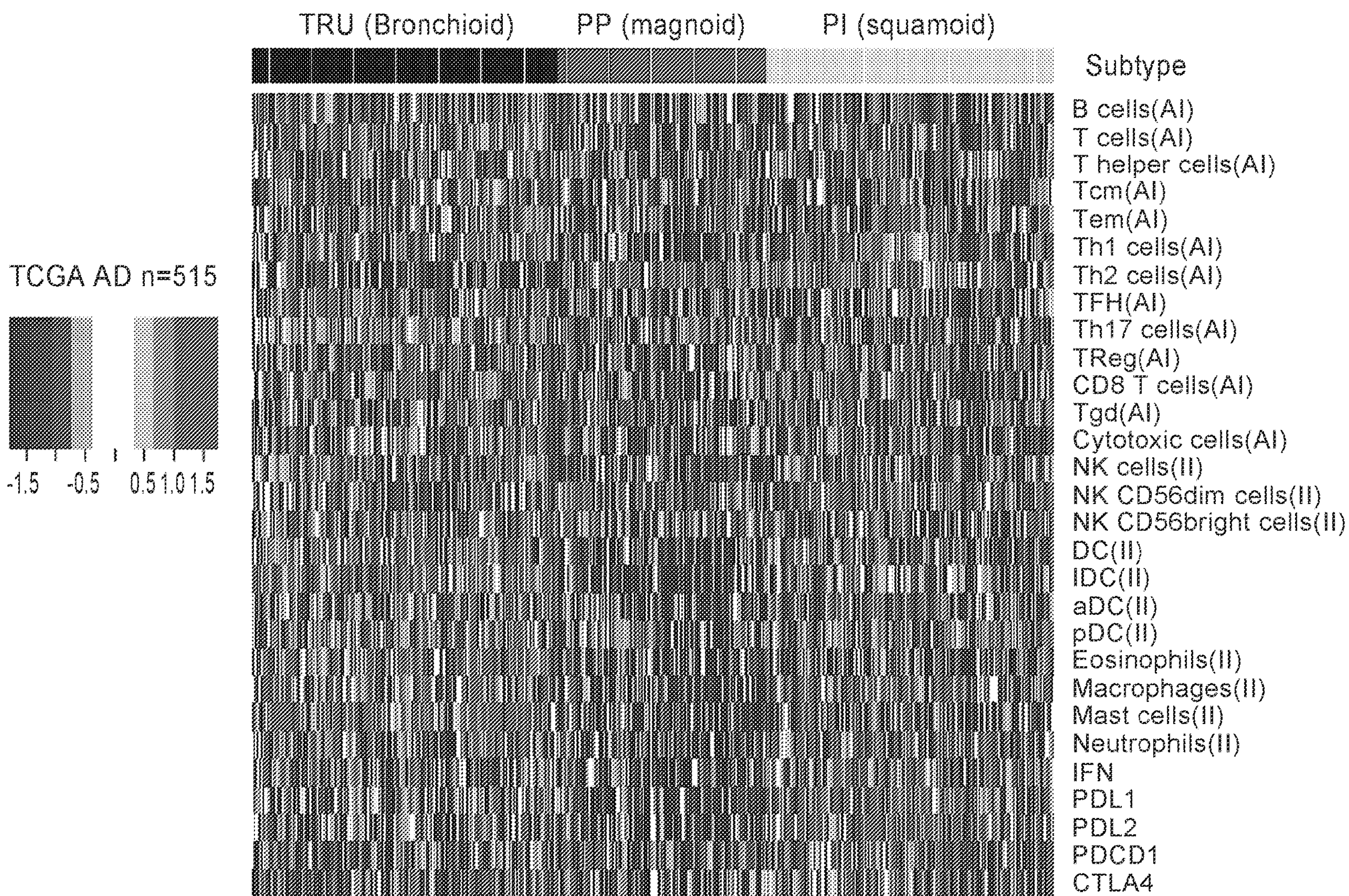
FIG. 14 illustrates a heatmap of immune cell signatures (i.e., Bindea et al reference from Example 3) and other immune markers in the Cancer Genome Atlas (TCGA) Lung AD datasets.
Figure 15:
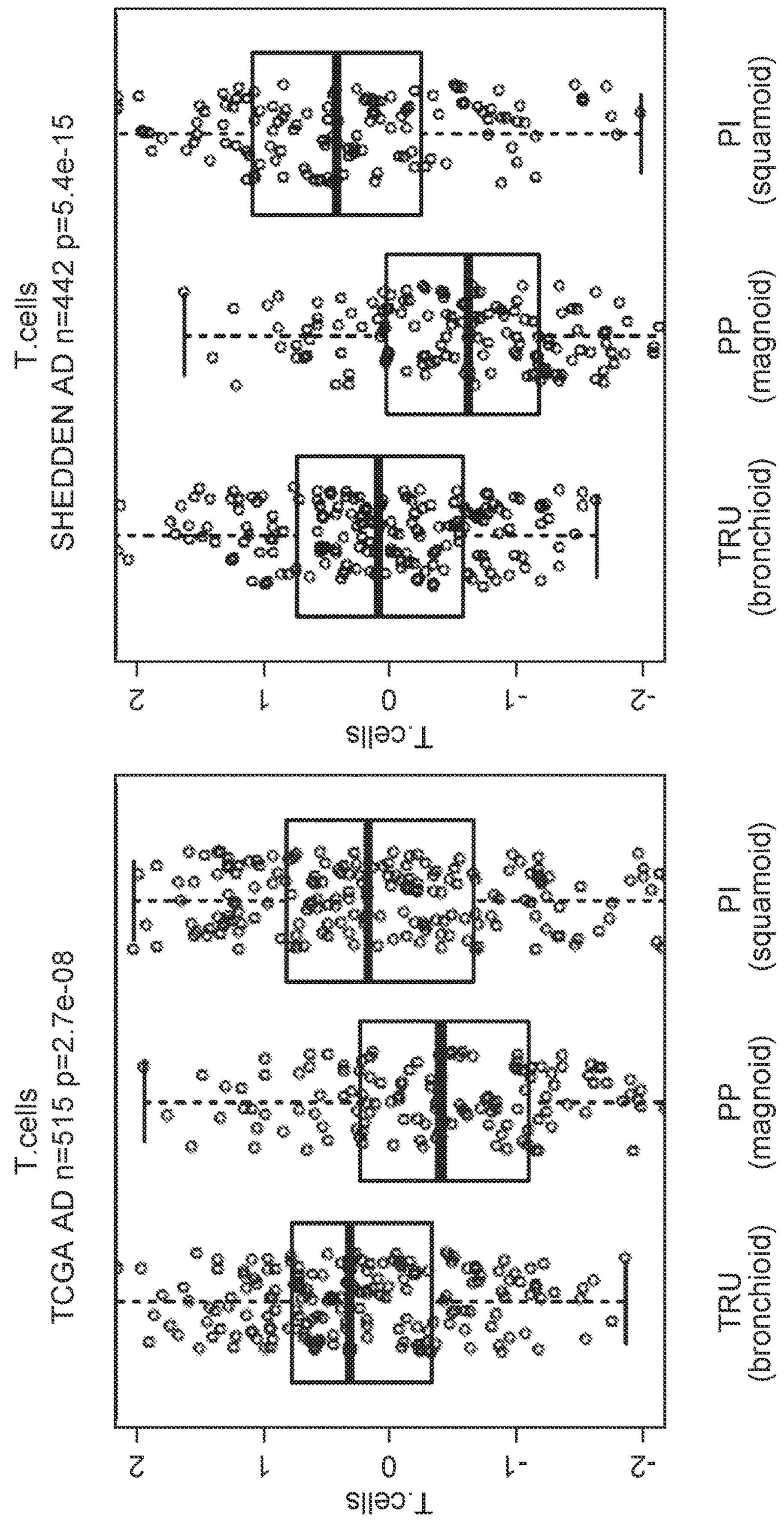
FIG. 15 illustrates reproducibility of T cell signature gene expression subtype patterns across multiple AD datasets as described in Example 3.
Figure 15:
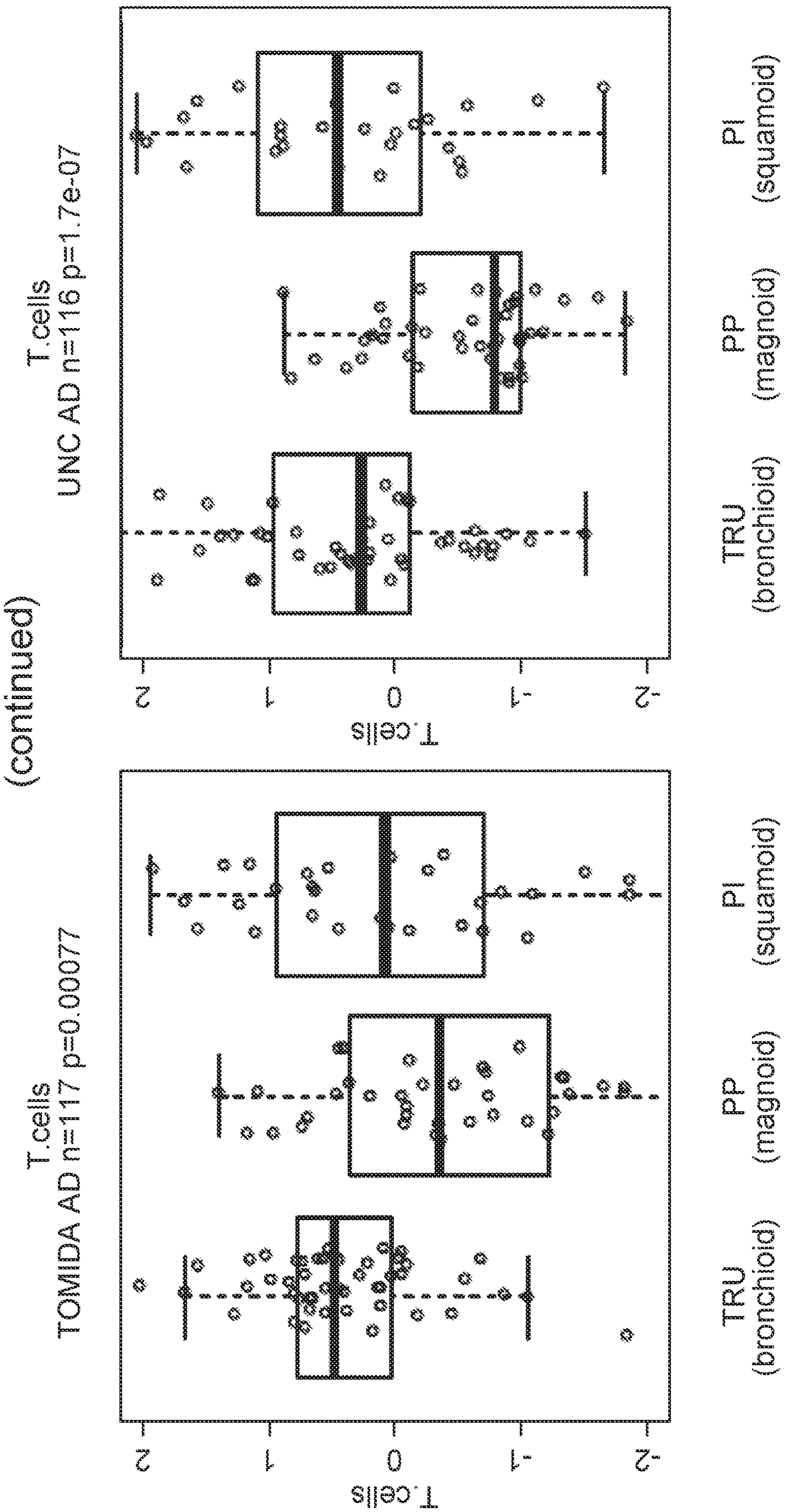
Figure 15:
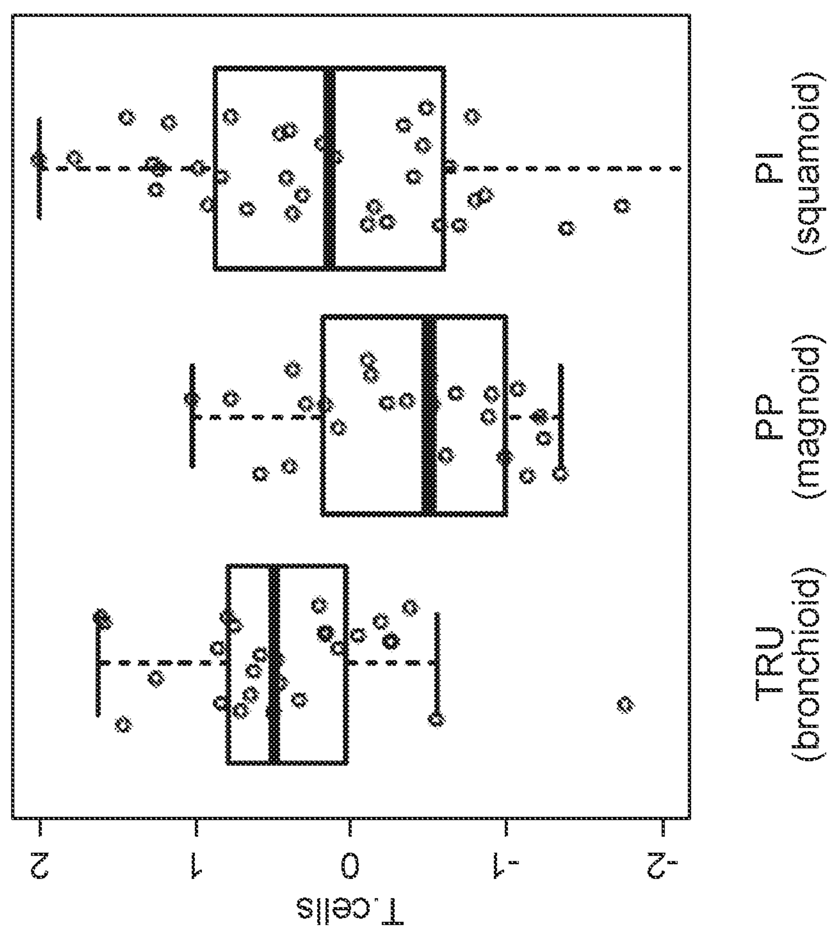
Figure 16:
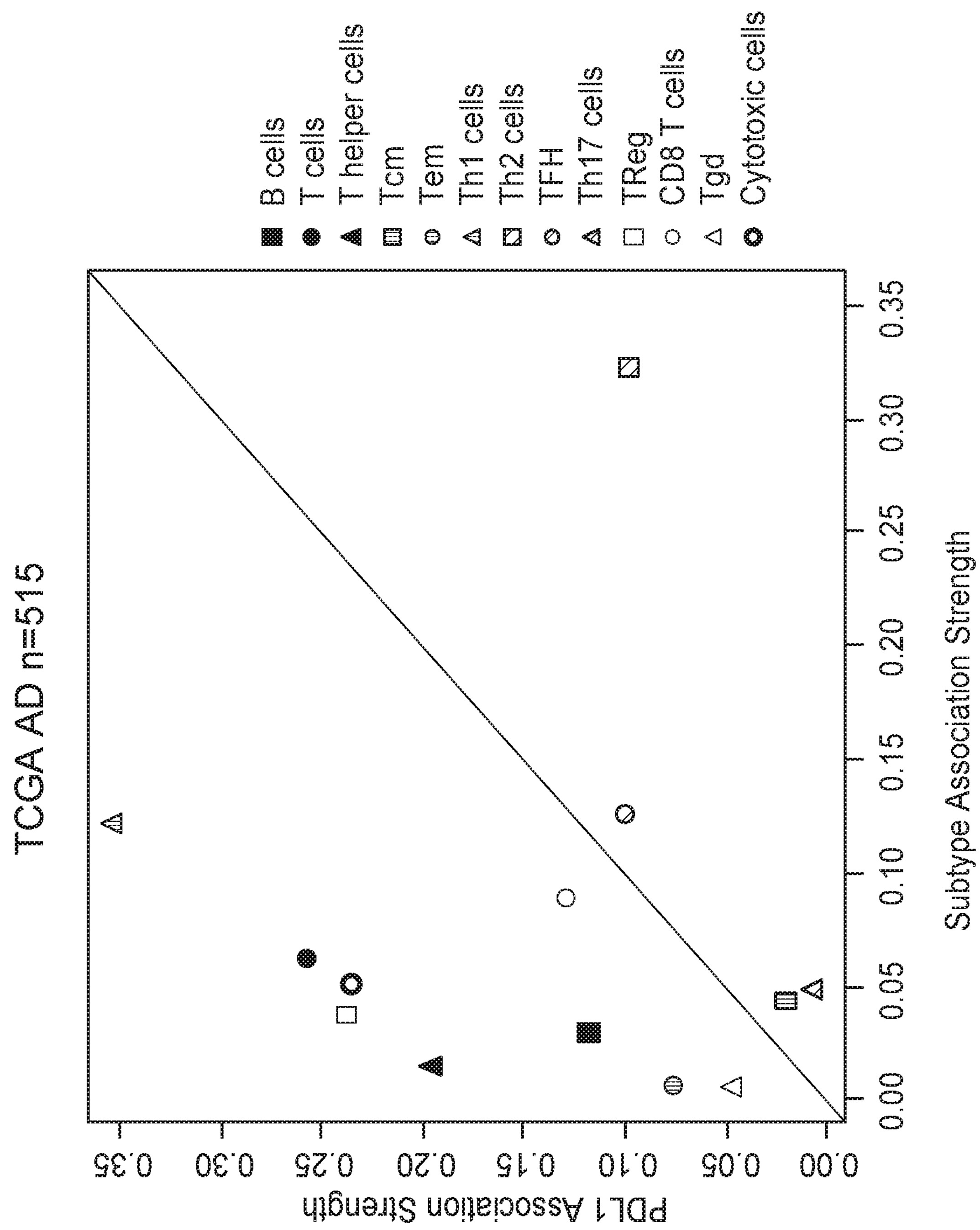
FIG. 16 illustrates an association (adjusted R-squared) between CD274 (PD-L1) expression and adaptive immune cell (AIC) signatures versus subtype and AIC signatures as described in Example 3. Tcm=central memory T cells, Tem=Effector Memory T cells, Th1=Type 1 T helper cells, Th2=Type 2 T helper cells, TFH=T follicular helper cells, Th17=T helper 17 cells, Treg=Tregulatory cells, Tgd=Gamma Delta Tells.

Using the TCGA AD dataset and the 48 gene AD subtyping signature of Example 2, heatmap analysis and unsupervised hierarchical clustering of immune cell gene signatures provided separation of intrinsic subtypes of AD in a similar fashion as to what was observed in Example 1 (see FIG. 3 and FIG. 14). Further, immune cell signature gene expression patterns were consistent across multiple AD (see FIG. 15) datasets similar to that observed in Example 1 (see FIG. 5). Strength of association of CD274 (PD-L1) expression with adaptive immune cell signatures, as compared to AD subtype was conducted. As shown in FIG. 16 (like in FIG. 6 of Example 1), for AD subtypes, association strengths (adjusted R squared) were mixed showing CD274 association greater for some cells (Bcells, Tcells, Th1, Treg, cytotoxic cells, Thelper, Tem, Tgd), while AD subtype association greater for others (TFH, Th2, CD8, Th17, and Tcm). As in Example 1, immune activation was most prominent in the PI subtype of AD, while the PP subtype of AD demonstrated lower immune activation, and AD subtype and CD274 expression were similarly predictive of AIC expression (see FIG. 6 and FIG. 16).

Figure 17:
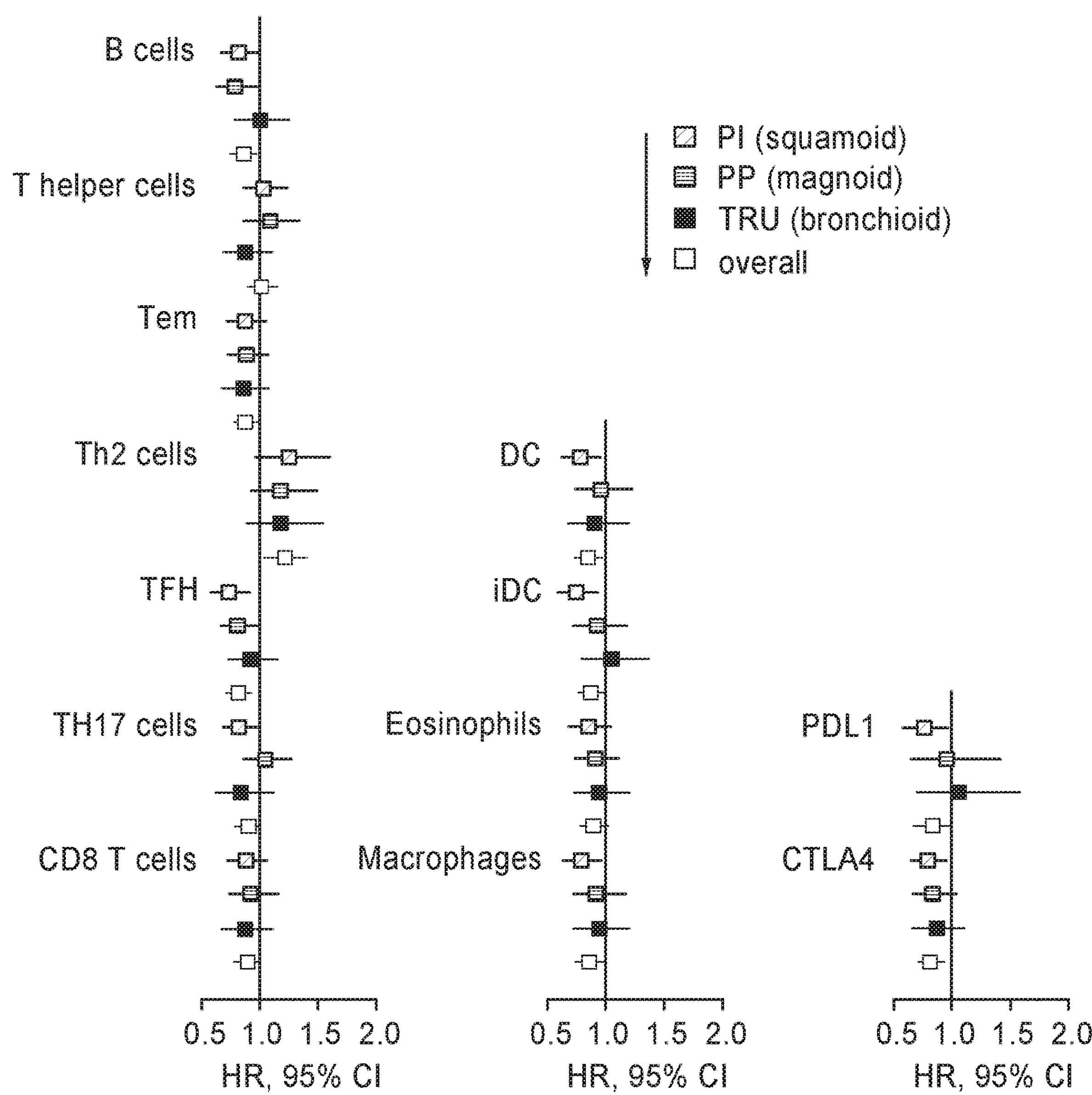
FIG. 17 illustrates for AD signature-survival associations overall and by subtype as described in Example 3. Hazard Ratios (HR) and confidence intervals calculated from stratified cox models. Subtype specific HR's were adjusted for stage (overall adjusted by stage and subtype) and only immune features with significant associations ($p<0.05$) are shown.

Using cox proportional hazard models, subtype specific hazard ratios for one unit of increased expression were calculated. Subtype specific HR's were adjusted for pathologic stage and confidence intervals were calculated. The HR and CI for cell signatures or genes showing significant survival associations for one or more of the subtypes are shown in FIG. 17. For AD subtypes, like in Example 1, a unit increase in expression of many innate and adaptive immune cells, CD274 (PD-L1) and CTLA4 was significantly associated with improved survival in the PI subtype of AD but not in other subtypes (see FIGS. 7A-7B and 17). Overall, like in Example 1, survival analysis of immune cell signatures suggested T Helper 17 and T Follicular Helper immune cells predicted improved survival in AD ($p<0.001$) (see FIGS. 7A-7B and 17).

Conclusion

The 48 gene signature for AD subtyping described in Example 2 shows similar results to the AD subtyping gene signature(s) used in Example 1 in terms of showing how Lung AD subtypes vary in their immune landscape. In agreement with the AD subtyping gene signatures of Example 1, the AD subtyping gene signature used in this example shows that Lung AD gene expression subtypes vary in their immune landscape. Intrinsic biologic subtypes of AD revealed key differences in immune cell activation, which were not always correlated with CD274 expression and demonstrated variable association with survival. AD PP subtype showed minimal immune infiltration suggesting reduced response to immunoRX. AD PI subtype showed immune feature expression associated with improved survival.

INCORPORATION BY REFERENCE

The following references are incorporated by reference in their entireties for all purposes.

1.) Wilkerson M D, et al. PLoS One 2012; 7(5): e36530. PMID 22590557
2.) TCGA Lung AdenoC. Nature 2014; 511(7511): 543-550. PMID 25079552
3.) Bindea et al., Immunity 2013; 39(4): 782-95. PMID 24138885
4.) Shedden K. et al. Nat Med 2008; 14(8): 822-827. PMID 18641660
5.) Tomida S, et al. J Clin Oncol 2009; 27(17): 2793-99. PMID 19414676
6.) Lee E S, et al. Cancer Res 2008; 14(22): 7397-7404. PMID 19010856
7.) Raponi M, et al. Cancer Res 2006; 66(7): 466-72. PMID 16885343

Example 4—Expression Subtypes of Lung Adenocarcinoma Reveal a Varied Immune Landscape and Unique Somatic Genetic Features Suggesting Differential Response to Multiple Drug Targets Introduction:

Gene expression based subtyping in Lung Adenocarcinoma (AD) classifies AD tumors into distinct subtypes with variable outcomes and potential response to therapy. Gene expression based subtyping has consistently identified 3 distinct biologic types in Lung AD, Terminal Respiratory Unit (TRU), formerly Bronchioid, Proximal Proliferative (PP), formerly Magnoid, and Proximal Inflammatory (PI), formerly Squamoid (1,2) (see FIG. 1). AD subtypes demonstrate key differences in genomic alterations, tumor drivers, prognosis, and likely response to various therapies (1-2).

Methods:

As a follow up to the experiments conducted in Example 1, differential drug target gene expression was evaluated in the lung AD subtypes from Example 1 that were determined using the TCGA lung cancer gene expression dataset (AD n=515)[2] shown in FIG. 2. Previously published AD subtypes (TRU, PP and P1) were defined in Example 1 using gene expression patterns. In this example, the variable expression of genes from a clinical oncology solid tumor mutation panel (322 genes, see Table 8),[3] was examined in relation to AD subtypes from Example 1 as a supplement to the examination of the immune cell gene signatures (Bindea et al. 24 immune cell types),[4]expression of single immune gene biomarkers (CTLA4, PDCD1 (P1)-1), and CD274 (PD-L1)), proliferation (11 gene signature; see Table 9),[5] and non-silent mutation burden done in Example 1. Differential gene expression was assessed using the Kruskal-Wallis (KW) test with Bonferroni correction, while linear regression and Spearman correlations were used to evaluate association of non-silent mutation burden, tumor subtype, and CD274 (PD-L1) expression with immune cell expression.

Figure 20:
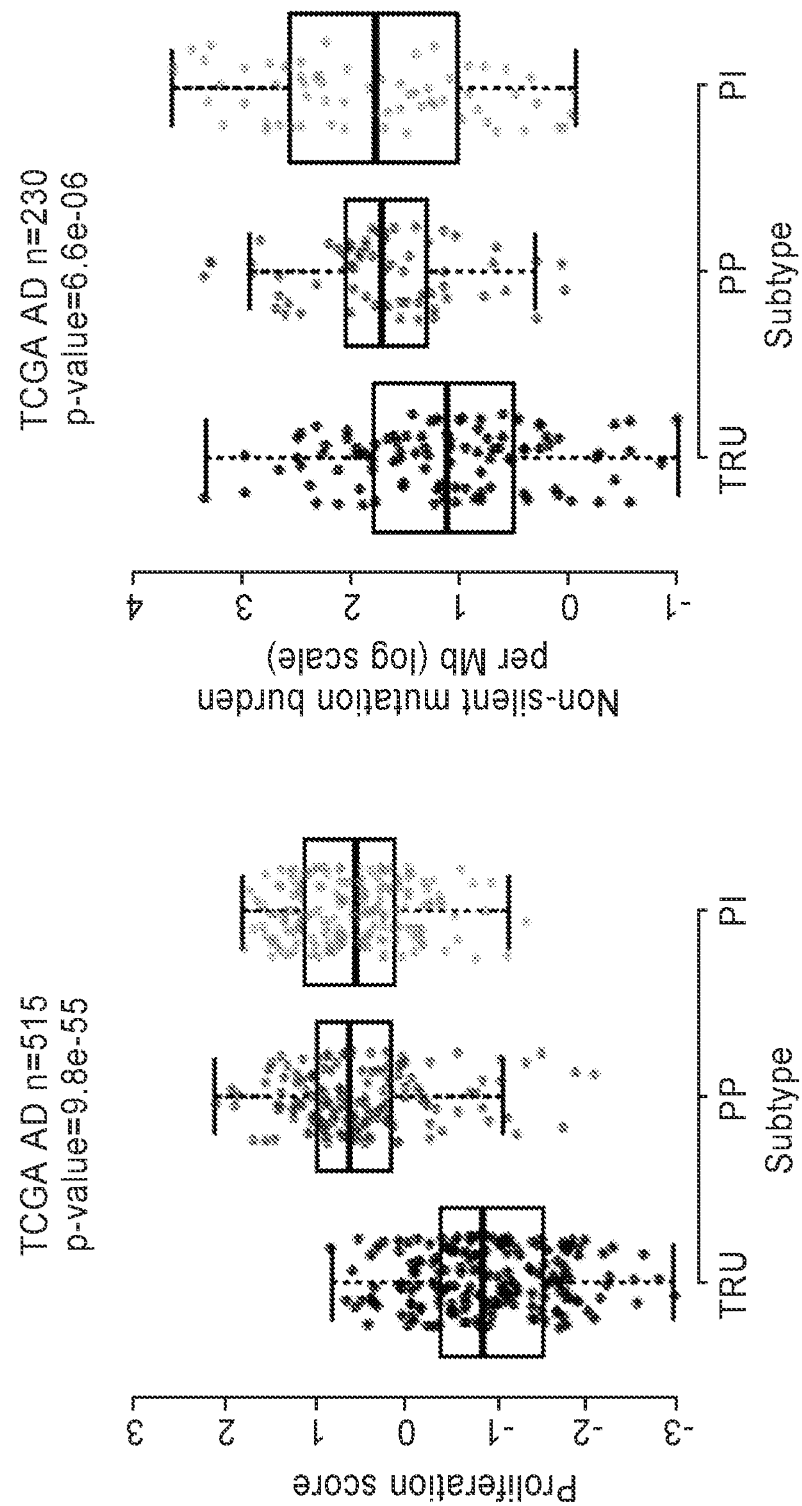
FIG. 20 illustrates significant Adenocarcinoma (AD) subtype differences in proliferation, non-silent mutation burden, and key drug targets: CD274 (PD-L1), PDCD1 (PD-1), and CTLA4. AD was determined as described in Example 4.
Figure 20:
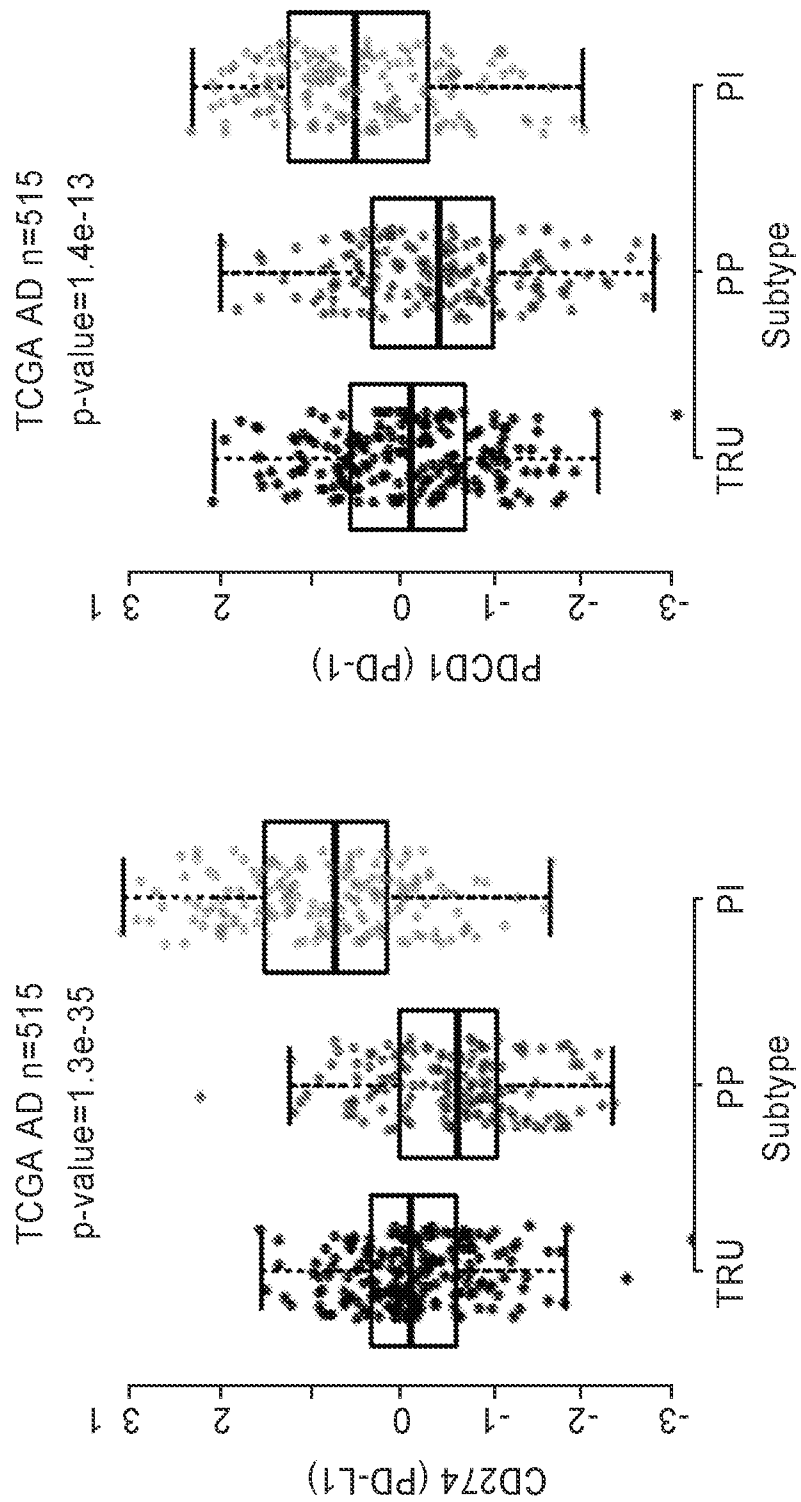
Figure 20:
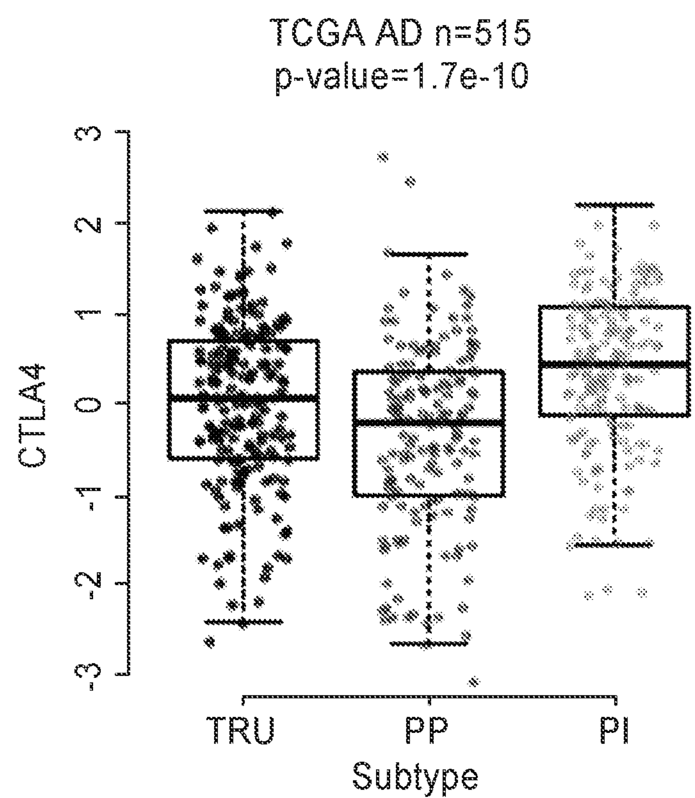
Figure 21:
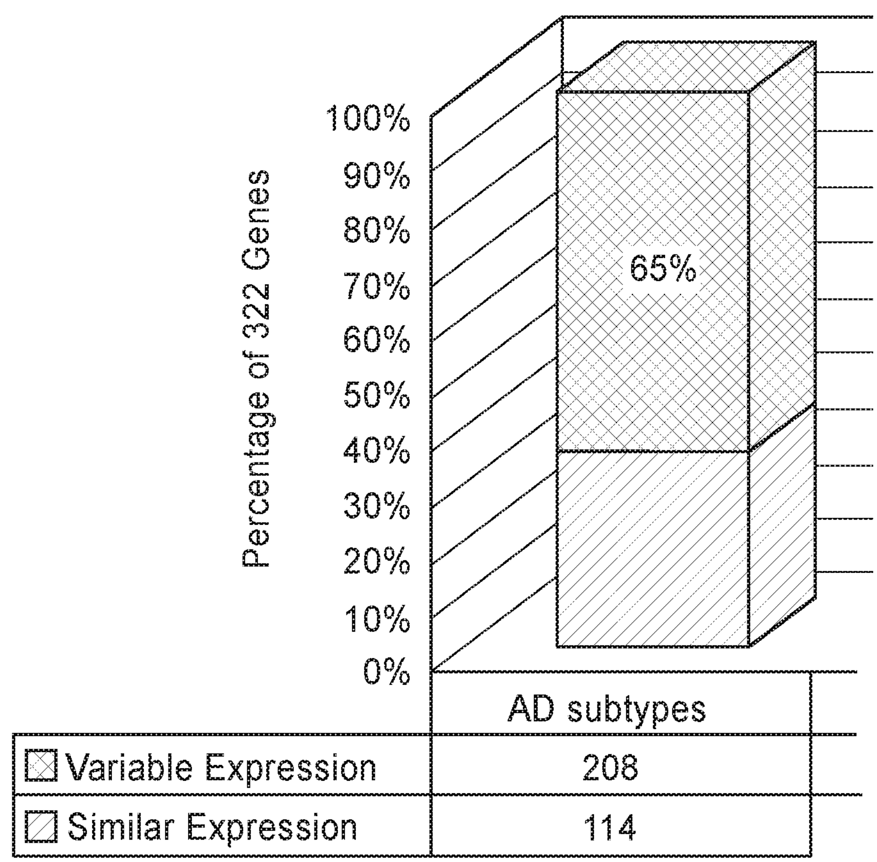
FIG. 21 illustrates significant drug target gene expression differences of AD subtypes for the majority of genes in a clinical solid tumor mutation panel (322 genes disclosed in Table 8). In AD subtypes, 65% of panel genes showed significantly variable expression (KW Bonferroni threshold $p<0.000155$). AD subtyping was determined as described in Example 4.

Results:

As shown in FIG. 21, variable expression of 208/322 tumor panel genes (65%) in AD subtypes were observed (KW Bonferroni threshold $p<0.000155$). Most drug target genes, including but not limited to AURKA, CHEK1, ROS1, CD274 (PD-L1), CSF1R and ERBB4 in AD exhibited strong differential expression across the subtypes ($p<1E-28$). Further, the top 25 genes from the 322 genes of the clinical oncology solid tumor mutation panel showing differential gene expression across the AD subtypes can be seen in Table 10. Immune cell expression was also highly variable across subtypes (see FIG. 3). The PI subtype of AD demonstrated the greatest immune cell expression while the PP subtype of AD demonstrated low expression of immune cells (see FIG. 3). Non-silent mutation burden was not strongly correlated with immune cell expression (Spearman correlation=−0.07 in AD) however, the PI subtype of AD, which is enriched for TP53 mutations, was associated with elevated immune cell expression and a high mutation burden (see FIG. 20). Overall, as shown in FIG. 20, there were significant AD subtype differences in proliferation, non-silent mutation burden, and key drug targets CD274 (PD-L1), PDCD1 (PD-1), and CTLA4.

Conclusion:

Molecular subtypes of lung AD vary in expression of the majority of key drug target genes included in a clinical solid tumor sequencing panel. Molecular subtypes of lung AD revealed differential expression of host immune response and immune targets. Evaluation of subtypes as potential biomarkers for drug sensitivity should be investigated alone, and in combination with immune cell features and key mutation targets.

INCORPORATION BY REFERENCE

The following references are incorporated by reference in their entireties for all purposes.

1.) Wilkerson M D, et al. PLoS One 2012; 7(5): e36530. PMID 22590557
2.) TCGA Lung AdenoC. Nature 2014; 511(7511): 543-550. PMID 25079552
3.) Foundation Medicine Solid Tumor Mutation Panel accessed October 2014.
4.) Bindea et al., Immunity 2013; 39(4): 782-95. PMID 24138885

5.) Neilson T O, et al. Clin Cancer Res 2010; 16(21): 522-5232. PMID 20837693.

Example 5: Expression Subtypes of Lung Adenocarcinoma Reveal a Varied Immune Landscape and Unique Somatic Genetic Features Suggesting Differential Response to Multiple Drug Targets Introduction:

Just like in Example 4, the purpose of this Example was to assess the differential expression of clinically important genes across previously defined gene expression subtypes of Adenocarcinoma (AD). In contrast to Example 4 where the AD and gene expression based subtyping was performed using the TCGA lung cancer gene expression dataset (AD n=515)[2] as described in Example 1, gene expression based AD subtyping in this Example was performed using the 48 gene sets described in Example 2. Further, the clinically important genes were 322 genes (see Table 8) that constituted a clinical solid tumor mutation sequencing panel used in the management of oncology patients to identify genomic alterations impacting therapeutic management and/or to determine eligibility for targeted drug clinical trials. Just like in Example 4, differences in tumor proliferation were also assessed across the AD subtypes using an 11 gene proliferation signature (see Table 9).

Methods:

Using the TCGA lung cancer gene expression dataset (Adenocarcinoma (AD) n=515),[1] differential drug target gene expression was evaluated in lung AD subtypes. Subtype was defined in AD using the Clanc48 AD subtyper (see Example 2 and described herein) as previously described (nearest centroid prediction).[2] AD subtypes Terminal Respiratory Unit (TRU), Proximal Proliferative (PP), and Proximal Inflammatory (PI) were examined. Variable expression of genes from a clinical oncology solid tumor mutation panel (322 genes),[3] was examined in relation to AD. Differential gene expression was assessed using the Kruskal-Wallis (KW) test with Bonferroni correction. Further, a proliferation score was calculated as the average expression (log 2(RSEM+1)) of available genes in the 11-gene PAM50 proliferation signature[4]. Subtype-proliferation association was tested using the Kruskal-Wallis test.

Figure 22:
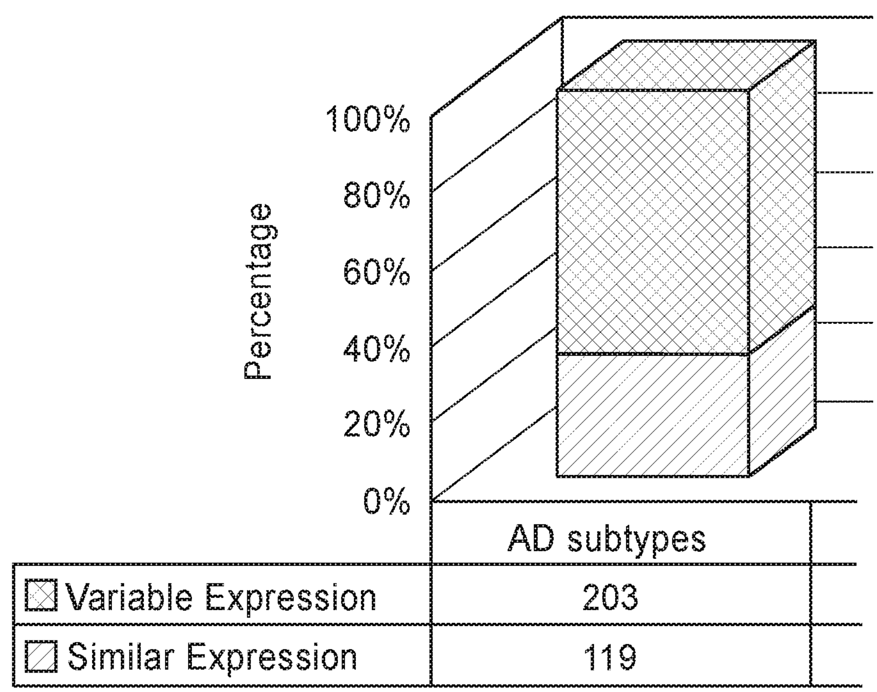
FIG. 22 illustrates significant drug target gene expression differences of AD for the majority of genes in a clinical solid tumor mutation panel (322 genes disclosed in Table 8). In AD subtypes, 63% of panel genes showed significantly variable expression (KW Bonferroni threshold $p<0.000155$). AD subtyping was determined as described in Example 5.
Figure 23:
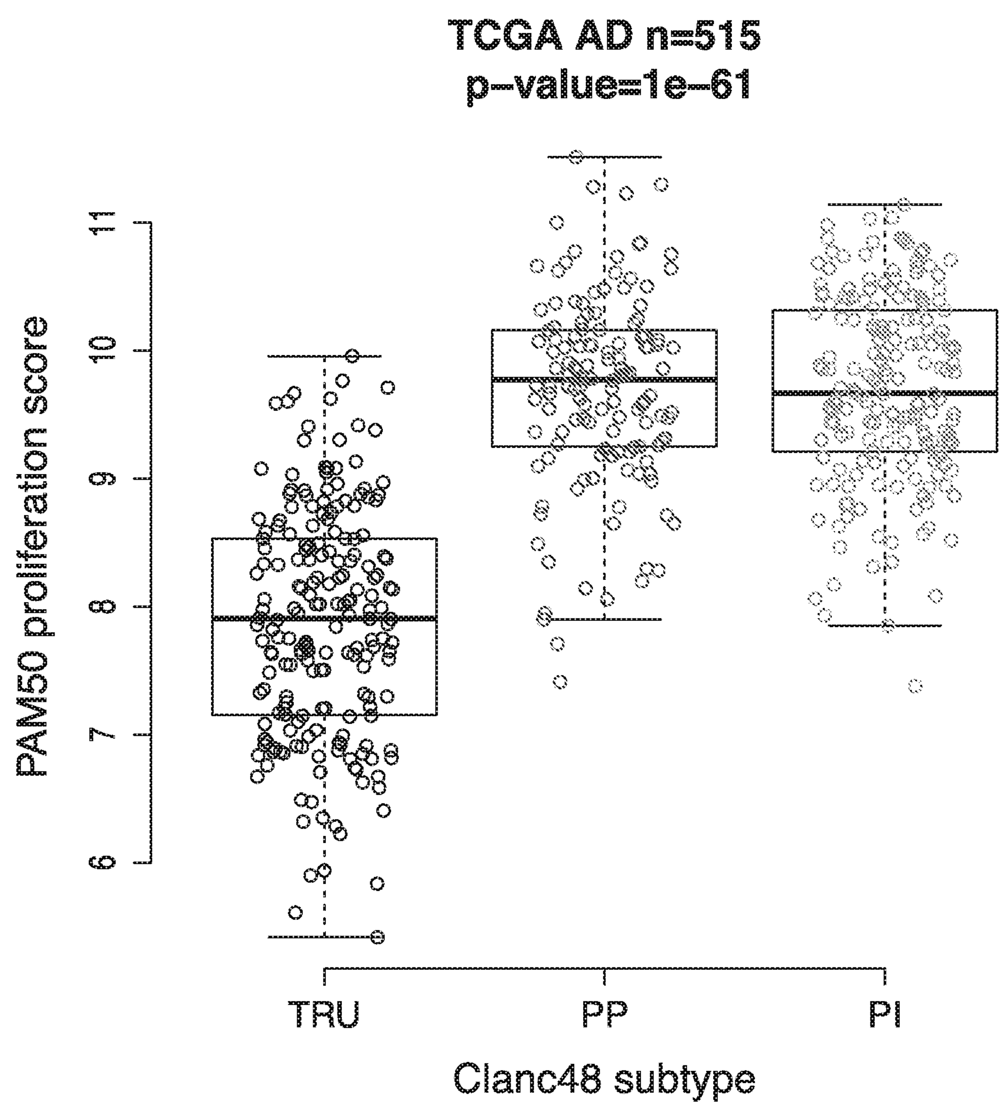
FIG. 23 illustrates significant Adenocarcinoma (AD) subtype differences in proliferation. AD subtyping was determined as described in Example 5.

Results:

Similar to FIG. 21, FIG. 22 showed variable expression of 203/322 tumor panel genes (63%) across the AD subtypes observed (KW Bonferroni threshold $p<0.000155$). Further, just like in FIG. 20 in Example 4, there were significant AD subtype differences in proliferation (see. FIG. 23). Moreover, the top 25 genes from the 322 genes of the clinical oncology solid tumor mutation panel showing differential gene expression across the AD subtypes seen in Table 11 are very similar to those found in Table 10.

Conclusion:

Just like in Example 4, molecular subtypes of lung AD vary in expression of the majority of key drug target genes included in a clinical solid tumor sequencing panel. Molecular subtypes of lung AD revealed differential expression of host immune response and immune targets.

INCORPORATION BY REFERENCE

The following references are incorporated by reference in their entireties for all purposes.

1.) TCGA Lung A D. Nature 2014; 511(7511): 543-550. PMID 25079552

2.) Wilkerson M D, et al. PLoS One 2012; 7(5): e36530. PMID 22590557

3.) Foundation Medicine Solid Tumor Mutation Panel accessed Oct. 6, 2014.

4.) Neilson T O, Parker J S, Leung S, et al. Clin Cancer Res 2010; 16(21): 5222-5232. PMID 20837693

TABLE 8

322 genes of a clinical solid tumor mutation sequencing panel[3]

| | | | | | | | | |
|---|---|---|---|---|---|---|---|---|
| ABL1 | C11orf30 (EMSY) | DDR2 | FGFR4 | IL7R | MET | PIK3CA | SDHD | TSHR |
| ABL2 | CARD11 | DICER1 | FH | INHBA | MITF | PIK3CB | SETD2 | U2AF1 |
| ACVR1B | CBFB | DNMT3A | FLCN | INPP4B | MLH1 | PIK3CG | SF3B1 | VEGFA |
| AKT1 | CBL | DOT1L | FLT1 | IRF2 | MPL | PIK3R1 | SLIT2 | VHL |
| AKT2 | CCND1 | EGFR | FLT3 | IRF4 | MRE11A | PIK3R2 | SMAD2 | WISP3 |
| AKT3 | CCND2 | EP300 | FLT4 | IRS2 | MSH2 | PLCG2 | SMAD3 | WT1 |
| ALK | CCND3 | EPHA3 | FOXL2 | JAK1 | MSH6 | PMS2 | SMAD4 | XPO1 |
| AMER1 (FAM123B) | CCNE1 | EPHA5 | FOXP1 | JAK2 | MTOR | POLD1 | SMARCA4 | ZBTB2 |
| APC | CD274 | EPHA7 | FRS2 | JAK3 | MUTYH | POLE | SMARCB1 | ZNF217 |
| AR | CD79A | EPHB1 | FUBP1 | JUN | MYC | PPP2R1A | SMO | ZNF703 |
| ARAF | CD79B | ERBB2 | GABRA6 | KAT6A (MYST3) | MYCL (MYCL1) | PRDM1 | SNCAIP | ETV4 |
| ARFRP1 | CDC73 | ERBB3 | GATA1 | KDM5A | MYCN | PREX2 | SOCS1 | ETV5 |
| ARID1A | CDH1 | ERBB4 | GATA2 | KDM5C | MYD88 | PRKAR1A | SOX10 | ETV6 |
| ARID1B | CDK12 | ERG | GATA3 | KDM6A | NF1 | PRKCI | SOX2 | ETV1 |
| ARID2 | CDK4 | ERRFI1 | GATA4 | KDR | NF2 | PRKDC | SOX9 | NFKBIA |
| ASXL1 | CDK6 | ESR1 | GATA6 | KEAP1 | NFE2L2 | PRSS8 | SPEN | |
| ATM | CDK8 | EZH2 | GID4 (C17orf39) | KEL | NFKBIA | PTCH1 | SPOP | |
| ATR | CDKN1A | FAM46C | GLI1 | KIT | NKX2-1 | PTEN | SPTA1 | |
| ATRX | CDKN1B | FANCA | GNA11 | KLHL6 | NOTCH1 | PTPN11 | SRC | |
| AURKA | CDKN2A | FANCC | GNA13 | KMT2A (MLL) | NOTCH2 | QKI | STAG2 | |
| AURKB | CDKN2B | FANCD2 | GNAQ | KMT2C (MLL3) | NOTCH3 | RAC1 | STAT3 | |
| AXIN1 | CDKN2C | FANCE | GNAS | KMT2D (MLL2) | NPM1 | RAD50 | STAT4 | |
| AXL | CEBPA | FANCF | GPR124 | KRAS | NRAS | RAD51 | STK11 | |
| BAP1 | CHD2 | FANCG | GRIN2A | LMO1 | NSD1 | RAF1 | SUFU | |

TABLE 8-continued

| 322 genes of a clinical solid tumor mutation sequencing panel[3] | | | | | | | |
|---|---|---|---|---|---|---|---|
| BARD1 | CHD4 | FANCL | GRM3 | LRP1B | NTRK1 | RANBP2 | SYK |
| BCL2 | CHEK1 | FAS | GSK3B | LYN | NTRK2 | RARA | TAF1 |
| BCL2L1 | CHEK2 | FAT1 | H3F3A | LZTR1 | NTRK3 | RB1 | TBX3 |
| BCL2L2 | CIC | FBXW7 | HGF | MAGI2 | NUP93 | RBM10 | TERC |
| BCOR | CREBBP | FGF10 | HNF1A | MAP2K1 | PAK3 | RET | TERT (promoter only) |
| BCORL1 | CRKL | FGF14 | HRAS | MAP2K2 | PALB2 | RICTOR | TET2 |
| BLM | CRLF2 | FGF19 | HSD3B1 | MAP2K4 | PARK2 | RNF43 | TGFBR2 |
| BRAF | CSF1R | FGF23 | HSP90AA1 | MAP3K1 | PAX5 | ROS1 | TNFAIP3 |
| BRCA1 | CTCF | FGF3 | IDH1 | MCL1 | PBRM1 | RPTOR | TNFRSF14 |
| BRCA2 | CTNNA1 | FGF4 | IDH2 | MDM2 | PDCD1LG2 | RUNX1 | TOP1 |
| BRD4 | CTNNB1 | FGF6 | IGF1R | MDM4 | PDGFRA | RUNX1T1 | TOP2A |
| BRIP1 | CUL3 | FGFR1 | IGF2 | MED12 | PDGFRB | SDHA | TP53 |
| BTG1 | CYLD | FGFR2 | IKBKE | MEF2B | PDK1 | SDHB | TSC1 |
| BTK | DAXX | FGFR3 | IKZF1 | MEN1 | PIK3C2B | SDHC | TSC2 |

TABLE 9

| 11 gene proliferation gene signature | | | |
|---|---|---|---|
| BIRC5 | CDCA1 (NUF2) | MKI67 | TYMS |
| CCNB1 | CEP55 | PTTG1 | UBE2C |
| CDC20 | KNTC2 (NDC80) | RRM2 | |

TABLE 10

Top 25 differentiated genes of the 322 tumor panel[3] for the AD expression subtypes as determined in Example 4.

| AD Genes | KW p value |
|---|---|
| AURKA | 1.40E−50 |
| AURKB | 1.06E−49 |
| TOP2A | 1.88E−46 |
| RAD51 | 2.28E−46 |
| CHEK1 | 3.40E−44 |
| BLM | 1.40E−43 |
| TMPRSS2 | 6.34E−40 |
| FAS | 9.42E−39 |
| ROS1 | 1.07E−37 |
| EZH2 | 2.18E−37 |
| BRCA1 | 1.16E−36 |
| CD274 | 1.26E−35 |
| CCNE1 | 4.95E−35 |
| BRIP1 | 2.50E−34 |
| ERBB4 | 2.16E−33 |
| CSF1R | 2.97E−33 |
| PDCD1LG2 | 9.44E−33 |
| FANCG | 1.22E−32 |
| BTK | 3.48E−32 |
| CHEK2 | 3.13E−30 |
| CEBPA | 4.87E−30 |
| AXL | 2.12E−29 |
| FANCD2 | 3.93E−29 |
| ETV1 | 1.66E−27 |
| DNMT3A | 5.53E−26 |

TABLE 11

Top 25 differentiated genes of the 322 tumor panel[3] for the AD expression subtypes as determined in Example 5.

| AD Genes | KW p value |
|---|---|
| AURKA | 9.48E−57 |
| AURKB | 1.81E−56 |
| TOP2A | 1.74E−54 |
| RAD51 | 6.87E−53 |
| CHEK1 | 6.77E−49 |
| BLM | 2.08E−48 |
| BRCA1 | 3.25E−44 |
| CCNE1 | 7.10E−42 |
| EZH2 | 2.19E−41 |
| TMPRSS2 | 4.67E−41 |
| BRIP1 | 4.52E−39 |
| FANCG | 1.34E−35 |
| CHEK2 | 1.83E−35 |
| FAS | 3.16E−34 |
| FANCD2 | 1.54E−33 |
| ROS1 | 3.42E−32 |
| CEBPA | 6.55E−31 |
| ERBB4 | 1.05E−30 |
| FANCA | 2.63E−29 |
| MSH6 | 5.67E−29 |
| BRCA2 | 4.75E−27 |
| CD274 | 4.95E−27 |
| TGFBR2 | 1.12E−26 |
| POLE | 2.82E−26 |
| ETV1 | 2.32E−25 |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of assaying a lung sample obtained from a human patient, the method comprising measuring a nucleic acid expression level of each biomarker from a plurality of biomarkers consisting of only C-fos-induced growth factor (FIGF), Cathepsin H (CTSH), Secretin receptor (SCTR), Cytochrome P450 family 4 subfamily B member 1 (CYP4B1), G protein-coupled receptor 116 (GPR116), Alcohol dehydrogenase 1B (class I) (ADH1B), Chromobox 7 (CBX7), Hepatic leukemia factor (HLF), Centrosomal protein 55 (CEP55), Tpx2, Microtubule-associated (TPX2), BUB1 mitotic checkpoint serine/threonine kinase B (BUB1B), Kinesin family member 4A (KIF4A), Cyclin B2 (CCNB2), Kinesin family member 14 (KIF14), Maternal embryonic leucine zipper kinase (MELK), Kinesin family member 11 (KIF11), Fibrinogen like 1 (FGL1), PDZ binding kinase (PBK), Heat shock protein family D (Hsp60) member 1 (HSPD1), Thymine DNA glycosylase (TDG), Protein regulator of cytokinesis 1 (PRC1), Dual specificity phosphatase 4 (DUSP4), GTP binding protein 4 (GTPBP4), ZW10 interacting kinetochore protein (ZWINT), Toll like receptor 2 (TLR2), CD74 molecule (CD74), Major histocompatibility complex, class II, DP beta 1 (HLA-DPB1), Major histocompatibility complex, class II, DP alpha 1 (HLA-DPA1), Major histocompatibility complex, class II, DR alpha (HLA-DRA), Integrin subunit beta 2 (ITGB2), Fas cell surface death receptor (FAS), Major histocompatibility complex, class II, DR beta 1 (HLA-DRB1), Plasminogen activator, urokinase (PLAU), Guanylate binding protein 1 (GBP1), Dermatan sulfate epimerase (DSE), Coiled-coil domain containing 109B (CCDC109B), Transforming growth factor beta induced (TGFBI), C-X-C motif chemokine ligand 10 (CXCL10), Lectin, galactoside binding soluble 1 (LGALS1), Tubulin beta 6 class V (TUBB6), Gap junction protein beta 1 (GJB1), RAP1 GTPase activating protein (RAP1GAP), Calcium voltage-gated channel auxiliary subunit alpha2delta 2 (CACNA2D2), Selenium binding protein 1 (SELENBP1), Transcription factor CP2-like 1 (TFCP2L1), Sorbin and SH3 domain containing 2 (SORBS2), Unc-13 homolog B (UNC13B) and Transforming acidic coiled-coil containing protein 2 (TACC2) in the lung sample obtained from the human patient.

2. The method of claim 1, wherein the lung sample was previously diagnosed as being adenocarcinoma.

3. The method of claim 1, wherein the measuring is performed by an amplification, hybridization and/or sequencing assay, wherein the amplification, hybridization and/or sequencing assay is selected from the group consisting of quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, and Northern blotting.

4. The method of claim 1, wherein the lung sample is selected from the group consisting of a formalin-fixed, paraffin-embedded (FFPE) lung tissue sample, fresh or a frozen tissue sample, an exosome, wash fluids, cell pellets, and a bodily fluid obtained from the patient.

5. A method of treating lung cancer in a subject, the method comprising: (a) determining the subtype of a lung sample obtained from the subject, wherein the lung sample is an adenocarcinoma lung cancer sample, wherein the determining the subtype comprises:

(i) measuring a nucleic acid expression level of each biomarker of a plurality of biomarkers consisting of only FIGF, CTSH, SCTR, CYP4B1, GPR116, ADH1B, CBX7, HLF, CEP55, TPX2, BUB1B, KIF4A, CCNB2, KIF14, MELK, KIF11, FGL1, PBK, HSPD1, TDG, PRC1, DUSP4, GTPBP4, ZWINT, TLR2, CD74, HLA-DPB1, HLA-DPA1, HLA-DRA, ITGB2, FAS, HLA-DRB1, PLAU, GBP1, DSE, CCDC109B, TGFBI, CXCL10, LGALS1, TUBB6, GJB1, RAP1GAP, CACNA2D2, SELENBP1, TFCP2L1, SORBS2, UNC13B and TACC2 in the lung sample obtained from the subject;

(ii) comparing the measured nucleic acid expression levels of each biomarker of the plurality of the biomarkers of (α)(i) in at least one sample training set(s), wherein the at least one sample training set is a reference lung adenocarcinoma bronchioid (terminal respiratory unit) sample, a reference lung adenocarcinoma magnoid (proximal proliferative) sample, a reference lung adenocarcinoma squamoid (proximal inflammatory) sample or a combination thereof; and (iii) classifying the subtype of lung adenocarcinoma as bronchioid (terminal respiratory unit), magnoid (proximal proliferative) or squamoid (proximal inflammatory) based on the results of the comparing step; and (b) administering a therapeutic agent based on the subtype of the lung adenocarcinoma, wherein a squamoid (proximal inflammatory) subtype is administered a checkpoint inhibitor, a magnoid (proximal proliferative) subtype is administered a chemotherapeutic agent and a bronchioid (terminal respiratory unit) subtype is administered a therapeutic agent selected from a chemotherapeutic agent and an angiogenesis inhibitor.

6. The method of claim 5, wherein the lung sample was previously diagnosed as being an adenocarcinoma lung cancer sample.

7. The method of claim 5, wherein the measuring the expression level is conducted using an amplification, hybridization and/or sequencing assay, wherein the amplification, hybridization and/or sequencing assay is selected from the group consisting of quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, and Northern blotting.

8. The method of claim 5, wherein the lung sample is selected from the group consisting from a formalin-fixed, paraffin-embedded (FFPE) lung tissue sample, fresh or a frozen tissue sample, an exosome, wash fluids, cell pellets, and a bodily fluid obtained from the subject.

9. The method of claim 1, further comprising measuring a nucleic acid expression level of each biomarker from the plurality of biomarkers consisting of only FIGF, CTSH, SCTR, CYP4B1, GPR116, ADH1B, CBX7, HLF, CEP55, TPX2, BUB1B, KIF4A, CCNB2, KIF14, MELK, KIF11, FGL1, PBK, HSPD1, TDG, PRC1, DUSP4, GTPBP4, ZWINT, TLR2, CD74, HLA-DPB1, HLA-DPA1, HLA-DRA, ITGB2, FAS, HLA-DRB1, PLAU, GBP1, DSE, CCDC109B, TGFBI, CXCL10, LGALS1, TUBB6, GJB1, RAP1GAP, CACNA2D2, SELENBP1, TFCP2L1, SORBS2, UNC13B and TACC2 in a normal lung sample, a squamoid (proximal inflammatory) sample, a bronchioid (terminal respiratory unit) sample or a magnoid (proximal proliferative) sample.

10. The method of claim 5, wherein the comparing step comprises applying a statistical algorithm which comprises determining a correlation between the nucleic acid expression levels of each biomarker from the plurality of biomarkers obtained from the lung sample and the nucleic acid expression levels of each biomarker from the plurality of biomarkers from the at least one training set(s); and classifying the subtype of the lung adenocarcinoma sample as a bronchioid (terminal respiratory unit), magnoid (proximal proliferative) or squamoid (proximal inflammatory) subtype based on the results of the statistical algorithm.

11. The method of claim 5, wherein the chemotherapeutic agent administered to the bronchioid (terminal respiratory unit) subtype is selected from EGFR inhibitors and Pemetrexed.

* * * * *

SEQUENCE LISTING

<160> NUMBER OF SEQ ID NOS: 48

<210> SEQ ID NO 1
<211> LENGTH: 2122
<212> TYPE: DNA
<213> ORGANISM: Homo sapiens

<400> SEQUENCE: 1

```
ctctagcttc tagcacaatg tctgtcattt aatgggcatt cagtacataa tagataggta     60

attgaatgaa tggatttaga tgcctgggtg ttttctttct acttgtattc tattccccac    120

atcctctcca aagatttcag catcatcaag acatattatc ctgtgtcttc cttctgaaga    180

tttaaattat agtgatcacc aaatccatgt tgatatgata acaatggtta agaagtttga    240

atatgttatt ttctctaagc aatacagttg tatattaatc agaatctccc agagaaagcc    300

ccttagagca ggcagttcca taaaaggaat gtcaggaact tctgcaggct ggatgaggac    360

atacactgag tgaacaagtc tgtcaactgc tctaaagaca ctgtcaatgc catataaaag    420

ctggccttgt tcatctagca gatcatgggg gtgagacagt ccagtgcctc tctgccccta    480

caatatatga agaaagggga agaaacacac attgcctcct ggtagattag gggaggactt    540

cttgtacatt tttagcaaaa tccgagttca gacccagcaa ttagacaaaa gggtcagcaa    600

actatggtcg atgggctaca tctgcccact gcatgttttt gtaaatgaag ttttattggg    660

acacagccat acctattcac ttttgcatta tctatggctg cttttgcact ttgatgaaag    720

agttgagtag ttgagacaga cactgtttga cccacaaaat ctaaaataca tactatctag    780

cccttcctag caaacatttg ccaaccccta gaaaactttt aaaaaatgat gctcttcgac    840

ttgaaatttt tataatcttc tgtttattgt caataggtgc tgctgatttt caaaaaatga    900

cttagaatcc tcaaataagt atacagcctt atatgctgct tagacaccaa agctatgata    960

agatttgtca gttctttgta tcagatgggt tcaattcttg acatcagcta atgttataaa   1020

aataactaca aaattggttg taatagaacc aaatctaaga ctctttttaa taaaaaagat   1080

caccattgct ggtgagaaac ctatactgaa tgggtgagat gccattgcat ttatctgaag   1140

tttcgtcttt ataatcaata atcatataca atcctagtca agaaactcat cttacagtcc   1200

ttggggattg aacactgtga aaataaactt ttactcttcg gatgtgcttg gattttgttt   1260

taaattaaga actacagaaa tatatatcat ttctagtggt agaggaaaat attgccaccc   1320

agaactttct gaatgtctct ttctgcccta ggtccatttg tgatgaacac caatgaagag   1380

atttctcaag ctattcttga tttcagaaac gcaaaaaatg ggtttgaaag ggccaaaacc   1440

tggaaatcaa agattgggaa ctagtggaaa gcggaagagc aggtcttgat gtgtcctaga   1500

attttgccat ttctgagatt gagccattga aggcattcca tttctaaagc ttatttagcc   1560

ggtgcttcta aagaattcca cactaacgtg ataacatggt ttttgtaaca ataaatgtag   1620

gatatttcct ggcacatgca aataaaccta atcattgttt ctttaaaaat cagtgttttt   1680

catttgagat acctaagtta ctaagcttct gtttaaaaag tcgttttgtg tatgtttgcc   1740

tttttttgca tgtatggatg gatgttttta ttatttttgt gcatgtgcag gttttaaaaa   1800

tcatatttga ttgctttctg tgtgtcattg gcagcagatg catgagcatc tgaggtccct   1860

tcttaagcaa tcccactgag atacaaaggt caaagctatg tgctggggtt tcatgttaca   1920

ggttatctgc tttaaaataa cggcagccct gaacatttga gtcagttctt aaaactgccc   1980

tgctattggt agggacgcaa caggattaca gccaagactt ctctgcattt tctgccaaaa   2040

tctgtgtcag atttaagaca catgcttctg caagcttcca tgaaggttgt gcaaaaaagt   2100
```

```
ttcaatccag agttgggttc ca                                          2122

<210> SEQ ID NO 2
<211> LENGTH: 1514
<212> TYPE: DNA
<213> ORGANISM: Homo sapiens

<400> SEQUENCE: 2

ttcgcgctcc cgccgctcct ccacgctcgt gccgctcccc ccccgcgctc ccagttgacg    60

ctctgggccg ccacctccgc ggaccctgag cgcaagagcc aagccgccag cgctgcgatg   120

tgggccacgc tgccgctgct ctgcgccggg gcctggctcc tgggagtccc cgtctgcggt   180

gccgccgaac tgtgcgtgaa ctccttagag aagtttcact tcaagtcatg gatgtctaag   240

caccgtaaga cctacagtac ggaggagtac caccacaggc tgcagacgtt tgccagcaac   300

tggaggaaga taaacgccca caacaatggg aaccacacat ttaaaatggc actgaaccaa   360

ttttcagaca tgagctttgc tgaaataaaa cacaagtatc tctggtcaga gcctcagaat   420

tgctcagcca ccaaaagtaa ctaccttcga ggtactggtc cctacccacc ttccgtggac   480

tggcggaaaa aaggaaattt tgtctcacct gtgaaaaatc agggtgcctg cggcagttgc   540

tggactttct ccaccactgg ggccctggag tctgcgatcg ccatcgcaac cggaaagatg   600

ctgtccttgg cggaacagca gctggtggac tgcgcccagg acttcaataa tcacggctgc   660

caagggggtc tccccagcca ggctttcgag tatatcctgt acaacaaggg gatcatgggt   720

gaagacacct acccctacca gggcaaggat ggttattgca agttccaacc tggaaaggcc   780

atcggctttg tcaaggatgt agccaacatc acaatctatg acgaggaagc gatggtggag   840

gctgtggccc tctacaaccc tgtgagcttt gcctttgagg tgactcagga cttcatgatg   900

tatagaacgg gcatctactc cagtacttcc tgccataaaa ctccagataa agtaaaccat   960

gcagtactgg ctgttgggta tggagaaaaa aatgggatcc cttactggat cgtgaaaaac  1020

tcttggggtc cccagtgggg aatgaacggg tacttcctca tcgagcgcgg aaagaacatg  1080

tgtggcctgg ctgcctgcgc ctcctacccc atccctctgg tgtgagccgt ggcagccgca  1140

gcgcagactg gcggagaagg agaggaacgg gcagcctggg cctgggtgga aatcctgccc  1200

tggaggaagt tgtggggaga tccactggga cccccaacat tctgccctca cctctgtgcc  1260

cagcctggaa acctacagac aaggaggagt tccaccatga gctcacccgt gtctatgacg  1320

caaagatcac cagccatgtg ccttagtgtc cttcttaaca gactcaaacc acatggacca  1380

cgaatattct ttctgtccag aagggctact ttccacatat agagctccag ggactgtctt  1440

ttctgtattc gctgttcaat aaacattgag tgagcacctc cccagatgga gcatgctggt  1500

cctggaaaaa aaaa                                                   1514

<210> SEQ ID NO 3
<211> LENGTH: 1833
<212> TYPE: DNA
<213> ORGANISM: Homo sapiens

<400> SEQUENCE: 3

aaagccgcgt cctgatcaat ggggcgggcg gcttagcgcg cgcggccacc tggtccgagg    60

aggagcagtc ccggggcccg ccgcaggtcg ggtggctcag ccatggctcc tcggggcgca   120

gcggccggcc ggagcccggg accctgcgcg gggcgctgag ctcccgagcg ggcagagggc   180

acgggcaggc ggacgtcggg gcgccctcgg ggaacgtgcg ggcaccatgc gtccccacct   240
```

```
gtcgccgccg ctgcagcagc tactactgcc ggtgctgctc gcctgcgccg cgcactcgac    300

tggagccctt ccccgactat gtgacgtgct acaagtgctg tgggaagagc aagaccagtg    360

cctgcaggaa ctctccagag agcagacagg agacctgggc acggagcagc cagtgccagg    420

ttgtgagggg atgtgggaca acataagctg ctggccctct tctgtgccgg gccggatggt    480

ggaggtggaa tgcccgagat tcctccggat gctcaccagc agaaatggtt ccttgttccg    540

aaactgcaca caggatggct ggtcagaaac cttccccagg cctaatctgg cctgtggcgt    600

taatgtgaac gactcttcca acgagaagcg gcactcctac ctgctgaagc tgaaagtcat    660

gtacaccgtg ggctacagct cctccctggt catgctcctg gtcgcccttg gcatcctctg    720

tgctttccgg aggctccact gcactcgcaa ctacatccac atgcacctgt tcgtgtcctt    780

catccttcgt gccctgtcca acttcatcaa ggacgccgtg ctcttctcct cagatgatgt    840

cacctactgc gatgcccaca gggcgggctg caagctggtc atggtgctgt tccagtactg    900

catcatggcc aactactcct ggctgctggt ggaaggcctc taccttcaca cactcctcgc    960

catctccttc ttctctgaaa gaaagtacct ccagggattt gtggcattcg gatggggttc   1020

tccagccatt tttgttgctt tgtgggctat tgccagacac tttctggaag atgttgggtg   1080

ctgggacatc aatgccaacg catccatctg gtggatcatt cgtggtcctg tgatcctctc   1140

catcctgatt aatttcatcc ttttcataaa cattctaaga atcctgatga gaaaacttag   1200

aacccaagaa acaagaggaa atgaagtcag ccattataag cgcctggcca ggtccactct   1260

cctgctgatc cccctctttg gcatccacta catcgtcttc gccttctccc cagaggacgc   1320

tatggagatc cagctgtttt ttgaactagc ccttggctca ttccagggac tggtggtggc   1380

cgtcctctac tgcttcctca atggggaggt gcagctggag gttcagaaga agtggcagca   1440

atggcacctc cgtgagttcc cactgcaccc cgtggcctcc ttcagcaaca gcaccaaggc   1500

cagccacttg gagcagagcc agggcacctg caggaccagc atcatctgag aggctggagc   1560

agggtcaccc acggacagag accaagagag gtcctgcgaa ggctgggcac tgctgtggga   1620

cagccagtct tcccagcaga caccctgtgt cctccttcag ctgaagatgc ccctccccag   1680

gccttggact cttccgaagg gatgtgaggc actgtggggc aggacaaggg cctgggattt   1740

ggttcgtttg ctcttctggg aagagaagtt caggggtccc agaaagggac agggaaataa   1800

atggtgcctg ggatgagatt caaaaaaaaa aaa                                1833
```

<210> SEQ ID NO 4
<211> LENGTH: 2128
<212> TYPE: DNA
<213> ORGANISM: Homo sapiens

<400> SEQUENCE: 4

```
aagatgcatg ggtccagagt ataaaggaac ccaggagcag ctgaaggcag gtcagatgaa     60

ggctaggtgg ctggaactgc aaccatggtg cccagcttcc tctccctgag cttctcctcc    120

ttgggcctgt gggcttctgg gctgatcttg gtcttaggct ttctcaagct catccacctg    180

ctgctgcgga ggcagacgtt ggctaaggct atggacaaat tcccagggcc tcccacccac    240

tggctttttg gacatgccct cgagatccag gagacgggga gcctggacaa agtggtgtcc    300

tgggcccacc agttcccgta tgcccaccca ctctggttcg gacagttcat tggcttcctg    360

aacatctatg agcctgacta tgccaaagct gtgtacagcc gtgggggggag aggcctgctg    420

gttcttgagg ggcccaagtg gttgcagcac cgcaagctgc tcacacctgg ctttcattat    480

gatgtgctga agccctatgt ggccgtgttc actgagtcta cacgtatcat gctggacaag    540
```

```
tgggaagaga aagctcggga gggtaagtcc tttgacatct tctgcgatgt gggtcacatg    600
gcgctgaaca cactcatgaa gtgcaccttt ggaagaggag acaccggcct gggccacagc    660
agggacagca gctactacct tgcagtcagc gatctcactc tgttgatgca gcagcgcctt    720
gtgtccttcc agtaccataa tgacttcatc tactggctca ccccacatgg ccgccgcttc    780
ctgcgggcct gccaggtggc ccatgaccat acagaccagg tcatcaggga gcggaaggca    840
gccctgcagg atgagaaggt gcggaagaag atccagaacc ggaggcacct ggacttcctg    900
gacattctcc tgggtgcccg ggatgaagat gacatcaaac tgtcagatgc agacctccgg    960
gctgaagtgg acacattcat gtttgaaggc catgacacca ccaccagtgg tatctcctgg   1020
tttctctact gcatggccct gtaccctgag caccagcatc gttgtagaga ggaggtccgc   1080
gagatcctag gggaccagga cttcttccag tgggatgatc tgggcaaaat gacttatctg   1140
accatgtgca tcaaggagag cttccgcctc tacccacctg tgccccaggt gtaccgccag   1200
ctcagcaagc ctgtcacctt tgtggatggc cggtctctac ctgcaggaag cctgatctct   1260
atgcatatct atgccctcca taggaacagt gctgtatggc ccgaccctga ggtctttgac   1320
tctctgcgct tttccactga gaatgcatcc aaacgccatc cctttgcctt tatgcccttc   1380
tctgctgggc ccaggaactg cattgggcag cagtttgcca tgagtgagat gaaggtggtc   1440
acagccatgt gcttgctccg ctttgagttc tctctggacc cctcacggct gcccatcaag   1500
atgccccagc ttgtcctgcg ctccaagaat ggctttcacc tccacctgaa gccactgggc   1560
cctgggtctg ggaagtagct ctgatgagaa tggggtccca gatggctcag gctgtgacct   1620
ccctgggcac caccctcccc aggctgggtg tggaggagtt ggggccccct gccttcagga   1680
ggcttgtagt ttagaaggga agtaggcatt accatagacg actcctagag gacagtgcta   1740
tgtaaaaatg tgtgtctata aatgtttatc atgcatgtat tctagagctc attcatttat   1800
tcaacaaaca tttggtgagc acctatttcg ttcgagaaac ttcatttatc tcctataatt   1860
ggcaaactta aaaatgcagc agaaacttac attccaacct tagagactca tagtgagcac   1920
aaggaaagtt ttgccctgag attcatggtt atggctgggt accaccaaat agaagaatgg   1980
cttaggggag tgccccttca ctgagatgtg tttctttgtt gaactttgtg tgtgtgtgtt   2040
tagaatataa cagacataag aaaaaattac ctaaatgaag actgtacaaa ataataaata   2100
attctgaagc agaaaaaaaa aaaaaaaa                                      2128

<210> SEQ ID NO 5
<211> LENGTH: 3903
<212> TYPE: DNA
<213> ORGANISM: Homo sapiens

<400> SEQUENCE: 5

atgaaatccc caaggagaac cactttgtgc ctcatgttta ttgtgattta ttcttccaaa     60
gctgcactga actggaatta cgagtctact attcatcctt tgagtcttca tgaacatgaa    120
ccagctggtg aagaggcact gaggcaaaaa cgagcagttg ccacaaaaag tcctacggct    180
gaagaataca ctgttaatat tgagatcagt tttgaaaatg catccttcct ggatcctatc    240
aaagcctact tgaacagcct cagttttcca attcatggga ataacactga ccaaattacc    300
gacattttga gcataaatgt gacaacagtc tgcagacctg ctggaaatga aatctggtgc    360
tcctgcgaga caggttatgg gtggcctcgg gaaaggtgtc ttcacaatct catttgtcaa    420
gagcgtgacg tcttcctccc agggcaccat tgcagttgcc ttaaagaact gcctcccaat    480
```

-continued

```
ggaccttttt gcctgcttca ggaagatgtt accctgaaca tgagagtcag actaaatgta    540
ggctttcaag aagacctcat gaacacttcc tccgccctct ataggtccta caagaccgac    600
ttggaaacag cgttccggaa gggttacgga attttaccag gcttcaaggg cgtgactgtg    660
acagggttca agtctggaag tgtggttgtg acatatgaag tcaagactac accaccatca    720
cttgagttaa tacataaagc caatgaacaa gttgtacaga gcctcaatca gacctacaaa    780
atggactaca actcctttca agcagttact atcgaaagca atttctttgt cacaccagaa    840
atcatctttg aaggggacac agtcagtctg gtgtgtgaaa aggaagtttt gtcctccaat    900
gtgtcttggc gctatgaaga acagcagttg gaaatccaga acagcagcag attctcgatt    960
tacaccgcac ttttcaacaa catgacttcg gtgtccaagc tcaccatcca caacatcact   1020
ccaggtgatg caggtgaata tgtttgcaaa ctgatattag acatttttga atatgagtgc   1080
aagaagaaaa tagatgttat gcccatccaa attttggcaa atgaagaaat gaaggtgatg   1140
tgcgacaaca atcctgtatc tttgaactgc tgcagtcagg gtaatgttaa ttggagcaaa   1200
gtagaatgga agcaggaagg aaaaataaat attccaggaa cccctgagac agacatagat   1260
tctagctgca gcagatacac cctcaaggct gatggaaccc agtgcccaag cgggtcgtct   1320
ggaacaacag tcatctacac ttgtgagttc atcagtgcct atggagccag aggcagtgca   1380
aacataaaag tgacattcat ctctgtggcc aatctaacaa taaccccgga cccaatttct   1440
gtttctgagg gacaaaactt ttctataaaa tgcatcagtg atgtgagtaa ctatgatgag   1500
gtttattgga acacttctgc tggaattaaa atataccaaa gattttatac cacgaggagg   1560
tatcttgatg gagcagaatc agtactgaca gtcaagacct cgaccaggga gtggaatgga   1620
acctatcact gcatatttag atataagaat tcatacagta ttgcaaccaa agacgtcatt   1680
gttcacccgc tgcctctaaa gctgaacatc atggttgatc ctttggaagc tactgtttca   1740
tgcagtggtt cccatcacat caagtgctgc atagaggagg atggagacta caaagttact   1800
ttccatacgg gttcctcatc ccttcctgct gcaaaagaag ttaacaaaaa acaagtgtgc   1860
tacaaacaca atttcaatgc aagctcagtt tcctggtgtt caaaaactgt tgatgtgtgt   1920
tgtcacttta ccaatgctgc taataattca gtctggagcc catctatgaa gctgaatctg   1980
gttcctgggg aaaacatcac atgccaggat cccgtaatag gtgtcggaga gccggggaaa   2040
gtcatccaga agctatgccg gttctcaaac gttcccagca gccctgagag tcccattggc   2100
gggaccatca cttacaaatg tgtaggctcc cagtgggagg agaagagaaa tgactgcatc   2160
tctgccccaa taaacagtct gctccagatg gctaaggctt tgatcaagag cccctctcag   2220
gatgagatgc tccctacata cctgaaggat ctttctatta gcatagacaa agcggaacat   2280
gaaatcagct cttctcctgg gagtctggga gccattatta acatccttga tctgctctca   2340
acagttccaa cccaagtaaa ttcagaaatg atgacgcacg tgctctctac ggttaatgtc   2400
atccttggca agcccgtctt gaacacctgg aaggttttac aacagcaatg gaccaatcag   2460
agttcacagc tactacattc agtggaaaga ttttcccaag cattacagtc gggagatagc   2520
cctcctttgt ccttctccca aactaatgtg cagatgagca gcatggtaat caagtccagc   2580
cacccagaaa cctatcaaca gaggtttgtt ttcccatact ttgacctctg ggcaatgtg   2640
gtcattgaca agagctatct agaaaacttg cagtcggatt cgtctattgt caccatggct   2700
ttcccaactc tccaagccat ccttgcccag gatatccagg aaaataactt tgcagagagc   2760
ttagtgatga caaccactgt cagccacaat acaactatgc cattcaggat ttcaatgact   2820
tttaagaaca atagcccttc aggcggcgaa acgaagtgtg tcttctggaa cttcaggctt   2880
```

```
gccaacaaca caggggggtg ggacagcagt gggtgctatg tagaagaagg tgatggggac   2940

aatgtcacct gtatctgtga ccacctaaca tcattctcca tcctcatgtc ccctgactcc   3000

ccagatccta gttctctcct gggaatactc ctggatatta tttcttatgt tggggtgggc   3060

ttttccatct tgagcttggc agcctgtcta gttgtggaag ctgtggtgtg gaaatcggtg   3120

accaagaacc ggacttctta tatgcgccac acctgcatag tgaatatcgc tgcctccctt   3180

ctggtcgcca acacctggtt cattgtggtc gctgccatcc aggacaatcg ctacatactc   3240

tgcaagacag cctgtgtggc tgccaccttc ttcatccact tcttctacct cagcgtcttc   3300

ttctggatgc tgacactggg cctcatgctg ttctatcgcc tggttttcat tctgcatgaa   3360

acaagcaggt ccactcagaa agccattgcc ttctgtcttg gctatggctg cccacttgcc   3420

atctcggtca tcacgctggg agccacccag ccccgggaag tctatacgag gaagaatgtc   3480

tgttggctca actgggagga caccaaggcc ctgctggctt tcgccatccc agcactgatc   3540

attgtggtgg tgaacataac catcactatt gtggtcatca ccaagatcct gaggccttcc   3600

attggagaca agccatgcaa gcaggagaag agcagcctgt ttcagatcag caagagcatt   3660

ggggtcctca caccactctt gggcctcact tggggttttg gtctcaccac tgtgttccca   3720

gggaccaacc ttgtgttcca tatcatattt gccatcctca atgtcttcca gggattattc   3780

attttactct ttggatgcct ctgggatctg aagtcaacat ccctgggttc atccacacct   3840

gtgttttcta tgagttctcc aatatcaagg agatttaaca atttgtttgg taaaacaggt   3900

taa                                                                 3903
```

<210> SEQ ID NO 6
<211> LENGTH: 2829
<212> TYPE: DNA
<213> ORGANISM: Homo sapiens

<400> SEQUENCE: 6

```
acaagcaaac aaaataaata tctgtgcaat atatctgctt tatgcactca agcagagaag     60

aaatccacaa agactcacag tctgctggtg ggcagagaag acagaaacga catgagcaca    120

gcaggaaaag aaagttgtct gacagaagtt tgatgagagg aatttgactc agaagactga    180

aatatccttt aaccttacta taaaatatct tacaaaatac tcattgattt cacagcatta    240

gaatcatcaa ggtaatcaaa tgcaaagcag ctgtgctatg ggaggtaaag aaaccctttt    300

ccattgagga tgtggaggtt gcacctccta aggcttatga agttcgcatt aagatggtgg    360

ctgtaggaat ctgtcacaca gatgaccacg tggttagtgg caacctggtg acccccccttc    420

ctgtgatttt aggccatgag gcagccggca tcgtggagag tgttggagaa ggggtgacta    480

cagtcaaacc aggtgataaa gtcatcccgc tctttactcc tcagtgtgga aaatgcagag    540

tttgtaaaaa cccggagagc aactactgct tgaaaaatga tctaggcaat cctcggggga    600

ccctgcagga tggcaccagg aggttcacct gcagggggaa gcccattcac cacttccttg    660

gcaccagcac cttctcccag tacacggtgg tggatgagaa tgcagtggcc aaaattgatg    720

cagcctcgcc cctggagaaa gtctgcctca ttggctgtgg attctcgact ggttatgggt    780

ctgcagttaa cgttgccaag gtcaccccag gctctacctg tgctgtgttt ggcctgggag    840

gggtcggcct atctgctgtt atgggctgta aagcagctgg agcagccaga atcattgcgg    900

tggacatcaa caaggacaaa tttgcaaagg ccaaagagtt gggtgccact gaatgcatca    960

accctcaaga ctacaagaaa cccattcagg aagtgctaaa ggaaatgact gatggaggtg   1020
```

```
tggatttttc gtttgaagtc atcggtcggc ttgacaccat gatggcttcc ctgttatgtt   1080

gtcatgaggc atgtggcaca agcgtcatcg taggggtacc tcctgcttcc cagaacctct   1140

caataaaccc tatgctgcta ctgactggac gcacctggaa gggggctgtt tatggtggct   1200

ttaagagtaa agaaggtatc ccaaaacttg tggctgattt tatggctaag aagttttcac   1260

tggatgcgtt aataacccat gttttacctt ttgaaaaaat aaatgaagga tttgacctgc   1320

ttcactctgg gaaaagtatc cgtaccgtcc tgacgttttg aggcaataga gatgccttcc   1380

cctgtagcag tcttcagcct cctctaccct acaagatctg gagcaacagc taggaaatat   1440

cattaattca gctcttcaga gatgttatca ataaattaca catgggggct ttccaaagaa   1500

atggaaattg atgggaaatt atttttcagg aaaatttaaa attcaagtga gaagtaaata   1560

aagtgttgaa catcagctgg ggaattgaag ccaacaaacc ttccttctta accattctac   1620

tgtgtcacct ttgccattga ggaaaaatat tcctgtgact tcttgcattt ttggtatctt   1680

cataatcttt agtcatcgaa tcccagtgga ggggaccctt ttacttgccc tgaacataca   1740

catgctgggc cattgtgatt gaagtcttct aactctgtct cagttttcac tgtcgacatt   1800

ttcctttttc taataaaaat gtaccaaatc cctggggtaa aagctagggt aaggtaaagg   1860

atagactcac atttacaagt agtgaaggtc caagagttct aaatacagga aatttcttag   1920

gaactcaaat aaaatgcccc acattttact acagtaaatg gcagtgtttt tatgactttt   1980

atactatttc tttatggtcg atatacaatt gatttttttaa aataatagca gatttcttgc   2040

ttcatatgac aaagcctcaa ttactaattg taaaaactga actattccca gaatcatgtt   2100

caaaaaatct gtaatttttg ctgatgaaag tgcttcattg actaaacagt attagtttgt   2160

ggctataaat gattatttag atgatgactg aaaatgtgta taaagtaatt aaaagtaata   2220

tggtggcttt aagtgtagag atgggatggc aaatgctgtg aatgcagaat gtaaaattgg   2280

taactaagaa atggcacaaa caccttaagc aatatatttt cctagtagat atatatatac   2340

acatacatat atacacatat acaaatgtat atttttgcaa aattgttttc aatctagaac   2400

ttttctatta actaccatgt cttaaaatca agtctataat cctagcatta gtttaatatt   2460

ttgaatatgt aaagacctgt gttaatgctt tgttaatgct tttcccactc tcatttgtta   2520

atgctttccc actctcaggg gaaggatttg cattttgagc tttatctcta aatgtgacat   2580

gcaaagatta ttcctggtaa aggaggtagc tgtctccaaa aatgctattg ttgcaatatc   2640

tacattctat ttcatattat gaaagacctt agacataaag taaaatagtt tatcatttac   2700

tgtgtgatct tcagtaagtc tctcaggctc tctgagcttg ttcatccttt gttttgaaaa   2760

aattactcaa ccaatccatt acagcttaac caagattaaa tgggatgatg ttaaaaaaaa   2820

aaaaaaaaa                                                           2829
```

<210> SEQ ID NO 7
<211> LENGTH: 4081
<212> TYPE: DNA
<213> ORGANISM: Homo sapiens

<400> SEQUENCE: 7

```
ccgaggaaaa cgttgcgcag gttcaaaaat ggaacgtcgg cggcgtgagg gagcgcgagg     60

gggtgtgcgc gcgtgcgcgt gcgcgtgcgc gcccggacga gggtgacggg gaccccgcca    120

gccccagcat cgcgcgccgc agccgcggcc ccgcagctcc gcccccggcc cggcccggcc    180

ccgggcccgc tcgcccgccg ccccgcatgg agctgtcagc catcggcgag caggtgttcg    240

ccgtggagag catccggaag aagcgcgtgc ggaagggtaa agtcgagtat ctggtgaagt    300
```

```
ggaaaggatg gcccccaaag tacagcacgt gggagccaga agagcacatc ttggaccccc    360
gcctcgtcat ggcctacgag gagaaggagg agagagaccg agcatcgggg tataggaaga    420
gaggtccgaa acccaagcgg cttctgctgc agcggctgta cagcatggac ctgcggagct    480
cccacaaggc caagggcaag gagaagctct gcttctccct gacgtgccca ctcggcagcg    540
ggagccctga gggggtggtc aaggcggggg cacctgagct ggtggacaag ggcccccttgg   600
tgcccaccct gcccttcccg ctccgcaagc cccgaaaggc ccacaagtac ctgcggctct    660
cgcgcaagaa gttcccgccc cgcgggccca acctggagag ccacagccat cgacgggagc    720
tcttcctgca ggagccaccg gccccagacg tcctgcaggc ggctggcgag tgggagcctg    780
ctgcgcagcc ccctgaagag gaggcagatg ccgacctggc cgagggggccc cctccctgga   840
cacctgcgct cccctcaagt gaggtgaccg tgaccgacat caccgccaac tccatcaccg    900
tcaccttccg cgaggcccag gcagctgagg gcttcttccg agaccgcagt gggaagttct    960
gaatcaccgt tttactcttt cttaaactgt tttcttttgg gcttggggtg ggacttccag   1020
agatagggat gggttggggg cggggtaatt attttattta aaaaaatacc gagcagcaaa   1080
aggggagaag atcccactac tctcccacca cctgcccttt ctctgaggga cgtttaccac   1140
gaggcctcag gctggggatg gagagagttg ctctgggagt tggggtacca cccccagggc   1200
aggatgggga caggatcacc tgcccgggac accaccatta tcattctcct ctagtgacgc   1260
agcagctggt tctgggagtt aaaggagcat tggaaggccc aaaccctctc ccttgagtgg   1320
ccaccccagc ctggttggct ggttttcccc ttttctcttg tttcaattgg gtctttacct   1380
tgaactctcc tctctggctt tgcggtgggc tgtggaggct ggttttgacc aaaagtgagt   1440
ggggcgggag gaaggggcag gaggaagggt tgaggttact tggggcgagt cccttcccct   1500
tcagagaggc ttctatcctt cccagggagg aggcgccgct gagacccttc tgctgagagc   1560
tctgccctcc cctcatcacc tggcctgtgc agaaacgctc atgcacacct ggctgcacag   1620
gtgtgcacgc attacccttc gcgtgtacgt tcccatgtgc cccgtgaaag catgtgtggc   1680
tgcagacgtg tccacatggg ccttgcgaac ctgggttaga aaccctggcc aggcgaacgt   1740
ggggtgattc acagcacaaa agacctcacc accacacctg cactcacccc accttgcatg   1800
caccttgcta cctgcttgcg gctttcagtg gagggcaggg gtctggcaca ggtgcgatgg   1860
caccccatgc tccaggcata cagatgtggt ttctcggctg caccgggcca ggctgcgggt   1920
gtgcaggcgt ctgctaagtt gtgtgatgta tcagcacagg ctttgagacg tctggaccct   1980
gtccttcctc ccgtgagggg ttcttgttct ttctgactca ggtgactttt cagcccttcc   2040
aattcccctc tttttctgcc ctcccctcca actcagccaa cccaggtgtg ggcagtcagg   2100
gagggaggga gtgtcccacc acgttctcag ggcagccctt gactcctaag ccccttcctc   2160
cttccattct gcatcccctc cccatccaac ctaaatgcca cagctggggc tgagctgtat   2220
tcctgtggag ggacctctgc cgtgcctctc tgaggtcagg ctgtgctgtg tgatgggcag   2280
gctttgcccc agcccacccc tggcaaggtg cacttgtttt ctggtttgta caaggtgtcc   2340
tgggggcccg tggcttccct gccagtgagg agtgacttct ccctctcttc cagtcctgta   2400
ggggagacaa aaccagattg gggggcccaa ggggagcatg gaaaaggccg gctcccctgt   2460
ctttccttgg ctgtcagagt cagggtaaca cacaccaaga gtggagtgcg gccagcaagt   2520
ttgagacctg cccgccctcc tcgcagctct gctctgtgtc ctcaggaagt cacagagtct   2580
actgaggcaa ggagagggtg attctttccc caaatccctt cttccctggt tcccaaacca   2640
```

```
aagacagcct gcagcccttt ctgcatgggg tgctctgttg acaggcttcc cagatccctg   2700

agtctctctt tccttcctcc tcgatcttta gttgtccacg gtcaattcag tgcttccatt   2760

gggggacagt cccctccggg atgacctgat tcacctccag cccagggaat ggaatctaga   2820

ggaatacgtg gggtgggtct ggacaaggag cggcaggaat caccacccat ctccagctgt   2880

ggagccctgt ggaggggaag gggaagcttg gggttcagag gggactcttc caggagaggg   2940

gtgcccagcg gaggtaaaga tgatagaggg ttgtgggggg tctctagttg aatgttttgg   3000

cccatgactt tggaacatgg ctggcagctt ccagcagaag tcacgctccc catcccccag   3060

gggacatagg acctttttcc tgcttcctgg tcactttcaa agaactattt gcgcaatctg   3120

tgggtctgtg gattcacggg gctttctgtg tgggtgctgc agttgctttt gtctgcagca   3180

gcaggacaca tctttcctct tactcagccc tttatggccc atggggaact ccgtggctca   3240

gggagagctg aactccaggg gtgtgacctg ggacgggtgg gcctgaggtg cccagctcag   3300

ggcagccagg tggctcatgg gctgtagtga gccagctccc tgggggaaaa ggctgtgggc   3360

cgttaggacc atcctccagg acaggtgacc tctatgaggt cacctacggc tgtggccgtg   3420

caggcctcct tccagcccag agtggcccag tagagcaagg cagacagtga cctccacccc   3480

cgcagccctc ttaaaaggcc agtactcttg gggtggggg gagggtttag aaagcatttg   3540

cccatctgcc tttctttccc ccagccccca cccgctttga atgtagagac ccgtgggcac   3600

ttttcctttt gtggtggggg gtgcggagga ggtaccccca cccctggcac agccgcctgg   3660

aatgcaggac tgtcactgct gttcgggtga tgacctcgtt gccaagctcc tcctgtcccc   3720

ttgttctggg ggcaggcgct gtgcttctgt gaggtggttt agcttttgct ttcgaagtgg   3780

ccagctgcgg ccaccaggtc tcagcacaag agcgcttcct ttgcacagaa tgagcttcga   3840

gctttgttca gactaaatga atgtatctgg gaggggtcgg gggcacgagt tgattccaag   3900

cacatgcctt tgctgagtgt gtgtgtgctg ggagagtcag agtggatgta gagcgcggtt   3960

ttatttttgt actgacattg gtaagagact gtatagcatc tatttattta gatgatttat   4020

ctggtaaatg aggcaaaaaa attattaaaa atacattaaa gatgatttaa aaaaaagaaa   4080

a                                                                  4081
```

<210> SEQ ID NO 8
<211> LENGTH: 3865
<212> TYPE: DNA
<213> ORGANISM: Homo sapiens

<400> SEQUENCE: 8

```
tttttcaatt ttgaacattt tgcaaaacga ggggttcgag gcaggtgaga gcatcctgca     60

cgtcgccggg gagcccgcgg gcacttggcg cgctctcctg ggaccgtctg cactggaaac    120

ccgaaagttt ttttttaata tatattttta tgcagatgta tttataaaga tataagtaat    180

tttttcttc cctttctcc accgccttga gagcgagtac ttttggcaaa ggacggagga    240

aaagctcagc aacattttag gggcggttg tttctttctt tcttatttct tttttaaggg    300

gaaaaaattt gagtgcatcg cgatggagaa aatgtcccga ccgctccccc tgaatcccac    360

ctttatcccg cctccctacg gcgtgctcag gtccctgctg gagaacccgc tgaagctccc    420

ccttcaccac gaagacgcat ttagtaaaga taaagacaaa gaaaagaagc tggatgatga    480

gagtaacagc ccgacggtcc cccagtcggc attcctgggg cctaccttat gggacaaaac    540

ccttccctat gacggagata ctttccagtt ggaatacatg gacctggagg agtttttgtc    600

agaaaatggc attcccccca gcccatctca gcatgaccac agccctcacc ctcctgggct    660
```

```
gcagccagct tcctcggctg ccccctcggt catggacctc agcagccggg cctctgcacc    720
ccttcaccct ggcatcccat ctccgaactg tatgcagagc cccatcagac caggtcagct    780
gttgccagca aaccgcaata caccaagtcc cattgatcct gacaccatcc aggtcccagt    840
gggttatgag ccagacccag cagatcttgc cctttccagc atccctggcc aggaaatgtt    900
tgaccctcgc aaacgcaagt tctctgagga agaactgaag ccacagccca tgatcaagaa    960
agctcgcaaa gtcttcatcc ctgatgacct gaaggatgac aagtactggg caaggcgcag   1020
aaagaacaac atggcagcca agcgctcccg cgacgcccgg aggctgaaag agaaccagat   1080
cgccatccgg gcctcgttcc tggagaagga gaactcggcc ctccgccagg aggtggctga   1140
cttgaggaag gagctgggca aatgcaagaa catacttgcc aagtatgagg ccaggcacgg   1200
gcccctgtag gatggcattt ttgcaggctg gctttggaat agatggacag tttgtttcct   1260
gtctgatagc accacacgca aaccaacctt tctgacatca gcactttacc agaggcataa   1320
acacaactga ctcccatttt ggtgtgcatc tgtgtgtgtg tgcgtgtata tgtgcttgtg   1380
ctcatgtgtg tggtcagcgg tatgtgcgtg tgcgtgttcc tttgctcttg ccattttaag   1440
gtagccctct catcgtcttt tagttccaac aaagaaaggt gccatgtctt tactagactg   1500
aggagccctc tcgcgggtct cccatcccct ccctccttca ctcctgcctc ctcagctttg   1560
cttcatgttc gagcttacct actcttccag gactctctgc ttggattcac taaaaagggc   1620
cctggtaaaa tagtggatct cagtttttaa gagtacaagc tcttgtttct gtttagtccg   1680
taagttacca tgctaatgag gtgcacacaa taacttagca ctactccgca gctctagtcc   1740
tttataagtt gctttcctct tactttcagt tttggtgata atcgtcttca aattaaagtg   1800
ctgtttagat ttattagatc ccatatttac ttactgctat ctactaagtt tccttttaat   1860
tctaccaacc ccagataagt aagagtacta ttaatagaac acagagtgtg tttttgcact   1920
gtctgtacct aaagcaataa tcctattgta cgctagagca tgctgcctga gtattactag   1980
tggacgtagg atattttccc tacctaagaa tttcactgtc ttttaaaaaa caaaaagtaa   2040
agtaatgcat ttgagcatgg ccagactatt ccctaggaca aggaagcaga gggaaatggg   2100
aggtctaagg atgaggggtt aatttatcag tacatgagcc aaaaactgcg tcttggatta   2160
gcctttgaca ttgatgtgtt cggttttgtt gttccccttc cctcacaccc tgcctcgccc   2220
ccacttttct agttaacttt ttccatatcc ctcttgacat tcaaaacagt tacttaagat   2280
tcagttttcc cactttttgg taatatatat atttttgtga attatacttt gttgttttta   2340
aaaagaaaat cagttgatta agttaataag ttgatgtttt ctaaggccct ttttcctagt   2400
ggtgtcattt ttgaatgcct cataaattaa tgattctgaa gcttatgttt cttattctct   2460
gtttgctttt gaacgtatgt gctcttataa agtggacttc tgaaaaatga atgtaaaaga   2520
cactggtgta tctcagaagg ggatggtgtt gtcacaaact gtggttaatc caatcaattt   2580
aaatgtttac tatagaccaa aaggagagat tattaaatcg tttaatgttt atacagagta   2640
attataggaa gttctttttt gtacagtatt tttcagatat aaatactgac aatgtatttt   2700
ggaagacata tattatatat agaaaagagg agaggaaaac tattccatgt tttaaaatta   2760
tatagcaaag atatatattc accaatgttg tacagagaag aagtgcttgg gggtttttga   2820
agtctttaat attttaagcc ctatcactga cacatcagca tgttttctgc tttaaattaa   2880
aattttatga cagtatcgag gcttgtgatg acgaatcctg ctctaaaata cacaaggagc   2940
tttcttgttt cttattaggc ctcagaaaga agtcagttaa cgtcacccaa aagcacaaaa   3000
```

```
tggattttag tcaaatattt attggatgat acagtgtttt ttaggaaaag catctgccac   3060

aaaaatgttc acttcgaaat tctgagttcc tggaatggca cgttgctgcc agtgccccag   3120

acagttcttt tctaccctgc gggcccgcac gttttatgag gttgatatcg gtgctatgtg   3180

tttggtttat aatttgatag atgtttgact ttaaagatga ttgttctttt gtttcattaa   3240

gttgtaaaat gtcaagaaat tctgctgtta cgacaaagaa acattttacg ctagattaaa   3300

atatcctttc atcaatggga ttttctagtt tcctgccttc agagtatcta atcctttaat   3360

gatctggtgg tctcctcgtc aatccatcag caatgcttct ctcatagtgt catagacttg   3420

ggaaacccaa ccagtaggat atttctacaa ggtgttcatt ttgtcacaag ctgtagataa   3480

cagcaagaga tgggggtgta ttggaattgc aatacattgt tcaggtgaat aataaaatca   3540

aaaacttttg caatcttaag cagagataaa taaaagatag caatatgaga cacaggtgga   3600

cgtagagttg gcctttttac aggcaaagag gcgaattgta gaattgttag atggcaatag   3660

tcattaaaaa catagaaaaa tgatgtcttt aagtggagaa ttgtggaagg attgtaacat   3720

ggaccatcca aatttatggc cgtatcaaat ggtagctgaa aaaactatat ttgagcactg   3780

gtctctcttg gaattagatg tttatatcaa atgagcatct caaatgtttt ctgcagaaaa   3840

aaataaaaag attctaataa aaaaa                                         3865
```

<210> SEQ ID NO 9
<211> LENGTH: 2656
<212> TYPE: DNA
<213> ORGANISM: Homo sapiens

<400> SEQUENCE: 9

```
cacacctgat ggtgtgactc ggccgacgcg agcgccgcgc ttcgcttcag ctgctagctg     60

gcccaaggga ggcgaccgcg gagggtggcg aggggcggcc aggacccgca gccccggggc    120

cgggccggtc cggaccgcca gggagggcag gtcagtgggc agatcgcgtc cgcgggattc    180

aatctctgcc cgctctgata acagtccttt tccctggcgc tcacttcgtg cctggcaccc    240

ggctgggcgc ctcaagaccg ttgtctcttc gatcgcttct ttggacttgg cgaccatttc    300

agagatgtct tccagaagta ccaaagattt aattaaaagt aagtggggat cgaagcctag    360

taactccaaa tccgaaacta cattagaaaa attaaaggga gaaattgcac acttaaagac    420

atcagtggat gaaatcacaa gtgggaaagg aaagctgact gataaagaga gacacagact    480

tttggagaaa attcgagtcc ttgaggctga gaaggagaag aatgcttatc aactcacaga    540

gaaggacaaa gaaatacagc gactgagaga ccaactgaag gccagatata gtactaccgc    600

attgcttgaa cagctggaag agacaacgag agaaggagaa aggagggagc aggtgttgaa    660

agccttatct gaagagaaag acgtattgaa acaacagttg tctgctgcaa cctcacgaat    720

tgctgaactt gaaagcaaaa ccaatacact ccgtttatca cagactgtgg ctccaaactg    780

cttcaactca tcaataaata atattcatga aatggaaata cagctgaaag atgctctgga    840

gaaaaatcag cagtggctcg tgtatgatca gcagcgggaa gtctatgtaa aaggactttt    900

agcaaagatc tttgagttgg aaaagaaaac ggaaacagct gctcattcac tcccacagca    960

gacaaaaaag cctgaatcag aaggttatct tcaagaagag aagcagaaat gttacaacga   1020

tctcttggca agtgcaaaaa aagatcttga ggttgaacga caaaccataa ctcagctgag   1080

ttttgaactg agtgaatttc gaagaaaata tgaagaaacc caaaaagaag ttcacaattt   1140

aaatcagctg ttgtattcac aaagaagggc agatgtgcaa catctggaag atgataggca   1200

taaaacagag aagatacaaa aactcaggga agagaatgat attgctaggg gaaaacttga   1260
```

```
agaagagaag aagagatccg aagagctctt atctcaggtc cagtttcttt acacatctct   1320

gctaaagcag caagaagaac aaacaagggt agctctgttg gaacaacaga tgcaggcatg   1380

tactttagac tttgaaaatg aaaaactcga ccgtcaacat gtgcagcatc aattgcatgt   1440

aattcttaag gagctccgaa aagcaagaaa tcaaataaca cagttggaat ccttgaaaca   1500

gcttcatgag tttgccatca cagagccatt agtcactttc caaggagaga ctgaaaacag   1560

agaaaaagtt gccgcctcac caaaaagtcc cactgctgca ctcaatgaaa gcctggtgga   1620

atgtcccaag tgcaatatac agtatccagc cactgagcat cgcgatctgc ttgtccatgt   1680

ggaatactgt tcaaagtagc aaaataagta tttgttttga tattaaaaga ttcaatactg   1740

tattttctgt tagcttgtgg gcattttgaa ttatatattt cacattttgc ataaaactgc   1800

ctatctacct ttgacactcc agcatgctag tgaatcatgt atcttttagg ctgctgtgca   1860

tttctcttgg cagtgatacc tccctgacat ggttcatcat caggctgcaa tgacagaatg   1920

tggtgagcag cgtctactga gactactaac attttgcact gtcaaaatac ttggtgagga   1980

aaagatagct caggttattg ctaatgggtt aatgcaccag caagcaaaat attttatgtt   2040

ttgggggttt tgaaaaatca aagataatta accaaggatc ttaactgtgt tcgcattttt   2100

tatccaagca cttagaaaac ctacaatcct aatttgatg tccattgtta agaggtggtg   2160

atagatacta ttttttttt catattgtat agcggttatt agaaaagttg ggattttct   2220

tgatctttat tgctgcttac cattgaaact taacccagct gtgttcccca actctgttct   2280

gcgcacgaaa cagtatctgt ttgaggcata atcttaagtg gccacacaca atgttttctc   2340

ttatgttatc tggcagtaac tgtaacttga attacattag cacattctgc ttagctaaaa   2400

ttgttaaaat aaactttaat aaacccatgt agccctctca tttgattgac agtattttag   2460

ttatttttgg cattcttaaa gctgggcaat gtaatgatca gatctttgtt tgtctgaaca   2520

ggtattttta tacatgcttt ttgtaaacca aaaactttta aatttcttca ggtttctaa    2580

catgcttacc actgggctac tgtaaatgag aaaagaataa aattatttaa tgttttaaaa   2640

aaaaaaaaaa aaaaaa                                                   2656
```

<210> SEQ ID NO 10
<211> LENGTH: 3685
<212> TYPE: DNA
<213> ORGANISM: Homo sapiens

<400> SEQUENCE: 10

```
agtggactca cgcaggcgca ggagactaca cttcccagga actccgggcc gcgttgttcg     60

ctggtacctc cttctgactt ccggtattgc tgcggtctgt agggccaatc gggagcctgg    120

aattgctttc ccggcgctct gattggtgca ttcgactagg ctgcctgggt tcaaaatttc    180

aacgatactg aatgagtccc gcggcgggtt ggctcgcgct tcgttgtcag atctgaggcg    240

aggctaggtg agccgtggga agaaaagagg gagcagctag ggcgcgggtc tccctcctcc    300

cggagtttgg aacggctgaa gttcaccttc cagcccctag cgccgttcgc gccgctaggc    360

ctggcttctg aggcggttgc ggtgctcggt cgccgcctag gcggggcagg gtgcgagcag    420

gggcttcggg ccacgcttct cttggcgaca ggattttgct gtgaagtccg tccgggaaac    480

ggaggaaaaa aagagttgcg ggaggctgtc ggctaataac ggttcttgat acatatttgc    540

cagacttcaa gatttcagaa aaggggtgaa agagaagatt gcaactttga gtcagacctg    600

taggcctgat agactgatta aaccacagaa ggtgacctgc tgagaaaagt ggtacaaata    660
```

```
ctgggaaaaa cctgctcttc tgcgttaagt gggagacaat gtcacaagtt aaaagctctt    720
attcctatga tgccccctcg gatttcatca atttttcatc cttggatgat gaaggagata    780
ctcaaaacat agattcatgg tttgaggaga aggccaattt ggagaataag ttactgggga    840
agaatggaac tggagggctt tttcagggca aaactccttt gagaaaggct aatcttcagc    900
aagctattgt cacacctttg aaaccagttg acaacactta ctacaaagag gcagaaaaag    960
aaaatcttgt ggaacaatcc attccgtcaa atgcttgttc ttccctggaa gttgaggcag   1020
ccatatcaag aaaaactcca gcccagcctc agagaagatc tcttaggctt tctgctcaga   1080
aggatttgga acagaaagaa aagcatcatg taaaaatgaa agccaagaga tgtgccactc   1140
ctgtaatcat cgatgaaatt ctaccctcta agaaaatgaa agtttctaac aacaaaaaga   1200
agccagagga agaaggcagt gctcatcaag atactgctga aaagaatgca tcttccccag   1260
agaaagccaa gggtagacat actgtgcctt gtatgccacc tgcaaagcag aagtttctaa   1320
aaagtactga ggagcaagag ctggagaaga gtatgaaaat gcagcaagag gtggtggaga   1380
tgcggaaaaa gaatgaagaa ttcaagaaac ttgctctggc tggaataggg caacctgtga   1440
agaaatcagt gagccaggtc accaaatcag ttgacttcca cttccgcaca gatgagcgaa   1500
tcaaacaaca tcctaagaac caggaggaat ataaggaagt gaactttaca tctgaactac   1560
gaaagcatcc ttcatctcct gcccgagtga ctaagggatg taccattgtt aagcctttca   1620
acctgtccca aggaaagaaa agaacatttg atgaaacagt ttctacatat gtgccccttg   1680
cacagcaagt tgaagacttc cataaacgaa cccctaacag atatcatttg aggagcaaga   1740
aggatgatat taacctgtta ccctccaaat cttctgtgac caagatttgc agagacccac   1800
agactcctgt actgcaaacc aaacaccgtg cacgggctgt gacctgcaaa agtacagcag   1860
agctggaggc tgaggagctc gagaaattgc aacaatacaa attcaaagca cgtgaacttg   1920
atcccagaat acttgaaggt gggcccatct tgcccaagaa accacctgtg aaaccaccca   1980
ccgagcctat tggctttgat ttggaaattg agaaaagaat ccaggagcga gaatcaaaga   2040
agaaaacaga ggatgaacac tttgaatttc attccagacc ttgccctact aagattttgg   2100
aagatgttgt gggtgttcct gaaaagaagg tacttccaat caccgtcccc aagtcaccag   2160
cctttgcatt gaagaacaga attcgaatgc ccaccaaaga agatgaggaa gaggacgaac   2220
cggtagtgat aaaagctcaa cctgtgccac attatggggt gccttttaag ccccaaatcc   2280
cagaggcaag aactgtggaa atatgccctt tctcgtttga ttctcgagac aaagaacgtc   2340
agttacagaa ggagaagaaa ataaaagaac tgcagaaagg ggaggtgccc aagttcaagg   2400
cacttccctt gcctcatttt gacaccatta acctgccaga gaagaaggta aagaatgtga   2460
cccagattga acctttctgc ttggagactg acagaagagg tgctctgaag gcacagactt   2520
ggaagcacca gctggaagaa gaactgagac agcagaaaga agcagcttgt ttcaaggctc   2580
gtccaaacac cgtcatctct caggagccct ttgttcccaa gaaagagaag aaatcagttg   2640
ctgagggcct ttctggttct ctagttcagg aaccttttca gctggctact gagaagagag   2700
ccaaagagcg gcaggagctg gagaagagaa tggctgaggt agaagcccag aaagcccagc   2760
agttggagga ggccagacta caggaggaag agcagaaaaa agaggagctg gccaggctac   2820
ggagagaact ggtgcataag gcaaatccaa tacgcaagta ccagggtctg gagataaagt   2880
caagtgacca gcctctgact gtgcctgtat ctcccaaatt ctccactcga ttccactgct   2940
aaactcagct gtgagctgcg gataccgccc ggcaatggga cctgctctta acctcaaacc   3000
taggaccgtc ttgctttgtc attgggcatg gagagaaccc atttctccag acttttacct   3060
```

```
acccgtgcct gagaaagcat acttgacaac tgtggactcc agttttgttg agaattgttt   3120
tcttacatta ctaaggctaa taatgagatg taactcatga atgtctcgat tagactccat   3180
gtagttactt cctttaaacc atcagccggc cttttatatg ggtcttcact ctgactagaa   3240
tttagtctct gtgtcagcac agtgtaatct ctattgctat tgccccttac gactctcacc   3300
ctctccccac ttttttaaa aattttaacc agaaaataaa gatagttaaa tcctaagata   3360
gagattaagt catggtttaa atgaggaaca atcagtaaat cagattctgt cctcttctct   3420
gcataccgtg aatttatagt taaggatccc tttgctgtga gggtagaaaa cctcaccaac   3480
tgcaccagtg aggaagaaga ctgcgtggat tcatggggag cctcacagca gccacgcagc   3540
aggctctggg tggggctgcc gttaaggcac gttctttcct tactggtgct gataacaaca   3600
gggaaccgtg cagtgtgcat tttaagacct ggcctggaat aaatacgttt tgtctttccc   3660
tcaaaaaaaa aaaaaaaaaa aaaaa                                          3685
```

<210> SEQ ID NO 11
<211> LENGTH: 3670
<212> TYPE: DNA
<213> ORGANISM: Homo sapiens

<400> SEQUENCE: 11

```
ccggtttgtt agggagtcgt gtacgtgcct tggtcgcttc tgtagctccg agggcaggtt     60
gcggaagaaa gcccaggcgg tctgtggccc agaggaaagg cctgcagcag gacgaggacc    120
tgagccagga atgcaggatg gcggcggtga agaaggaagg gggtgctctg agtgaagcca    180
tgtccctgga gggagatgaa tgggaactga gtaaagaaaa tgtacaacct ttaaggcaag    240
ggcggatcat gtccacgctt cagggagcac tggcacaaga atctgcctgt aacaatactc    300
ttcagcagca gaaacgggca tttgaatatg aaattcgatt ttacactgga aatgaccctc    360
tggatgtttg ggataggtat atcagctgga cagagcagaa ctatcctcaa ggtgggaagg    420
agagtaatat gtcaacgtta ttagaaagag ctgtagaagc actacaagga gaaaaacgat    480
attatagtga tcctcgattt ctcaatctct ggcttaaatt agggcgttta tgcaatgagc    540
ctttggatat gtacagttac ttgcacaacc aagggattgg tgtttcactt gctcagttct    600
atatctcatg ggcagaagaa tatgaagcta gagaaaactt taggaaagca gatgcgatat    660
ttcaggaagg gattcaacag aaggctgaac cactagaaag actacagtcc cagcaccgac    720
aattccaagc tcgagtgtct cggcaaactc tgttggcact tgagaaagaa gaagaggagg    780
aagtttttga gtcttctgta ccacaacgaa gcacactagc tgaactaaag agcaaaggga    840
aaaagacagc aagagctcca atcatccgtg taggaggtgc tctcaaggct ccaagccaga    900
acagaggact ccaaaatcca tttcctcaac agatgcaaaa taatagtaga attactgttt    960
ttgatgaaaa tgctgatgag gcttctacag cagagttgtc taagcctaca gtccagccat   1020
ggatagcacc ccccatgccc agggccaaag agaatgagct gcaagcaggc ccttggaaca   1080
caggcaggtc cttggaacac aggcctcgtg gcaatacagc ttcactgata gctgtacccg   1140
ctgtgcttcc cagtttcact ccatatgtgg aagagactgc acgacagcca gttatgacac   1200
catgtaaaat tgaacctagt ataaaccaca tcctaagcac cagaaagcct ggaaaggaag   1260
aaggagatcc tctacaaagg gttcagagcc atcagcaagc gtctgaggag aagaaagaga   1320
agatgatgta ttgtaaggag aagatttatg caggagtagg ggaattctcc tttgaagaaa   1380
ttcgggctga agttttccgg aagaaattaa aagagcaaag ggaagccgag ctattgacca   1440
```

```
gtgcagagaa gagagcagaa atgcagaaac agattgaaga gatggagaag aagctaaaag   1500
aaatccaaac tactcagcaa gaaagaacag gtgatcagca agaagagacg atgcctacaa   1560
aggagacaac taaactgcaa attgcttccg agtctcagaa aataccagga atgactctat   1620
ccagttctgt ttgtcaagta aactgttgtg ccagagaaac ttcacttgcg gagaacattt   1680
ggcaggaaca acctcattct aaaggtccca gtgtaccttt ctccattttt gatgagtttc   1740
ttctttcaga aaagaagaat aaaagtcctc ctgcagatcc cccacgagtt ttagctcaac   1800
gaagacccct tgcagttctc aaaacctcag aaagcatcac ctcaaatgaa gatgtgtctc   1860
cagatgtttg tgatgaattt acaggaattg aacccttgag cgaggatgcc attatcacag   1920
gcttcagaaa tgtaacaatt tgtcctaacc cagaagacac ttgtgacttt gccagagcag   1980
ctcgttttgt atccactcct tttcatgaga taatgtcctt gaaggatctc ccttctgatc   2040
ctgagagact gttaccggaa gaagatctag atgtaaagac ctctgaggac cagcagacag   2100
cttgtggcac tatctacagt cagactctca gcatcaagaa gctgagccca attattgaag   2160
acagtcgtga agccacacac tcctctggct tctctggttc ttctgcctcg gttgcaagca   2220
cctcctccat caaatgtctt caaattcctg agaaactaga acttactaat gagacttcag   2280
aaaaccctac tcagtcacca tggtgttcac agtatcgcag acagctactg aagtccctac   2340
cagagttaag tgcctctgca gagttgtgta tagaagacag accaatgcct aagttggaaa   2400
ttgagaagga aattgaatta ggtaatgagg attactgcat taaacgagaa tacctaatat   2460
gtgaagatta caagttattc tgggtggcgc caagaaactc tgcagaatta acagtaataa   2520
aggtatcttc tcaacctgtc ccatgggact tttatatcaa cctcaagtta aaggaacgtt   2580
taaatgaaga ttttgatcat ttttgcagct gttatcaata tcaagatggc tgtattgttt   2640
ggcaccaata tataaactgc ttcacccttc aggatcttct ccaacacagt gaatatatta   2700
cccatgaaat aacagtgttg attatttata accttttgac aatagtggag atgctacaca   2760
aagcagaaat agtccatggt gacttgagtc caaggtgtct gattctcaga aacagaatcc   2820
acgatcccta tgattgtaac aagaacaatc aagctttgaa gatagtggac ttttcctaca   2880
gtgttgacct tagggtgcag ctggatgttt ttaccctcag cggctttcgg actgtacaga   2940
tcctggaagg acaaaagatc ctggctaact gttcttctcc ctaccaggta gacctgtttg   3000
gtatagcaga tttagcacat ttactattgt tcaaggaaca cctacaggtc ttctgggatg   3060
ggtccttctg gaaacttagc caaaatattt ctgagctaaa agatggtgaa ttgtggaata   3120
aattctttgt gcggattctg aatgccaatg atgaggccac agtgtctgtt cttggggagc   3180
ttgcagcaga aatgaatggg gtttttgaca ctacattcca aagtcacctg aacaaagcct   3240
tatggaaggt agggaagtta actagtcctg gggctttgct ctttcagtga gctaggcaat   3300
caagtctcac agattgctgc ctcagagcaa tggttgtatt gtggaacact gaaactgtat   3360
gtgctgtaat ttaatttagg acacatttag atgcactacc attgctgttc tacttttttgg   3420
tacaggtata ttttgacgtc actgatattt tttatacagt gatatactta ctcatggcct   3480
tgtctaactt ttgtgaagaa ctattttatt ctaaacagac tcattacaaa tggttacctt   3540
gttatttaac ccatttgtct ctacttttcc ctgtactttt cccatttgta atttgtaaaa   3600
tgttctctta tgatcaccat gtattttgta aataataaaa tagtatctgt taaaaaaaaa   3660
aaaaaaaaaa                                                          3670
```

<210> SEQ ID NO 12
<211> LENGTH: 4504

<212> TYPE: DNA
<213> ORGANISM: Homo sapiens

<400> SEQUENCE: 12

```
gggcagtccg cactgcaatt ggttggcgtc tccgggacgg atttgaaact tggcggttaa     60
agctccggct gggacagggc ggcgggaggc ccagggagaa cggggaaggg acatttagtt    120
tgagacggtg ctgagatagg atcatgaagg aagaggtgaa gggaattcct gtaagagtgg    180
cgctgcgttg tcgccctctg gtccccaaag agattagcga gggctgccag atgtgccttt    240
ccttcgtgcc cggagagcct caggtggtgg ttggtacaga taaatccttc acctacgatt    300
ttgtatttga tccctctact gaacaggaag aagtcttcaa tacagcagta gcgccactca    360
taaaaggtgt atttaaagga tataatgcaa cggtcctggc ctatgggcag actggctctg    420
gaaaaaccta ttcaatggga ggtgcatata ctgcagagca agagaatgaa ccaacagttg    480
gggttattcc tagggtaata caactgctct tcaaagaaat tgataaaaag agtgactttg    540
aatttactct gaaagtgtct tacttagaga tttacaatga agaaattttg gatcttctat    600
gcccatctcg tgagaaagct caaataaata tacgagagga tcctaaggaa ggcataaaga    660
ttgtgggact cactgagaag actgttttgg ttgccttgga tactgtttcc tgtttggaac    720
agggcaacaa ctctaggact gtggcctcca cggctatgaa ctcccagtcg tcccgatctc    780
atgccatctt tacaatctcc ttagagcaaa gaaagaaaag tgacaagaat agcagctttc    840
gctccaagct gcatcttgta gacctcgctg gatcagaaag acagaagaaa accaaggctg    900
aaggggatcg tctaaaagag ggtattaata ttaaccgagg cctcctatgc ttgggaaatg    960
taatcagtgc tcttggagat gacaaaaagg gtggctttgt gccctacaga gattccaagt   1020
tgactcgact gcttcaagat tctctaggag gtaatagcca tactcttatg atagcctgtg   1080
tgagtcctgc tgactccaat ctagaggaaa cattaaatac ccttcgctat gctgacagag   1140
caagaaaaat caagaacaaa cctattgtta atattgatcc ccagacagct gaacttaatc   1200
atctaaagca acaggtacaa cagctacaag tcttgttgct acaggcccat ggaggtaccc   1260
tgcctggatc tataactgtg gaaccatcag agaatctaca atccctgatg gagaagaatc   1320
agtccctggt agaggagaat gaaaaattaa gtcgtggtct gagcgaggca gctggtcaga   1380
cagcccagat gttggagagg atcattttga cagagcaagc gaatgaaaaa atgaacgcca   1440
agctagaaga gctcaggcag catgcggcct gcaaactgga tcttcaaaag ctagtggaga   1500
ctttggaaga ccaggaattg aaagaaaatg tagagataat ttgtaacctg cagcaattga   1560
ttacccagtt atcggatgaa actgttgctt gcatggctgc agccattgat actgcggtgg   1620
agcaagaagc ccaagtagaa accagtccag agacgagcag gtcttctgac gcttttacca   1680
ctcagcatgc tctccgtcaa gcgcagatgt ctaaggagct ggttgagttg aataaagcgc   1740
ttgcactgaa agaggccctg gctaggaaga tgactcagaa tgacagccaa ctgcagccca   1800
ttcagtacca ataccaggat aacataaaag agctagaatt agaagtcatc aatctgcaaa   1860
aggaaaagga agaattggtt cttgaacttc agacagcaaa gaaggatgcc aaccaagcca   1920
agttgagtga gcgccgccgc aaacgtctcc aggagctgga gggtcaaatt gctgatctga   1980
agaagaaact gaatgagcag tccaaacttc tgaaactaaa ggaatccaca gagcgtactg   2040
tctccaaact gaaccaggag atacggatga tgaaaaacca gcgggtacag ttaatgcgtc   2100
aaatgaaaga agatgctgag aagtttagac agtggaagca gaaaaaagac aaagaagtaa   2160
tacagttaaa agaacgagac cgtaagaggc aatatgagct gctgaaactt gaaagaaact   2220
```

```
tccagaaaca atccaatgtg ctcagacgta aaacggagga ggcagcagct gccaacaagc   2280
gtctcaagga tgctctccag aaacaacggg aggttgcaga taagcggaaa gagactcaga   2340
gccgtggaat ggaaggcact gcagctcgag tgaagaattg gcttggaaac gaaattgagg   2400
ttatggtcag tactgaggaa gccaaacgcc atctgaatga cctccttgaa gatagaaaga   2460
tcctggctca agatgtggct caactcaaag aaaaaaagga atctggggag aatccacctc   2520
ctaaactccg gaggcgtaca ttctccctta ctgaagtgcg tggtcaagtt tcggagtcag   2580
aagattctat tacaaagcag attgaaagcc tagagactga aatggaattc aggagtgctc   2640
agattgctga cctacagcag aagctgctgg atgcagaaag tgaagacaga ccaaaacaac   2700
gctgggagaa tattgccacc attctggaag ccaagtgtgc cctgaaatat ttgattggag   2760
agctggtctc ctccaaaata caggtcagca aacttgaaag cagcctgaaa cagagcaaga   2820
ccagctgtgc tgacatgcag aagatgctgt ttgaggaacg aaatcatttt gccgagatag   2880
agacagagtt acaagctgag ctggtcagaa tggagcaaca gcaccaagag aaggtgctgt   2940
accttctcag ccagctgcag caaagccaaa tggcagagaa gcagttagag gaatcagtca   3000
gtgaaaagga acagcagctg ctgagcacac tgaagtgtca ggatgaagaa cttgagaaaa   3060
tgcgagaagt gtgtgagcaa aatcagcagc ttctccgaga gaatgaaatc atcaagcaga   3120
aactgaccct cctccaggta gccagcagac agaaacatct tcctaaggat acccttctat   3180
ctccagactc ttcttttgaa tatgtcccac ctaagccaaa accttctcgt gttaaagaaa   3240
agttcctgga gcaaagcatg gacatcgagg atctaaaata ttgttcagag cattctgtga   3300
atgagcatga ggatggtgat ggtgatgatg atgaggggga tgacgaggaa tggaagccaa   3360
caaaattagt taaggtgtcc aggaagaaca tccaagggtg ttcctgcaag ggctggtgtg   3420
gaaacaagca gtgtgggtgc aggaagcaaa agtcagactg tggtgtggac tgttgctgtg   3480
accccacaaa gtgtcggaac cgccagcaag gcaaggatag cttgggcact gttgaacgga   3540
cccaggattc cgaaggctcc ttcaaactgg aggatcctac cgaggtgacc ccaggattga   3600
gcttctttaa tcccgtctgt gccacccccca atagcaagat cctgaaagag atgtgcgatg   3660
tggagcaggt gctgtcaaag aagactcccc cagctccctc ccctttttgac ctcccagagt   3720
tgaaacatgt agcaacagaa taccaagaaa acaaggctcc agggaagaaa aagaaacggg   3780
ctctggccag caacaccagc ttcttctctg gctgctcccc tatcgaagaa gaggcccact   3840
gaagttggag tcatcatctc tacccccagt ctggcttggg agatgctttc aggttgcagc   3900
cagaaggggt tttttaaatg acttctctgg atttcaggtt tcttgctgtt gaaaaaagga   3960
acaaagcgtt actgaaaaga aggtaacctt tgttggatgt gggccttagc ctccaggtcc   4020
agactactac tctatgttct ccagaagggt gctaagtcac ctactgaaga gagaaccaac   4080
tgactttcct attgactcat caggaaccag tcctcagtct ggtcaagttg tttcttattt   4140
gtgagcagtt caggctatct cctgatgggg atgaggccaa ggctttctta tcttttggtt   4200
gtctctgctt aatggaggag cctggcctag gatggaggcc tggcttagat ctttcattcc   4260
acctcaggaa tgaggttgtg atctttcctg tcctgaccct ctctgaatta tgtttcaata   4320
gtactcttga ttgtctgcca tgttgttgaa gcaaatgaat tatttttaaa tgttaagtaa   4380
gtaaataaac cttagcccgt ctactgtttg ggaagatcct tctgtgctag agggagaaat   4440
aaaatttcaa cctgtgttcc tcagcccctg aggaagctat taaggggatt cattacaagt   4500
aaaa                                                                4504
```

<210> SEQ ID NO 13
<211> LENGTH: 1566
<212> TYPE: DNA
<213> ORGANISM: Homo sapiens

<400> SEQUENCE: 13

```
gggccgccca atggggcgca agcgacgcgg tatttgaatc ctggaacaag gctacagcgt     60
cgaagatccc cagcgctgcg ggctcggaga gcagtcctaa cggcgcctcg tacgctagtg    120
tcctcccttt tcagtccgcg tccctccctg ggccgggctg gcactcttgc cttccccgtc    180
cctcatggcg ctgctccgac gcccgacggt gtccagtgat ttggagaata ttgacacagg    240
agttaattct aaagttaaga gtcatgtgac tattaggcga actgttttag aagaaattgg    300
aaatagagtt acaaccagag cagcacaagt agctaagaaa gctcagaaca ccaaagttcc    360
agttcaaccc accaaaacaa caaatgtcaa caaacaactg aaacctactg cttctgtcaa    420
accagtacag atggaaaagt tggctccaaa gggtccttct cccacacctg aggatgtctc    480
catgaaggaa gagaatctct gccaagcttt ttctgatgcc ttgctctgca aaatcgagga    540
cattgataac gaagattggg agaaccctca gctctgcagt gactacgtta aggatatcta    600
tcagtatctc aggcagctgg aggttttgca gtccataaac ccacatttct tagatggaag    660
agatataaat ggacgcatgc gtgccatcct agtggattgg ctggtacaag tccactccaa    720
gtttaggctt ctgcaggaga ctctgtacat gtgcgttggc attatggatc gatttttaca    780
ggttcagcca gtttcccgga agaagcttca attagttggg attactgctc tgctcttggc    840
ttccaagtat gaggagatgt tttctccaaa tattgaagac tttgtttaca tcacagacaa    900
tgcttatacc agttcccaaa tccgagaaat ggaaactcta attttgaaag aattgaaatt    960
tgagttgggt cgacccttgc cactacactt cttaaggcga gcatcaaaag ccggggaggt   1020
tgatgttgaa cagcacactt tagccaagta tttgatggag ctgactctca tcgactatga   1080
tatggtgcat tatcatcctt ctaaggtagc agcagctgct tcctgcttgt ctcagaaggt   1140
tctaggacaa ggaaaatgga acttaaagca gcagtattac acaggataca cagagaatga   1200
agtattggaa gtcatgcagc acatggccaa gaatgtggtg aaagtaaatg aaaacttaac   1260
taaattcatc gccatcaaga ataagtatgc aagcagcaaa ctcctgaaga tcagcatgat   1320
ccctcagctg aactcaaaag ccgtcaaaga ccttgcctcc ccactgatag gaaggtccta   1380
ggctgccgtg gcccctgggg atgtgtgctt cattgtgccc tttttcttat tggtttagaa   1440
ctcttgattt tgtacatagt cctctggtct atctcatgaa acctcttctc agaccagttt   1500
tctaaacata tattgaggaa aaataaagcg attggttttt cttaaggtaa aaaaaaaaaa   1560
aaaaaa                                                               1566
```

<210> SEQ ID NO 14
<211> LENGTH: 7293
<212> TYPE: DNA
<213> ORGANISM: Homo sapiens

<400> SEQUENCE: 14

```
ctggggagcc ggcgctggag gtggtgagtg gcgtggggac tgtgtcgagg gggtccccaa     60
ggtgccggac cctgcggagg ggcgaagttt cggcactggg gagggcgtgc ggacgctttc    120
cctacaggcg accactgctc tgcgggcggg tggtcttagc tccagtcccc cattcagttc    180
ctcagcattc caggtcggcg gcgaaggggt ccccgaacga agggcgcaag gcagcgtctc    240
tgctgggacc gggaagccgg acttcagggc ctctcggccc gtgggcttct ccccgagtct    300
```

-continued

```
ccccgagtcg gttggcatta agagtttagc agatactttc agaaatggat acataagaaa    360
tggctggaaa tcaaatgaat gtccaaagaa gagcttaggg tcttagtaac attctttttt    420
aaaataactg tctgccaaaa tgtcattaca cagtactcat aatagaaata acagcggtga    480
tattcttgat attccttctt cccaaaatag ttcatcactg aatgccctca cccacagtag    540
ccgacttaag ctgcatttga agtcggatat gtcagaatgt gaaaatgatg atccattatt    600
gagatctgca ggtaaagtca gagacataaa tagaacttat gttatttctg ccagtagaaa    660
aacagcagac atgcccctta cccctaatcc tgtaggtaga ttggcacttc agaggagaac    720
tacaaggaac aaagaatcat ctttgcttgt tagtgagttg gaagacacaa ctgaaaaaac    780
agcagaaaca cgtcttacat tacaacgtcg tgctaaaaca gattctgcag aaaagtggaa    840
aacagctgaa atagattctg tcaaaatgac actgaatgtg ggaggtgaaa cagaaaataa    900
tggtgtttct aaggaaagta gaacaaatgt aaggattgta aataatgcta aaaactcttt    960
tgttgcctct tctgtacctt tagatgaaga tccacaggtc attgaaatga tggctgataa   1020
gaaatacaaa gaaacatttt ctgcccccag tagagcaaat gaaaatgttg cacttaagta   1080
ctcaagtaat agaccaccca ttgcttccct gagtcagact gaagttgtta gatcaggaca   1140
cttgacaacg aaacctactc agagcaagtt ggatatcaaa gtgttgggaa caggaaactt   1200
gtatcataga agtattggga aggaaattgc aaaaacttca aataaatttg ggagcttaga   1260
aaaaagaaca cctacaaaat gtacaacaga acacaaactg acaacaaagt gcagcctgcc   1320
tcagcttaag agcccagctc catcaatact gaagaataga atgtctaacc ttcaagttaa   1380
acaaagacca aaaagttcct ttcttgcaaa taaacaggaa agatccgcag aaaatacaat   1440
tcttcccgaa gaagaaactg tagttcagaa cacctctgca ggaaaagacc ccttaaaagt   1500
agagaatagt caagtgacag tggcagtacg cgtaagacct ttcaccaaga gagagaagat   1560
tgaaaaagca tcccaggtag tcttcatgag tgggaaagaa ataactgtgg aacaccctga   1620
cacgaaacaa gtttataatt ttatttatga tgtttcattc tggtcttttg atgaatgtca   1680
tcctcactac gctagccaga caactgtcta tgagaagcta gcagcaccac tcctagaaag   1740
agccttcgaa ggcttcaata cctgtctttt tgcttatggt cagactggct ctggaaaatc   1800
atatacgatg atgggattta gtgaagaacc aggaataatt ccaagatttt gtgaagatct   1860
tttttctcaa gtagccagaa aacaaaccca agaggtcagc tatcacattg aaatgagctt   1920
ctttgaagta tataatgaaa aaattcacga ccttctggtt tgtaaagatg aaaatgggca   1980
gagaaagcaa ccactgagag tgagggaaca tcctgtttat ggaccatatg ttgaagcact   2040
gtcaatgaac attgtcagtt cttacgctga tatccagagt tggctagaat tgggaaataa   2100
acaaagagct actgctgcta ctggtatgaa tgataaaagt tcccgatctc attcagtttt   2160
caccctggtg atgacccaga ccaagacaga atttgtggaa ggggaagaac acgatcacag   2220
aataacaagt cgaattaacc taatagatct ggcaggcagt gagcgctgct ctacggctca   2280
cactaatgga gatcgactaa aggaaggtgt gagtattaat aagtccttgc taactttggg   2340
aaaagttata tctgcacttt cggaacaagc aaaccaaagg agtgttttta ttccttatcg   2400
tgaatctgtt cttacatggc tgttaaaaga aagtctgggt ggaaattcaa aaactgcaat   2460
gattgctacg attagtcccg ctgccagcaa catagaagaa acattaagca cacttagata   2520
tgctaaccaa gcccgtttaa tagtcaacat tgctaaagta aatgaagata tgaacgctaa   2580
gttaattaga gaattgaagg cagaaattgc aaagctaaaa gctgctcaga gaaacagtcg   2640
gaatattgac cctgaacgat acaggctctg tcggcaagaa ataacatcct taagaatgaa   2700
```

```
actgcatcaa caggagagag acatggcaga aatgcaaaga gtgtggaaag aaaagtttga   2760
acaagctgaa aaaagaaaac ttcaagaaac aaaagagtta cagaaagcag gaattatgtt   2820
tcaaatggac aatcatttac caaaccttgt taatctgaat gaagatccac aactatctga   2880
gatgctgcta tatatgataa aagaaggaac aactacagtt ggaaagtata aaccaaactc   2940
aagccatgat attcagttat ctggggtgct gattgctgat gatcattgta ctatcaaaaa   3000
ttttggtggg acagtgagta ttatcccagt tggggaagca aagacatatg taaatggaaa   3060
acatattttg gaaatcacag tattacgtca tggtgatcga gtgattcttg gtggagatca   3120
ttattttaga tttaatcatc cagtagaagt ccagaaagga aaaaggccat ctggaagaga   3180
tactcctata agtgagggtc caaaagactt tgaatttgca aaaaatgagt tgctcatggc   3240
acagagatca caacttgaag cagaaataaa agaggctcag ttgaaggcaa aggaagaaat   3300
gatgcaagga atccagattg caaaagaaat ggctcagcaa gagctttctt ctcaaaaagc   3360
tgcatatgaa agcaaaataa aagcactgga agcagaactg agagaagagt ctcaaaggaa   3420
aaaaatgcag gaaataaata accagaaggc taatcacaaa attgaggaat tagaaaaggc   3480
aaagcagcat cttgaacagg aaatatatgt caacaaaaag cgattagaaa tggaaacatt   3540
ggctacaaaa caggctttag aagaccatag catccgccat gcaagaattc tggaagcttt   3600
agaaactgaa aagcaaaaaa ttgctaaaga agtacaaatt ctacagcaga atcggaataa   3660
tagggataaa acttttacag tgcagacaac ttggagctct atgaaactct caatgatgat   3720
tcaggaagcc aatgctatca gcagcaaatt gaaaacatac tatgtttttg gcagacatga   3780
tatatcagat aaaagtagtt ctgacacttc tattcgggtt cgtaacctga aactaggaat   3840
ctcaacattc tggagtctgg aaaagtttga atctaaactt gcagcaatga aagaacttta   3900
tgagagtaat ggtagtaaca ggggtgaaga tgccttttgt gatcctgaag atgaatggga   3960
acccgacatt acagatgcac cagtttcttc actttctaga aggaggagta ggagtttgat   4020
gaagaacaga agaatttctg gttgtttaca tgacatacaa gtccatccaa ttaagaattt   4080
gcattcttca cattcatcag gtttaatgga caaatcaagc actatttact caaattcagc   4140
agagtccttt cttcctggaa tttgcaaaga attgattggt tcttcgttag atttttttgg   4200
acagagttat gatgaagaaa gaactatagc agacagccta attaatagtt ttcttaaaat   4260
ttataatggg ctatttgcca tttccaaggc tcatgaagaa caagatgaag aaagtcaaga   4320
taacttgttt tcttctgatc gagcaatcca gtcacttact attcagactg catgtgcttt   4380
tgagcagcta gtagtgctaa tgaaacactg gctgagtgat ttactgcctt gtaccaacat   4440
agcaagactt gaggatgagt tgagacaaga agttaaaaaa ctgggaggct acttacagtt   4500
atttttgcag ggatgctgtt tggatatttc atcaatgata aaagaggctc aaaagaatgc   4560
aatccaaatt gtacaacaag ctgtaaagta tgtggggcag ttagcagttc tgaaagggag   4620
caagctacat tttctagaaa acggtaacaa taaagctgcc agtgtccagg aggaattcat   4680
ggatgctgtt tgtgatggtg taggcttagg aatgaagatt ttattagatt ctggactgga   4740
aaaagcaaaa gaacttcagc atgaactctt taggcagtgt acaaaaaatg aggttaccaa   4800
agaaatgaaa actaatgcca tgggattgat tagatctctt gaaaacatct ttgctgaatc   4860
gaaaattaaa agtttcagaa ggcaagtaca agaagaaaac tttgaatacc aagatttcaa   4920
gaggatggtt aatcgtgctc cagaattctt aaagttaaaa cattgcttag agaaagctat   4980
tgaaattatt atttctgcac tgaaaggatg ccatagtgat ataaatcttc tccagacttg   5040
```

```
tgttgaaagt attcgcaact tggccagtga tttttacagt gacttcagtg tgccttctac   5100
ttctgttggc agctatgaga gtagagtaac tcacattgtc caccaggaac tagaatctct   5160
agctaagtct ctcctctttt gttttgaatc tgaagaaagc cctgatttgt tgaaaccctg   5220
ggaaacttat aatcaaaata ccaaagaaga acaccaacaa tctaaatcaa gcgggattga   5280
cggcagtaag aataaaggtg taccaaagcg tgtctatgag ctccatggct catccccagc   5340
agtgagctca gaggaatgca cacccagtag gattcagtgg gtgtgaatac tgatgtgtag   5400
gcacttttat gaccacccat gaaagaaaaa gaacacttgc tcggtaattt tctttatgca   5460
ggagagttta agagaaatca gcacagatat ttcaaaaaag tccatgtctt tttatcttta   5520
aaatatctat ttatcaaagg ccagacacag tggctcacgc ctgtaatccc agcactttgg   5580
gaggcgggca gatcacaagg tcaggagttt gagaccggcc tggccaacat ggcgaaaccc   5640
cgtctctact aaaaatacaa aaatttgctg ggcatggtgg cgcgtgcctg taatcccagc   5700
tactaggggg gctgaggcag gaggatcgct tgaacctgag aggcagaggt tgcagtgagc   5760
caagatcatg ccactttact ccagtctgag caacagaacg agacttagtc aaaataaata   5820
aataaataaa taaataaata aataaataaa taaataaaat atatttttat ctttaaagtg   5880
tttaacattg gtatactgtc tgtagttggt tcattagtcg tttataaagg gttattttct   5940
catgagtgga aacctgaaca atcagttacc tttgtgccta tgccttctct ctcctcagac   6000
agctgggatg tttatggtga aatggcctgt acaagtttaa ctaagacaac ttaacttgca   6060
ttgttaatca aaaattcttt tctcaaaggg ttaactggtt gccattttga atagtatgtt   6120
caagggtgta gcttcctgtt tctttccaaa ttataagtag ctacctaaat atagtataat   6180
tatatattaa taatatggct tgctggcaca gtagtttacc ctgttatctg tgtttcataa   6240
tgggggctgt atgaatatta tttaaaacta ataaaatgtt gccagaatta tactaaactg   6300
ttggatgaga ttaggagatc agaggctgga ccttctcttg ataatgcttg ttttgttaaa   6360
ggtataatga aataatttgt atatgatttg atgaagatta aagaccctta ttttccacag   6420
ctttaaaaaa aaacctttat ttatgatcaa gtaataaaga taatattcta cttgtgggat   6480
cttacattac ggaaatagtt tgacgttttt gacctcaaga gtatgtataa tttgaagaga   6540
tactttgtaa ctatgcttgg gtgatattga gcagttccta aagaataatt catttaaaaa   6600
aaaagaagaa aaaaaaagaa gaattcattt aaataacctg atcctttcat ttgccctttt   6660
cgaatttaca gatactactt gtacatttgg cataactagt tgaaattggc cattcgtacc   6720
atgaataaat ctgatagttt ccttgttagg aagagattgt aagtaaatac agtcattgca   6780
gtcagaacag tattagtgaa ccttgtgtgg tgttttcaag ctctttaaaa tggtacaatg   6840
tagcacattt gctttcattt cttttttat ttttggcatt tgaccttgta ttctttctga   6900
agctctatat gtgtttttat tagtcaataa tctggcaagt agcactttgc ctgtgcagtt   6960
tgctggagtg tagatgtaca tatgaggatt tcccgggagg tgcacttctt tgaagaactt   7020
cctaaagtac ctgtatagta gttttcatct taatattcag tatttaatct tcagtttgtg   7080
ctttgtaaac tcatgactta attggtcaga aactttttag tgtctttata aaattttgta   7140
tacatattta tactaaacac attgtgatac tgtatttgaa tgaatggtga aaaaatattt   7200
gctattggaa ttatgtgcac tgacaagaaa tgttataaag agaatgcctt taataaatct   7260
tttcagcatt agaattgaaa aaaaaaaaaa aaa                                7293
```

<210> SEQ ID NO 15
<211> LENGTH: 2486

<212> TYPE: DNA
<213> ORGANISM: Homo sapiens

<400> SEQUENCE: 15

```
gagatttgat tcccttggcg ggcggaagcg gccacaaccc ggcgatcgaa aagattctta     60
ggaacgccgt accagccgcg tctctcagga cagcaggccc ctgtccttct gtcgggcgcc    120
gctcagccgt gccctccgcc cctcaggttc tttttctaat tccaaataaa cttgcaagag    180
gactatgaaa gattatgatg aacttctcaa atattatgaa ttacatgaaa ctattgggac    240
aggtggcttt gcaaaggtca aacttgcctg ccatatcctt actggagaga tggtagctat    300
aaaaatcatg gataaaaaca cactagggag tgatttgccc cggatcaaaa cggagattga    360
ggccttgaag aacctgagac atcagcatat atgtcaactc taccatgtgc tagagacagc    420
caacaaaata ttcatggttc ttgagtactg ccctggagga gagctgtttg actatataat    480
ttcccaggat cgcctgtcag aagaggagac ccgggttgtc ttccgtcaga tagtatctgc    540
tgttgcttat gtgcacagcc agggctatgc tcacagggac ctcaagccag aaaatttgct    600
gtttgatgaa tatcataaat taaagctgat tgactttggt ctctgtgcaa aacccaaggg    660
taacaaggat taccatctac agacatgctg tgggagtctg gcttatgcag cacctgagtt    720
aatacaaggc aaatcatatc ttggatcaga ggcagatgtt tggagcatgg gcatactgtt    780
atatgttctt atgtgtggat ttctaccatt tgatgatgat aatgtaatgg ctttatacaa    840
gaagattatg agaggaaaat atgatgttcc caagtggctc tctcccagta gcattctgct    900
tcttcaacaa atgctgcagg tggacccaaa gaaacggatt tctatgaaaa atctattgaa    960
ccatccctgg atcatgcaag attacaacta tcctgttgag tggcaaagca agaatccttt   1020
tattcacctc gatgatgatt gcgtaacaga actttctgta catcacagaa acaacaggca   1080
aacaatggag gatttaattt cactgtggca gtatgatcac ctcacggcta cctatcttct   1140
gcttctagcc aagaaggctc ggggaaaacc agttcgttta aggctttctt ctttctcctg   1200
tggacaagcc agtgctaccc cattcacaga catcaagtca aataattgga gtctggaaga   1260
tgtgaccgca agtgataaaa attatgtggc gggattaata gactatgatt ggtgtgaaga   1320
tgatttatca acaggtgctg ctactccccg aacatcacag tttaccaagt actggacaga   1380
atcaaatggg gtggaatcta aatcattaac tccagcctta tgcagaacac ctgcaaataa   1440
attaaagaac aaagaaaatg tatatactcc taagtctgct gtaaagaatg aagagtactt   1500
tatgtttcct gagccaaaga ctccagttaa taagaaccag cataagagag aaatactcac   1560
tacgccaaat cgttacacta caccctcaaa agctagaaac cagtgcctga aagaaactcc   1620
aattaaaata ccagtaaatt caacaggaac agacaagtta atgacaggtg tcattagccc   1680
tgagaggcgg tgccgctcag tggaattgga tctcaaccaa gcacatatgg aggagactcc   1740
aaaaagaaag ggagccaaag tgtttgggag ccttgaaagg gggttggata aggttatcac   1800
tgtgctcacc aggagcaaaa ggaagggttc tgccagagac gggcccagaa gactaaagct   1860
tcactataac gtgactacaa ctagattagt gaatccagat caactgttga atgaaataat   1920
gtctattctt ccaaagaagc atgttgactt tgtacaaaag ggttatacac tgaagtgtca   1980
aacacagtca gattttggga aagtgacaat gcaatttgaa ttagaagtgt gccagcttca   2040
aaaacccgat gtggtgggta tcaggaggca gcggcttaag ggcgatgcct gggtttacaa   2100
aagattagtg gaagacatcc tatctagctg caaggtataa ttgatggatt cttccatcct   2160
gccggatgag tgtgggtgtg atacagccta cataaagact gttatgatcg ctttgatttt   2220
```

-continued

```
aaagttcatt ggaactacca acttgtttct aaagagctat cttaagacca atatctcttt   2280

gtttttaaac aaaagatatt attttgtgta tgaatctaaa tcaagcccat ctgtcattat   2340

gttactgtct tttttaatca tgtggttttg tatattaata attgttgact ttcttagatt   2400

cacttccata tgtgaatgta agctcttaac tatgtctctt tgtaatgtgt aatttctttc   2460

tgaaataaaa ccatttgtga atatag                                          2486
```

<210> SEQ ID NO 16
<211> LENGTH: 5101
<212> TYPE: DNA
<213> ORGANISM: Homo sapiens

<400> SEQUENCE: 16

```
agcgcagcca ttggtccggc tactctgtct ctttttcaaa ttgaggcgcc gagtcgttgc     60

ttagtttctg gggattcggg cggagacgag attagtgatt tggcggctcc gactggcgcg    120

ggacaaacgc cacggccaga gtaccgggta gagagcgggg acgccgacct gcgtgcgtcg    180

gtcctccagg ccacgccagc gcccgagagg gaccagggag actccggccc ctgtcggccg    240

ccaagcccct ccgcccctca cagcgcccag gtccgcggcc gggccttgat tttttggcgg    300

ggaccgtcat ggcgtcgcag ccaaattcgt ctgcgaagaa gaaagaggag aaggggaaga    360

acatccaggt ggtggtgaga tgcagaccat ttaatttggc agagcggaaa gctagcgccc    420

attcaatagt agaatgtgat cctgtacgaa aagaagttag tgtacgaact ggaggattgg    480

ctgacaagag ctcaaggaaa acatacactt ttgatatggt gtttggagca tctactaaac    540

agattgatgt ttaccgaagt gttgtttgtc caattctgga tgaagttatt atgggctata    600

attgcactat ctttgcgtat ggccaaactg gcactggaaa aacttttaca atggaaggtg    660

aaaggtcacc taatgaagag tatacctggg aagaggatcc cttggctggt ataattccac    720

gtacccttca tcaaattttt gagaaactta ctgataatgg tactgaattt tcagtcaaag    780

tgtctctgtt ggagatctat aatgaagagc tttttgatct tcttaatcca tcatctgatg    840

tttctgagag actacagatg tttgatgatc cccgtaacaa gagaggagtg ataattaaag    900

gtttagaaga aattacagta cacaacaagg atgaagtcta tcaaatttta gaaaaggggg    960

cagcaaaaag gacaactgca gctactctga tgaatgcata ctctagtcgt tcccactcag   1020

ttttctctgt tacaatacat atgaaagaaa ctacgattga tggagaagag cttgttaaaa   1080

tcggaaagtt gaacttggtt gatcttgcag gaagtgaaaa cattggccgt tctggagctg   1140

ttgataagag agctcgggaa gctggaaata taaatcaatc cctgttgact ttgggaaggg   1200

tcattactgc ccttgtagaa agaacacctc atgttcctta tcgagaatct aaactaacta   1260

gaatcctcca ggattctctt ggagggcgta caagaacatc tataattgca acaatttctc   1320

ctgcatctct caatcttgag gaaactctga gtacattgga atatgctcat agagcaaaga   1380

acatattgaa taagcctgaa gtgaatcaga aactcaccaa aaaagctctt attaaggagt   1440

atacggagga gatagaacgt ttaaaacgag atcttgctgc agcccgtgag aaaaatggag   1500

tgtatatttc tgaagaaaat tttagagtca tgagtggaaa attaactgtt caagaagagc   1560

agattgtaga attgattgaa aaaattggtg ctgttgagga ggagctgaat agggttacag   1620

agttgtttat ggataataaa aatgaacttg accagtgtaa atctgacctg caaaataaaa   1680

cacaagaact tgaaaccact caaaaacatt tgcaagaaac taaattacaa cttgttaaag   1740

aagaatatat cacatcagct ttggaaagta ctgaggagaa acttcatgat gctgccagca   1800

agctgcttaa cacagttgaa gaaactacaa aagatgtatc tggtctccat tccaaactgg   1860
```

```
atcgtaagaa ggcagttgac caacacaatg cagaagctca ggatattttt ggcaaaaacc   1920
tgaatagtct gtttaataat atggaagaat taattaagga tggcagctca aagcaaaagg   1980
ccatgctaga agtacataag accttatttg gtaatctgct gtcttccagt gtctctgcat   2040
tagataccat tactacagta gcacttggat ctctcacatc tattccagaa aatgtgtcta   2100
ctcatgtttc tcagattttt aatatgatac taaaagaaca atcattagca gcagaaagta   2160
aaactgtact acaggaattg attaatgtac tcaagactga tcttctaagt tcactggaaa   2220
tgattttatc cccaactgtg gtgtctatac tgaaaatcaa tagtcaacta aagcatattt   2280
tcaagacttc attgacagtg gccgataaga tagaagatca aaaaaaggaa ctagatggct   2340
ttctcagtat actgtgtaac aatctacatg aactacaaga aaataccatt tgttccttgg   2400
ttgagtcaca aaagcaatgt ggaaacctaa ctgaagacct gaagacaata aagcagaccc   2460
attcccagga actttgcaag ttaatgaatc tttggacaga gagattctgt gctttggagg   2520
aaaagtgtga aaatatacag aaaccactta gtagtgtcca ggaaaatata cagcagaaat   2580
ctaaggatat agtcaacaaa atgacttttc acagtcaaaa attttgtgct gattctgatg   2640
gcttctcaca ggaactcaga aattttaacc aagaaggtac aaaattggtt gaagaatctg   2700
tgaaacactc tgataaactc aatggcaacc tggaaaaaat atctcaagag actgaacaga   2760
gatgtgaatc tctgaacaca agaacagttt atttttctga acagtgggta tcttccttaa   2820
atgaaaggga acaggaactt cacaacttat tggaggttgt aagccaatgt tgtgaggctt   2880
caagttcaga catcactgag aaatcagatg gacgtaaggc agctcatgag aaacagcata   2940
acatttttct tgatcagatg actattgatg aagataaatt gatagcacaa aatctagaac   3000
ttaatgaaac cataaaaatt ggtttgacta agcttaattg ctttctggaa caggatctga   3060
aactggatat cccaacaggt acgacaccac agaggaaaag ttatttatac ccatcaacac   3120
tggtaagaac tgaaccacgt gaacatctcc ttgatcagct gaaaaggaaa cagcctgagc   3180
tgttaatgat gctaaactgt tcagaaaaca acaaagaaga gacaattccg gatgtggatg   3240
tagaagaggc agttctgggg cagtatactg aagaacctct aagtcaagag ccatctgtag   3300
atgctggtgt ggattgttca tcaattggcg gggttccatt tttccagcat aaaaaatcac   3360
atggaaaaga caaagaaaac agaggcatta acacactgga gaggtctaaa gtggaagaaa   3420
ctacagagca cttggttaca aagagcagat tacctctgcg agcccagatc aacctttaat   3480
tcacttgggg gttggcaatt ttatttttaa agaaaactta aaaataaaac ctgaaacccc   3540
agaacttgag ccttgtgtat agattttaaa agaatatata tatcagccgg gcgcggtggc   3600
tcatgcctgt aatcccagca ctttgggagg ctgaggcggg tggattgctt gagcccagga   3660
gtttgagacc agcctggcca acgtggcaaa acctcgtctc tgttaaaaat tagccgggcg   3720
tggtggcaca ctcctgtaat cccagctact ggggaggctg aggcacgaga atcacttgaa   3780
cccaggaagc ggggttgcag tgagccaaag gtacaccact acactccagc ctgggcaaca   3840
gagcaagact cggtctcaaa aacaaaattt aaaaaagata taaggcagta ctgtaaattc   3900
agttgaattt tgatatctac ccatttttct gtcatcccta tagttcactt tgtattaaat   3960
tgggtttcat ttgggatttg caatgtaaat acgtatttct agttttcata taaagtagtt   4020
cttttataac aaatgaaaag tatttttctt gtatattatt aagtaatgaa tatataagaa   4080
ctgtactctt ctcagcttga gcttacatag gtaaatatca ccaacatctg tccttagaaa   4140
ggaccatctc atgttttttt tcttgctatg acttgtgtat tttcttgcat cctccctaga   4200
```

```
cttccctatt tcgctttctc ctcggctcac tttctccctt tttatttttc accaaaccat   4260

ttgtagagct acaaaaggta tcctttctta ttttcagtag tcagaatttt atctagaaat   4320

cttttaacac ctttttagtg gttatttcta aaatcactgt caacaataaa tctaaccccta  4380

gttgtatccc tcctttcagt atttttcact tgttgcccca aatgtgaaag catttcattc   4440

ctttaagagg cctaactcat tcaccctgac agagttcaca aaaagcccac ttaagagtat   4500

acattgctat tatgggagac cacccagaca tctgactaat ggctctgtgc ccacactcca   4560

agacctgtgc cttttagaga agctcacaat gatttaagga ctgtttgaaa cttccaatta   4620

tgtctataat ttatattctt ttgtttacat gatgaaactt tttgttgttg cttgtttgta   4680

tataatacaa tgtgtacatg tatctttttc tcgattcaaa tcttaaccct taggactctg   4740

gtatttttga tctggcaacc atatttctgg aagttgagat gtttcagctt gaagaaccaa   4800

aacagaagga atatgtacaa agaataaatt ttctgctcac gatgagttta gtgtgtaaag   4860

tttagagaca tctgactttg atagctaaat taaaccaaac cctattgaag aattgaatat   4920

atgctacttc aagaaactaa attgatctcg tagaattatc ttaataaaat aatggctata   4980

atttctctgc aaaatcagat gtcagcataa gcgatggata atacctaata aactgccctc   5040

agtaaatcca tggttaataa atgtggtttc tacattaaaa aaaaaaaaaa aaaaaaaaaa   5100

a                                                                   5101
```

<210> SEQ ID NO 17
<211> LENGTH: 1285
<212> TYPE: DNA
<213> ORGANISM: Homo sapiens

<400> SEQUENCE: 17

```
aattacaaat tcccaatgca gttacaggat cctgggaagc agagtgtctg gatggaacct     60

gagctgggtc tctgactcac ttctgacttt agttttttca agggggaaca tggcaaaggt    120

gttcagtttc atccttgtta ccaccgctct gacaatgggc agggaaattt cggcgctcga    180

ggactgtgcc caggagcaga tgcggctcag agcccaggtg cgcctgcttg agacccgggt    240

caaacagcaa caggtcaaga tcaagcagct tttgcaggag aatgaagtcc agttccttga    300

taaaggagat gagaatactg tcattgatct tggaagcaag aggcagtatg cagattgttc    360

agagattttc aatgatgggt ataagctcag tggattttac aaaatcaaac ctctccagag    420

cccagcagaa ttttctgttt attgtgacat gtccgatgga ggaggatgga ctgtaattca    480

gagacgatct gatggcagtg aaaactttaa cagaggatgg aaagactatg aaaatggctt    540

tggaaatttt gtccaaaaac atggtgaata ttggctgggc aataaaaatc ttcacttctt    600

gaccactcaa gaagactaca ctttaaaaat cgaccttgca gattttgaaa aaaatagccg    660

ttatgcacaa tataagaatt tcaaagttgg agatgaaaag aatttctacg agttgaatat    720

tggggaatat tctggaacag ctggagattc ccttgcgggg aattttcatc ctgaggtgca    780

gtggtgggct agtcaccaaa gaatgaaatt cagcacgtgg gacagagatc atgacaacta    840

tgaagggaac tgcgcagaag aagatcagtc tggctggtgg tttaacaggt gtcactctgc    900

aaacctgaat ggtgtatact acagcggccc ctacacggct aaaacagaca atgggattgt    960

ctggtacacc tggcatgggt ggtggtattc tctgaaatct gtggttatga aaattaggcc   1020

aaatgatttt attccaaatg taatttaatt gctgctgttg ggctttcgtt tctgcaattc   1080

agctttgttt aaagtgattt gaaaaatact cattctgaac atatccatgc gcaatcatga   1140

taactgttgt gagtagtgct tttcattctt ctcacttgcc tttgttactt aatgtgcttt   1200
```

```
cagtacagca gatatgcaat attcaccaaa taaatgtaga ctgtgttaaa aaaaaaaaaa   1260

aaaaaaaaaa aaaaaaaaaa aaaaa                                         1285
```

<210> SEQ ID NO 18
<211> LENGTH: 2127
<212> TYPE: DNA
<213> ORGANISM: Homo sapiens

<400> SEQUENCE: 18

```
ataatcacga cacattcaac acagatgtga gcgtttggag agagcttcag ccttcagcac     60

aggcaactgt gttctattca ccgggctgtg ctcctcggaa gggctggtgg ttcctgtaaa    120

agtttgtgct ccccgcgcct ttccttcctt ccctcgtctt tggcgcctgc gggcaccggg    180

agtcctggga gagggaggag gaacggcgaa tcggcggggc gtgtccttca cgccgccccg    240

tagctcgggg ccgaagctgg cgcagcgcgc gactttttga aagccaggag ggttcgaatt    300

gcaacggcag ctgccgggcg tatgtgttgg tgctagaggc agctgcaggg tctcgctggg    360

ggccgctcgg gaccaatttt gaagaggtac ttggccacga cttattttca cctccgacct    420

ttccttccag gcggtgagac tctggactga gagtggcttt cacaatggaa gggatcagta    480

atttcaagac accaagcaaa ttatcagaaa aaaagaaatc tgtattatgt tcaactccaa    540

ctataaatat cccggcctct ccgtttatgc agaagcttgg ctttggtact ggggtaaatg    600

tgtacctaat gaaaagatct ccaagaggtt tgtctcattc tccttgggct gtaaaaaaga    660

ttaatcctat atgtaatgat cattatcgaa gtgtgtatca aaagagacta atggatgaag    720

ctaagatttt gaaaagcctt catcatccaa acattgttgg ttatcgtgct tttactgaag    780

ccaatgatgg cagtctgtgt cttgctatgg aatatggagg tgaaaagtct ctaaatgact    840

taatagaaga acgatataaa gccagccaag atccttttcc agcagccata attttaaaag    900

ttgctttgaa tatggcaaga gggttaaagt atctgcacca agaaaagaaa ctgcttcatg    960

gagacataaa gtcttcaaat gttgtaatta aaggcgattt tgaaacaatt aaaatctgtg   1020

atgtaggagt ctctctacca ctggatgaaa atatgactgt gactgaccct gaggcttgtt   1080

acattggcac agagccatgg aaacccaaag aagctgtgga ggagaatggt gttattactg   1140

acaaggcaga catatttgcc tttggcctta ctttgtggga aatgatgact ttatcgattc   1200

cacacattaa tctttcaaat gatgatgatg atgaagataa aacttttgat gaaagtgatt   1260

ttgatgatga agcatactat gcagcgttgg gaactaggcc acctattaat atggaagaac   1320

tggatgaatc ataccagaaa gtaattgaac tcttctctgt atgcactaat gaagacccta   1380

aagatcgtcc ttctgctgca cacattgttg aagctctgga aacagatgtc tagtgatcat   1440

ctcagctgaa gtgtggcttg cgtaaataac tgtttattcc aaaatattta catagttact   1500

atcagtagtt attagactct aaaattggca tatttgagga ccatagtttc ttgttaacat   1560

atggataact atttctaata tgaaatatgc ttatattggc tataagcact tggaattgta   1620

ctgggttttc tgtaaagttt tagaaactag ctacataagt actttgatac tgctcatgct   1680

gacttaaaac actagcagta aaacgctgta aactgtaaca ttaaattgaa tgaccattac   1740

ttttattaat gatctttctt aaatattcta tattttaatg gatctactga cattagcact   1800

ttgtacagta caaaataaag tctacatttg tttaaaacac tgaacctttt gctgatgtgt   1860

ttatcaaatg ataactggaa gctgaggaga atatgcctca aaaagagtag ctccttggat   1920

acttcagact ctggttacag attgtcttga tctcttggat ctcctcagat ctttggtttt   1980
```

tgctttaatt tattaaatgt attttccata ctgagtttaa aatttattaa tttgtacctt 2040
aagcatttcc cagctgtgta aaaacaataa aactcaaata ggatgataaa gaataaagga 2100
cactttgggt accagaaaaa aaaaaaa 2127

<210> SEQ ID NO 19
<211> LENGTH: 2339
<212> TYPE: DNA
<213> ORGANISM: Homo sapiens

<400> SEQUENCE: 19
acgcggtgcc gcggggcggg agtagaggcg gagggagggg acacgggctc attgcggtgt 60
gcgccctgca ctctgtccct cactcgccgc cgacgacctg tctcgccgag cgcacgcctt 120
gccgccgccc cgcagaaatg cttcggttac ccacagtctt tcgccagatg agaccggtgt 180
ccagggtact ggctcctcat ctcactcggg cttatgccaa agatgtaaaa tttggtgcag 240
atgcccgagc cttaatgctt caaggtgtag accttttagc cgatgctgtg gccgttacaa 300
tggggccaaa gggaagaaca gtgattattg agcagagttg gggaagtccc aaagtaacaa 360
aagatggtgt gactgttgca aagtcaattg acttaaaaga taaatacaaa aacattggag 420
ctaaacttgt tcaagatgtt gccaataaca caaatgaaga agctggggat ggcactacca 480
ctgctactgt actggcacgc tctatagcca aggaaggctt cgagaagatt agcaaaggtg 540
ctaatccagt ggaaatcagg agaggtgtga tgttagctgt tgatgctgta attgctgaac 600
ttaaaaagca gtctaaacct gtgaccaccc ctgaagaaat tgcacaggtt gctacgattt 660
ctgcaaacgg agacaaagaa attggcaata tcatctctga tgcaatgaaa aaagttggaa 720
gaaagggtgt catcacagta aaggatggaa aaacactgaa tgatgaatta gaaattattg 780
aaggcatgaa gtttgatcga ggctatattt ctccatactt tattaataca tcaaaaggtc 840
agaaatgtga attccaggat gcctatgttc tgttgagtga aaagaaaatt tctagtatcc 900
agtccattgt acctgctctt gaaattgcca atgctcaccg taagcctttg gtcataatcg 960
ctgaagatgt tgatggagaa gctctaagta cactcgtctt gaataggcta aaggttggtc 1020
ttcaggttgt ggcagtcaag gctccagggt ttggtgacaa tagaaagaac cagcttaaag 1080
atatggctat tgctactggt ggtgcagtgt ttggagaaga gggattgacc ctgaatcttg 1140
aagacgttca gcctcatgac ttaggaaaag ttggagaggt cattgtgacc aaagacgatg 1200
ccatgctctt aaaaggaaaa ggtgacaagg ctcaaattga aaaacgtatt caagaaatca 1260
ttgagcagtt agatgtcaca actagtgaat atgaaaagga aaaactgaat gaacggcttg 1320
caaaactttc agatggagtg gctgtgctga aggttggtgg gacaagtgat gttgaagtga 1380
atgaaaagaa agacagagtt acagatgccc ttaatgctac aagagctgct gttgaagaag 1440
gcattgtttt gggagggggt tgtgccctcc ttcgatgcat tccagccttg gactcattga 1500
ctccagctaa tgaagatcaa aaaattggta tagaaattat taaaagaaca ctcaaaattc 1560
cagcaatgac cattgctaag aatgcaggtg ttgaaggatc tttgatagtt gagaaaatta 1620
tgcaaagttc ctcagaagtt ggttatgatg ctatggctgg agattttgtg aatatggtgg 1680
aaaaaggaat cattgaccca acaaaggttg tgagaactgc tttattggat gctgctggtg 1740
tggcctctct gttaactaca gcagaagttg tagtcacaga aattcctaaa gaagagaagg 1800
accctggaat gggtgcaatg ggtggaatgg gaggtggtat gggaggtggc atgttctaac 1860
tcctagacta gtgctttacc tttattaatg aactgtgaca ggaagcccaa ggcagtgttc 1920
ctcaccaata acttcagaga agtcagttgg agaaaatgaa gaaaaaggct ggctgaaaat 1980

```
cactataacc atcagttact ggtttcagtt gacaaaatat ataatggttt actgctgtca   2040

ttgtccatgc ctacagataa tttattttgt atttttgaat aaaaaacatt tgtacattcc   2100

tgatactggg tacaagagcc atgtaccagt gtactgcttt caacttaaat cactgaggca   2160

tttttactac tattctgtta aaatcaggat tttagtgctt gccaccacca gatgagaagt   2220

taagcagcct ttctgtggag agtgagaata attgtgtaca aagtagagaa gtatccaatt   2280

atgtgacaac ctttgtgtaa taaaaatttg tttaaagtta aaaaaaaaaa aaaaaaaaa    2339
```

```
<210> SEQ ID NO 20
<211> LENGTH: 3251
<212> TYPE: DNA
<213> ORGANISM: Homo sapiens

<400> SEQUENCE: 20

gatttggctc cgaggaggcg gaagtgcagc acagaaaggg ggtccgtggg ggacggtaga     60

agcctggagg aggagcttga gtccagccac tgtctgggta ctgccagcca tcgggcccag    120

gtctctgggg ttgtcttacc gcagtgagta ccacgcggta ctacagagac cggctgcccg    180

tgtgcccggc aggtggagcc gcccgcatca gcggcctcgg ggaatggaag cggagaacgc    240

gggcagctat tcccttcagc aagctcaagc tttttatacg tttccatttc aacaactgat    300

ggctgaagct cctaatatgg cagttgtgaa tgaacagcaa atgccagaag aagttccagc    360

cccagctcct gctcaggaac cagtgcaaga ggctccaaaa ggaagaaaaa gaaaacccag    420

aacaacagaa ccaaaacaac cagtggaacc caaaaaacct gttgagtcaa aaaaatctgg    480

caagtctgca aaatcaaaag aaaaacaaga aaaaattaca gacacattta aagtaaaaag    540

aaaagtagac cgttttaatg gtgtttcaga agctgaactt ctgaccaaga ctctccccga    600

tattttgacc ttcaatctgg acattgtcat tattggcata aacccgggac taatggctgc    660

ttacaaaggg catcattacc ctggacctgg aaaccatttt tggaagtgtt tgtttatgtc    720

agggctcagt gaggtccagc tgaaccatat ggatgatcac actctaccag ggaagtatgg    780

tattggattt accaacatgg tggaaaggac cacgcccggc agcaaagatc tctccagtaa    840

agaatttcgt gaaggaggac gtattctagt acagaaatta cagaaatatc agccacgaat    900

agcagtgttt aatggaaaat gtatttatga aatttttagt aaagaagttt ttggagtaaa    960

ggttaagaac ttggaatttg ggcttcagcc ccataagatt ccagacacag aaactctctg   1020

ctatgttatg ccatcatcca gtgcaagatg tgctcagttt cctcgagccc aagacaaagt   1080

tcattactac ataaaactga aggacttaag agatcagttg aaaggcattg aacgaaatat   1140

ggacgttcaa gaggtgcaat atacatttga cctacagctt gcccaagagg atgcaaagaa   1200

gatggctgtt aaggaagaaa aatatgatcc aggttatgag gcagcatatg gtggtgctta   1260

cggagaaaat ccatgcagca gtgaaccttg tggcttctct tcaaatgggc taattgagag   1320

cgtggagtta agaggagaat cagctttcag tggcattcct aatgggcagt ggatgaccca   1380

gtcatttaca gaccaaattc cttcctttag taatcactgt ggaacacaag aacaggaaga   1440

agaaagccat gcttaagaat ggtgcttctc agctctgctt aaatgctgca gttttaatgc   1500

agttgtcaac aagtagaacc tcagtttgct aactgaagtg ttttattagt attttactct   1560

agtggtgtaa ttgtaatgta gaacagttgt gtggtagtgt gaaccgtatg aacctaagta   1620

gtttggaaga aaaagtaggg tttttgtata ctagcttttg tatttgaatt aattatcatt   1680

ccagcttttt atatactata tttcatttat gaagaaattg attttctttt gggagtcact   1740
```

```
tttaatctgt aattttaaaa tacaagtctg aatatttata gttgattctt aactgcataa   1800

acctagatat accattatcc cttttatacc taagaagggc atgctaataa ttaccactgt   1860

caaagaggca aaggtgttga tttttgtata tgaagttaag cctcagtgga gtctcatttg   1920

ttagttttta gtggtaacta agggtaaact cagggttccc tgagctatat gcacactcag   1980

acctctttgc tttaccagtg gtgtttgtga gttgctcagt agtaaaaact ggcccttacc   2040

tgacagagcc ctggctttga cctgctcagc cctgtgtgtt aatcctctag tagccaatta   2100

actactctgg ggtggcaggt tccagagaat gcagtagacc ttttgccact catctgtgtt   2160

ttacttgaga catgtaaata tgataggaa ggaactgaat ttctccattc atatttataa    2220

ccattctagt tttatcttcc ttggctttaa gagtgtgcca tggaaagtga taagaaatga   2280

acttctaggc taagcaaaaa gatgctggag atatttgata ctctcattta aactggtgct   2340

ttatgtacat gagatgtact aaaataagta atatagaatt tttcttgcta ggtaaatcca   2400

gtaagccaat aattttaaag attctttatc tgcatcattg ctgtttgtta ctataaatta   2460

aatgaacctc atggaaaggt tgaggtgtat acctttgtga ttttctaatg agttttccat   2520

ggtgctacaa ataatccaga ctaccaggtc tggtagatat taaagctggg tactaagaaa   2580

tgttatttgc atcctctcag ttactcctga atattctgat ttcatacgta cccagggagc   2640

atgctgtttt gtcaatcaat ataaaatatt tatgaggtct cccccacccc caggaggtta   2700

tatgattgct cttctcttta taataagaga aacaaattct tattgtgaat cttaacatgc   2760

tttttagctg tggctatgat ggattttatt ttttcctagg tcaagctgtg taaaagtcat   2820

ttatgttatt taaatgatgt actgtactgc tgtttacatg gacgttttgt gcgggtgctt   2880

tgaagtgcct tgcatcaggg attaggagca attaaattat tttttcacgg gactgtgtaa   2940

agcatgtaac taggtattgc tttggtatat aactattgta gctttacaag agattgtttt   3000

atttgaatgg ggaaaatacc ctttaaatta tgacggacat ccactagaga tgggtttgag   3060

gattttccaa gcgtgtaata atgatgtttt tcctaacatg acagatgagt agtaaatgtt   3120

gatatatcct atacatgaca gtgtgagact tttcattaa ataatattga aagattttaa    3180

aattcatttg aaagtctgat ggcttttaca ataaaagata ttaagaattg ttatccttaa   3240

cttaaaaaaa a                                                        3251
```

```
<210> SEQ ID NO 21
<211> LENGTH: 3207
<212> TYPE: DNA
<213> ORGANISM: Homo sapiens

<400> SEQUENCE: 21

gattgcgcac ccgcgacttc agcccgaggg gcggggattt tcttggagcg acgggacgcg     60

acgccaatcg cgacgaggct tcgccccgtg gcgcggtttg aaattttgcg gggctcaacg    120

gctcgcggag cggctacgcg gagtgacatc gccggtgttt gcgggtggtt gttgctctcg    180

gggccgtgtg gagtaggtct ggacctggac tcacggctgc ttggagcgtc cgccatgagg    240

agaagtgagg tgctggcgga ggagtccata gtatgtctgc agaaagccct aaatcacctt    300

cgggaaatat gggagctaat tgggattcca gaggaccagc ggttacaaag aactgaggtg    360

gtaaagaagc atatcaagga actcctggat atgatgattg ctgaagagga aagcctgaag    420

gaaagactca tcaaaagcat atccgtctgt cagaaagagc tgaacactct gtgcagcgag    480

ttacatgttg agccatttca ggaagaagga gagacgacca tcttgcaact agaaaaagat    540

ttgcgcaccc aagtggaatt gatgcgaaaa cagaaaaagg agagaaaaca ggaactgaag    600
```

```
ctacttcaag agcaagatca agaactgtgc gaaattcttt gtatgcccca ctatgatatt    660
gacagtgcct cagtgcccag cttagaagag ctgaaccagt tcaggcaaca tgtgacaact    720
ttgagggaaa caaaggcttc taggcgtgag gagtttgtca gtataaagag acagatcata    780
ctgtgtatgg aagaattaga ccacacccca gacacaagct ttgaaagaga tgtggtgtgt    840
gaagacgaag atgccttttg tttgtctttg gagaatattg caacactaca aaagttgcta    900
cggcagctgg aaatgcagaa atcacaaaat gaagcagtgt gtgaggggct gcgtactcaa    960
atccgagagc tctgggacag gttgcaaata cctgaagaag aaagagaagc tgtggccacc   1020
attatgtctg ggtcaaaggc caaggtccgg aaagcgctgc aattagaagt ggatcggttg   1080
gaagaactga aaatgcaaaa catgaagaaa gtgattgagg caattcgagt ggagctggtt   1140
cagtactggg accagtgctt ttatagccag gagcagagac aagcttttgc ccctttctgt   1200
gctgaggact acacagaaag tctgctccag ctccacgatg ctgagattgt gcggttaaaa   1260
aactactatg aagttcacaa ggaactcttt gaaggtgtcc agaagtggga agaaacctgg   1320
aggcttttct tagagtttga gagaaaagct tcagatccaa atcgatttac aaaccgagga   1380
ggaaatcttc taaaagaaga aaaacaacga gccaagctcc agaaaatgct gcccaagctg   1440
gaagaagagt tgaaggcacg aattgaattg tgggaacagg aacattcaaa ggcatttatg   1500
gtgaatgggc agaaattcat ggagtatgtg gcagaacaat gggagatgca tcgattggag   1560
aaagagagag ccaagcagga aagacaactg aagaacaaaa aacagacaga gacagagatg   1620
ctgtatggca gcgctcctcg aacacctagc aagcggcgag gactggctcc caatacaccg   1680
ggcaaagcac gtaagctgaa cactaccacc atgtccaatg ctacggccaa tagtagcatt   1740
cggcctatct ttggagggac agtctaccac tcccccgtgt ctcgacttcc tccttctggc   1800
agcaagccag tcgctgcttc cacctgttca gggaagaaaa caccccgtac tggcaggcat   1860
ggagccaaca aggagaacct ggagctcaac ggcagcatcc tgagtggtgg gtaccctggc   1920
tcggcccccc tccagcgcaa cttcagcatt aattctgttg ccagcaccta ttctgagttt   1980
gcgaaggatc cgtccctctc tgacagttcc actgttgggc ttcagcgaga actttcaaag   2040
gcttccaaat ctgatgctac ttctggaatc ctcaattcaa ccaacatcca gtcctgagaa   2100
gccctgatca gtcaaccagc tgtggcttcc tgtgcctaga ctggacctaa ttatatgggg   2160
gtgactttag tttttcttca gcttaggcgt gcttgaaacc ttggccaggt tccatgacca   2220
tgggcctaac ttaaagatgt gaatgagtgt tacagttgaa agcccatcat aggtttagtg   2280
gtcctaggag acttggtttt gacttatata catgaaaagt ttatggcaag aagtgcaaat   2340
tttagcatat ggggcctgac ttctctacca cataattcta cttgctgaag catgatcaaa   2400
gcttgtttta tttcaccact gtaggaaaat gattgactat gcccatccct gggggtaatt   2460
ttggcatgta tacctgtaac tagtaattaa catctttttt gtttaggcat gttcaattaa   2520
tgctgtagct atcatagctt tgctcttacc tgaagccttg tccccaccac acaggacagc   2580
cttcctcctg aagagaatgt ctttgtgtgt ccgaagttga gatggcctgc cctactgcca   2640
aagaggtgac aggaaggctg ggagcagctt tgttaaattg tgttcagttc tgttacacag   2700
tgcattgccc tttgttgggg gtatgcatgt atgaacacac atgcttgtcg gaacgctttc   2760
tcggcgtttg tcccttggct ctcatctccc ccattcctgt gcctactttg cctgagttct   2820
tctacccccg cagttgccag ccacattggg agtctgtttg ttccaatggg ttgagctgtc   2880
tttgtcgtgg agatctggaa ctttgcacat gtcactactg ggaggtgtt cctgctctag   2940
```

```
cttccacgat gaggcgccct ctttacctat cctctcaatc actactcttc ttgaagcact   3000

attatttatt cttccgctgt ctgcctgcag cagtactact gtcaacatag tgtaaatggt   3060

tctcaaaagc ttaccagtgt ggacttggtg ttagccacgc tgtttactca tacagtacgt   3120

gtcctgtttt taaaatatac aattattctt aaaaataaat taaaatctgt atacttacat   3180

ttcaaaaaga aaaaaaaaaa aaaaaaa                                       3207


<210> SEQ ID NO 22
<211> LENGTH: 5625
<212> TYPE: DNA
<213> ORGANISM: Homo sapiens

<400> SEQUENCE: 22

acctagcgcc ccctcccccg ggagcgcgga ggagcattaa taaacctcta agccgaggag     60

aaaactctgg ctggggcagt gcgctgagcg ccggaggagc gtaggcaggg cagcgctggc    120

gccagtggcg acaggagccg cgcgaccggc aaaaatacac gggaggccgt cgccgaaaag    180

agtccgcggt cctctctcgt aaacacactc tcctccaccg gcgcctcccc ctccgctctg    240

cgcgccgccc ggctgggcgc ccgaggccgc tccgactgct atgtgaccgc gaggctgcgg    300

gaggaagggg acagggaaga agaggctctc ccgcgggagc ccttgaggac caagtttgcg    360

gccacttctg caggcgtccc ttcttagctc tcgcccgccc ctttctgcag cctaggcggc    420

ccgggttctc ttctcttcct cgcgcgccca gccgcctcgg ttcccggcga ccatggtgac    480

gatggaggag ctgcgggaga tggactgcag tgtgctcaaa aggctgatga accgggacga    540

gaatggcggc ggcgcgggcg gcagcggcag ccacggcacc ctggggctgc cgagcggcgg    600

caagtgcctg ctgctggact gcagaccgtt cctggcgcac agcgcgggct acatcctagg    660

ttcggtcaac gtgcgctgta acaccatcgt gcggcggcgg gctaagggct ccgtgagcct    720

ggagcagatc ctgcccgccg aggaggaggt acgcgcccgc ttgcgctccg gcctctactc    780

ggcggtcatc gtctacgacg agcgcagccc gcgcgccgag agcctccgcg aggacagcac    840

cgtgtcgctg gtggtgcagg cgctgcgccg caacgccgag cgcaccgaca tctgcctgct    900

caaaggcggc tatgagaggt ttcctccga gtacccagaa ttctgttcta aaaccaaggc     960

cctggcagcc atcccacccc cggttccccc cagtgccaca gagcccttgg acctgggctg   1020

cagctcctgt gggaccccac tacacgacca ggggggtcct gtggagatcc ttcccttcct   1080

ctacctcggc agtgcctacc atgctgcccg gagagacatg ctggacgccc tgggcatcac   1140

ggctctgttg aatgtctcct cggactgccc aaaccacttt gaaggacact atcagtacaa   1200

gtgcatccca gtggaagata accacaaggc cgacatcagc tcctggttca tggaagccat   1260

agagtacatc gatgccgtga aggactgccg tgggcgcgtg ctggtgcact gccaggcggg   1320

catctcgcgg tcggccacca tctgcctggc ctacctgatg atgaagaaac gggtgaggct   1380

ggaggaggcc ttcgagttcg ttaagcagcg ccgcagcatc atctcgccca acttcagctt   1440

catggggcag ctgctgcagt tcgagtccca ggtgctggcc acgtcctgtg ctgcggaggc   1500

tgctagcccc tcgggacccc tgcgggagcg gggcaagacc cccgccaccc ccacctcgca   1560

gttcgtcttc agctttccgg tctccgtggg cgtgcactcg gcccccagca gcctgcccta   1620

cctgcacagc cccatcacca cctctcccag ctgttagagc cgccctgggg gccccagaac   1680

cagagctggc tcccagcaag ggtaggacgg gccgcatgcg ggcagaaagt tgggactgag   1740

cagctgggag caggcgaccg agctccttcc ccatcatttc tccttggcca acgacgaggc   1800

cagccagaat ggcaataagg actccgaata cataataaaa gcaaacagaa cactccaact   1860
```

```
tagagcaata acggctgccg cagcagccag ggaagacctt ggtttggttt atgtgtcagt   1920
ttcacttttc cgatagaaat ttcttacctc attttttaa gcagtaaggc ttgaagtgat   1980
gaaacccaca gatcctagca aatgtgccca accagcttta ctaaaggggg aggaagggag   2040
ggcaaaggga tgagaagaca agtttcccag aagtgcctgg ttctgtgtac ttgtcccttt   2100
gttgtcgttg ttgtagttaa aggaatttca tttttaaaa gaaatcttcg aaggtgtggt   2160
tttcatttct cagtcaccaa cagatgaata attatgctta ataataaagt atttattaag   2220
actttcttca gagtatgaaa gtacaaaaag tctagttaca gtggatttag aatatattta   2280
tgttgatgtc aaacagctga gcaccgtagc atgcagatgt caaggcagtt aggaagtaaa   2340
tggtgtcttg tagatatgtg caaggtagca tgatgagcaa cttgagtttg ttgccactga   2400
gaagcaggcg ggttgggtgg gaggaggaag aaagggaaga attaggtttg aattgctttt   2460
taaaaaaaaa agaaaagaaa aagacagcat ctcactatgt tgccaaggct catcttgaga   2520
agcaggcggg ttgggtggga ggaggaagaa agggaagaat taggtttgaa ttgctttttt   2580
aaaaaaaaag aaaagaaaaa aaaagacagc atctcactat gttgccaagg ctcatctcaa   2640
gctcttgggc tcaagagatc ctcccacctc ggcctcctga gtagctggga ctgcaggtgt   2700
gtgtcatcat gaccaatgtg aattgctttt gaagctggtt catgggcatg taggccaccg   2760
aagcaatttt agaccacagt aagtcaagct tttttccctc cgatgatcac tgggtggttg   2820
cagcattttt tgcataaacc tgcctaagac ttgtctatcg tctgtgatca atatgccata   2880
ttacactaag gtgctcctgg aaaattgggt gcagttcaaa ttttcctaca gcaaatcatt   2940
tggcaaggcc agccattggg gaaaccagac aactagagat aaccctgaaa tgaatccttt   3000
tgtaaattga agcaccatct tttcttttt tgcataaatt ggaggtttta attttagggc   3060
agttacctga agtgaaatat accaacaatt tcttgtgttc tttaaattcc tagttaggtg   3120
aatattttg aaggtcctct tttgaataaa gaggggaatg gacaccacat ttcaggtctt   3180
ctcgaagtgt ggaagggcaa gagagcatca gtgagctgat ggtggattgc ttacatcgga   3240
ttccattggt atgaatttcc caaactggaa atcaaagcgc cagggtgggg ttggggctga   3300
ctgctggtga gggggctggc cgctggctcc cgtgacgtgc gtcatgggca cgcaggcgcc   3360
attttgaatc tatcgtcggc acgtgggtgc cattttgaat ccttagttgg gcctttctaa   3420
atggagaatg gctttggagg gagacacgtt ttctgtgggg agggtttggg ggggagggag   3480
gagggaacaa gctacatgct attttgtttg tagtattgtg gaacagtctt gttatggagt   3540
gccagcttag aggttgttgc aaacttgtct agaagtgaga gcatggtttt ttttagccct   3600
ttgagagtct acatctaatg aacattcttg ctcacccata aataacgtca agcctcaatg   3660
tcaccgtcac gttgggatac tctttctcat ctggcatcct agacaggaca aggttggtta   3720
cctttccttc catgaaccat gaacctgtga cggcatcatt catcctgact tcaccaagct   3780
ccgcctgtgg gtgaggccag agctcccact ggcaattttt agaagagcca gaggctccct   3840
gcttcctcta gaaataacag ttcagggtga agcatggagg gtttcagttc ccagacaatg   3900
gaaccattta gagacaacac agttggacat ttccactttt tccttgattc ctggaagtcc   3960
agtgggttct gcagctgaaa aagccctggg tcccagcagc agagagacag gacagagggg   4020
atgcttgggc ggggagggac ggtaacctgc agaacagatt ccatttttat agaacgagta   4080
cacgtttgct aaaacagtcc tgctttccca gactggattc ccaccacagg gacagtcgga   4140
actcaggact agctccagcg acatctttcc tccgaattca agccttctat cacaatgtca   4200
```

```
aaacagctat ttataaagcc attttcattg tacttgataa cagcacgagt cccaaaactt   4260
ttagaaataa aataggacat tggcttgatt gaaaagaggg actttttaaa aattgttctt   4320
tcgtcagaag ccttttggat gacttacaat agctctgatg aagataccac cccagcgtca   4380
gtccaatagg tcagtgagtt tcaacaggca tccatccctc ccatgaaggg attctggtga   4440
tgggaagttt ctgtaatgac aggaaagcat tgaccctcat tgattgtcaa ctttggtatt   4500
agccatgaaa gacaggatgc tcattgggtg ttctgtagag tgaggaatgc tgcctattcc   4560
ctcccagaac gtctgaccca ggggtgtgtg ttgaggagcc ctgggggaaa tggaccaagt   4620
tttcccacag agcagtatta ggctgaagag caggtgactg gtaggcccca gctcccatca   4680
ttccctccca aagccatttt gttcagttgc tcatccacgc tggattccag agagttttcc   4740
aatttgggaa gccatgagaa aggtttttaa atcttgggaa gatggagaga gggacatagg   4800
atagttgact ccaacatgac aggaagaggc tggagattgg gaattggcca tcaaccaagc   4860
ctgtagtagt aaagccatgg tcccgcattg gaattacttg gggaacttat acagttctga   4920
tacccaggct ctcctagacc agttcaacca attctaggtg gggactcag gcatcagtgt   4980
gtttcgtagc tccccgggtg ttttccctgt gcagccgagc ttgggaaact gccatgcttt   5040
ttggatgtca aggcgctgtt ggaggctggg tgtgacagca cagagccagg ttgtcttgtg   5100
gaaaccacag ccacgggttt gccactggct cagcatggcc tcactgccag tcccagcctg   5160
gctgagggac aagatggttt ctcttgggag ttcctgagtg gagcaccctt ccaggctttt   5220
tgaaagccag ctgatctgtg gagccttgtt aagggactca atacggtgtt tggatattga   5280
tgtttttcct tgagactgtc ttgtccatca ataaagatgg aggatgtctc ctctttgaac   5340
cccgcttccc caccagtact ctctctccct tagagtttat gagttattca aggaggagac   5400
ttcttaaaga cagcaacgca attcttgtaa cttgtgtaaa tagccccatc tttcagagtg   5460
ataccatttc tacatttgat aatgcctgta ttcctgtagg atgtatatag tttaggggat   5520
tttttttttg tttggttttg ttttttagaa gtcaatatgt ctggttttat ttattgcttg   5580
aaaaagatca tttgaaaaaa ataaatacat tttcaaccac taaaa                   5625
```

<210> SEQ ID NO 23
<211> LENGTH: 2537
<212> TYPE: DNA
<213> ORGANISM: Homo sapiens

<400> SEQUENCE: 23

```
ggaagtccca cctgcgcccg acggcggaag ttccgggagt gccaagtacc cgcgtgcata     60
cggctgccgg catggcacat tacaacttca agaaaattac ggtggtgccg tccgccaagg    120
acttcataga cctcacgttg tcgaagactc aacgaaagac tccaaccgtt attcataaac    180
attaccaaat acatcgcatt agacattttt acatgagaaa agtcaaattt actcaacaga    240
attaccatga tagactttca caaattctaa cagatttccc caaattggat gatattcatc    300
cgttctatgc tgatttgatg aatattctct acgacaagga tcattacaag ttggctctgg    360
ggcaaataaa tattgccaaa aatttagtgg acaatgttgc taaagattat gtgcgactga    420
tgaagtatgg cgactctctc taccgctgca aacagctgaa gcgtgcggcc ctgggacgga    480
tgtgcacagt gatcaagagg cagaagcaga gtttggagta tttggagcaa gtgcgtcagc    540
atttatcccg tttgccaacc attgatccga ataccaggac cctgcttttg tgtgggtacc    600
caaatgttgg gaagtccagc ttcatcaaca aggtgacgag agcagacgtg gatgtccagc    660
cctatgcgtt cacaaccaag tctctgtttg ttgggcacat ggattataag tatctacgtt    720
```

```
ggcaggttgt agacactcct gggatcctgg accaccctct ggaggatagg aacaccatcg    780

agatgcaggc catcactgcc ctggcccacc tccgtgctgc ggtcctgtat gtgatggatt    840

tgtctgagca gtgtgggcat gggctgaggg agcagctaga actcttccag aacatcagac    900

ctctcttcat caacaagcct ctcatagttg tagccaacaa atgtgatgtg aagagaatag    960

ctgaactttc tgaagatgat cagaaaatat ttacagattt gcagtctgaa ggattccctg   1020

taatagagac cagcaccctg actgaggaag gtgttattaa agttaaaaca gaggcttgcg   1080

ataggctttt ggctcatcga gtggaaacca aaatgaaggg aaataaagtg aatgaggtgc   1140

tgaatagact gcacctggct atcccaacca ggagggacga taaggagagg ccccctttca   1200

tccctgaagg agtggtggct cgcaggaaga ggatggaaac tgaggagtcc aggaagaaga   1260

gggaacgaga tcttgagctg gaaatgggag atgattatat tttggatctt cagaagtact   1320

gggatttaat gaatttgtct gaaaaacatg ataagatacc agaaatctgg gaaggccata   1380

atatagctga ttatattgat ccagccatca tgaagaaatt ggaagaatta gaaaaagaag   1440

aagagctgag aacagctgct ggagagtatg acagtgtatc tgagagtgaa gacgaagaga   1500

tgctggaaat ccgacagctg gcaaagcaaa ttcgagagaa aaagaagttg aaaattctgg   1560

agtccaaaga aaagaataca cagggaccca ggatgccgcg aactgctaag aaggttcaga   1620

ggacagtttt ggagaaggag atgcgtagtc ttggtgttga catggacgat aaagacgatg   1680

cccattacgc agtccaggca agaagatccc ggagcatcac taggaaaaga aagcgggaag   1740

actctgctcc cccgtcctct gtggcccgga gtgggagttg ctctcgaact ccacgtgacg   1800

tttctggtct tagggatgtc aagatggtga agaaagccaa gactatgatg aagaatgctc   1860

agaagaagat gaatcggttg gggaagaaag gggaggcgga tagacacgtg tttgatatga   1920

agcccaagca cttgctgtct gggaagagga aagctggtaa aaaggacagg agatagtatc   1980

cgtttggttg gcgtggcttc gctagagtgt tgctgtttat ttcctggttt ggcacagtat   2040

ggtttcatga aattggagct ctgtataaac tgaaaaagac aaaataagta aagcacttgt   2100

tgctttgctg aaaactatgg ttaaccctat ataggtgtgg gaaatttttg tcactgcata   2160

atattacaaa tattttgagt agacagtgtt tccacattta atggagtatc agttgcttca   2220

gattttcaga actgggaaga tttactggtg taactgggtt gtttttgatg gagaaaaacc   2280

ttattttctt ttgtaagagc tgggagcaaa cacgtttatg agtgtgtcgg aatcccgtgc   2340

ttaaaatacg ctcttaaatt attttctagt cttattttac aatgtctcat tgtagtctgt   2400

cttcaactat tttatccaaa ataaacctcc agaagaaagt agttttcatt tacttagctc   2460

atgttttggt ttagttatag tcgctatgga tttggccaaa taaaaaggca aacaacaaaa   2520

aaaaaaaaaa aaaaaaa                                                  2537
```

<210> SEQ ID NO 24
<211> LENGTH: 1687
<212> TYPE: DNA
<213> ORGANISM: Homo sapiens

<400> SEQUENCE: 24

```
gattgtggga aggcagctga actcggcgcc tggaaagatg gaggcagcgg agacagaggc     60

ggaagctgca gccctagagg tcctggctga ggtggcaggc atcttggaac ctgtaggcct    120

gcaggaggag gcagaactgc cagccaagat cctggttgag tttgtggtgg actctcagaa    180

gaaagacaag ctgctctgca gccagcttca ggtagcggat ttcctgcaga acatcctggc    240
```

```
tcaggaggac actgctaagg gtctcgaccc cttggcttct gaagacacga gccgacagaa    300

ggcaattgca gctaaggaac aatggaaaga gctgaaggcc acctacaggg agcacgtaga    360

ggccatcaaa attggcctca ccaaggccct gactcagatg gaggaagccc agaggaaacg    420

gacacaactc cgggaagcct ttgagcagct ccaggccaag aaacaaatgg ccatggagaa    480

acgcagagca gtccagaacc agtggcagct acaacaggag aagcatctgc agcatctggc    540

ggaggtttct gcagaggtga gggagcgtaa gacagggact cagcaggagc ttgacagggt    600

gtttcagaaa cttggaaacc tgaagcagca ggcagaacag gagcgggaca agctgcagag    660

gtatcagacc ttcctccagc ttctgtatac cctgcagggt aagctgttgt tccctgaggc    720

tgaggctgag gcagagaatc ttccagatga taaaccccag cagccgactc gaccccagga    780

gcagagtaca ggagacacca tggggagaga ccctggtgtg tccttcaagg ctgttggtct    840

acaacctgct ggagatgtaa atttgccatg acttcctgga ggacagcagc atggagaaag    900

atcctagaaa aggcctctga cttccctcac ctcccaacca tcattacagg aaagactgtg    960

aactcctgag ttcagcttga tttctgacta catcccagca agctctggca tctgtggatt   1020

aaaatccctg gatctctctc agttgtgtat ttgttcatct tcatatgctg gcaggaacaa   1080

ctattaatac agatactcag aagccaataa catgacagga gctgggactg gtttgaacac   1140

agggtgtgca gatggggagg gggtactggc cttgggcctc ctatgatgca gacatggtga   1200

atttaattca aggaggagga gaatgtttta ggcaggtggt tatatgtggg aagataattt   1260

tattcatgga tccaaatgtt tgttgagtcc tttctttgtg ctaaggttct tgcggtgaac   1320

cagaattata acagtgagct catctgactg ttttaggatg tacagcctag tgttaacatt   1380

cttggtatct ttttgtgcct tatctaaaac atttctcgat cactggtttc agatgttcat   1440

ttattatatt cttttcaaag attcagagat tggcttttgt catccactat tgtatgtttt   1500

gtttcattga cctctagtga taccttgatc tttcccactt tctgttttcg gattggagaa   1560

gatgtacctt ttttgtcaac tcttactttt atcagatgat caactcacgt atttggatct   1620

ttatttgttt tctcaaataa atatttaagg ttatacattt aaaaaaaaaa aaaaaaaaaa   1680

aaaaaaa                                                             1687
```

```
<210> SEQ ID NO 25
<211> LENGTH: 3849
<212> TYPE: DNA
<213> ORGANISM: Homo sapiens

<400> SEQUENCE: 25

ccctttttgct tacttcctag tcccgggcag gccggctcgg aggcagcgag aaagcgcagc    60

caggcggctg ctcggcgttc tctcaggtga ctgctcggag ttctcccagt gtttggtgtt   120

gcaagcagga tccaaaggag acctatagtg actcccagga gctcttagtg accaagtgaa   180

ggcaggaaga cagggttctg atggtgtgag tctccttcaa ctcagcaaac caccttggtc   240

tgcctcgagt ttccaacacc cctcctgcct gctagtgata ggtgtgaggc aggttgatga   300

acatggaact tttttctttt ggtcccaaag catgctactc ctggagtttc attcagtgaa   360

tgagaactat agtttggttc tgtgagatct ctatgaatca aggcggccac tgaagcggag   420

aaaagaaatg cttaaatgtt aagaaagttt gaagtgcaga aaaaggttga agcactggac   480

aatgccacat actttgtgga tggtgtgggt cttgggggtc atcatcagcc tctccaagga   540

agaatcctcc aatcaggctt ctctgtcttg tgaccgcaat ggtatctgca agggcagctc   600

aggatcttta aactccattc cctcagggct cacagaagct gtaaaaagcc ttgacctgtc   660
```

```
caacaacagg atcacctaca ttagcaacag tgacctacag aggtgtgtga acctccaggc    720
tctggtgctg acatccaatg gaattaacac aatagaggaa gattcttttt cttccctggg    780
cagtcttgaa catttagact tatcctataa ttacttatct aatttatcgt cttcctggtt    840
caagcccctt tcttctttaa cattcttaaa cttactggga aatccttaca aaaccctagg    900
ggaaacatct ctttttctc atctcacaaa attgcaaatc ctgagagtgg gaaatatgga     960
caccttcact aagattcaaa gaaaagattt tgctggactt accttccttg aggaacttga   1020
gattgatgct tcagatctac agagctatga gccaaaaagt ttgaagtcaa ttcagaatgt   1080
aagtcatctg atccttcata tgaagcagca tattttactg ctggagattt ttgtagatgt   1140
tacaagttcc gtggaatgtt tggaactgcg agatactgat ttggacactt tccatttttc   1200
agaactatcc actggtgaaa caaattcatt gattaaaaag tttacattta gaaatgtgaa   1260
aatcaccgat gaaagtttgt ttcaggttat gaaacttttg aatcagattt ctggattgtt   1320
agaattagag tttgatgact gtacccttaa tggagttggt aattttagag catctgataa   1380
tgacagagtt atagatccag gtaaagtgga aacgttaaca atccggaggc tgcatattcc   1440
aaggttttac ttattttatg atctgagcac tttatattca cttacagaaa gagttaaaag   1500
aatcacagta gaaaacagta aagtttttct ggttccttgt ttactttcac aacatttaaa   1560
atcattagaa tacttggatc tcagtgaaaa tttgatggtt gaagaatact tgaaaaattc   1620
agcctgtgag gatgcctggc cctctctaca aactttaatt ttaaggcaaa atcatttggc   1680
atcattggaa aaaaccggag agactttgct cactctgaaa aacttgacta acattgatat   1740
cagtaagaat agttttcatt ctatgcctga aacttgtcag tggccagaaa agatgaaata   1800
tttgaactta tccagcacac gaatacacag tgtaacaggc tgcattccca agacactgga   1860
aattttagat gttagcaaca acaatctcaa tttattttct ttgaatttgc cgcaactcaa   1920
agaactttat atttccagaa ataagttgat gactctacca gatgcctccc tcttacccat   1980
gttactagta ttgaaaatca gtaggaatgc aataactacg ttttctaagg agcaacttga   2040
ctcatttcac acactgaaga ctttggaagc tggtggcaat aacttcattt gctcctgtga   2100
attcctctcc ttcactcagg agcagcaagc actggccaaa gtcttgattg attggccagc   2160
aaattacctg tgtgactctc catcccatgt gcgtggccag caggttcagg atgtccgcct   2220
ctcggtgtcg gaatgtcaca ggacagcact ggtgtctggc atgtgctgtg ctctgttcct   2280
gctgatcctg ctcacggggg tcctgtgcca ccgtttccat ggcctgtggt atatgaaaat   2340
gatgtgggcc tggctccagg ccaaaaggaa gcccaggaaa gctcccagca ggaacatctg   2400
ctatgatgca tttgtttctt acagtgagcg ggatgcctac tgggtggaga accttatggt   2460
ccaggagctg gagaacttca atcccccctt caagttgtgt cttcataagc gggacttcat   2520
tcctggcaag tggatcattg acaatatcat tgactccatt gaaaagagcc acaaaactgt   2580
ctttgtgctt tctgaaaact ttgtgaagag tgagtggtgc aagtatgaac tggacttctc   2640
ccatttccgt ctttttgatg agaacaatga tgctgccatt ctcattcttc tggagcccat   2700
tgagaaaaaa gccattcccc agcgcttctg caagctgcgg aagataatga acaccaagac   2760
ctacctggag tggcccatgg acgaggctca gcgggaagga ttttgggtaa atctgagagc   2820
tgcgataaag tcctaggttc ccatatttaa gaccagtctt tgtctagttg ggatctttat   2880
gtcactagtt atagttaagt tcattcagac ataattatat aaaaactacg tggatgtacc   2940
gtcatttgag gacttgctta ctaaaactac aaaacttcaa attttgtctg ggtgctgtt    3000
```

```
ttataaacat atgccagatt taaaaattgg tttttggttt ttcttttttc tatgagataa   3060

ccatgatcat aagtctatta ctgatatctg aatatagtcc cttggtatcc aagggaattg   3120

gttgcaggat cctcgtggat atcaaaattc atagatgatc aagtccctta taagagtggc   3180

atagtatttg catataacct gtgtacattc tcctgtatac tttaaatcat ctctagatta   3240

cttatgatac ccaatacaat gtaaatacta tgtaaatagt tgtactgtct ttttatttat   3300

attattattg ttattttta ttttcaaaat ttttaaaaca tacttttgat ccacagttgg   3360

ttgacttcat ggatgcagaa cccatggata tagagggcca actgtaatct gtagcaactg   3420

gcttagttca ttaggaaaca gcacaaatga acttaagatt ctcaatgact gtgtcattct   3480

ttcttcctgc taagagactc ctctgtggcc acaaaaggca ttctctgtcc tacctagctg   3540

tcacttctct gtgcagctga tctcaagagc aacaaggcaa agtatttggg gcactcccca   3600

aaacttgttg ctattcctag aaaaaagtgc tgtgtatttc ctattaaact ttacaggatg   3660

agaaatacta gagggtgtat tttcatgtga tctggatctg tctttctggc tattagatag   3720

gtttctccag ccatagttac ttgagagagt gagtacacag tgcaaggtac agtaaattat   3780

gtatttctgt aatttaacaa aataaatact cagtttagga gaatttgaaa gacaaaaaaa   3840

aaaaaaaaa                                                           3849
```

```
<210> SEQ ID NO 26
<211> LENGTH: 1698
<212> TYPE: DNA
<213> ORGANISM: Homo sapiens

<400> SEQUENCE: 26

ctgcctgggg agcccccccg ccccacatcc tgccccgcaa aaggcagctt caccaaagtg     60

gggtatttcc agcctttgta gctttcactt ccacatctac caagtgggcg gagtggcctt    120

ctgtggacga atcagattcc tctccagcac cgactttaag aggcgagccg gggggtcagg    180

gtcccagatg cacaggagga gaagcaggag ctgtcgggaa gatcagaagc cagtcatgga    240

tgaccagcgc gaccttatct ccaacaatga gcaactgccc atgctgggcc ggcgccctgg    300

ggccccggag agcaagtgca gccgcggagc cctgtacaca ggcttttcca tcctggtgac    360

tctgctcctc gctggccagg ccaccaccgc ctacttcctg taccagcagc agggccggct    420

ggacaaactg acagtcacct cccagaacct gcagctggag aacctgcgca tgaagcttcc    480

caagcctccc aagcctgtga gcaagatgcg catggccacc ccgctgctga tgcaggcgct    540

gcccatggga gccctgcccc aggggcccat gcagaatgcc accaagtatg gcaacatgac    600

agaggaccat gtgatgcacc tgctccagaa tgctgacccc ctgaaggtgt acccgccact    660

gaaggggagc ttcccggaga acctgagaca ccttaagaac accatggaga ccatagactg    720

gaaggtcttt gagagctgga tgcaccattg gctcctgttt gaaatgagca ggcactcctt    780

ggagcaaaag cccactgacg ctccaccgaa agtactgacc aagtgccagg aagaggtcag    840

ccacatccct gctgtccacc cgggttcatt caggcccaag tgcgacgaga acggcaacta    900

tctgccactc cagtgctatg ggagcatcgg ctactgctgg tgtgtcttcc ccaacggcac    960

ggaggtcccc aacaccagaa gccgcgggca ccataactgc agtgagtcac tggaactgga   1020

ggacccgtct tctgggctgg gtgtgaccaa gcaggatctg ggcccagtcc ccatgtgaga   1080

gcagcagagg cggtcttcaa catcctgcca gccccacaca gctacagctt tcttgctccc   1140

ttcagccccc agcccctccc ccatctccca ccctgtacct catcccatga gaccctggtg   1200

cctggctctt tcgtcaccct tggacaagac aaaccaagtc ggaacagcag ataacaatgc   1260
```

```
agcaaggccc tgctgcccaa tctccatctg tcaacagggg cgtgaggtcc caggaagtgg   1320

ccaaaagcta gacagatccc cgttcctgac atcacagcag cctccaacac aaggctccaa   1380

gacctaggct catggacgag atgggaaggc acagggagaa gggataaccc tacacccaga   1440

ccccaggctg gacatgctga ctgtcctctc cctccagcc tttggccttg gcttttctag    1500

cctatttacc tgcaggctga gccactctct tccctttccc cagcatcact ccccaaggaa   1560

gagccaatgt tttccaccca taatcctttc tgccgacccc tagttccctc tgctcagcca   1620

agcttgttat cagctttcag ggccatggtt cacattagaa taaaaggtag taattagaac   1680

aaaaaaaaaa aaaaaaaa                                                 1698
```

```
<210> SEQ ID NO 27
<211> LENGTH: 1501
<212> TYPE: DNA
<213> ORGANISM: Homo sapiens

<400> SEQUENCE: 27

agcgagtcct tcttttcctg actgcagctc ttttcatttt gccatccttc tccagctcca     60

tgatggttct gcaggtttct gcggcccccc ggacagtggc tctgacggcg ttactgatgg    120

tgctgctcac atctgtggtc cagggcaggg ccactccaga gaattacgtg taccagggac    180

ggcaggaatg ctacgcgttt aatgggacac agcgcttcct ggagagatac atctacaacc    240

gggaggagta cgcgcgcttc gacagcgacg tgggggagtt ccgggcggtg acggagctgg    300

ggcggcctgc tgcggagtac tggaacagcc agaaggacat cctggaggag aagcgggcag    360

tgccggacag ggtatgcaga cacaactacg agctggacga ggccgtgacc ctgcagcgcc    420

gagtccagcc taaggtgaac gtttccccct ccaagaaggg gcccctgcag caccacaacc    480

tgcttgtctg ccacgtgaca gatttctacc caggcagcat tcaagtccga tggttcctga    540

atggacagga ggaaacagct ggggtcgtgt ccaccaacct gatccgtaat ggagactgga    600

ccttccagat cctggtgatg ctggaaatga ccccccagca gggagacgtc tacatctgcc    660

aagtggagca caccagcctg gacagtcctg tcaccgtgga gtggaaggca cagtctgatt    720

ctgcccagag taagacattg acgggagctg gggcttcgt gctggggctc atcatctgtg     780

gagtgggcat cttcatgcac aggaggagca agaaagttca acgaggatct gcataaacag    840

ggttcctgac ctcaccgaaa agactaatgt gccttagaac aagcatttgc tgtgttttgt    900

taacacctgg ttccaggaca gaccctcagc ttcccaagag gatactgctg ccaagaagtt    960

gctctgaagt cagtttctat cgttctgctc tttgattcaa agcactgttt ctctcactgg   1020

gcctccaacc atgttccctt cttcttagca ccacaaataa tcaaaaccca acataagtgt   1080

ttgctttcct ttaaaaatat gcatcaaatc gtctctcatt acttttctct gagggtttta   1140

gtaaacagta ggagttaata aagaagttca ttttggttta cacgtaggaa agaagagaag   1200

catcaaagtg gagatatgtt aactattgta taatgtggcc tgttatacat gacactcttc   1260

tgaattgact gtatttcagt gagctgcccc caaatcaagt ttagtgccct catccattta   1320

tgtctcagac cgctattctt aactattcaa tggtgagcag actgcaaatc tgcctgatag   1380

gacccatatt cccacagcac taattcaaca tatatcttac tgagagcatg ttttatcatt   1440

accattaaga agttaaatga acatcagaat ttaaaatcat aaatataatc taatacactt   1500

t                                                                   1501

<210> SEQ ID NO 28
```

<211> LENGTH: 1697
<212> TYPE: DNA
<213> ORGANISM: Homo sapiens

<400> SEQUENCE: 28

```
atttccagtg ctagaggccc acagtttcag tctcatctgc ctccactcgg cctcagttcc     60

tcatcactgt tcctgtgctc acagtcatca attatagacc ccacaacatg cgccctgaag    120

acagaatgtt ccatatcaga gctgtgatct tgagagccct ctccttggct ttcctgctga    180

gtctccgagg agctggggcc atcaaggcgg accatgtgtc aacttatgcc gcgtttgtac    240

agacgcatag accaacaggg gagtttatgt ttgaatttga tgaagatgag atgttctatg    300

tggatctgga caagaaggag accgtctggc atctggagga gtttggccaa gccttttcct    360

ttgaggctca gggcgggctg gctaacattg ctatattgaa caacaacttg aataccttga    420

tccagcgttc caaccacact caggccacca acgatccccc tgaggtgacc gtgtttccca    480

aggagcctgt ggagctgggc cagcccaaca ccctcatctg ccacattgac aagttcttcc    540

caccagtgct caacgtcacg tggctgtgca acggggagct ggtcactgag ggtgtcgctg    600

agagcctctt cctgcccaga acagattaca gcttccacaa gttccattac ctgacctttg    660

tgccctcagc agaggacttc tatgactgca gggtggagca ctggggcttg gaccagccgc    720

tcctcaagca ctgggaggcc caagagccaa tccagatgcc tgagacaacg gagactgtgc    780

tctgtgccct gggcctggtg ctgggcctag tcggcatcat cgtgggcacc gtcctcatca    840

taaagtctct gcgttctggc catgaccccc gggcccaggg gaccctgtga aatactgtaa    900

aggtgacaaa atatctgaac agaagaggac ttaggagaga tctgaactcc agctgcccta    960

caaactccat ctcagctttt cttctcactt catgtgaaaa ctactccagt ggctgactga   1020

attgctgacc cttcaagctc tgtccttatc cattacctca aagcagtcat tccttagtaa   1080

agtttccaac aaatagaaat taatgacact ttggtagcac taatatggag attatccttt   1140

cattgagcct tttatcctct gttctccttt gaagaacccc tcactgtcac cttcccgaga   1200

ataccctaag accaataaat acttcagtat ttcagagcgg ggagactctg agtcattctt   1260

actggaagtc taggaccagg tcacatgtga atactatttc ttgaaggtgt ggtttcaacc   1320

tctgttgccg atgtggttac taaaggttct gatcccactt gaacggaaag gtctgaggat   1380

attgattcag tcctgggttt ttccctaact acaggatagg gtggggtaga gaaaggatat   1440

ttgggggaaa ttttacttgg atgaagattt tcttggatgt agtttgaaga ctgcagtgtt   1500

tgaagtctct gagggaagag atttggtctg tctggatcaa gatttcaggc agattaggat   1560

tccattcaca gcccctgagc ttccttccca aggctgtatt gtaattatag caatatttca   1620

tggaggattt ttctacatga taaactaaga gccaagaaat aaaattttta aaatgcccta   1680

aaaaaaaaaa aaaaaaa                                                  1697
```

<210> SEQ ID NO 29
<211> LENGTH: 1312
<212> TYPE: DNA
<213> ORGANISM: Homo sapiens

<400> SEQUENCE: 29

```
ttttaatggt cagactctat tacaccccac attctctttt cttttattct tgtctgttct     60

gcctcactcc cgagctctac tgactcccaa cagagcgccc aagaagaaaa tggccataag    120

tggagtccct gtgctaggat ttttcatcat agctgtgctg atgagcgctc aggaatcatg    180

ggctatcaaa gaagaacatg tgatcatcca ggccgagttc tatctgaatc ctgaccaatc    240
```

```
aggcgagttt atgtttgact ttgatggtga tgagattttc catgtggata tggcaaagaa    300
ggagacggtc tggcggcttg aagaatttgg acgatttgcc agctttgagg ctcaaggtgc    360
attggccaac atagctgtgg acaaagccaa cctggaaatc atgacaaagc gctccaacta    420
tactccgatc accaatgtac ctccagaggt aactgtgctc acaaacagcc ctgtggaact    480
gagagagccc aacgtcctca tctgtttcat agacaagttc accccaccag tggtcaatgt    540
cacgtggctt cgaaatggaa aacctgtcac cacaggagtg tcagagacag tcttcctgcc    600
cagggaagac caccttttcc gcaagttcca ctatctcccc ttcctgccct caactgagga    660
cgtttacgac tgcagggtgg agcactgggg cttggatgag cctcttctca agcactggga    720
gtttgatgct ccaagccctc tcccagagac tacagagaac gtggtgtgtg ccctgggcct    780
gactgtgggt ctggtgggca tcattattgg gaccatcttc atcatcaagg gattgcgcaa    840
aagcaatgca gcagaacgca gggggcctct gtaaggcaca tggaggtgat ggtgtttctt    900
agagagaaga tcactgaaga aacttctgct ttaatggctt tacaaagctg gcaatattac    960
aatccttgac ctcagtgaaa gcagtcatct tcagcatttt ccagccctat agccacccca   1020
agtgtggata tgcctcttcg attgctccgt actctaacat ctagctggct tccctgtcta   1080
ttgccttttc ctgtatctat tttcctctat ttcctatcat tttattatca ccatgcaatg   1140
cctctggaat aaaacataca ggagtctgtc tctgctatgg aatgccccat ggggcatctc   1200
ttgtgtactt attgtttaag gtttcctcaa actgtgattt ttctgaacac aataaactat   1260
tttgatgatc ttgggtggaa aaaaaaaaaa aaaaaaaaaa aaaaaaaaaa aa           1312
```

<210> SEQ ID NO 30
<211> LENGTH: 2973
<212> TYPE: DNA
<213> ORGANISM: Homo sapiens

<400> SEQUENCE: 30

```
gggccgctct ctgacatcag agctgctgta gagcggagag gggcaggggt gaagggccac     60
ggtggtgcaa cccaccactt cctccaagga ggagctgaga ggaacaggaa gtgtcaggac    120
tttacgaccc gcgcctccag ctgaggtttc tagacgtgac ccagggcaga ctggtagcaa    180
agcccccacg cccagccagg agcaccgccg aggactccag cacaccgagg gacatgctgg    240
gcctgcgccc cccactgctc gccctggtgg ggctgctctc cctcgggtgc gtcctctctc    300
aggagtgcac gaagttcaag gtcagcagct gccgggaatg catcgagtcg gggcccggct    360
gcacctggtg ccagaagctg aacttcacag ggccggggga tcctgactcc attcgctgcg    420
acacccggcc acagctgctc atgaggggct gtgcggctga cgacatcatg gaccccacaa    480
gcctcgctga aacccaggaa gaccacaatg gggccagaa gcagctgtcc ccacaaaaag    540
tgacgcttta cctgcgacca ggccaggcag cagcgttcaa cgtgaccttc cggcgggcca    600
agggctaccc catcgacctg tactatctga tggacctctc ctactccatg cttgatgacc    660
tcaggaatgt caagaagcta ggtggcgacc tgctccgggc cctcaacgag atcaccgagt    720
ccggccgcat tggcttcggg tccttcgtgg acaagaccgt gctgccgttc gtgaacacgc    780
accctgataa gctgcgaaac ccatgcccca acaaggagaa agagtgccag cccccgtttg    840
ccttcaggca cgtgctgaag ctgaccaaca actccaacca gtttcagacc gaggtcggga    900
agcagctgat ttccggaaac ctggatgcac ccgagggtgg gctggacgcc atgatgcagg    960
tcgccgcctg cccggaggaa atcggctggc gcaacgtcac gcggctgctg gtgtttgcca   1020
```

```
ctgatgacgg cttccatttc gcgggcgacg ggaagctggg cgccatcctg acccccaacg   1080

acggccgctg tcacctggag gacaacttgt acaagaggag caacgaattc gactacccat   1140

cggtgggcca gctggcgcac aagctggctg aaaacaacat ccagcccatc ttcgcggtga   1200

ccagtaggat ggtgaagacc tacgagaaac tcaccgagat catccccaag tcagccgtgg   1260

gggagctgtc tgaggactcc agcaatgtgg tccatctcat taagaatgct tacaataaac   1320

tctcctccag ggtcttcctg gatcacaacg ccctccccga caccctgaaa gtcacctacg   1380

actccttctg cagcaatgga gtgacgcaca ggaaccagcc cagaggtgac tgtgatggcg   1440

tgcagatcaa tgtcccgatc accttccagg tgaaggtcac ggccacagag tgcatccagg   1500

agcagtcgtt tgtcatccgg gcgctgggct tcacggacat agtgaccgtg caggttcttc   1560

cccagtgtga gtgccggtgc cgggaccaga gcagagaccg cagcctctgc catggcaagg   1620

gcttcttgga gtgcggcatc tgcaggtgtg acactggcta cattgggaaa aactgtgagt   1680

gccagacaca gggccggagc agccaggagc tggaaggaag ctgccggaag gacaacaact   1740

ccatcatctg ctcagggctg gggggactgtg tctgcgggca gtgcctgtgc cacaccagcg   1800

acgtccccgg caagctgata tacgggcagt actgcgagtg tgacaccatc aactgtgagc   1860

gctacaacgg ccaggtctgc ggcggcccgg ggagggggct ctgcttctgc gggaagtgcc   1920

gctgccaccc gggctttgag ggctcagcgt gccagtgcga gaggaccact gagggctgcc   1980

tgaacccgcg gcgtgttgag tgtagtggtc gtggccggtg ccgctgcaac gtatgcgagt   2040

gccattcagg ctaccagctg cctctgtgcc aggagtgccc cggctgcccc tcaccctgtg   2100

gcaagtacat ctcctgcgcc gagtgcctga agttcgaaaa gggccccttt gggaagaact   2160

gcagcgcggc gtgtccgggc ctgcagctgt cgaacaaccc cgtgaagggc aggacctgca   2220

aggagaggga ctcagagggc tgctgggtgg cctacacgct ggagcagcag gacgggatgg   2280

accgctacct catctatgtg gatgagagcc gagagtgtgt ggcaggcccc aacatcgccg   2340

ccatcgtcgg gggcaccgtg gcaggcatcg tgctgatcgg cattctcctg ctggtcatct   2400

ggaaggctct gatccacctg agcgacctcc gggagtacag gcgctttgag aaggagaagc   2460

tcaagtccca gtggaacaat gataatcccc ttttcaagag cgccaccacg acggtcatga   2520

accccaagtt tgctgagagt taggagcact tggtgaagac aaggccgtca ggacccacca   2580

tgtctgcccc atcacgcggc cgagacatgg cttgccacag ctcttgagga tgtcaccaat   2640

taaccagaaa tccagttatt ttccgccctc aaaatgacag ccatggccgg ccgggtgctt   2700

ctgggggctc gtcgggggga cagctccact ctgactggca cagtctttgc atggagactt   2760

gaggagggag ggcttgaggt tggtgaggtt aggtgcgtgt ttcctgtgca agtcaggaca   2820

tcagtctgat taaaggtggt gccaatttat ttacatttaa acttgtcagg gtataaaatg   2880

acatcccatt aattatattg ttaatcaatc acgtgtatag aaaaaaaata aaacttcaat   2940

acaggctgtc catggaaaaa aaaaaaaaaa aaa                                2973
```

<210> SEQ ID NO 31
<211> LENGTH: 2755
<212> TYPE: DNA
<213> ORGANISM: Homo sapiens

<400> SEQUENCE: 31

```
cctacccgcg cgcaggccaa gttgctgaat caatggagcc ctccccaacc cgggcgttcc     60

ccagcgaggc ttccttccca tcctcctgac caccggggct tttcgtgagc tcgtctctga    120

tctcgcgcaa gagtgacaca caggtgttca aagacgcttc tggggagtga gggaagcggt    180
```

```
ttacgagtga cttggctgga gcctcagggg cgggcactgg cacggaacac accctgaggc    240
cagccctggc tgcccaggcg gagctgcctc ttctcccgcg ggttggtgga cccgctcagt    300
acggagttgg ggaagctctt tcacttcgga ggattgctca acaaccatgc tgggcatctg    360
gaccctccta cctctggttc ttacgtctgt tgctagatta tcgtccaaaa gtgttaatgc    420
ccaagtgact gacatcaact ccaagggatt ggaattgagg aagactgtta ctacagttga    480
gactcagaac ttggaaggcc tgcatcatga tggccaattc tgccataagc cctgtcctcc    540
aggtgaaagg aaagctaggg actgcacagt caatggggat gaaccagact gcgtgccctg    600
ccaagaaggg aaggagtaca cagacaaagc ccatttttct tccaaatgca gaagatgtag    660
attgtgtgat gaaggacatg gcttagaagt ggaaataaac tgcacccgga cccagaatac    720
caagtgcaga tgtaaaccaa actttttttg taactctact gtatgtgaac actgtgaccc    780
ttgcaccaaa tgtgaacatg gaatcatcaa ggaatgcaca ctcaccagca acaccaagtg    840
caaagaggaa ggatccagat ctaacttggg gtggctttgt cttcttcttt tgccaattcc    900
actaattgtt tgggtgaaga gaaaggaagt acagaaaaca tgcagaaagc acagaaagga    960
aaaccaaggt tctcatgaat ctccaacttt aaatcctgaa acagtggcaa taaatttatc   1020
tgatgttgac ttgagtaaat atatcaccac tattgctgga gtcatgacac taagtcaagt   1080
taaaggcttt gttcgaaaga atggtgtcaa tgaagccaaa ataggtgaga tcaagaatga   1140
caatgtccaa gacacagcag aacagaaagt tcaactgctt cgtaattggc atcaacttca   1200
tggaaagaaa gaagcgtatg acacattgat taaagatctc aaaaaagcca atctttgtac   1260
tcttgcagag aaaattcaga ctatcatcct caaggacatt actagtgact cagaaaattc   1320
aaacttcaga aatgaaatcc aaagcttggt ctagagtgaa aaacaacaaa ttcagttctg   1380
agtatatgca attagtgttt gaaaagattc ttaatagctg gctgtaaata ctgcttggtt   1440
ttttactggg tacattttat catttattag cgctgaagag ccaacatatt tgtagatttt   1500
taatatctca tgattctgcc tccaaggatg tttaaaatct agttgggaaa acaaacttca   1560
tcaagagtaa atgcagtggc atgctaagta cccaaatagg agtgtatgca gaggatgaaa   1620
gattaagatt atgctctggc atctaacata tgattctgta gtatgaatgt aatcagtgta   1680
tgttagtaca aatgtctatc cacaggctaa ccccactcta tgaatcaata gaagaagcta   1740
tgaccttttg ctgaaatatc agttactgaa caggcaggcc actttgcctc taaattacct   1800
ctgataattc tagagatttt accatatttc taaactttgt ttataactct gagaagatca   1860
tatttatgta aagtatatgt atttgagtgc agaatttaaa taaggctcta cctcaaagac   1920
ctttgcacag tttattggtg tcatattata caatatttca attgtgaatt cacatagaaa   1980
acattaaatt ataatgtttg actattatat atgtgtatgc attttactgg ctcaaaacta   2040
cctacttctt tctcaggcat caaaagcatt ttgagcagga gagtattact agagctttgc   2100
cacctctcca tttttgcctt ggtgctcatc ttaatggcct aatgcacccc caaacatgga   2160
aatatcacca aaaaatactt aatagtccac caaaaggcaa gactgccctt agaaattcta   2220
gcctggtttg gagatactaa ctgctctcag agaaagtagc tttgtgacat gtcatgaacc   2280
catgtttgca atcaaagatg ataaaataga ttcttatttt tcccccaccc ccgaaaatgt   2340
tcaataatgt cccatgtaaa acctgctaca aatggcagct tatacatagc aatggtaaaa   2400
tcatcatctg gatttaggaa ttgctcttgt cataccccca agtttctaag atttaagatt   2460
ctccttacta ctatcctacg tttaaatatc tttgaaagtt tgtattaaat gtgaatttta   2520
```

agaaataata tttatatttc tgtaaatgta aactgtgaag atagttataa actgaagcag 2580
atacctggaa ccacctaaag aacttccatt tatggaggat ttttttgccc cttgtgtttg 2640
gaattataaa atataggtaa aagtacgtaa ttaaataatg tttttggtaa aaaaaaaaaa 2700
aaaaaaaaaa aaaaaaaaaa aaaaaaaaaa aaaaaaaaaa aaaaaaaaaa aaaaa 2755

<210> SEQ ID NO 32
<211> LENGTH: 1280
<212> TYPE: DNA
<213> ORGANISM: Homo sapiens

<400> SEQUENCE: 32
cctataactt ggaatgtggg tggaggggtt catagttctc cctgagtgag acttgcctgc 60
ttctctggcc cctggtcctg tcctgttctc cagcatggtg tgtctgaagc tccctggagg 120
ctcctgcatg acagcgctga cagtgacact gatggtgctg agctccccac tggctttgtc 180
tggggacacc cgaccacgtt tcctgtggca gcctaagagg gagtgtcatt tcttcaatgg 240
gacggagcgg gtgcggttcc tggacagata cttctataac caggaggagt ccgtgcgctt 300
cgacagcgac gtgggggagt tccgggcggt gacggagctg gggcggcctg acgctgagta 360
ctggaacagc cagaaggaca tcctggagca ggcgcgggcc gcggtggaca cctactgcag 420
acacaactac ggggttgtgg agagcttcac agtgcagcgg cgagtccaac ctaaggtgac 480
tgtatatcct tcaaagaccc agcccctgca gcaccacaac ctcctggtct gctctgtgag 540
tggtttctat ccaggcagca ttgaagtcag gtggttcctg aacggccagg aagagaaggc 600
tgggatggtg tccacaggcc tgatccagaa tggagactgg accttccaga ccctggtgat 660
gctggaaaca gttcctcgaa gtggagaggt ttacacctgc caagtggagc acccaagcgt 720
gacaagccct ctcacagtgg aatggagagc acggtctgaa tctgcacaga gcaagatgct 780
gagtggagtc gggggctttg tgctgggcct gctcttcctt ggggccgggc tgttcatcta 840
cttcaggaat cagaaaggac actctggact tcagccaaca ggattcctga gctgaaatgc 900
agatgaccac attcaaggaa gaactttctg ccccggcttt gcaggatgaa aagctttcct 960
gcttggcagt tattcttcca caagagaggg ctttctcagg acctggttgc tactggttcg 1020
gcaactgcag aaaatgtcct cccttgtggc ttcctcagct cctgcccttg gcctgaagtc 1080
ccagcattga tggcagcgcc tcatcttcaa cttttgtgct cccctttgcc taaaccgtat 1140
ggcctcccgt gcatctgtat tcaccctgta tgacaaacac attacattat taaatgtttc 1200
tcaaagatgg agttaaaaaa aaaaaaaaaa aaaaaaaaaa aaaaaaaaaa aaaaaaaaaa 1260
aaaaaaaaaa aaaaaaaaaa 1280

<210> SEQ ID NO 33
<211> LENGTH: 2398
<212> TYPE: DNA
<213> ORGANISM: Homo sapiens

<400> SEQUENCE: 33
ctgatataga gcaggcgccg cgggtcgcag cacagtgcgg agaccgcagc cccggagccc 60
gggccagggt ccacctgtcc ccgcagcgcc ggctcgcgcc ctcctgccgc agccaccgag 120
ccgccgtcta gcgccccgac ctcgccacca tgagagccct gctggcgcgc ctgcttctct 180
gcgtcctggt cgtgagcgac tccaaaggca gcaatgaact tcatcaagtt ccatcgaact 240
gtgactgtct aaatggagga acatgtgtgt ccaacaagta cttctccaac attcactggt 300
gcaactgccc aaagaaattc ggagggcagc actgtgaaat agataagtca aaaacctgct 360

```
atgaggggaa tggtcacttt taccgaggaa aggccagcac tgacaccatg ggccggccct    420
gcctgccctg gaactctgcc actgtccttc agcaaacgta ccatgcccac agatctgatg    480
ctcttcagct gggcctgggg aaacataatt actgcaggaa cccagacaac cggaggcgac    540
cctggtgcta tgtgcaggtg ggcctaaagc cgcttgtcca agagtgcatg gtgcatgact    600
gcgcagatgg aaaaaagccc tcctctcctc cagaagaatt aaaatttcag tgtggccaaa    660
agactctgag gccccgcttt aagattattg gggagaatt caccaccatc gagaaccagc    720
cctggtttgc ggccatctac aggaggcacc ggggggctc tgtcacctac gtgtgtggag    780
gcagcctcat cagcccttgc tgggtgatca gcgccacaca ctgcttcatt gattacccaa    840
agaaggagga ctacatcgtc tacctgggtc gctcaaggct taactccaac acgcaagggg    900
agatgaagtt tgaggtggaa aacctcatcc tacacaagga ctacagcgct gacacgcttg    960
ctcaccacaa cgacattgcc ttgctgaaga tccgttccaa ggagggcagg tgtgcgcagc   1020
catcccggac tatacagacc atctgcctgc cctcgatgta taacgatccc cagtttggca   1080
caagctgtga gatcactggc tttggaaaag agaattctac cgactatctc tatccggagc   1140
agctgaaaat gactgttgtg aagctgattt cccaccggga gtgtcagcag ccccactact   1200
acggctctga agtcaccacc aaaatgctgt gtgctgctga cccacagtgg aaaacagatt   1260
cctgccaggg agactcaggg ggacccctcg tctgttccct ccaaggccgc atgactttga   1320
ctggaattgt gagctggggc cgtggatgtg ccctgaagga caagccaggc gtctacacga   1380
gagtctcaca cttcttaccc tggatccgca gtcacaccaa ggaagagaat ggcctggccc   1440
tctgagggtc cccagggagg aaacgggcac cacccgcttt cttgctggtt gtcatttttg   1500
cagtagagtc atctccatca gctgtaagaa gagactggga agataggctc tgcacagatg   1560
gatttgcctg tgccacccac cagggcgaac gacaatagct ttaccctcag gcataggcct   1620
gggtgctggc tgcccagacc cctctggcca ggatggaggg gtggtcctga ctcaacatgt   1680
tactgaccag caacttgtct ttttctggac tgaagcctgc aggagttaaa aagggcaggg   1740
catctcctgt gcatgggtga agggagagcc agctcccccg acggtgggca tttgtgaggc   1800
ccatggttga gaaatgaata atttcccaat taggaagtgt aacagctgag gtctcttgag   1860
ggagcttagc caatgtggga gcagcggttt ggggagcaga gacactaacg acttcagggc   1920
agggctctga tattccatga atgtatcagg aaatatatat gtgtgtgtat gtttgcacac   1980
ttgtgtgtgg gctgtgagtg taagtgtgag taagagctgg tgtctgattg ttaagtctaa   2040
atatttcctt aaactgtgtg gactgtgatg ccacacagag tggtctttct ggagaggtta   2100
taggtcactc ctggggcctc ttgggtcccc cacgtgacag tgcctgggaa tgtattattc   2160
tgcagcatga cctgtgacca gcactgtctc agtttcactt tcacatagat gtccctttct   2220
tggccagtta tcccttcctt ttagcctagt tcatccaatc ctcactgggt ggggtgagga   2280
ccactcctgt acactgaata tttatatttc actattttta tttatatttt tgtaatttta   2340
aataaaagtg atcaataaaa tgtgattttt ctgatgacaa aaaaaaaaaa aaaaaaa      2398
```

<210> SEQ ID NO 34
<211> LENGTH: 3050
<212> TYPE: DNA
<213> ORGANISM: Homo sapiens

<400> SEQUENCE: 34

```
ggagtcagtg atttgaacga agtactttca gtttcatatt actctaaatc cattacaaat     60
```

-continued

```
ctgcttagct tctaaatatt tcatcaatga ggaaatccca gccctacaac ttcggaacag    120
tgaaatatta gtccagggat ccagtgagag acacagaagt gctagaagcc agtgctcgtg    180
aactaaggag aaaaagaaca gacaagggaa cagcctggac atggcatcag agatccacat    240
gacaggccca atgtgcctca ttgagaacac taatgggcga ctgatggcga atccagaagc    300
tctgaagatc ctttctgcca ttacacagcc tatggtggtg gtggcaattg tgggcctcta    360
ccgcacaggc aaatcctacc tgatgaacaa gctggctgga aagaaaaagg gcttctctct    420
gggctccacg gtgcagtctc acactaaagg aatctggatg tggtgtgtgc ccaccccaa    480
gaagccaggc cacatcctag ttctgctgga caccgagggt ctgggagatg tagagaaggg    540
tgacaaccag aatgactcct ggatcttcgc cctggccgtc ctcctgagca gcaccttcgt    600
gtacaatagc ataggaacca tcaaccagca ggctatggac caactgtact atgtgacaga    660
gctgacacat agaatccgat caaaatcctc acctgatgag aatgagaatg aggttgagga    720
ttcagctgac tttgtgagct tcttcccaga ctttgtgtgg acactgagag atttctccct    780
ggacttggaa gcagatggac aacccctcac accagatgag tacctgacat actccctgaa    840
gctgaagaaa ggtaccagtc aaaaagatga aacttttaac ctgcccagac tctgtatccg    900
gaaattcttc ccaaagaaaa aatgctttgt ctttgatcgg cccgttcacc gcaggaagct    960
tgcccagctc gagaaactac aagatgaaga gctggacccc gaatttgtgc aacaagtagc   1020
agacttctgt tcctacatct ttagtaattc caaaactaaa actctttcag gaggcatcca   1080
ggtcaacggg cctcgtctag agagcctggt gctgacctac gtcaatgcca tcagcagtgg   1140
ggatctgccg tgcatggaga acgcagtcct ggccttggcc cagatagaga actcagctgc   1200
agtgcaaaag gctattgccc actatgaaca gcagatgggc cagaaggtgc agctgcccac   1260
agaaaccctc caggagctgc tggacctgca cagggacagt gagagagagg ccattgaagt   1320
cttcatcagg agttccttca aagatgtgga ccatctattt caaaaggagt tagcggccca   1380
gctagaaaaa aagcgggatg acttttgtaa acagaatcag gaagcatcat cagatcgttg   1440
ctcagcttta cttcaggtca ttttcagtcc tctagaagaa gaagtgaagg cgggaattta   1500
ttcgaaacca gggggctatc gtctctttgt tcagaagcta caagacctga agaaaaagta   1560
ctatgaggaa ccgaggaagg ggatacaggc tgaagagatt ctgcagacat acttgaaatc   1620
caaggagtct atgactgatg caattctcca gacagaccag actctcacag aaaaagaaaa   1680
ggagattgaa gtggaacgtg tgaaagctga gtctgcacag gcttcagcaa aaatgttgca   1740
ggaaatgcaa agaaagaatg agcagatgat ggaacagaag gagaggagtt atcaggaaca   1800
cttgaaacaa ctgactgaga agatggagaa cgacagggtc cagttgctga aagagcaaga   1860
gaggaccctc gctcttaaac ttcaggaaca ggagcaacta ctaaaagagg gatttcaaaa   1920
agaaagcaga ataatgaaaa atgagataca ggatctccag acgaaaatga gacgacgaaa   1980
ggcatgtacc ataagctaaa gaccagagcc ttcctgtcac ccctaaccaa ggcataattg   2040
aaacaatttt agaatttgga acaagcgtca ctacatttga taataattag atcttgcatc   2100
ataacaccaa aagtttataa aggcatgtgg tacaatgatc aaaatcatgt tttttcttaa   2160
aaaaaaaaaa agactgtaaa ttgtgcaaca aagatgcatt tacctctgta tcaactcagg   2220
aaatctcata agctggtacc actcaggaga agtttattct tccagatgac cagcagtaga   2280
caaatggata ctgagcagag tcttaggtaa aagtcttggg aaatatttgg gcattggtct   2340
ggccaagtct acaatgtccc aatatcaagg acaaccaccc tagcttctta gtgaagacaa   2400
tgtacagtta tccgttagat caagactaca cggtctatga gcaataatgt gatttctgga   2460
```

```
cattgcccat gtataatcct cactgatgat ttcaagctaa agcaaaccac cttatacaga   2520

gatctagaat ctctttatgt tctccagagg aaggtggaag aaaccatggg caggagtagg   2580

aattgagtga taaacaattg ggctaatgaa gaaaacttct cttattgttc agttcatcca   2640

gattataact tcaatgggac actttagacc attagacaat tgacactgga ttaaacaaat   2700

tcacataatg ccaaatacac aatgtattta tagcaacgta taatttgcaa agatggactt   2760

taaaagatgc tgtgtaacta aactgaaata attcaattac ttattattta gaatgttaaa   2820

gcttatgata gtcttttcta actcttaaca ctcatacttg aaaactttct gagtttcccc   2880

agaagagaat atgggatttt ttttgacatt tttgactcat ttaataatgc tcttgtgttt   2940

acctagtata tgtagacttt gtcttatgtg tgaaaagtcc taggaaagtg gttgatgttt   3000

cttatagcaa ttaaaaatta tttttgaact gaaaatacaa tgtatttcac              3050
```

<210> SEQ ID NO 35
<211> LENGTH: 4146
<212> TYPE: DNA
<213> ORGANISM: Homo sapiens

<400> SEQUENCE: 35

```
cggagcctca gcgcccgccg cgtccctccc tccgcccctt tcgcccacac ctacccgccc     60

ccgccggccc ggctctcagt agcgtcgccc gaggctgcag cagcgcatcc cggggcatgg    120

cgcggcgggg gcgcggaggg ctcggttcgg agggggccgg gagcccgggc gccctggagt    180

gaggaggacc gggagctggc tctggaggct gcggaggcga cgccggagag aacgaagcct    240

cggctgggag cggatctttc gaagatggtt tggctgcctt ggagatttgg agatctgatg    300

ccacgatgag gactcacaca cggggggctc ccagtgtgtt tttcatatat ttgctttgct    360

ttgtgtcagc ctacatcacc gacgagaacc cagaagttat gattcccttc accaatgcca    420

actacgacag ccatcccatg ctgtacttct ccagggcaga agtggcggag ctgcagctca    480

gggctgccag ctcgcacgag cacattgcag cccgcctcac ggaggctgtg cacacgatgc    540

tgtccagccc cttggaatac ctccctccct gggatcccaa ggactacagt gcccgctgga    600

atgaaatttt tggaaacaac ttgggtgcct tggcaatgtt ctgtgtgctg tatcctgaga    660

acattgaagc ccgagacatg gccaaagact acatggagag gatggcagcg cagcctagtt    720

ggttggtgaa agatgctcct tgggatgagg tcccgcttgc tcactccctg gttggttttg    780

ccactgctta tgacttcttg tacaactacc tgagcaagac acaacaggag aagtttcttg    840

aagtgattgc caatgcctca gggtatatgt atgaaacttc atacaggaga ggatggggat    900

ttcaatacct gcacaatcat cagcccacca actgtatggc tttgctcacg ggaagcctag    960

tcctgatgaa tcaaggatat cttcaagaag cctacttatg gaccaaacaa gttctgacca   1020

tcatggagaa atctctggtc ttgctcaggg aggtgacgga tggctccctc tatgaaggag   1080

ttgcgtatgg cagctacacc actagatcac tcttccaata catgtttctc gtccagaggc   1140

acttcaacat caaccacttt ggccatccgt ggcttaaaca acactttgca tttatgtata   1200

gaaccatcct gccagggttt caaaggactg tggctattgc ggactcaaat tacaactggt   1260

tttatggtcc agaaagccaa ttagtgttcc ttgataaatt tgtcatgcgt aatggcagtg   1320

gtaactggct agctgaccaa atcagaagga accgtgtggt ggaaggtcca ggaacaccat   1380

ccaaagggca gcgctggtgc actctgcaca cagaatttct ctggtatgat ggcagcttga   1440

aatcggttcc tcctccagac tttggcaccc ctacactgca ttattttgaa gactggggtg   1500
```

```
tcgtgactta tggaagtgca ctacctgcag aaatcaatag atctttcctt tccttcaagt   1560
ctggaaaact ggggggacgt gcaatatatg acattgtcca cagaaacaaa tacaaagatt   1620
ggatcaaagg atggagaaat tttaatgcag ggcatgaaca tcctgatcaa aactcattta   1680
cttttgctcc caatggtgtg cctttcatta ctgaggctct gtacgggcca aagtacacct   1740
tcttcaacaa tgttttgatg ttttccccag ctgtgtcaaa gagctgcttt tctccctggg   1800
tgggtcaggt cacagaagac tgctcatcaa aatggtctaa atacaagcat gacctggcag   1860
ctagttgtca ggggagggtg gttgcagcag aggagaaaaa tggggtggtt ttcatccgag   1920
gagaaggtgt gggagcttat aacccccagc tcaacctgaa gaatgttcag aggaatctca   1980
tcctcctaca tccacagctg cttctccttg tagaccaaat acacctggga gaggagagtc   2040
ccttggagac agcagcgagc ttcttccata atgtggatgt tccttttgag gagactgtgg   2100
tagatggtgt ccatggggct ttcatcaggc agagagatgg tctctataaa atgtactgga   2160
tggacgatac tggctacagc gagaaagcaa cctttgcctc agtgacatat cctcggggct   2220
atccctacaa cgggacaaac tatgtgaatg tcaccatgca cctccgaagt cccatcacca   2280
gggcagctta cctcttcata gggccatcta tagatgttca gagcttcact gtccacggag   2340
actctcagca actggatgtg ttcatagcca ccagcaaaca tgcctacgcc acatacctgt   2400
ggacaggtga ggccacagga cagtctgcct ttgcacaggt cattgctgat cgtcacaaaa   2460
ttctgtttga ccggaattca gccatcaaga gcagcattgt ccctgaggtg aaggactatg   2520
ctgctattgt ggaacagaac ttgcagcatt ttaaaccagt gtttcagctg ctggagaagc   2580
agatactgtc ccgagtccgg aacacagcta gctttaggaa gactgctgaa cgcctgctga   2640
gattttcaga taagagacag actgaggagg ccattgacag gatttttgcc atatcacagc   2700
aacagcagca gcaaagcaag tcaaagaaaa accgaagggc aggcaaacgc tataaatttg   2760
tggatgctgt ccctgatatt tttgcacaga ttgaagtcaa tgagaaaaag attagacaga   2820
aagctcagat tttggcacag aaagaactac ccatagatga agatgaagaa atgaaagacc   2880
ttttagattt tgcagatgta acatacgaga aacataaaaa tgggggcttg attaaaggcc   2940
ggtttggaca ggcacggatg gtgacaacta cacacagcag ggccccatca ctgtctgctt   3000
cctataccag gttgttcctg attctgaaca ttgctatttt ctttgtcatg ttggcaatgc   3060
aactgactta tttccagagg gcccagagcc tacatggcca aagatgtctt tatgcagttc   3120
ttctcataga tagctgtatt ttattatggt tgtactcttc ttgttcccaa tcacagtgtt   3180
agcactgaag ctataaatta cctggtcatt ttgtgatcac aagagtctat gcaaaaaaaa   3240
aaatttcttt accccagatt atcagatttt tttccctcag attcatttta acaaattaag   3300
ggaagatatt ttgacacaag aaagcaggaa cgtggagaaa ttggagcagg aaaagaaatt   3360
atcaaagcaa tagaaatagc ttggtggtcc tatggtgttt ttggaagtat ttggcattgc   3420
taattgagca gtccatatag tactactttt agaagaaaca aaaagtctat tttttaaagt   3480
aatgtttttt cttatgagaa aaaggtttag atagaattgg gttttattaa tattaattta   3540
atgctattag caatttccat atactatatt gtggaaaaga ctgaagaata caattctgag   3600
aaatataaaa aaattttaat ggtatactca tgttgaaaga taaatgttgc taagtcctgg   3660
tatgatggtg tgagcttcct tggggaagta cttcttgagt tatgtaacta acaggatgtt   3720
ttactacaga tctggatggc tattcagata acatggcaaa aaatgatagc agaagatcat   3780
taaaaactta aaatatattt tattagaaaa catttatcta tgaatgaata tttccttgat   3840
gctggtctct gcacacatat gcttggttac ttgcatgcat tcattggttg ttcaataagt   3900
```

```
gagatgatta cagataatac tgtattttcc ttatatggaa aaccgttata gacccaataa   3960

caactaaacc tttcaaaaga aaatattttc tattatgaat gttgattttc ataccaaaga   4020

agatggagag tctaaaattt ggatatgatt cttatgtttt tttaatagaa aaccttcttc   4080

aagtttattt tcctaaataa acatcataat tgtgaatttt ctctagtaaa aaaaaaaaaa   4140

aaaaaa                                                              4146
```

<210> SEQ ID NO 36
<211> LENGTH: 1236
<212> TYPE: DNA
<213> ORGANISM: Homo sapiens

<400> SEQUENCE: 36

```
caggcgctga cgaggagccc ggctgaggga ggatgcgccg ctgacgcctg cgggagccgc     60

gcgcctgggg cgggaggatg ctccagaggg gcctctggcc gtggcgcacg cggctgctgc    120

cgacccctgg cacctggcgc ccagcgcgcc cgtggccgct gccgcctccg ccccaggttt    180

tgcgtgtgaa gctgtgtgga aatgtgaaat actaccagtc acaccattat agtaccgtgg    240

tgccacctga tgaaataaca gttatttata gacatggcct tcccttggta acacttacct    300

tgccatctag aaaagaacgt tgtcaattcg tagtcaaacc aatgttgtca acagttggtt    360

cattccttca ggacctacaa aatgaagata agggtatcaa aactgcagcc atcttcacag    420

cagatggcaa catgatttca gcttctacct tgatggatat tttgctaatg aatgatttta    480

aacttgtcat taataaaata gcatatgatg tgcagtgtcc aaagagagaa aaaccaagta    540

atgagcacac tgctgagatg gaacacatga aatccttggt tcacagacta tttacaatct    600

tgcatttaga agagtctcag aaaaagagag agcaccattt actggagaaa attgaccacc    660

tgaaggaaca gctgcagccc cttgaacagg tgaaagctgg aatagaagct cattcggaag    720

ccaaaaccag tggactcctg tgggctggat tggcactgct gtccattcag ggtggggcac    780

tggcctggct cacgtggtgg gtgtactcct gggatatcat ggagccagtt acatacttca    840

tcacatttgc aaattctatg gtctttttg catactttat agtcactcga caggattata     900

cttactcagc tgttaagagt aggcaatttc ttcagttctt ccacaagaaa tcaaagcaac    960

agcactttga tgtgcagcaa tacaacaagt taaaagaaga ccttgctaag gctaaagaat   1020

ccctgaaaca ggcgcgtcat tctctctgtt tgcaaatgca agtagaagaa ctcaatgaaa   1080

agaattaatc ttacagtttt aaatgtcgtc agattttcca ttatgtattg attttgcaac   1140

ttaggatgtt tttgagtccc atggttcatt ttgattgttt aatctttgtt attaaattct   1200

tgtaaaacag aaaaaaaaaa aaaaaaaaaa aaaaaa                             1236
```

<210> SEQ ID NO 37
<211> LENGTH: 2805
<212> TYPE: DNA
<213> ORGANISM: Homo sapiens

<400> SEQUENCE: 37

```
ctccttgcac gggccggccc agcttccccg cccctggcgt ccgctccctc ccgctcgcag     60

cttacttaac ctggcccggg cggcggaggc gctctcactt ccctggagcc gcccgcttgc    120

ccgtcggtcg ctagctcgct cggtgcgcgt cgtcccgctc catggcgctc ttcgtgcggc    180

tgctggctct cgccctggct ctggccctgg gccccgccgc gaccctggcg ggtcccgcca    240

agtcgcccta ccagctggtg ctgcagcaca gcaggctccg ggccgccag cacggcccca     300
```

```
acgtgtgtgc tgtgcagaag gttattggca ctaataggaa gtacttcacc aactgcaagc    360
agtggtacca aaggaaaatc tgtggcaaat caacagtcat cagctacgag tgctgtcctg    420
gatatgaaaa ggtccctggg gagaagggct gtccagcagc cctaccactc tcaaaccttt    480
acgagaccct gggagtcgtt ggatccacca ccactcagct gtacacggac cgcacggaga    540
agctgaggcc tgagatggag gggcccggca gcttcaccat cttcgcccct agcaacgagg    600
cctgggcctc cttgccagct gaagtgctgg actccctggt cagcaatgtc aacattgagc    660
tgctcaatgc cctccgctac catatggtgg gcaggcgagt cctgactgat gagctgaaac    720
acggcatgac cctcacctct atgtaccaga attccaacat ccagatccac cactatccta    780
atgggattgt aactgtgaac tgtgcccggc tgctgaaagc cgaccaccat gcaaccaacg    840
ggtggtgca cctcatcgat aaggtcatct ccaccatcac caacaacatc cagcagatca    900
ttgagatcga ggacaccttt gagacccttc gggctgctgt ggctgcatca gggctcaaca    960
cgatgcttga aggtaacggc cagtacacgc ttttggcccc gaccaatgag gccttcgaga   1020
agatccctag tgagactttg aaccgtatcc tgggcgaccc agaagccctg agagacctgc   1080
tgaacaacca catcttgaag tcagctatgt gtgctgaagc catcgttgcg gggctgtctg   1140
tagagaccct ggagggcacg acactggagg tgggctgcag cggggacatg ctcactatca   1200
acgggaaggc gatcatctcc aataaagaca tcctagccac caacggggtg atccactaca   1260
ttgatgagct actcatccca gactcagcca agacactatt tgaattggct gcagagtctg   1320
atgtgtccac agccattgac cttttcagac aagccggcct cggcaatcat ctctctggaa   1380
gtgagcggtt gaccctcctg gctcccctga attctgtatt caaagatgga acccctccaa   1440
ttgatgccca tacaaggaat ttgcttcgga accacataat taaagaccag ctggcctcta   1500
agtatctgta ccatggacag accctggaaa ctctgggcgg caaaaaactg agagtttttg   1560
tttatcgtaa tagcctctgc attgagaaca gctgcatcgc ggcccacgac aagaggggga   1620
ggtacgggac cctgttcacg atggaccggg tgctgacccc cccaatgggg actgtcatgg   1680
atgtcctgaa gggagacaat cgctttagca tgctggtagc tgccatccag tctgcaggac   1740
tgacggagac cctcaaccgg gaaggagtct acacagtctt tgctcccaca aatgaagcct   1800
tccgagccct gccaccaaga gaacggagca gactcttggg agatgccaag gaacttgcca   1860
acatcctgaa ataccacatt ggtgatgaaa tcctggttag cggaggcatc ggggccctgg   1920
tgcggctaaa gtctctccaa ggtgacaagc tggaagtcag cttgaaaaac aatgtggtga   1980
gtgtcaacaa ggagcctgtt gccgagcctg acatcatggc cacaaatggc gtggtccatg   2040
tcatcaccaa tgttctgcag cctccagcca acagacctca ggaaagaggg gatgaacttg   2100
cagactctgc gcttgagatc ttcaaacaag catcagcgtt ttccagggct tcccagaggt   2160
ctgtgcgact agcccctgtc tatcaaaagt tattagagag gatgaagcat tagcttgaag   2220
cactacagga ggaatgcacc acggcagctc tccgccaatt tctctcagat ttccacagag   2280
actgtttgaa tgttttcaaa accaagtatc acactttaat gtacatgggc cgcaccataa   2340
tgagatgtga gccttgtgca tgtgggggag gagggagaga gatgtacttt ttaaatcatg   2400
ttccccctaa acatggctgt taacccactg catgcagaaa cttggatgtc actgcctgac   2460
attcacttcc agagaggacc tatcccaaat gtggaattga ctgcctatgc caagtccctg   2520
gaaaaggagc ttcagtattg tggggctcat aaaacatgaa tcaagcaatc cagcctcatg   2580
ggaagtcctg gcacagtttt tgtaaagccc ttgcacagct ggagaaatgg catcattata   2640
agctatgagt tgaaatgttc tgtcaaatgt gtctcacatc tacacgtggc ttggaggctt   2700
```

ttatggggcc ctgtccaggt agaaaagaaa tggtatgtag agcttagatt tccctattgt 2760
gacagagcca tggtgtgttt gtaataataa aaccaaagaa acata 2805

<210> SEQ ID NO 38
<211> LENGTH: 1227
<212> TYPE: DNA
<213> ORGANISM: Homo sapiens

<400> SEQUENCE: 38
ctttgcagat aaatatggca cactagcccc acgttttctg agacattcct caattgctta 60
gacatattct gagcctacag cagaggaacc tccagtctca gcaccatgaa tcaaactgcc 120
attctgattt gctgccttat ctttctgact ctaagtggca ttcaaggagt acctctctct 180
agaactgtac gctgtacctg catcagcatt agtaatcaac ctgttaatcc aaggtcttta 240
gaaaaacttg aaattattcc tgcaagccaa ttttgtccac gtgttgagat cattgctaca 300
atgaaaaaga agggtgagaa gagatgtctg aatccagaat cgaaggccat caagaattta 360
ctgaaagcag ttagcaagga aaggtctaaa agatctcctt aaaaccagag gggagcaaaa 420
tcgatgcagt gcttccaagg atggaccaca cagaggctgc ctctcccatc acttccctac 480
atggagtata tgtcaagcca taattgttct tagtttgcag ttacactaaa aggtgaccaa 540
tgatggtcac caaatcagct gctactactc ctgtaggaag gttaatgttc atcatcctaa 600
gctattcagt aataactcta ccctggcact ataatgtaag ctctactgag gtgctatgtt 660
cttagtggat gttctgaccc tgcttcaaat atttccctca cctttcccat cttccaaggg 720
tactaaggaa tctttctgct ttggggttta tcagaattct cagaatctca aataactaaa 780
aggtatgcaa tcaaatctgc tttttaaaga atgctcttta cttcatggac ttccactgcc 840
atcctcccaa ggggcccaaa ttctttcagt ggctacctac atacaattcc aaacacatac 900
aggaaggtag aaatatctga aaatgtatgt gtaagtattc ttatttaatg aaagactgta 960
caaagtagaa gtcttagatg tatatatttc ctatattgtt ttcagtgtac atggaataac 1020
atgtaattaa gtactatgta tcaatgagta acaggaaaat tttaaaaata cagatagata 1080
tatgctctgc atgttacata agataaatgt gctgaatggt tttcaaaata aaaatgaggt 1140
actctcctgg aaatattaag aaagactatc taaatgttga aagatcaaaa ggttaataaa 1200
gtaattataa ctaagaaaaa aaaaaaa 1227

<210> SEQ ID NO 39
<211> LENGTH: 586
<212> TYPE: DNA
<213> ORGANISM: Homo sapiens

<400> SEQUENCE: 39
agttaaaagg gtgggagcgt ccgggggccc atctctctcg ggtggagtct tctgacagct 60
ggtgcgcctg cccgggaaca tcctcctgga ctcaatcatg gcttgtggtc tggtcgccag 120
caacctgaat ctcaaacctg gagagtgcct tcgagtgcga ggcgaggtgg ctcctgacgc 180
taagagcttc gtgctgaacc tgggcaaaga cagcaacaac ctgtgcctgc acttcaaccc 240
tcgcttcaac gcccacggcg acgccaacac catcgtgtgc aacagcaagg acggcggggc 300
ctgggggacc gagcagcggg aggctgtctt tcccttccag cctggaagtg ttgcagaggt 360
gtgcatcacc ttcgaccagg ccaacctgac cgtcaagctg ccagatggat acgaattcaa 420
gttccccaac cgcctcaacc tggaggccat caactacatg gcagctgacg gtgacttcaa 480

```
gatcaaatgt gtggcctttg actgaaatca gccagcccat ggcccccaat aaaggcagct    540

gcctctgctc cctctgaaaa aaaaaaaaaa aaaaaaaaaa aaaaaa                   586


<210> SEQ ID NO 40
<211> LENGTH: 2078
<212> TYPE: DNA
<213> ORGANISM: Homo sapiens

<400> SEQUENCE: 40

ttttccgccc ggctcccggc aagggtcccc cgactggcgc ccgcgcgtcc tccctcggct     60

gctgcaggcc gggccgcggc gtcgagcggg ggcggcgggg cggggcccgc agccattggc    120

gagcggcggg gcgggggcgg gggcgcggag ggtcggcccc gggacgcgcg cagccggccc    180

gcagttgccg ctgtcgtccg cagagccagt tcctagcgca gagccgcgcc cgccatgagg    240

gagatcgtgc acatccaggc gggccagtgc gggaaccaga tcggcaccaa gttttgggaa    300

gtgatcagcg atgagcacgg catcgacccg gccggaggct acgtgggaga ctcggcgctg    360

cagctggaga gaatcaacgt ctactacaat gagtcatcgt ctcagaaata tgtgcccagg    420

gccgccctgg tggacttaga gccaggcacc atggacagcg tgcggtctgg gccttttggg    480

cagcttttcc ggcctgacaa cttcatcttt ggccagacgg gtgcagggaa caactgggcg    540

aaagggcact acacggaggg cgcggagctg gtggacgcag tgctggacgt ggtgcggaag    600

gagtgcgagc actgcgactg cctgcagggc ttccagctca cgcactcgct gggcggcggc    660

acgggctcag gcatgggcac gctgctcatc agcaagatcc gtgaggagtt cccggaccgc    720

atcatgaaca ccttcagcgt catgccctcg cccaaggtgt cggacacggt ggtggagccc    780

tacaatgcca cactgtcggt gcaccagctg gtggagaata cagacgagac ctactgcatc    840

gacaacgagg cgctctatga catctgcttc cgcactctga agctgacaac gcccacctac    900

ggggacctca accacctggt gtccgccacc atgagtgggg tcaccacctc gctgcgcttc    960

ccgggccagc tcaatgctga cctgcgcaag ctggcggtga acatggtgcc cttcccgcgc   1020

ctgcacttct tcatgcctgg cttcgcgccg ctcaccagcc gcggcagcca gcagtaccgg   1080

gccctgaccg tgcccgagct cacccagcag atgttcgacg ccaggaacat gatggccgcc   1140

tgcgatccgc gccatggccg ctacctgacc gtggccaccg tgttccgcgg gcccatgtcc   1200

atgaaggagg tggacgagca gatgctggcc atccagagta agaacagcag ctacttcgtg   1260

gagtggattc ccaacaacgt gaaggtggcc gtgtgcgaca tcccgccccg cggcctgaag   1320

atggcctcca ccttcatcgg caacagcacg gccatccagg agctgttcaa gcgcatctcc   1380

gagcagttct cagccatgtt ccggcgcaag gccttcctgc actggttcac gggtgagggc   1440

atggatgaaa tggagttcac cgaggcggag agcaacatga acgacctggt atccgagtac   1500

cagcagtacc aggatgccac cgccaatgac ggggaggaag cttttgagga tgaggaagag   1560

gagatcgatg gatagtcgga atagagccgc cccaactcag atcctacaac acgcaagttc   1620

cttcttgaac cctggtgcct cctaccctat ggccctgaat ggtgcactgg tttaattgtg   1680

ttggtgtcgg cccctcacaa atgcagccaa gtcatgtaat tagtcatctg gaacaaagac   1740

taaaaacagc agagaattgc gggttctacc cagtcagaag atcacaccat ggagactttc   1800

tactagagga cttgaaagag aactgagggg ccacaaaata aacttcacct tccattaagt   1860

gttcaagcat gtctgcaaat taggagggag ttagaaacag tctttttcat cctttgtgat   1920

gaagcctgaa attgtgccgt gttgccttat atgaatatgc agtatgggac tttgaaataa   1980

tgattcataa taaaatacta aacgtgtgtc ttcatctctc tagccatgtg cataaatgac   2040
```

gtaagttact ttgtatggtt aaaaaaaaaa aaaaaaaa 2078

<210> SEQ ID NO 41
<211> LENGTH: 1623
<212> TYPE: DNA
<213> ORGANISM: Homo sapiens

<400> SEQUENCE: 41
ctggtggcat agggcagaca cgcctgcaga cattctctgg gaaagggcag cagcagccag 60
gtgtggcagt gacagggagg tgtgaatgag gcaggatgaa ctggacaggt ttgtacacct 120
tgctcagtgg cgtgaaccgg cattctactg ccattggccg agtatggctc tcggtcatct 180
tcatcttcag aatcatggtg ctggtggtgg ctgcagagag tgtgtggggt gatgagaaat 240
cttccttcat ctgcaacaca ctccagcctg gctgcaacag cgtttgctat gaccaattct 300
tccccatctc ccatgtgcgg ctgtggtccc tgcagctcat cctagtttcc accccagctc 360
tcctcgtggc catgcacgtg gctcaccagc aacacataga gaagaaaatg ctacggcttg 420
agggccatgg ggacccccta cacctggagg aggtgaagag gcacaaggtc cacatctcag 480
ggacactgtg gtggacctat gtcatcagcg tggtgttccg gctgttgttt gaggccgtct 540
tcatgtatgt cttttatctg ctctaccctg gctatgccat ggtgcggctg gtcaagtgcg 600
acgtctaccc ctgccccaac acagtggact gcttcgtgtc ccgccccacc gagaaaaccg 660
tcttcaccgt cttcatgcta gctgcctctg gcatctgcat catcctcaat gtggccgagg 720
tggtgtacct catcatccgg gcctgtgccc gccgagccca gcgccgctcc aatccacctt 780
cccgcaaggg ctcgggcttc ggccaccgcc tctcacctga atacaagcag aatgagatca 840
acaagctgct gagtgagcag gatggctccc tgaaagacat actgcgccgc agccctggca 900
ccggggctgg gctggctgaa aagagcgacc gctgctcggc ctgctgatgc cacataccag 960
gcaacctccc atcccacccc cgaccctgcc ctgggcgagc cctccttct cccctgccgg 1020 tgcacaggcc tctgcctgct ggggattact cgatcaaaac cttccttccc tggctacttc 1080
ccttcctccc ggggccttcc ttttgaggag ctggaggggt ggggagctag aggccaccta 1140
tgccagtgct caaggttact gggagtgtgg gctgcccttg ttgcctgcac ccttccctct 1200
tccctctccc tctctctggg accactgggt acaagagatg ggatgctccg acagcgtctc 1260
caattatgaa actaatctta accctgtgct gtcagatacc ctgtttctgg agtcacatca 1320
gtgaggaggg atgtgggtaa gaggagcaga gggcaggggt gctgtggaca tgtgggtgga 1380
gaagggaggg tggccagcac tagtaaagga ggaatagtgc ttgctggcca caaggaaaag 1440
gaggaggtgt ctggggtgag ggagttaggg agagagaagc aggcagataa gttggagcag 1500
gggttggtca aggccacctc tgcctctagt ccccaaggcc tctctctgcc tgaaatgtta 1560
cacattaaac aggattttac agtaaatgaa gaggtggctt gtgaaaaaaa aaaaaaaaaa 1620
aaa 1623

<210> SEQ ID NO 42
<211> LENGTH: 3310
<212> TYPE: DNA
<213> ORGANISM: Homo sapiens

<400> SEQUENCE: 42
gcgcgggccg ggccgggcgg cggcggcggc accatgagcg gccggaagcg cagcttcacc 60
ttcggggcct acggcggggt ggacaagtcc ttcacttctc gccggagtgt gtggaggagc 120

-continued

```
gatgggcaga accagcactt ccctcaggca ctagacctgt cacgagtgaa cttagttccc    180
tcctatactc cttcactcta ccctaagaac acagatctat ttgagatgat tgagaagatg    240
cagggaagca ggatggatga acaacgctgc tccttcccgc cgcccctcaa aacagaggag    300
gactacattc catacccgag cgtgcacgag gtcttggggc gagaaggacc cttccccctc    360
atcctgctgc cccagtttgg gggctactgg attgagggca ccaaccacga aatcaccagc    420
atccccgaga cagagccact gcagtcgccc acaaccaagg tgaagctcga gtgcaacccc    480
acagcccgca tctaccggaa gcactttctc ggcaaggagc atttcaatta ctactcactg    540
gacgctgccc tcggccacct tgtcttctca ctcaagtacg atgtcatcgg ggaccaagag    600
cacctgcggc tgctgctcag gaccaagtgc cggacatacc atgatgtcat ccccatctcc    660
tgcctcaccg agttccctaa tgttgtccag atggcaaagt tggtgtgtga agacgtcaat    720
gtggatcggt tctatcctgt gctctacccc aaggcttccc ggctcatcgt cacctttgac    780
gagcatgtca tcagcaataa cttcaagttt ggcgtcattt atcagaagct tgggcagacc    840
tccgaggaag aactcttcag caccaatgag gaaagtcccg ctttcgtgga gttccttgaa    900
tttcttggcc agaaggtcaa actgcaggac tttaaggggt tccgaggagg cctggacgtg    960
acccacgggc agacggggac cgaatctgtg tactgcaact tccgcaacaa ggagatcatg   1020
tttcacgtgt ccaccaagct gccatacacg gaaggggacg cccagcagtt gcagcggaag   1080
cggcacatcg ggaacgacat cgtggctgtg gtcttccagg atgagaacac tcctttcgtg   1140
cccgacatga tcgcgtccaa cttcctgcat gcctacgtcg tggtgcaggc tgagggcggg   1200
ggccctgatg gccccctcta caaggtctct gtcactgcaa gagatgatgt gcccttcttt   1260
ggacccccc tcccggaccc cgctgtgttc aggaaggggc ctgagttcca ggaatttttg   1320
ctgacaaagc tgatcaatgc tgaatatgcc tgctacaagg cagagaagtt tgccaaactg   1380
gaggagcgga cgcgggccgc cctcctggag acgctctatg aggaactaca catccacagc   1440
cagtccatga tgggcttggg cggcgacgag gacaagatgg agaatggcag tgggggcggc   1500
ggcttctttg agtctttcaa gcgggtcatc cggagccgca gccagtccat ggatgccatg   1560
gggctgagca acaagaagcc caacaccgtg tccaccagcc acagcgggag cttcgcgccc   1620
aacaaccccg acctggccaa ggcggctgga atatcactga ttgtccctgg gaagagcccc   1680
acgaggaaga agtcgggccc gttcggctcc cgccgcagca gcgccattgg catcgagaac   1740
atacaggagg tgcaggagaa gagggagagc cctccggctg gtcagaagac cccagacagc   1800
gggcacgtct cacaggagcc caagtcggag aactcatcca ctcagagctc cccagagatg   1860
cccacgacca agaacagagc ggagaccgca gcgcagagag cagaggcgct caaggacttc   1920
tcccgctcct cgtccagtgc cagcagcttc gccagcgtgg tggaggagac ggagggtgtg   1980
gacggagagg acacaggcct ggagagcgtg tcatcctcag gaacacccca caagcgggac   2040
tccttcatct atagcacgtg gctggaggac agtgtcagca ccactagtgg gggcagctcc   2100
ccaggcccct ctcgatcacc ccacccagac gccggcaagt tgggggaccc tgcgtgtccc   2160
gagatcaaga tccagctgga agcatctgag cagcacatgc cccagctggg ctgttagccg   2220
ggccaccccc tctgaaggtg aaactgagca gatgaggcca cagaagcaca aggggaaggt   2280
gccgtgtcaa gcccaggcag acgagacctc tgccctgaag accaacacca gcccgtgggc   2340
tgccccctgc ctccccaccc tccccatggc ccacccatct gggctgtctc tgcagggcag   2400
agccgtccag acctgggatc agggaagctg ctggcatcgt ccccaccccc agcctggggg   2460
tctgggctgg ggcagggatt gctcagtgga agcaggactg gggtctggc ttgcccctc   2520
```

```
cctgggcctc catcacccct gagcatccct ctggactcag agggaacaag gtgggagaga   2580

gagtttgaga cagctccgtg tggagagctt agcccctgga ggcagcacaa ggaggatgtg   2640

atatgtgggg gagtgagcac tgggttggga gccgggtcct ggtttccaat ttgggttctg   2700

ctgtgtgact ctgggcaagt cactctccct ctctgggcat gtctgctaca aatggacaag   2760

attatttcag aggtcactga agactgtgat tacatgcacc tgccttagaa ggtaggattt   2820

tcttcccagg gacctcctat caccctaccc tgcttcttga ggtccctgga gccccaggtg   2880

ggctgagggg cagggagccg gctgtgccca gtatgcctcc tggaccctcc agttctgcca   2940

caggtctgcc gatgccctgt ccactgccta cacatgacag acaagtaacc ccctcatggg   3000

ggatggggac ctacctggct cctcagccag cacccagctt aacccctgcc atcccatgct   3060

gggccctcca ggccaagagt ctcagctggc cgagagtcca ggccttgcct cccccgaccg   3120

ccatggaggg ggcagcccgg cacagctgct gggagccctt gtgtgtctgg tcacactttt   3180

taggcgtcac gccaaaggcc agcctcctgg ccccaatacc cattttggaa gcccctgtgg   3240

ccgtgtggat gtcggtaaca gttgtataaa ataaattcta tttatcgcta ttgtaaaaaa   3300

aaaaaaaaaa                                                          3310
```

<210> SEQ ID NO 43
<211> LENGTH: 5665
<212> TYPE: DNA
<213> ORGANISM: Homo sapiens

<400> SEQUENCE: 43

```
gcgcagcccg cagaggcgct gcggcccgtg cagccccgga ggcccctcgc ggagaaggcg     60

gcggcggagg agaggccgag ttaccgcccg ccgcccgcgc ccccccaacc ccgccgccgc    120

cgccgccgcc gccactgccc cccctccccg cggcgccgca tcttgaatgg aaacatggcg    180

gtgccggctc ggacctgcgg cgcctctcgg cccggcccag cgcggactgc gcgcccctgg    240

cccggctgcg gcccccaccc tggccccggc acccggcgcc cgacgtccgg gcccccgcgc    300

ccgctgtggc tgctgctgcc gcttctaccg ctgctcgccg cccccggcgc ctctgcctac    360

agcttccccc agcagcacac gatgcagcac tgggcccggc gtctggagca ggaggtcgac    420

ggcgtgatgc ggatttttgg aggcgtccag cagctccgtg agatttacaa ggacaaccgg    480

aacctgttcg aggtacagga gaatgagcct cagaagttgg tggagaaggt ggcaggggac    540

attgagagcc ttctggacag gaaggtgcag gccctgaaga gactggctga tgctgcagag    600

aacttccaga aagcacaccg ctggcaggac aacatcaagg aggaagacat cgtgtactat    660

gacgccaagg ctgacgctga gctggacgac cctgagagtg aggatgtgga aagggggtct    720

aaggccagca ccctaaggct ggacttcatc gaggacccaa acttcaagaa caaggtcaac    780

tattcatacg cggctgtaca gatccctacg gacatctaca aaggctccac tgtcatcctc    840

aatgagctca actggacaga ggccctggag aatgtgttca tggaaaaccg cagacaagac    900

cccacactgc tgtggcaggt cttcggcagc gccacaggag tcactcgcta ctacccggcc    960

accccgtggc gagcccccaa gaagatcgac ctgtacgatg tccgaaggag accctggtat   1020

atccaggggg cctcgtcacc caaagacatg gtcatcatcg tggatgtgag tggcagtgtg   1080

agcggcctga ccctgaagct gatgaagaca tctgtctgcg agatgctgga cacgctgtct   1140

gatgatgact atgtgaatgt ggcctcgttc aacgagaagg cacagcctgt gtcatgcttc   1200

acacacctgg tgcaggccaa tgtgcgcaac aagaaggtgt tcaaggaagc tgtgcagggc   1260
```

-continued

```
atggtggcca agggcaccac aggctacaag gccggctttg agtatgcctt tgaccagctg   1320
cagaactcca acatcactcg ggccaactgc aacaagatga tcatgatgtt cacggatggt   1380
ggtgaggacc gcgtgcagga cgtctttgag aagtacaatt ggccaaaccg gacggtgcgc   1440
gtgtttactt tctccgtggg gcagcataac tatgacgtca caccgctgca gtggatggcc   1500
tgtgccaaca aaggctacta ttttgagatc ccttccatcg gagccatccg catcaacaca   1560
caggaatatc tagatgtgtt gggcaggccc atggtgctgg caggcaagga ggccaagcag   1620
gtgcagtgga ccaacgtgta tgaggatgca ctgggactgg ggttggtggt aacagggacc   1680
ctccctgttt tcaacctgac acaggatggc cctggggaaa agaagaacca gctgatcctg   1740
ggcgtgatgg gcattgacgt ggctctgaat gacatcaaga ggctgacccc caactacacg   1800
cttggagcca acggctatgt gtttgccatt gacctgaacg gctacgtgtt gctgcacccc   1860
aatctcaagc cccagaccac caacttccgg gagcctgtga ctctggactt cctggatgcg   1920
gagctagagg atgagaacaa ggaagagatc cgtcggagca tgattgatgg caacaagggc   1980
cacaagcaga tcagaacgtt ggtcaagtcc ctggatgaga ggtacataga tgaggtgaca   2040
cggaactaca cctgggtgcc tataaggagc actaactaca gcctggggct ggtgctccca   2100
ccctacagca ccttctacct ccaagccaat ctcagtgacc agatcctgca ggtcaagtat   2160
tttgagttcc tgctccccag cagctttgag tctgaaggac acgttttcat tgctcccaga   2220
gagtactgca aggacctgaa tgcctcagac aacaacaccg agttcctgaa aaactttatt   2280
gagctcatgg agaaagtgac tccagactcc aagcagtgca acaacttcct tctgcacaac   2340
ctgatcttgg acacgggcat cacgcagcag ctggtagagc gtgtgtggag ggaccaggat   2400
ctcaacacgt acagcctact ggccgtgttc gctgccacag acggtggcat cacccgagtc   2460
ttccccaaca aggcagctga ggactggaca gagaaccctg agcccttcaa tgccagcttc   2520
taccgccgca gcctggataa ccacggttat gtcttcaagc ccccacacca ggatgccctg   2580
ttaaggccgc tggagctgga gaatgacact gtgggcatcc tcgtcagcac agctgtggag   2640
ctcagcctag gcaggcgcac actgaggcca gcagtggtgg gcgtcaagct ggacctagag   2700
gcttgggctg agaagttcaa ggtgctagcc agcaaccgta cccaccaaga ccagcctcag   2760
aagtgcggcc ccaacagcca ctgtgagatg gactgcgagg ttaacaatga ggacttactc   2820
tgtgtcctca ttgatgatgg aggattcctg gtgctgtcaa accagaacca tcagtgggac   2880
caggtgggca ggttcttcag tgaggtggat gccaacctga tgctggcact ctacaataac   2940
tccttctaca cccgcaagga gtcctatgac tatcaggcag cctgtgcccc tcagccccct   3000
ggcaacctgg gtgctgcacc ccggggtgtc tttgtgccca ccgttgcaga tttccttaac   3060
ctggcctggt ggacctctgc tgccgcctgg tccctgttcc agcagcttct ctacggcctc   3120
atctaccaca gctggttcca agcagacccc gcggaggccg aggggagccc cgagacgcgc   3180
gagagcagct gcgtcatgaa acagacccag tactacttcg gctcggtaaa cgcctcctac   3240
aacgccatca tcgactgcgg aaactgctcc aggctgttcc acgcgcagag actgaccaac   3300
accaatcttc tctttgtggt ggccgagaag ccgctgtgca gccagtgcga ggctggccgg   3360
ctgctgcaga aggagacgca ctgcccagcg gacggcccgg agcagtgtga gctagtgcag   3420
agaccgcgat accggagagg cccgcacatc tgcttcgact acaacgcgac agaagatacc   3480
tcagactgtg gccgcggggc ctccttcccg ccgtcgctgg gcgtcctggt ctccctgcaa   3540
ctgctgctcc tcctgggcct gccgccccgg ccgcagcctc aagtcctcgt ccacgcctct   3600
cgccgcctct gagcaccctg ccccacccca cctccactcc cacctcaccc ggcctcttcg   3660
```

cctttcccac cctcctgccc cacactcccc gccttagagc ctcgtccctc cctcactgaa 3720
ggacctgagc tggccaggcc ctgagagtct ggtctgcgcc ttgggatggg gagtcccaaa 3780
gcgggacgcc gcaggtgttt ggcacccaaa tcacatctca cctccgaact gttcaagtgt 3840
ccccagaccc ttcttgcctg ctgggctccc cccagtggga tgggacaggg aggccacacg 3900
cactggtgcc aaaaccaggc ctctgctgcc gcccttcctg gaggctgcct atgttggggg 3960
ggaccctgcc tcagctgacc cggcctctct gccccaccca agcccaaact tggtttctgt 4020
gagaatagtg gaggaaggtg agatggccag tttgaagcct gtgcctccca gcttaaatcc 4080
tagcaggaga gaggctctgg ggcagccccc atgggctcct gcccctttca ggcctacagc 4140
cacatcccca agcccaccag gtgtcaggat agtcacagtg ataccagttc agacactacc 4200
ccatatacac ctggaacatt gaggatggaa actggactca cattcgacat accccactgg 4260
gcacacgcac aaacacacac actatggggt ggggtgggtg taggggctta caaagcctta 4320
cacagggcga ggggttggtg ggagggttgg cacctgcaca ctccatctcc tgctcaccac 4380
ctgcctctaa tctgagctgc agcctggctg gtcctcccat ttctaaagct gaatgtcaaa 4440
cagtgccaaa tgctggggca gggggtgaag aaccctctgt cccacccccta gccaccagtg 4500 tcctccaagt gccccctcac ctctccaggt gctcattgta accatttctc actagtgtca 4560
ggcccccagt gggaccacat gccactgcct gcacctttcg gcagaggaac ccccaccaga 4620
catcaccctt tgccttagca ggggtgactt tgtctctcct ggctgggcca tccttccgcc 4680
aatctggccc ttacacactc aggcctgtgc ccactcccta tctccttccc accccctacac 4740 acacactccc tgcttgcagg aggccaaact gtccctccct tgctgaacac acacacacac 4800
acacacacac aggtggggac tgggcacagc tcttcacacc attcattctg gtcatttccc 4860
ccaaaggcat cccagcctgg gggccagtgg ggaactgagg gcaaggggat atagtgatgg 4920
ggctcagatg gactgggagg agggggaggg tgatgcatta attaatggct tcgttaatta 4980
atgtcatgtt gcttgtcgct ttctcagtgt gtgtgtgtgg tccatgccca ctgctggtgc 5040
cagggtgggt gtccatgtgc acccggcctg gatgccagct gtgtccttcg gggggcgtgcg 5100 tgtaactgta gtgtagtcag gtgctcaatg gagaatataa acatatacag aaaaatatat 5160
attttaagtt taaaaaacag aaaaacagac aaaacaatcc ccatcaggta gctgtctaac 5220
ccccagctgg gtctaatcct tctcattacc cacccgacct ggctgcccct caccttgggc 5280
tgggggactg gggggccatt tccttttctc tgccctttt ttgttgttct attttgtaca 5340
gacaagttgg aaaaacaaca gcgacaaaaa agtcaagaaa ctttgtaaaa tatcgtgtgt 5400
gtgattcctt gtaaaatatt ttcaaatggt ttattacaga agatcagtta ttaaataatg 5460
ttcatatttt cacttcaaat ggttcccatc cactgtatca gcttgggggt gaggactggg 5520
tagctatgaa gacagttggc caagacctca gagtcccact tagtgctctg caggggggtga 5580 agaccatggt agcccaggtc cctgtcaacc acagggcatg gcacttgctt ccaccagtta 5640
taataggtgc caggcccttg acata 5665

<210> SEQ ID NO 44
<211> LENGTH: 1768
<212> TYPE: DNA
<213> ORGANISM: Homo sapiens

<400> SEQUENCE: 44
tataaattcc ctcccttcgc tccttccccg gaacagcggc ctctgacacc agcacagcaa 60

```
acccgccggg atcaaagtgt accagtcggc agcatggcta cgaaatgtgg gaattgtgga    120

cccggctact ccacccctct ggaggccatg aaaggaccca gggaagagat cgtctacctg    180

ccctgcattt accgaaacac aggcactgag gccccagatt atctggccac tgtggatgtt    240

gaccccaagt ctccccagta ttgccaggtc atccaccggc tgcccatgcc caacctgaag    300

gacgagctgc atcactcagg atggaacacc tgcagcagct gcttcggtga tagcaccaag    360

tcgcgcacca agctggtgct gcccagtctc atctcctctc gcatctatgt ggtggacgtg    420

ggctctgagc cccgggcccc aaagctgcac aaggtcattg agcccaagga catccatgcc    480

aagtgcgaac tggcctttct ccacaccagc cactgcctgg ccagcgggga agtgatgatc    540

agctccctgg gagacgtcaa gggcaatggc aaagggggtt ttgtgctgct ggatggggag    600

acgttcgagg tgaaggggac atgggagaga cctgggggtg ctgcaccgtt gggctatgac    660

ttctggtacc agcctcgaca caatgtcatg atcagcactg agtgggcagc tcccaatgtc    720

ttacgagatg gcttcaaccc cgctgatgtg gaggctggac tgtacgggag ccacttatat    780

gtatgggact ggcagcgcca tgagattgtg cagaccctgt ctctaaaaga tgggcttatt    840

cccttggaga tccgcttcct gcacaaccca gacgctgccc aaggctttgt gggctgcgca    900

ctcagctcca ccatccagcg cttctacaag aacgagggag gtacatggtc agtggagaag    960

gtgatccagg tgccccccaa gaaagtgaag ggctggctgc tgcccgaaat gccaggcctg   1020

atcaccgaca tcctgctctc cctggacgac cgcttcctct acttcagcaa ctggctgcat   1080

ggggacctga ggcagtatga catctctgac ccacagagac cccgcctcac aggacagctc   1140

ttcctcggag gcagcattgt taagggaggc cctgtgcaag tgctggagga cgaggaacta   1200

aagtcccagc cagagcccct agtggtcaag ggaaaacggg tggctggagg ccctcagatg   1260

atccagctca gcctggatgg gaagcgcctc tacatcacca cgtcgctgta cagtgcctgg   1320

gacaagcagt tttaccctga tctcatcagg gaaggctctg tgatgctgca ggttgatgta   1380

gacacagtaa aaggagggct gaagttgaac cccaacttcc tggtggactt cgggaaggag   1440

ccccttggcc cagcccttgc ccatgagctc cgctaccctg gggcgattg tagctctgac    1500

atctggattt gaactccacc ctcatcaccc acactcccta ttttgggccc tcacttcctt   1560

ggggacctgg cttcattctg ctctctcttg gcacccgacc cttggcagca tgtaccacac   1620

agccaagctg agactgtggc aatgtgttga gtcatataca tttactgacc actgttgctt   1680

gttgctcact gtgctgcttt tccatgagct cttggaggca ccaagaaata aactcgtaac   1740

cctgtccttc agaaaaaaaa aaaaaaaa                                      1768
```

```
<210> SEQ ID NO 45
<211> LENGTH: 9306
<212> TYPE: DNA
<213> ORGANISM: Homo sapiens

<400> SEQUENCE: 45

gggttcggag cgcgaagccg ccgctgggtc ctcggcgcgc cccgcgtctg cgcttgctgc     60

cgcgccccgg tcggcgcgct gggagttcca gccatgctct tctggcacac gcagcccgag    120

cactacaacc agcacaactc cggcagctac ctgcgtgatg tgctcgctct gcccatcttc    180

aagcaggagg aaccccagct gtcccccgag aacgaggccc gcctgccacc cctgcaatat    240

gtgttgtgtg ctgccacgtc cccagccgtg aagctgcatg aagagacgct gacctacctc    300

aaccaaggtc agtcttatga aatccgacta ctggagaatc ggaagctggg agactttcaa    360

gatctgaaca caaaatatgt caagagcatc atccgtgtgg tcttccatga ccgccggctg    420
```

```
cagtatacgg agcaccagca gctggagggc tggcggtgga gtcggccagg ggaccggatc    480
ctggacatcg atattccact gtctgttggt atcttggacc ccagggccag cccgacccag    540
ctgaatgcag tcgagttttt gtgggaccct gcgaagagag cttctgcatt cattcaggta    600
cactgcatca gcacagaatt cacccccagg aagcacgggg gcgagaaggg agtgcccttt    660
cgagtccaga ttgacacgtt taagcagaac gagaatgggg agtacacgga gcacctgcac    720
tcagccagct gccagatcaa ggtgttcaag ccgaagggag ccgatcggaa acagaagact    780
gaccgggaga agatggagaa aagaactgcc caagagaagg agaaatacca gccgtcctat    840
gaaaccacca tcctcacaga gtgctctcca tggcccgacg tggcctacca ggtgaacagc    900
gccccgtccc caagctacaa tggttctcca aacagctttg gcctcggcga aggcaacgcc    960
tctccgaccc acccggtgga ggccctgccc gtgggcagtg accacctgct cccatcagct   1020
tcgatccagg atgcccagca gtggcttcac cgcaacaggt tctcgcagtt ctgccggctc   1080
tttgccagct tctcaggtgc tgacttgctg aagatgtccc gagatgattt ggtccagatc   1140
tgtggtcccg cagatgggat ccggctcttc aacgccatca aaggccggaa tgtgaggcca   1200
aagatgacca tttatgtctg tcaggagctg gagcagaatc gagtgcccct gcagcagaag   1260
cgggacggca gtggagacag caacctgtct gtgtaccacg ccatcttcct ggaagagctg   1320
accaccttgg agctgattga gaagatcgcc aacctgtaca gcatctcccc ccagcacatc   1380
caccgagtct accggcaggg ccccacgggc atccatgtgg tggtgagcaa cgagatggtg   1440
cagaacttcc aagatgaatc ctgttttgtc ctcagcacaa ttaaagctga gagcaatgat   1500
ggctaccaca tcatcctgaa atgtggactc tgagcagcag tggacctcat acctgtctcc   1560
agctcccagc cctgtggatc cccgtggatg tagacattgc cccactgtaa gctgtggcct   1620
caccaggcaa gctgaggcca ggagggaccc tgcccagtct gtgaaagcta cagagcacca   1680
accagcagaa gcctgtggac accaagtacg gtgtacagaa agccagtggc tcctttctcc   1740
cttcctcttg gcctccagat tttgaatggt tccttgttct tttctattgg tccaaccctg   1800
acgttctaaa agggcaaaca gtggagacgt ctgctctgaa atccctcatc ccttagttgg   1860
aagctgattg ggtatcttgg tgctgcctgt attggtccct tctgaccact ctcctgcctc   1920
cagagaaagc tctgcttcac cctggaagct ggtaccttta cctcctcctc tgggagttgg   1980
ctgcatggcc agcactgccg acttgatggg agcagtttgc cctcattctc ctgtttcagg   2040
tttgcttccc ttctcagtga ccctggtgag catccgcctt tcctgttctt ggatgaattg   2100
atgggagtgg ggctattctg tgccttctac ctctttcttc tctacgttgt ttctaaggat   2160
ctgctgctgc ggaacccaaa gatgtgctcc tgtctctgca ctggcgcatt ggcatggtag   2220
atgccacaat gtatgtgcac ggcctttctc agagacatta gttctgaggc cctttgtggg   2280
gaggttaggg ggatggtaat agaaaaagac tattttattt cctggcaatc acgggtaagg   2340
aggattagga atgagtattc cattcctagg tgtcatcaga tgaccttgac caccacaata   2400
ccaggccctc ttggatggac ttatagaaag ttagagaaga ccttgttgaa ccgctgctaa   2460
acttgccaca ggagcgatgt gttttctctg agtgcccctc acttacatgt ttatctttgt   2520
ttgtagaggc tatgtttagg atattttgcc tgcatcagaa tgggtgcatc atctttctta   2580
atggcctaac tatcgggaaa tttgagtgtc agtaactgtg gtagactcag aaattcgtct   2640
ttgtcttgcc tctggttcct gggatccagt gatctctact ggcccagggc ttcagctctt   2700
ggttaattta ggttcatggg gaaccctctg accacctgaa tgggatgtca tagcttctaa   2760
```

```
atggagcttc tgtggaatga agtgctagac tgaaggacta ccagaataaa acagggtcta   2820
caatggggag aacttgtttt atagatgagg aaaccaaggc tcagaggggc aaagtcacct   2880
gcatggtagc acatagtgat agggtagcga tataaattta tcatataaac caggacatct   2940
cggaataaaa ggggctctgt tagtcattat gttgggtaat agccgtggca ttcctacaga   3000
acagagtgag gacaggctcc tgattcctct tccttcttta gaggagaagc ggggagtggg   3060
ttaactaaca gctttattga gatgtcattc acatgccatt cagtttaccc attgctagtg   3120
tccaattgta ttcacagaac caccatcaat tcacagaatt acagtcaacg ttggtacatt   3180
ttcatcaccc ccagtaaaac cccgtaccct tggtctgtca ctcctgcttt cctaactcct   3240
gcagtccaag gcagccatga atctactttc tatgtaagat taacctactc tggacatttc   3300
atatatctgg aatcatgtga tatctctttt gtgactggct tcttccactg aatgttttct   3360
agggccgtcc aagttgagga tgtatcagta cttcattctt ttgtattgct gaataatact   3420
tcattgtata gatagaccac atttgtttat tgattcatca gttgatggac atttgtgtgt   3480
ttttactttt tggctactct gaatgatgct gctatgaaca tatttctaca agattttgtg   3540
tggacatatg ttttcatttc ttttagcaat atacatagga gtggaattgc taggtcttac   3600
agtaactccg tgttttaact ttttgagaaa ctgccagact gttttctata gcagctgtac   3660
cattttacat tcccaccagc aatgtatcca ggtttcaatt tgtctacatc ctcatcaaca   3720
cttgctatta tctgtctttt tgcttttagc atcctaatga gtatgaaatg ctatcttgtg   3780
gttttgattt gcattcccct gatggcaact gatgctgagt gtcttttcct gtgcttacgg   3840
gccatgcgta tttctttgga gaaaggtcta tccaggtcct ttgcctattt ttaattgagt   3900
tgtctttttt tttttaagtt ttctgttttc ctaaccacta gactaccagg gatgagcctt   3960
ctttttatta ttgagttggg tgagctattt gtatattcta gacgccagtc ttttatcagg   4020
tatatgactg gtaaaaatgt tctccccttc tgtggattgt tttcagtttc ttgttggtgt   4080
cctttgagac acaaaacttt ttaactttga tgatttccaa gatacgtatt tttttttctat   4140
tgtcacttgt gcttttggtg ccatatctag aaaaccattg cctaatccaa ggtcaagaag   4200
attaatgcct gtgttttctt ctaagaacta tacttttagt tctcacaatg gtctttgatc   4260
catttcgagt atatttttat atatgatgtg atgtaggggt ccagcttcat tcttttgctt   4320
gtggatctcc acttgtccca ctgctgatta ttgagaaaaa tatcctttct ccacggaatt   4380
gtcttggcat ccttgctaaa ggcctctgct tcttactgga tcttctttcc tgggacatgg   4440
tgtcgttggg aagcttacct tttttttttt tttacttagt ctgtgtttgg ttccaccagt   4500
tttatgctgc ctttctactc tgttcttgct gtctccctct ttacctgagt caacggtact   4560
gagtcctatc tctctctgat gttccccagt cttccttggt gcatgttcta gctccacaca   4620
ctagtccttg gaggaaggtt gagaccaatg atttcctgtt atgagtcatg aggaaactga   4680
atcacctaga agtggaataa tgtgctcagg gtcaccatag cccattagtg gaaggaccag   4740
gactagacct ttagtcttct gaggtccagc cccttaggct gtctgtcatc actgtaccca   4800
agtgatgtca ctaccaaggc caaatgatgg tgggctaaat tttaattctc aaaagtgtag   4860
gaggctaata ttgtcttcta agttccaaaa gaagatgtaa taaaagtctg ttaccttaag   4920
tgtgctatta gtagagtctt ccatttttct ggcatgcccc tggcatctgc tcttcttacc   4980
ttctcgtggt tgtagttaaa gcttatagct tatgaaagaa tagaaaataa taaataccaa   5040
aaaaaagtac acatggtaat ttggtaccaa aatatctcag ctgcctaatt tagcagctca   5100
tcccttccac aggggtcaga tgagctaaag ctccaggttt tatttttcat ttgattgaca   5160
```

```
tacagaaaag ccatagccct tcccacagct gtccagggtc tttcctgtga gtccggaggt   5220
gctggcctat tgagcaggac agctcttccc agggcattcc caccaacctg tggcttctga   5280
actgtagctt ctttttacag tgaaccccag agggaaataa gacagacaca tgtgctcagg   5340
ccaccatctt gaactggaag cccaaagctg agttccttac tcttaggtcg tcacggtttt   5400
tgcggggtat ctgcaaggtt gagataaacc ctttcctgtt taccaggttg tcctttctgg   5460
atgaagggac agaggctgtt gaatggagga ataataggtt tgctggagga ggggcatggt   5520
atgcctgtgg aaaggacagg atggggtggg gaggtcgagg ctttgacttg ggtcctaaa    5580
caaaggtcag gtgttgccct agtgacctct tgcccagaca gcccagagcc ccttacacag   5640
agctattaac ctagggaagg ctttaccagc agtggactgg agccagccag ggtcacaagt   5700
ttccaagtcc agcattgctt caggggctgg cctgagtaac tgaagatctg aaaatcatta   5760
acaagtcgat gaaataaacg gaaaagcctc ttaggctgtt gtcagtggag cagagggaga   5820
aagtccctag gcgctcagag ggggtgagaa agcagtggat gattgggcgg gggtggggga   5880
ttagatgttg acactgcctg gggtgtagga agaggaacag agaacccaga gtcagggtcc   5940
tagatcccag accctcgctc agtatgagtc tctttgcctc tctgggtctc tatctcctcc   6000
tcttacaaat acaggcttgg tgatctctga agatggcacc aacctgccat gaaatgaatc   6060
tgaggggttt tcccattttt ccctccatca aaatcgtaca aaaagctgga cgtggtggcc   6120
catgcctcta atcctagcat tttgggaggc cgaggtggga gaatcacttg acgccaagag   6180
ttcgagacca gcctgggcat cgtagtgaga ctccatctct gtctttttga aaataaaaaa   6240
tctttgaaaa ttgcacaaca ggcaggagac ctttacgtgt gcccatcctg gttgtacaca   6300
gtgccaccag tgctcctgca gtgcaaggcg gcatgcttct tgacatgggt cagattgtgt   6360
ccatcgtgtc tttgggaatc agccctagct cctaactggg ctgactactt cctccgcaaa   6420
cttatggggg ctcccagata ttccttgcca gccaggggcc agacacagtg caggcacagt   6480
ctgtgtcatt ggtgcacatg tgcgtgttta catgtgtacc tgggttcctt cccttgccca   6540
tgaatttgcc atgagcacag ccagaagcag cctcagcttg gcaaggtgtg gagatgactg   6600
ctgttccctt cgcatttggg gaaaacaggc tccctcggta gctcgatgat cctcttttga   6660
tcttgtgtga cctcctggag agtggatgaa gctggtggcc ttagcttttc tagacagtgt   6720
aagtggcact gggcaaggcc cccagagcag ggcaaggtct ctagagcggg tctcccacat   6780
gactggcttc acacaggcac ttccgctcgg gttgcatgct ctgtgtcatc ttaccggtcc   6840
agggttgcag gtaggaaatg tttgtaccct cttctgattg ccacctcctt cccatcgccc   6900
cttagggaca gggcttgagg gccagtgagg cgctggtcag gcaccccagg cctccttggg   6960
acctgcccag gggcaccctg agagctcctg aaaccccccac ttagcttcca gacctttctg  7020
caaaagctcc tcctggcttt cctccctccc ccaatctatg ggtcacagct aacagatctg   7080
agggcaactg ctgtgctagt ggccagggct gcacctgcca tccccggctc tgccacttta   7140
gggccttcta gaggcagtgt ccttaggaag tagctctgag gcatgggttt tctgctcctg   7200
tgcagggcag ctgatgggat aaggtgggga aggacggtca gtgcttgggc cccagctggc   7260
cagcctggcg atggggaaac caaaccatgt cccccagcga agggccagag tgggaacctg   7320
tcctcatgcc cttcgtcctg aggagccctg aggtgggcag caggggccag gggaagtttt   7380
caggccttca tcaaagagaa caacatcctc agctccgcac ccctcatcct gtatcagcac   7440
ttaccggtgt gtgactgccc ttgtcagcta gcatacggtg ggcccacctg gcccactggc   7500
```

```
tgtttatgcc actgatttat gatagggaat attatctttg aacccaatga agtgtttttct   7560

cccccatcac aaaaaaaaaa attcttattt ttagtagaca tgtatttacc aaaaatatgt   7620

actcaattat tgtattttgg attttatcaa tttaaaaatt gtggaaattt gtttgctctt   7680

acgccaacat aatattgatt ttgcctcttg gctctgaaag cccaaaatat ttaccgtcta   7740

gcccgttaca gaaaaagtct gctgactact gagccagacc tccattacct ccatccctgt   7800

tggattattt aaagaaagcc tcagacagta agggcttttt taaaagaata aaatgacttg   7860

gtttgcgctt ggaagcaggg gaagcattca gatgagcggt ttctgcatta accctgccta   7920

tcacgcatct cgtgtcctgt gtggctggcg agcccccctt ggaaggttct ggtgcttcag   7980

ctggctcctg cagagtccac cccgcctcgt ggtgggaatg cagagccctt tgctttcctt   8040

cttgccgcct gcttcctgtt cctggggacc cgctgggcct ttggtctgca tcccctggcc   8100

aggtccctca gggttgatgc gtggagaagg actttgagca gtggtgggca gcagtggcct   8160

cctggccagc tcacactctt gtcctgggag gggcagcctg atctcacctc cacctagtac   8220

cttggggact gaggaccttt tggcttctct ggagcctgca agcctcttcc catgtgtcca   8280

gctgctcttc ctgctacaaa ggggactgct cacagtggcc tcagcttggt ggttttgagg   8340

ggccgccccc cggccctcca taagggtatc ctgggcctga gaattctgca tctgccattg   8400

gaggatggac agcctcaaat ggaaggagtc ccacgggaga tgggtccgag gtccggctgt   8460

ggccatccag ccccctgtgg cttgtccagc ctctgtgcac ccctggtgtc ttcactccag   8520

gggcagacag cagccactgc agttcctttc ttcgtgagta acagtagtga tagcagctgg   8580

ggctaacagg ctaggctttg tgttctgcgc atttggtcag cttctcactc gatcctccct   8640

aaagcaatgg ggaggccccc actagcccag ttttcaggaa gtcaactggg aggttagatg   8700

ggggccaggg tcccacagct actgatggcc cgagccaggt tgagcttcct ggtgtccagt   8760

ccggatccca cttgcagatc tcatgctctc agataggtgg gacaagttct tttgtcacag   8820

tgctggctct gtcctgaggc ctcattgctg gctgggtgtg ctctgctggg aaaagctttg   8880

cggggcttgc ttggttaacc acagaagaga aggggactgt ttggggtgcc tctctgcagc   8940

ctccccgtgc tgggtggaag cacggttact gtgttctcta atgttcatgt atttaaaatg   9000

atttctttct aaagatgtaa cctccacacc tttctccaga ttgggtgact cttttctaaa   9060

ggtggtggga gtatctgtcg ggtggtggtg gcccttggat gggtcaggtg ggtgtgagag   9120

gtcctgggga ggtgggcgtt gagctcaaag ttgtcctact gccatgtttt tgtacctgaa   9180

ataaagcata ttttgcactt gttactgtac catagtgcgg acgagaagtc tgtatgtggg   9240

atctgtgctt gggttagaat gcaaataaaa ctcacatttg taagaaaaaa aaaaaaaaaa   9300

aaaaaa                                                                9306
```

<210> SEQ ID NO 46
<211> LENGTH: 6564
<212> TYPE: DNA
<213> ORGANISM: Homo sapiens

<400> SEQUENCE: 46

```
atgcattaaa ctccaggtat tttcagggag gaatcatgaa gccgctcctg ttaaatcata     60

tccattttat tacgtctctc cttgtggatt acgtagaact ttggaaaatt aaacattaga    120

catcttcata gaaaatcatg tcactgattt ttaaagccag ctcaatttaa cctgccactg    180

attccctaac cagctcttct ctgactgtat cccgagggaa aatgtattga acgcagcaga    240

aggttaaggc agaggagttc ggctagaccg ggtagcagcc aatcagatgg ggagggtcca    300
```

```
aggatctgat gcctccaggc gagcagcgcc aagctgagct ggttagtctc cttttattgt    360
ggatgaacac cacgtacatg ccgtaaatgc tccctaggct ggctgcggct acaaggcaga    420
cccgggagct gagaatagag gaatacctgc ccaagcaact cattctgcac agcagccgac    480
aagacagcga ttttcctgtg ctggaatgtg cccatccaaa gccaaccaat ttgttggaaa    540
atcagtcaaa atctaatttt gatgttctgc aagttccctg ggggccatga agcacctgac    600
acttggattg gacttaatct taaacctctg gagttcaaga ccttttaaaa agggctaaat    660
aaacaatctc tacatgtaaa aggccactga ctcctacttc ctctgtatag agcaactgtt    720
gaactcagct gcctgtagga aaactgaaga ctttaataac aaactctcca aggtgaaaat    780
gaacacagat agcggtgggt gtgctcgcaa acgtgccgcc atgtctgtta cgctaacatc    840
tgtgaagaga gtgcaaagtt ctccaaacct attggctgca gggcgtgatt ctcagtcacc    900
agactcagct tggagatctt acaatgatgg caatcaggag acactgaacg gagatgctac    960
atattcctct cttgcagcaa aaggttttag aagcgttcga ccaaacctac aagataaaag   1020
atcaccaact cagagccaga taacagtgaa tggaaactca ggaggtgccg tgagtcccat   1080
gagttactat cagaggccgt tttccccctc ggcatattct ctcccagcct cactcaactc   1140
cagcattgtc atgcagcacg gcacatccct cgattccaca gacacatatc cccagcatgc   1200
gcagtctctg gatggcacca ccagcagctc tatccccctg taccgatcct cagaggaaga   1260
gaagagagtg acagtcatca aagccccgca ttacccaggg atcgggcccg tggatgaatc   1320
cggaatcccc acagcaatta gaacgacagt cgaccggccc aaggactggt acaagacgat   1380
gtttaagcaa attcacatgg tgcacaagcc ggatgatgac acagacatgt ataatactcc   1440
ttatacatac aatgcaggtc tgtacaaccc accctacagt gctcagtcac accctgctgc   1500
aaagacccaa acctacagac ctctttccaa aagccactcc gacaacagcc ccaatgcctt   1560
taaggatgcg tcctccccag tgcctccccc acatgttcca cctccagtcc cgccgcttcg   1620
accaagagat cggtcttcaa cagaaaagca tgactgggat cctccagaca gaaaagtgga   1680
cacaagaaaa tttcggtctg agccaaggag tatttttgaa tatgaacctg gcaagtcatc   1740
aattcttcag catgaaagac cagcctcctt gtatcagtcc tctatagaca gaagcctgga   1800
aagacccatg agttctgcaa gcatggccag tgacttcagg aagcggagga agagcgagcc   1860
tgcagtgggt ccaccacggg gcttgggaga tcaaagtgcg agcaggacta gcccaggccg   1920
agtggacctc ccaggatcaa gcaccactct tacaaagtct ttcactagct cttctccttc   1980
ttccccatca agagcaaaag gtggggatga tagcaaaata tgtccatccc tttgcagtta   2040
ctcagggctc aacggcaacc cctccagtga gttagattac tgtagcactt acagacagca   2100
cttggatgtc cctcgggact caccaagagc cattagtttc aagaacggct ggcaaatggc   2160
ccggcaaaac gcagaaatct ggagcagcac ggaagaaacc gtctctccca aaatcaaatc   2220
ccggagctgt gacgatctcc taaacgacga ctgcgatagc ttcccggacc cgaaagtcaa   2280
gtcggaaagc atgggctccc tgttatgtga ggaggactcc aaggagagct gccccatggc   2340
gtgggggtcc ccctacgtcc cggaggttcg cagtaacggc agatcaagga tcagacacag   2400
gtcagcccgc aacgccccgg ggttcctgaa gatgtacaag aaaatgcacc gcatcaaccg   2460
caaggacctg atgaactccg aggtgatctg ctccgtgaag tccaggattc tgcagtacga   2520
gagcgagcag cagcacaagg acctgctgcg cgcctggagc cagtgctcca cggaggaggt   2580
gccccgggac atggtgccca cacgcatctc cgaattcgaa aagctgatcc agaagtccaa   2640
```

```
atccatgcca aatttagggg atgacatgct gtctcccgta accctagaac caccgcaaaa   2700
tggcctatgt cccaagaggc ggttttccat tgagtatttg ctggaggaag aaaatcaaag   2760
cggccccccc gctcggggcc ggcgaggctg ccagtctaac gccctggtgc ccattcacat   2820
tgaagtcacc agcgatgagc agccccgagc acacgtggag ttttccgaca gcgaccagga   2880
cggggttgtg tccgaccaca gtgactacat tcacctagag ggtcatcct tctgcagtga   2940
aagtgacttt gatcactttt ccttcacatc ctccgaaagc ttttacggat ccagccacca   3000
ccaccaccat caccaccacc accaccaccg ccacctcatc agctcctgca aaggcaggtg   3060
cccggcctcc tacactcgat ttaccacaat gttaaaacac gaaagagcca gacacgaaaa   3120
caccgaggag cccagaaggc aagaaatgga ccctggcctt tctaaacttg cttttctagt   3180
cagtcctgtg cctttccgga ggaaaaaaaa ttcggctcct aagaaacaga ctgaaaaggc   3240
aaaatgtaaa gcatctgtgt ttgaggctct ggactctgcc cttaaagaca tctgtgacca   3300
aattaaagct gaaaagaaaa gggggagctt gccggacaac agcatcctgc accgcctcat   3360
cagtgagctg ctgccagatg ttcccgagag gaactcatcc ctgagagcgc tgaggaggag   3420
cccccctgcac cagcctctcc acccactgcc tcccgatggt gctattcatt gtccacccta   3480
ccagaatgac tgcgggagaa tgccccgcag tgcctctttc caagacgtgg acacagccaa   3540
cagcagctgc caccaccaag accgtggcgg tgcactccaa gaccgtgagt cccctagaag   3600
ttactcatcc actttgactg acatggggag aagtgcacca agggaaagaa gaggaactcc   3660
agaaaaagag aaattgcctg caaaagctgt ttatgatttt aaggctcaga catctaagga   3720
gttgtcattt aagaaaggag atactgtcta catcctcagg aaaattgatc aaaattggta   3780
tgagggagaa caccacggga gagtgggcat cttcccgatc tcatacgtag agaaactcac   3840
acctcctgag aaagcacagc ctgcaagacc acctccgcca gcccagcccg gagaaatcgg   3900
agaagctata gccaaataca acttcaacgc agacacaaat gtggagctgt cactgagaaa   3960
gggagataga gttattcttc ttaaaagagt tgatcaaaac tggtatgaag gtaaaatccc   4020
aggaaccaac agacaaggca tcttccctgt ttcctatgtg gaggtcgtca agaagaacac   4080
aaaaggtgct gaggactacc ctgaccctcc aataccccac agctattcta gtgataggat   4140
tcacagcttg agctcaaata agccacagcg tcctgtgttt actcatgaaa atattcaagg   4200
tgggggggaa ccgtttcagg ctctgtataa ctatactccc aggaatgaag atgagctgga   4260
gctcagagaa agtgatgtca ttgatgtcat ggaaaagtgt gatgacggct ggtttgtggg   4320
gacctcaaga agaaccaaat tctttggtac tttccccgga aactacgtca agaggctgtg   4380
aattgcgctc cctccttctg tagaggccgc ctgccagcca tgcacctgcg tcaacgcgcc   4440
tgaaacaccc cgcgggcctc ccgttgtcat gccttacggt ttccaatgcg ccgtcaccat   4500
ctccacctgc caccaaacca ccagcagagt agccgccgct gctgtgagcc tggggacgac   4560
atggcaggct ggtccccctc cgtgaaagtg tggattccta cttcctgctc taagctttga   4620
cacgtcaaaa tgtgggatca gaaagaaaaa aatcatgata tttaaaaatg gtcaaatatt   4680
tgaggcaaaa aaaaaaaaaa aaagtgtctc caggaggctg tccagcctcg tggctccatt   4740
tcaacatctc cccccaggcg atgttctccc ccaagacgac cagaaaattg tttattgggg   4800
aatgctgtgg tttgcatttt catattcttc gcttggcagt gtgtattctt ttcacaagtt   4860
tgcctagtgt cttggtttac acaatatgac aactgtaact gtactttagc tattgtttgc   4920
ctgcacatac atgttgtaat atgcacagtg attacaacct ttaaagcaag aggaggcgag   4980
ttaatttgga tgagtgtgat tttgctgatt gaatgtgagt tttcaaatag gagtcttttt   5040
```

```
ctgcaatttg tttgcatttt ttagaagtgc aaacagtaag taaataaaag ccttcggtaa   5100

taatcatgac aatacaagag gctgagctag gctacagggg aaaactattg tgttgtaaag   5160

ttgcatcgct attttatatt aaaatgtaat gatcagcatc atgaacaatg agctcttagt   5220

gttttattta tctgaaaaaa tgtaagtaaa agcagtgtta gtgagaggtg caaagaatta   5280

ttctaacaga cacctgaaag tatctgtaag caatactagt aggtaagatt tcactgtgtg   5340

tacacataca catttgagat tgtatgagaa catataatcc atatgatatg ttgtacattt   5400

tatggaaatg taatagaatc tcacacatta ttttatagaa atagagtaca gaagcatcac   5460

aagtattaaa gttggtttta gcaaggatta ggattactac aattattttt actataataa   5520

ttatttttct tctatggaac tcagaatcct ggctacattt gaggacagga atatgttgag   5580

cctgattttc ctggtgtgtg taaaatattt cctaggaata aattaggcac tttttagaag   5640

caatgttaaa tcattcaggt tttattttct gccctgaagc agaaatttaa aaaatgatat   5700

tgggacctgg aaggtttaat atggttcaca gtgcctgaat tacacctgct ccgaaaacta   5760

gctttgtatt tcttatgact ttgcataaga actgttcatc tttggatctt gagcacctta   5820

cagataaaac tttttatggc atctctttca tggacagtga tattgatctt ttcacaatgt   5880

acgtagcctc tagaattttg tacatatgtt tgctcttttt ttgtacagac tagttgttga   5940

gaaaacaggg gcgtttccta atttggtctt tatcctgcga caacactttc agcagactag   6000

cctctcctta tctcacagat cacaagcacc cctagatagt gtgattctgt cagatagcat   6060

ttatgcaaaa atctatgaag ttaaaagatc gtagaagcca aatgaaatgt acatatctac   6120

tgactgatga caagggaatt tcattaggaa gaaggtaaag aaacatcgtt gagtagccta   6180

ccttgatttc tgtcaagttc ataaccagct tcatatttta aaggcttcag gtttgaaatt   6240

aagtcaactg catgcagctt tgctgataaa tgaataattc tctttgatgc catttatgag   6300

aaaagacttc aatatctgtt gcctgtcata tttaagaaaa attactgttt ctactctctg   6360

tatctgattt taaaagaaaa aactattcat acctggcttc caggtaattg actttgaatt   6420

cttacaagca aaggtcattg tgtttttctt gaatagacat ctaataaatt ttgcttggaa   6480

gtatacttca gtttttcttc ttgacattta tctttataaa aattgtgtat tttattccaa   6540

cttgttaaac taagagaaaa tgca                                          6564
```

<210> SEQ ID NO 47
<211> LENGTH: 6398
<212> TYPE: DNA
<213> ORGANISM: Homo sapiens

<400> SEQUENCE: 47

```
gtggaatgac gggagggagt cccggcagct cctacctccc agcgatggcg tcgctgtgcc     60

gcgcccagtc cccagcctgc cggccggtac tcaccgctac ccggagttcg ctcagacggt    120

gagatttggg gcgggtccga ggcagcggcg ggacgctacc tgcgaccggg accatgagga    180

gctgccagac ccgtggggcc ggtaacgaga gcagtcgcgg cacctgctga gaggaaagag    240

ggagcggtcc ggcgcggctg gggcgcggca gaggcttgcc cgatcctcgg ccatgtcact    300

gctctgcgtg cgcgttaaaa gggccaaatt ccagggttca ccagataaat ttaacacata    360

tgtgaccctg aaagtacaga atgtgaagag cacaactgta gcagttcgtg gtgatcagcc    420

ttcctgggaa caggatttca tgtttgagat tagtcgcctg gacctgggtc taagtgtgga    480

ggtatggaac aaaggactga tctgggacac catggtgggg actgtgtgga ttgcgctgaa    540
```

-continued

```
gactattcgt cagtcggatg aggaagggcc tggggaatgg tccacattag aggcagagac    600
gttaatgaaa gacgatgaga tctgtggaac tagaaaccca actcctcata aaattttgct    660
tgatacaaga tttgagttgc cttttgatat cccagaggag gaagccagat attggaccta    720
caaatgggag caaatcaatg ccttgggagc tgacaatgag tattctagtc aagaagaaag    780
ccagaggaag ccattgccca ctgctgccgc ccagtgttct tttgaagacc ctgatagtgc    840
cgtcgatgac cgagatagtg actatcgcag tgagaccagc aacagcttcc cacctcctta    900
ccatacagct tcccagccca acgcttctgt gcaccagttc cctgtgccgg tgcgatcgcc    960
acagcagctg ctacttcaag gcagttcccg ggactcttgt aatgactcta tgcaaagtta   1020
tgaccttgat tatccagagc ggcgggctat cagccccacc agcagcagta ggtatggctc   1080
ctcctgtaat gtgagtcaag gaagctctca gctaagtgaa ctagaccagt atcacgaaca   1140
agatgacgac catcgggaga cggactcgat tcattcttgc cacagctctc acagcctgtc   1200
cagagatggc caagcaggtt ttggagaaca agagaaaccc ttggaggtga caggtcaagc   1260
agagaaggag gcagcatgtg aacccaagga gatgaaagaa gatgccacaa cccaccctcc   1320
cccagatctg gtgctgcaaa aagaccactt cctaggtccc caggagagtt ttcctgagga   1380
gaatgcatct tcaccattta cccaagccag agcacattgg atccgagcag ttaccaaggt   1440
tcgactccag ctgcaggaga ttccagatga tggtgacccc tctctgcctc agtggctccc   1500
ggaagggcca gccggagggc tctatggcat tgacagcatg ccagatttac gcagaaagaa   1560
gccactgcca cttgtcagtg atctgtcact ggtccagtct cggaaggcag gaatcacttc   1620
tgcaatggct acacgcactt ctcttaagga cgaagagctg aaatcccacg tgtataagaa   1680
aaccctgcag gccttaatct accccatttc gtgcaccact cctcataact ttgaggtctg   1740
gacggccact accccaacct actgctatga gtgtgaaggc ctgctctggg gcattgcccg   1800
gcagggcatg cgctgcagcg aatgtggagt caagtgccat gagaagtgcc aggatctgct   1860
caatgctgac tgcctgcagc gggctgcaga aaagagctgt aaacatggag ctgaggaccg   1920
gacccagaac attatcatgg ccatgaagga ccgcatgaag atccgagagc gaaataagcc   1980
agagatcttt gaagttatcc gggacgtctt cacagtgaac aaagctgccc atgtgcagca   2040
gatgaaaaca gtgaagcaga gtgtactgga tggcacctcc aaatggtcag ccaagatcac   2100
cattactgtg gtgtgtgccc agggcctaca agccaaggac aaaacaggat ccagtgaccc   2160
ttacgtgact gtgcaagtca gcaaaactaa gaagcgtacc aagaccattt ttggaaactt   2220
gaatcctgtt tgggaggaga agttccattt tgagtgccac aactcctctg accgcattaa   2280
ggtgcgtgta tgggatgagg atgatgacat caagtcaaga gtaaagcaac gcctaaagcg   2340
agagtctgat gatttccttg gccaaaccat cattgaggtt cggaccctaa gtggcgagat   2400
ggacgtctgg tacaacttgg agaagaggac agacaaatca gccgtctcag ggggctatccg   2460
actacaaatc agtgtggaga tcaaggggga ggagaaagta gccccatacc acgtgcagta   2520
tacatgtctc catgagaatc ttttccatta cctcacagac attcagggca gtggaggagt   2580
ccgcatccct gaagctcgag gagacgatgc ctggaaggtg tactttgatg agacagccca   2640
agaaattgtg gatgaatttg ccatgcgtta tggcattgag tccatatatc aggccatgac   2700
gcactttgca tgtttatcat ccaagtacat gtgtcctggt gtgccagcag tgatgagcac   2760
cttactggcc aacatcaacg cctactatgc ccacacaact gcctctacca atgtctctgc   2820
atctgatcgc tttgcagcct ccaactttgg gaaagagaga tttgtaaaac tgctggacca   2880
gctacacaac tcactgagga tcgacctctc tacatacagg aataatttcc ctgctgggag   2940
```

```
tcctgaacgg cttcaggact taaaatccac agtggatttg ctgaccagca ttactttctt   3000
cagaatgaag gtacaagaac tgcaaagccc tccaagagcc agccaggtgg taaaggattg   3060
tgtgaaggcc tgtttgaact ccacatatga atatatcttc aacaactgcc acgacttata   3120
cagccgccag taccagctga agcaggagct acctccagag gaacaagggc ccagcattcg   3180
gaacctggat ttctggccca agctcatcac actcatcgtg tcaatcatag aggaagataa   3240
gaattcctac acacctgttc tgaaccagtt tcctcaggag ttgaatgtgg gaaaagtcag   3300
cgcagaagtg atgtggcatt tgtttgccca agacatgaaa tatgcattgg aggagcatga   3360
gaaagaccac ctgtgtaaaa gtgctgacta catgaacctg cacttcaagg tgaagtggct   3420
ccacaatgaa tacgtgcggg atctgcctgt cctccagggg caggtgcctg agtacccagc   3480
gtggtttgag cagttcgtgc tacaatggct ggatgagaat gaggatgtat ccctggaatt   3540
cctgcgtggg gccctggaac gagataagaa ggatggattc cagcagacat cagagcatgc   3600
actcttttcc tgctctgtgg tggatgtctt cacacaactc aatcagagct ttgagatcat   3660
ccggaagctg gaatgcccag accccagcat ccttgcccac tacatgagga ggtttgctaa   3720
gaccatcggg aaggtgctga tgcagtatgc agacatcttg tcaaaggact tcccagccta   3780
ttgcacaaag gagaaactgc cctgcatcct gatgaacaac gtgcagcaac tgagggtcca   3840
gctggagaaa atgtttgagg ccatgggagg caaggagctg gaccttgaag ctgcagacag   3900
tctgaaggag ctgcaggtga aactgaatac ggttctggat gagctcagca tggtgtttgg   3960
aaacagtttc caggtacgga ttgatgagtg tgttcgacaa atggccgaca tcctgggcca   4020
ggttcggggc acagggaatg catctccaga cgccagggcc tcagcggctc aggatgcaga   4080
tagcgtactc cggcctctca tggacttcct ggatggcaac ctcaccctct ttgccactgt   4140
gtgtgagaag acggttctga agcgtgtact gaaggagctc tggcgcgtgg tgatgaacac   4200
aatggagagg atgattgttc tgccccccact cactgaccag acgggcaccc agctgatctt   4260
cactgctgcc aaggagctga gccatctttc caaactcaag gatcacatgg tacgagagga   4320
aacacggaat ctcactccaa agcagtgtgc agtccttgac ctcgccctgg acaccatcaa   4380
gcaatacttc catgcaggag gcaatgggct gaagaaaacc ttcctggaga agagcccaga   4440
tctgcagtct ctacgctatg ccctgtctct gtacacacag actactgaca ctctcatcaa   4500
gacctttgtg cgctcgcaga ccacccaagg gtctggtgtg gacgatcctg tgggagaagt   4560
ctctattcag gtggacttgt ttacacaccc tggtactggg gagcacaagg tcacagtgaa   4620
agtggtggct gccaatgacc tcaagtggca gacagcgggt atgttccggc ctttcgtgga   4680
ggtgactatg gttggcccac accaaagtga taagaagagg aagttcacaa ccaaatccaa   4740
aagcaacaac tgggccccca agtacaatga gacattccac ttcctcctgg gaaatgagga   4800
ggggcccgag tcctatgagt tgcagatatg cgtgaaggat tactgctttg cccgggaaga   4860
tcgcgtgcta gggctggctg tgatgcctct gagggatgtc acagccaagg gcagctgtgc   4920
ctgctggtgc cccttgggcc ggaagatcca tatggatgag acaggcctga ccattctccg   4980
gattttatct cagaggagca atgacgaggt ggcccgagaa tttgtgaaac tcaaatcaga   5040
gtctcgttcc acggaggagg ggagctgaac accttcgact cctgtgccaa tcaggcagca   5100
gcaatttcac aaatcagggc cagtgggagt tagctgtgta accggcttag ggtctttgca   5160
gtcaagaggc tgaccccttc agttaaagat atttaaggaa aaatttgggg tggtgataat   5220
atggcttttc acagaaaggg tcatgaagcc ctggcccaac aggactgtgg tactaggggc   5280
```

```
tgggatgtgg ggttaccaca tggagagatt ttccattaag agagaaggac aaacatttct   5340
gagagtgtca gccattcttg gtagacacct ctccactcct catcccacct ctacccatct   5400
ccatgccaca ccttatccag ttagacacat acataccaat cattagaaga acaagtttag   5460
aaggtgtgga acttgtgcct ggctggctgg gtagtcagct gagcctgttg ctgagcccgg   5520
tggtctggat tggagtatgg ccagggcagg agtacacaga atagaattta gactgtccct   5580
tgagtagaat ccactgattt tctgtggctc cagtgagaac aaggctttga aactgaacaa   5640
gataacttct agaaatgaac tgtactaatc cctttcccca gattgtatca tgagtagaat   5700
caggttcacg tggtgcttca aagccctgag aagaatattt ctttggaccc caggcactag   5760
gggccacctg cctgggagtc tccctgcctc actcctctag gcaggggagt gatgcttcag   5820
gacgtgacag gctgttctaa catgtgtcta cctgagggct agttgaagga tccaggagta   5880
ttttcttctt gggtgggccc tgaacaaagc caaaaattgt agaaaccagt ctagaaaaag   5940
tcctgctcat ctgtggccac tgccttctag ccgtcctcca ccttgcagaa agaatctagc   6000
ctttggtctc tctctctctc atcggggtca tttgctattc ccctctgata ttcaacccta   6060
tagaaggagc ctggactctg atccctctgt acaggctgga tggaaggggc cctccacact   6120
tcctgggagg tcagagacaa actgtttcag agagtcagat ggacttccca agacttgttg   6180
agagatgtga catggttctt ggatttcctc tgtagcagcc tcctggactt cctgaggact   6240
cgacattgtc cacagatgta ctggccatta catgaaacaa gaaaccaagc atctttgctg   6300
ttgttaatta ttatatgtgc cattgttaca ggagattata ggctagtctg taataaatta   6360
tcttatagca aaaaaaaaaa aaaaaaaaaa aaaaaaaa                           6398
```

<210> SEQ ID NO 48
<211> LENGTH: 3311
<212> TYPE: DNA
<213> ORGANISM: Homo sapiens

<400> SEQUENCE: 48

```
cgcccgggca ggtgaaaggt tttgtctatt tctgttcctt gttgaatctc tagtacctag     60
aaccatgtct ggtcctgatt aggcacttgg tgaatgtttt tgaatgaata ctctgagctg    120
ttctttaatc ggtcctcatg atcctcattg tacagatgag ggaactctgg gcgaacctgg    180
cctgggtctt gagctaatta cgggtaggtc aggttctgta cccaagtagt acacacagtg    240
atgggcgggg tggcctgggg ccgtggtttg tcaaccccta cgctggaggg tgatgttttg    300
gtacaagagg agaggtgccc caatgcgtcc tgtgtctgta attgatggcg ttgtctgtgt    360
ttccccagga tgtggttctg agacagtccc tgtccctgat ggcccacgga gcgactcggt    420
ggaaggaagt cccttccgtc ccccgtcaca ctccttctct gccgtcttcg atgaagacaa    480
gccgatagcc agcagtggga cttacaactt ggactttgac aacattgagc ttgtggatac    540
ctttcagacc ttggagcctc gtgcctcaga cgctaagaat caggagggca aagtgaacac    600
acggaggaag tccacggatt ccgtccccat ctctaagtct acactgtccc ggtcgctcag    660
cctgcaagcc agtgactttg atggtgcttc ttcctcaggc aatcccgagg ccgtggccct    720
tgccccagat gcatatagca cgggttccag cagtgcttct agtaccctta agcgaactaa    780
aaaaccgagg ccgccttcct taaaaaagaa acagaccacc aagaaaccca cagagacccc    840
cccagtgaag gagacgcaac aggagccaga tgaagagagc cttgtcccca gtggggagaa    900
tctagcatct gagacgaaaa cggaatctgc caagacggaa ggtcctagcc cagccttatt    960
ggaggagacg ccccttgagc ccgctgtggg gcccaaagct gcctgccctc tggactcaga   1020
```

```
gagtgcagaa ggggttgtcc ccccggcttc tggaggtggc agagtgcaga actcaccccc   1080
tgtcgggagg aaaacgctgc ctcttaccac ggccccggag gcaggggagg taaccccatc   1140
ggatagcggg ggcaagaggg actctccagc caaagggctc tccgtaaggc tggagtttga   1200
ctattctgag gacaagagta gttgggacaa ccagcaggaa aaccccccctc ctaccaaaaa   1260
gataggcaaa aagccagttg ccaaaatgcc cctgaggagg ccaaagatga aaaagacacc   1320
cgagaaactt gacaacactc ctgcctcacc tcccagatcc cctgctgaac ccaatgacat   1380
ccccattgct aaaggtactt acacctttga tattgacaag tgggatgacc ccaattttaa   1440
cccttttttct tccacctcaa aaatgcagga gtctcccaaa ctgccccaac aatcatacaa   1500
ctttgaccca gacacctgtg atgagtccgt tgacccctttt aagacatcct ctaagacccc   1560
cagctcacct tctaaatccc cagcctcctt tgagatccca gccagtgcta tggaagccaa   1620
tggagtggac ggggatgggc taaacaagcc cgccaagaag aagaagacgc ccctaaagac   1680
tgacacattt agggtgaaaa agtcgccaaa acggtctcct ctctctgatc caccttccca   1740
ggaccccacc ccagctgcta caccagaaac accaccagtg atctctgcgg tggtccacgc   1800
cacagatgag gaaaagctgg cggtcaccaa ccagaagtgg acgtgcatga cagtggacct   1860
agaggctgac aaacaggact acccgcagcc ctcggacctg tccacctttg taaacgagac   1920
caaattcagt tcacccactg aggagttgga ttacagaaac tcctatgaaa ttgaatatat   1980
ggagaaaatt ggctcctcct tacctcagga cgacgatgcc ccgaagaagc aggccttgta   2040
ccttatgttt gacacttctc aggagagccc tgtcaagtca tctcccgtcc gcatgtcaga   2100
gtccccgacg ccgtgttcag ggtcaagttt tgaagagact gaagcccttg tgaacactgc   2160
tgcgaaaaac cagcatcctg tcccacgagg actggcccct aaccaagagt cacacttgca   2220
ggtgccagag aaatcctccc agaaggagct ggaggccatg ggcttgggca ccccttcaga   2280
agcgattgaa attagagagg ctgctcaccc aacagacgtc tccatctcca aaacagcctt   2340
gtactcccgc atcgggaccg ctgaggtgga gaaacctgca ggccttctgt tccagcagcc   2400
cgacctggac tctgccctcc agatcgccag agcagagatc ataaccaagg agagagaggt   2460
ctcagaatgg aaagataaat atgaagaaag caggcgggaa gtgatggaaa tgaggaaaat   2520
agtggccgag tatgagaaga ccatcgctca gatgatagag gacgaacaga gagagaagtc   2580
agtctcccac cagacggtgc agcagctggt tctggagaag gagcaagccc tggccgacct   2640
gaactccgtg gagaagtctc tggccgacct cttcagaaga tatgagaaga tgaaggaggt   2700
cctagaaggc ttccgcaaga atgaagaggt gttgaagaga tgtgcgcagg agtacctgtc   2760
ccgggtgaag aaggaggagc agaggtacca ggccctgaag gtgcacgcgg aggagaaact   2820
ggacagggcc aatgctgaga ttgctcaggt tcgaggcaag gcccagcagg agcaagccgc   2880
ccaccaggcc agcctgcgga aggagcagct gcgagtggac gccctggaaa ggacgctgga   2940
gcagaagaat aaagaaatag aagaactcac caagatttgt gacgaactga ttgccaaaat   3000
ggggaaaagc taactctgaa ccgaatgttt tggacttaac tgttgcgtgc aatatgaccg   3060
tcggcacact gctgttcctc cagttccatg gacaggttct gttttcactt tttcgtatgc   3120
actactgtat ttcctttcta aataaaattg atttgattgt atgcagtact aaggagacta   3180
tcagaatttc ttgctattgg tttgcatttt cctagtataa ttcatagcaa gttgacctca   3240
gagttcctgt atcagggaga ttgtctgatt ctctaataaa agacacattg ctgaaaaaaa   3300
aaaaaaaaaa a                                                         3311
```